United States Patent
Fan et al.

(10) Patent No.: US 11,642,342 B2
(45) Date of Patent: May 9, 2023

(54) COMBINATIONS OF ESTROGEN RECEPTOR DEGRADERS AND CYCLIN-DEPENDENT KINASE INHIBITORS FOR TREATING CANCER

(71) Applicant: Accutar Biotechnology, Brooklyn, NY (US)

(72) Inventors: Jie Fan, Brooklyn, NY (US); Yimin Qian, Plainsboro, NJ (US); Wei He, Zionsville, IN (US)

(73) Assignee: ACCUTAR BIOTECHNOLOGY, Brooklyn, NY (US)

( * ) Notice: Subject to any disclaimer, the term of this patent is extended or adjusted under 35 U.S.C. 154(b) by 0 days.

(21) Appl. No.: 17/140,664

(22) Filed: Jan. 4, 2021

(65) Prior Publication Data

US 2021/0213012 A1     Jul. 15, 2021

Related U.S. Application Data

(63) Continuation of application No. PCT/US2020/066798, filed on Dec. 23, 2020.

(60) Provisional application No. 62/952,695, filed on Dec. 23, 2019.

(51) Int. Cl.
| | |
|---|---|
| A61K 31/496 | (2006.01) |
| A61K 31/519 | (2006.01) |
| A61K 31/506 | (2006.01) |
| A61P 35/00 | (2006.01) |
| A61K 31/4995 | (2006.01) |
| A61K 31/501 | (2006.01) |
| A61K 31/444 | (2006.01) |
| A61K 31/551 | (2006.01) |
| A61K 31/5386 | (2006.01) |
| A61K 31/4985 | (2006.01) |
| A61K 31/4439 | (2006.01) |

(52) U.S. Cl.
CPC .......... *A61K 31/496* (2013.01); *A61K 31/444* (2013.01); *A61K 31/4439* (2013.01); *A61K 31/4985* (2013.01); *A61K 31/4995* (2013.01); *A61K 31/501* (2013.01); *A61K 31/506* (2013.01); *A61K 31/519* (2013.01); *A61K 31/5386* (2013.01); *A61K 31/551* (2013.01); *A61P 35/00* (2018.01)

(58) Field of Classification Search
CPC .............. A61K 31/496; A61K 31/4995; A61K 31/519; A61K 31/501; A61K 31/4439; A61K 31/506; A61K 31/5386; A61K 31/551; A61K 31/444; A61K 31/4985; A61P 35/00

See application file for complete search history.

(56) References Cited

U.S. PATENT DOCUMENTS

| | | |
|---|---|---|
| 6,875,775 B2 | 4/2005 | Södervall et al. |
| 7,151,102 B2 | 12/2006 | Martin et al. |
| 7,449,464 B2 | 11/2008 | Martin et al. |
| 7,855,211 B2 | 12/2010 | Coates et al. |
| 7,981,889 B2 | 7/2011 | Barr Martin et al. |
| 8,143,241 B2 | 3/2012 | Ashworth et al. |
| 8,247,416 B2 | 8/2012 | Menear et al. |
| 8,415,355 B2 | 4/2013 | Brain et al. |
| 8,475,842 B2 | 7/2013 | Bechtold et al. |
| 8,518,972 B2 | 8/2013 | Man et al. |
| 8,685,980 B2 | 4/2014 | Besong et al. |
| 8,841,312 B2 | 9/2014 | Connors et al. |
| 8,859,562 B2 | 10/2014 | Helleday |
| 8,912,187 B2 | 12/2014 | Martin et al. |
| 10,519,136 B2 | 12/2019 | Fan |
| 10,550,103 B2 | 2/2020 | Fan |
| 10,696,659 B2 | 6/2020 | Fan et al. |

(Continued)

FOREIGN PATENT DOCUMENTS

| | | |
|---|---|---|
| WO | WO 03/063859 A1 | 8/2003 |
| WO | WO 2013/097773 | 7/2013 |

(Continued)

OTHER PUBLICATIONS

Spring et al. (Discovery Medicine, Jan. 2016, 21:113, p. 65-74).*
Potter (Carcinogenesis vol. 35 No. 5 pp. 974-982, 2014).*
Kubinyi (3D QSAR in Drug Design: Ligand-Protein Interactions and Molecular Similarity, vol. 2-3, Springer, 1998, 800 pages). p. 243-44 provided.*

(Continued)

*Primary Examiner* — Robert H Havlin
(74) *Attorney, Agent, or Firm* — MH2 Technology Law Group, LLP

(57) ABSTRACT

Provided herein are pharmaceutical combinations, compositions, and methods of using a compound with estrogen receptor (ER) degradation activity, such as a compound of formula (I) or a tautomer, stereoisomer or a mixture of stereoisomers, or a pharmaceutically acceptable salt, or hydrate thereof, wherein $R_1$, Y, $R_{22}$, $R_{33}$, $R_2$, p, $X_3$, $X_4$, and Z are defined herein and a cyclin-dependent kinase (CDK) inhibitor.

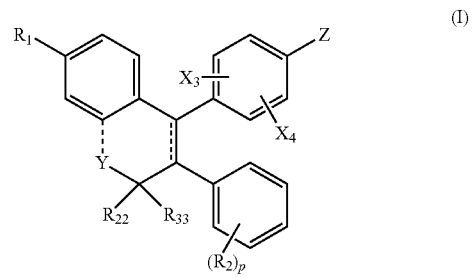

6 Claims, 4 Drawing Sheets

(56) References Cited

U.S. PATENT DOCUMENTS

| | | | |
|---|---|---|---|
| 10,800,770 | B1 | 10/2020 | Fan et al. |
| 2001/0021710 | A1 | 9/2001 | Poul et al. |
| 2002/0059198 | A1 | 4/2002 | Littman |
| 2003/0225130 | A1 | 12/2003 | Marja-Liisa et al. |
| 2009/0325930 | A1 | 12/2009 | Hamaoka et al. |
| 2011/0196150 | A1 | 8/2011 | Man et al. |
| 2014/0271460 | A1 | 9/2014 | Sharpless et al. |
| 2015/0018341 | A1 | 1/2015 | Xiao et al. |
| 2016/0008367 | A1 | 1/2016 | Borland et al. |
| 2018/0155322 | A1* | 6/2018 | Crew ................. A61K 31/5386 |
| 2018/0208590 | A1 | 7/2018 | Fan et al. |
| 2019/0202806 | A1 | 7/2019 | Fan |
| 2019/0202807 | A1 | 7/2019 | Fan |

FOREIGN PATENT DOCUMENTS

| | | | |
|---|---|---|---|
| WO | WO 2015/000868 A1 | 1/2015 | |
| WO | WO2018013559 * | 1/2018 | ............... A61K 9/00 |
| WO | WO 2019/133864 | 7/2019 | |
| WO | WO 2019/196812 A1 | 10/2019 | |
| WO | WO 2019/241231 A1 | 12/2019 | |
| WO | WO 2020/103878 A1 | 5/2020 | |
| WO | WO 2020142227 * | 7/2020 | ........... C07D 409/14 |

OTHER PUBLICATIONS

Wermuth, The Practice of Medicinal Chemsitry, 2d ed. (2003), 768 pages. Chs. 9-10 provided.*
Demidenko et al. ("Statistical determination of synergy based on Bliss definition of drugs independence" PLoS One 14(11): e0224137, 22 pages).*
International Search Report and Written Opinion dated Mar. 28, 2019, for PCT/US2018/067947, 8 pages.
International Search Report and Written Opinion dated Mar. 3, 2020, for PCT/US2019/062564, 11 pages.
Lahoz, et al., "High efficiency amplified spontaneous emission from a fluorescent anticancer drug-dye complex," Organic Electronics, 14 (2013), pp. 1225-1230.
Spring et al., "Targeting the cyclin D-cyclin-dependent kinase (CDK)4/6-retinoblastoma pathway with selective CDK4/6 inhibitors in hormone receptor-positive breast cancer: rationale, current status, and future directions," Discov Med. Jan. 2016; 21(113): 65-74.
Bliss, The Toxicity of Poisons Applied Jointly, "Laboratory of Insect Toxicology of the Institute for Plant Protection," Jan. 12, 1939, pp. 585-615.
Roell et al., "An Introduction to Terminology and Methodology of Chemical Synergy—Perspectives from Across Disciplines," Frontiers in Pharmacology, Apr. 2017, vol. 8, Article 158, 11 pages.
International Search Report and Written Opinion dated Jun. 22, 2020, for PCT/US2020/027895.
International Search Report and Written Opinion dated May 7, 2021, for PCT/US20/66798, 11 pages.
Kargbo, R., "PROTAC-Mediated Degradation of Estrogen Receptor in the Treatment of Cancer," *ACS Med. Chem. Lett. 10*:1367-1369, 2019.
Patel, H. et al., "Selective estrogen receptor modulators (SERMs) and selective estrogen receptor degraders (SERDs) in cancer treatment," *Pharmacology & Therapeutics 186*, 2018. (24 pages).

* cited by examiner

COMBINATIONS OF ESTROGEN RECEPTOR DEGRADERS AND CYCLIN-DEPENDENT KINASE INHIBITORS FOR TREATING CANCER

CROSS-REFERENCE TO RELATED APPLICATIONS

This application is a continuation of International PCT Application No. PCT/US/2020/066798, filed Dec. 23, 2020, which claims priority to U.S. Provisional Application Ser. No. 62/952,695, filed Dec. 23, 2019, the contents of each of which are hereby incorporated by reference in their entireties for all purposes.

BACKGROUND

Estrogen, a female sex hormone, through binding to its cognate Estrogen receptors, ERα and ERβ, governs a wide range of physiological processes, e.g., the development of the female reproductive system, the maintenance of bone mass, and the protection of cardiovascular tissue and the central nervous system. Upon estrogen's binding to an estrogen receptor ("ER"), the receptor undergoes a conformational change resulting in its homodimerization. The ER homodimer then binds to estrogen-response elements ("EREs") that are present in the promoters of a specific set of target genes and regulates their expression with the help of transcriptional coregulators.

Because ER signaling is implicated in many pathways, it is well known that deregulation of ER signaling, specifically through ERα, results in uncontrolled cellular proliferation which eventually results into cancer. ER+ breast cancer accounts for approximately 75% of all breast cancers diagnosed, as well as some ovarian and endometrial cancers.

The prevalence of ER+ cancer has led to decades of investigation and development of antiestrogens as therapeutic agents. Antiestrogen (i.e., hormonal) therapy is the first choice for treatment of most ER+ breast cancers. There are three major classes of antiestrogen therapies, including aromatase inhibitors (e.g., letrozole and anastrozole); selective estrogen modulators (e.g., tamoxifen, toremifene, and raloxifene); and selective estrogen receptor degraders (e.g., fulvestrant). These classes of antiestrogen therapy operate by different mechanisms of action, such as inhibiting aromatase enzyme, competitively binding to ERα, and/or causing ERα degradation.

The aforementioned therapies may result in deleterious effects. For example, administration of aromatase inhibitors results in a decrease in bone mineral density, which can result in an increased risk of fractures. Administration of selective estrogen modulators can result in development of endometrial cancer and/or cardiovascular issues, e.g., deep thrombosis and pulmonary embolism. Additionally, the aforementioned therapies may suffer from insufficient clinical efficacy.

Recently, new small molecules have been developed that selectively target and degrade ER (referred to herein as "ER degraders"). These small molecules down regulate ER activity, thereby ameliorating cellular proliferation that would otherwise cause cancer. While ER degraders may effectively down regulate ER signaling, cancer cell proliferation may proceed through other pathways.

Cyclin-dependent kinases (CDKs), and their associated proteins, play pivotal roles in coordinating and driving the cell cycle in proliferating cells. Progression through the cell cycle is governed by a series of checkpoint controls, otherwise referred to as restriction points, which are regulated CDKs. In turn, the CDKs are regulated at many levels, for instance by binding to cyclins. Tumor development is closely associated with genetic alteration and deregulation of CDKs and their regulators, suggesting that inhibitors of CDKs may be useful anti-cancer therapeutics.

There remains a need for effective and safe therapeutic agents and a need for their use in combination therapy. In particular, there is a need for effective methods of treating or preventing cancers, such as ER+ cancer.

SUMMARY

Described herein are methods of treating cancer in a patient in need thereof, comprising administering an estrogen receptor (ER) degrader and a cyclin-dependent kinase (CDK) inhibitor.

Also provided herein, are pharmaceutical combinations, and formulations comprising an estrogen receptor (ER) degrader and a cyclin-dependent kinase (CDK) inhibitor.

In some embodiments, the estrogen receptor (ER) degrader is a compound of formula (I):

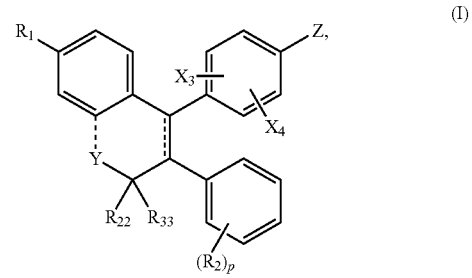

or a tautomer, stereoisomer or a mixture of stereoisomers, or a pharmaceutically acceptable salt, or hydrate thereof, wherein:

═ is a single or double bond;

--- is a single bond or absent;

Y is —CH₃, or —O—;

wherein, when Y is —CH₃, --- is absent, and ═ is a double bond; and when Y is —O—, --- and ═ are both single bonds;

Z is

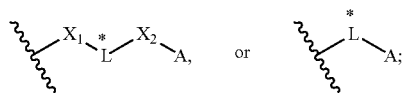

$X^3$ and $X^4$ are each independently selected from H or halo;

$X^1$ and $X^2$ are each independently selected from the group consisting of $C(R^3)_2$, $NR^4$, O, S, cycloalkyl, aryl, heterocycle, and heteroaryl, each of which is independently substituted with 0, 1, 2, or 3 $R^5$;

A is selected from:

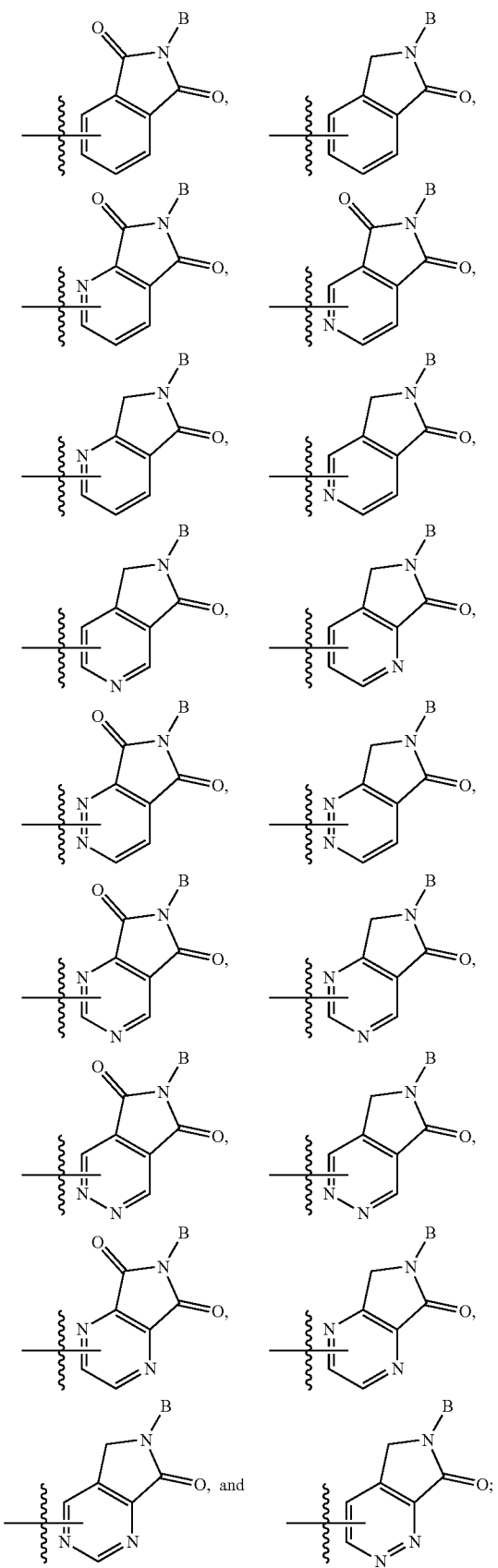

each of which is substituted with $R^{55}$ or 0, 1, 2, or 3 $R^5$;

B is selected from 5- to 6-membered cycloalkyl, 5- to 6-membered aryl, 5- to 6-membered heterocycle, and 5- to 6-membered heteroaryl, each of which is substituted with 0, 1, 2, or 3 $R^5$;

L* is a linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$;

$R^1$ and $R^2$ are each independently selected from the group consisting of H, $C_1$-$C_6$ acyl, cyano, $C_1$-$C_6$ alkyl, $C_1$-$C_6$ haloalkyl, halo, alkoxy, acyloxy, hydroxy, and sulfhydryl, each of which is substituted with 0, 1, 2, or 3 $R^5$;

each $R^3$ is independently selected from H, $C_1$-$C_6$ alkyl, halo, and hydroxy;

each $R^4$ is independently selected from H, $C_1$-$C_6$ alkyl, and acyl, each of which is substituted with 0, 1, 2, or 3 $R^5$;

each $R^{55}$ is independently selected from halogen, hydroxy, $C_1$-$C_3$ alkyl, $C_1$-$C_3$ alkoxy, $C_1$-$C_3$ haloalkyl, —$N(R^7)_2$, and —CN, each of which is substituted with 0, 1, 2, or 3 $R^5$;

each $R^7$ is independently selected from hydrogen, $C_1$-$C_6$ alkyl, and acyl, each of which is substituted with 0, 1, 2, or 3 $R^6$, or two $R^7$ groups are taken together to form a 3- to 6-membered heterocycle or heteroaryl.

each $R^5$ is independently selected from $C_1$-$C_6$ alkyl, $C_1$-$C_6$ alkoxy, $C_1$-$C_6$ haloalkyl, oxo, halo, cyano, and hydroxy;

$R^{22}$ and $R^{33}$ are each independently selected from H, $C_1$-$C_3$ alkyl, or $C_1$-$C_3$ haloalkyl, each of which is substituted with 0, 1, 2, or 3 $R^5$;

wherein

represents the point of attachment of A to $X^2$; and p is 1, or 2.

In some embodiments, the estrogen receptor (ER) degrader is a compound of formula (I-A):

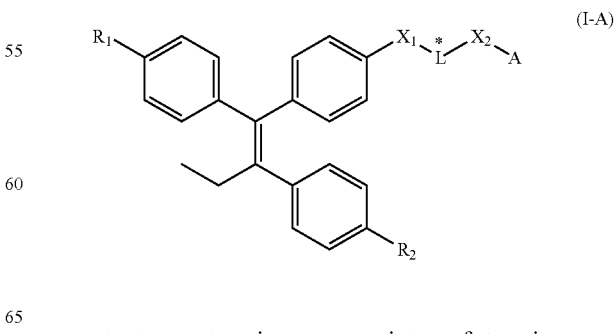

(I-A)

or a tautomer, stereoisomer or a mixture of stereoisomers, or a pharmaceutically acceptable salt, or hydrate thereof.

In some embodiments, the estrogen receptor (ER) degrader is a compound of Formula (I-B):

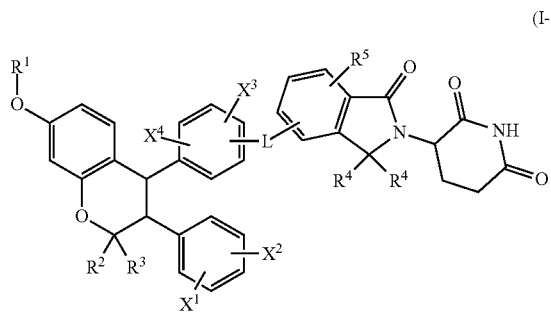

(I-B)

or a tautomer, stereoisomer or a mixture of stereoisomers, or a pharmaceutically acceptable salt, or hydrate thereof.

In some embodiments, the estrogen receptor (ER) degrader is a compound of Formula (I-B)*:

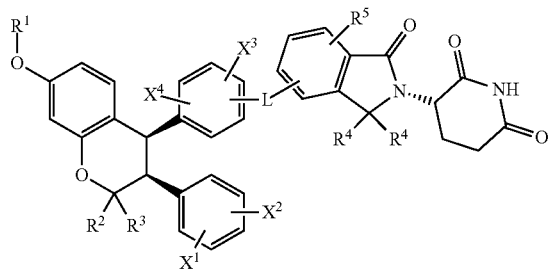

(I-B)* or a tautomer, stereoisomer or a mixture of stereoisomers, or a pharmaceutically acceptable salt, or hydrate thereof.

In some embodiments, the CDK inhibitor is a CDK1 inhibitor. In some embodiments, the CDK inhibitor is a CDK4/6 inhibitor.

In some embodiments, the CDK inhibitor has a structure according to Formula (II):

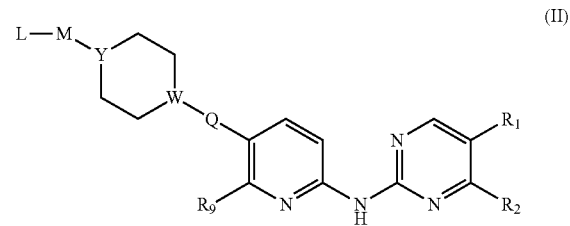

(II)

or a tautomer, stereoisomer or a mixture of stereoisomers, or a pharmaceutically acceptable salt, or hydrate thereof, wherein:

M is a bond, —NH—, or —C(O)—;

L is a H, alkyl, carbocyclyl, arylalkyl, heteroarylalkyl, or heterocycle, each of which is optionally substituted with one or more substituents;

Q is $CH_2$, O, S or a bond;

W and Y are independently CH or N, provided that at least one of W or Y is N, and when W is CH, Q is O or S; and $R_1$ and $R_2$ are independently selected from hydrogen, halogen, alkyl, and heterocycle, wherein each of alkyl and heterocycle are optionally substituted with one or more substituents; or $R_1$ and $R_2$ together with the atoms are to which they are attached form a carbocyclyl or heterocycle, each of which is optionally substituted with one or more substituents; and $R_9$ is hydrogen, halogen, or alkyl, wherein alkyl is optionally substituted.

In some embodiments, the CDK inhibitor has a structure according to Formula (III):

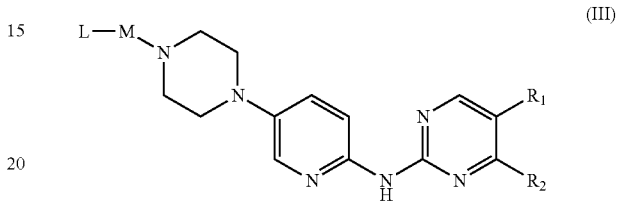

(III)

or a tautomer, stereoisomer or a mixture of stereoisomers, or a pharmaceutically acceptable salt, or hydrate thereof.

In some embodiments, the CDK4/6 inhibitor is selected from the group consisting of palbociclib, ribociclib, and abemaciclib or a pharmaceutically acceptable salt, hydrate polymorph, or solvate thereof.

DEFINITIONS

Figure 1:
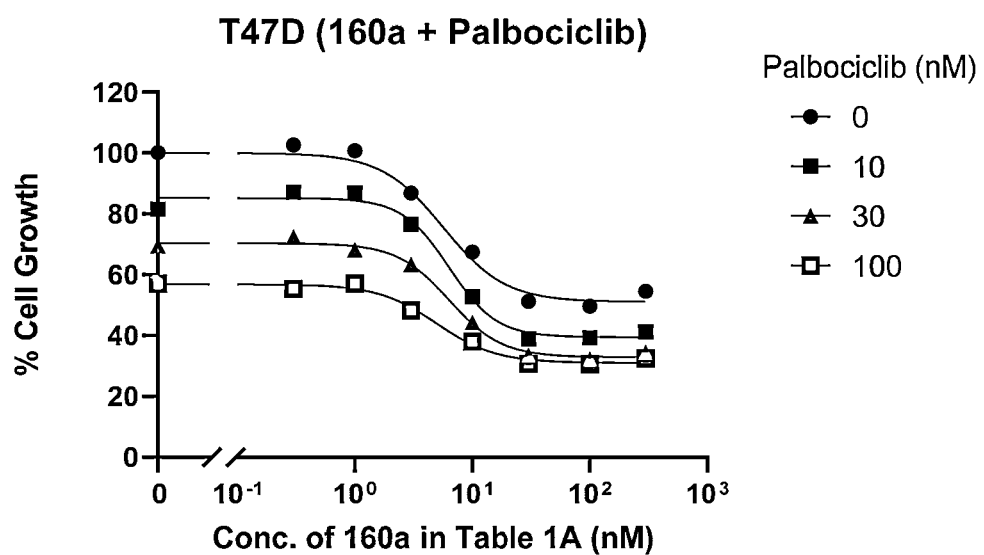
FIG. 1 is a cell growth inhibition curve depicting cell growth (%) in ER-positive T47D cells treated with palbociclib alone at 10, 30, and 100 nM, and with ER degrader 160a alone or in combination with palbociclib at 10, 30, and 100 nM.

While the following terms are believed to be well understood by one of ordinary skill in the art, the following definitions are set forth to facilitate explanation of the presently disclosed subject matter.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

The term "about" when immediately preceding a numerical value means a range of plus or minus an acceptable degree of variation in the art. In some embodiments, the term "about" encompasses 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

"Subject" refers to an animal, such as a mammal, that has been or will be the object of treatment, observation, or experiment. The methods described herein is useful for both human therapy and veterinary applications. In one embodiment, the subject is a human.

By "optional" or "optionally" it is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The term "pharmaceutically acceptable esters" include those obtained by replacing a hydrogen on an acidic group with an alkyl group, for example by reacting the acid group with an alcohol or a haloalkyl group. Examples of esters include, but are not limited to, replacing the hydrogen on an —C(O)OH group with an alkyl to form an —C(O)Oalkyl.

The term "pharmaceutically acceptable solvate" refers to a complex of solute (e.g., active compound, salt of active compound) and solvent. If the solvent is water, the solvate may be referred to as a hydrate, for example, a mono-hydrate, a di-hydrate, a tri-hydrate, etc.

The terms "pharmaceutical combination," "therapeutic combination" or "combination" as used herein, refers to a single dosage form comprising at least two therapeutically active agents, or separate dosage forms comprising at least two therapeutically active agents together or separately for use in combination therapy. For example, one therapeutically active agent is formulated into one dosage form and the other therapeutically active agent is formulated into a single or different dosage forms. For example, one therapeutically active agent is formulated into a solid oral dosage form whereas the second therapeutically active agent is formulated into a solution dosage form for parenteral administration.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

The term "therapeutically effective" applied to dose or amount refers to that quantity of a compound or pharmaceutical formulation that is sufficient to result in a desired clinical benefit after administration to a patient in need thereof.

All weight percentages (i.e., "% by weight" and "wt. %" and w/w) referenced herein, unless otherwise indicated, are measured relative to the total weight of the pharmaceutical composition.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "acyl" as used herein refers to R C(O) groups such as, but not limited to, (alkyl)-C(O)—, (alkenyl)-C(O)—, (alkynyl)-C(O)—, (aryl)-C(O)—, (cycloalkyl)-C(O), (heteroaryl)-C(O)—, and (heterocyclyl)-C(O)—, wherein the group is attached to the parent molecular structure through the carbonyl functionality. In some embodiments, it is a $C_{1-10}$ acyl radical which refers to the total number of chain or ring atoms of the, for example, alkyl, alkenyl, alkynyl, aryl, cycloalkyl, or heteroaryl, portion plus the carbonyl carbon of acyl. For example, a $C_4$-acyl has three other ring or chain atoms plus carbonyl.

"Alkyl" or "alkyl group" as used interchangeably herein refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. In some embodiments, "alkyl" is a straight-chain hydrocarbon. In some embodiments, "alkyl" is a branched hydrocarbon. Unless stated otherwise specifically in the specification, an alkyl group can be optionally substituted.

"Alkoxy" refers to a group of the formula —OR$_a$ where R$_a$ is an alkyl, alkenyl or alkynyl as defined above containing one to twelve carbon atoms. Unless stated otherwise specifically in the specification, an alkoxy group can be optionally substituted.

"Alkylene" or "alkylene chain" as used interchangeably herein refers to a fully saturated, straight or branched divalent hydrocarbon chain, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the group through a single bond. The points of attachment of the alkylene chain to the rest of the molecule and to the group can be through one carbon or any two carbons within the chain. Unless stated otherwise specifically in the specification, an alkylene chain can be optionally substituted.

"Alkenyl" or "alkenyl group" as used interchangeably herein refers to a straight or branched hydrocarbon chain having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkynyl" or "alkynyl group" as used interchangeably herein refers to a straight or branched hydrocarbon chain having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Aryl" refers to a hydrocarbon ring system comprising hydrogen, 6 to 18 carbon atoms and at least one aromatic ring, which is attached to the rest molecule by a single bond. For purposes of this invention, the aryl can be a monocyclic, bicyclic, tricyclic or tetracyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the aryl can be optionally substituted.

"Aralkyl" or "arylalkyl" as used interchangeably herein refers to a group of the formula —R$_b$—R$_c$ where R$_b$ is an alkylene group as defined above and R$_c$ is one or more aryls as defined above, for example, benzyl, diphenylmethyl and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon, and which is attached to the rest of the molecule by a single bond. Carbocyclic rings can comprise from 3 to 20 carbon atoms in the ring. Carbocyclic rings include aryls and cycloalkyl, cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon consisting solely of carbon and hydrogen atoms, which can include fused, spirocyclic, or bridged ring systems (e.g., fused, or bridged ring systems), having from three to twenty carbon atoms, and which is attached to the rest of the molecule by a single bond. Monocyclic cycloalkyl include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl include, for example, cyclopentenyl, cyclohexenyl, cycloheptenyl, cyclooctenyl, and the like.

Polycyclic cycloalkenyls include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon consisting solely of carbon and hydrogen atoms, having from 3 to 20 carbon atoms and one or more carbon-carbon triple bonds, which can include fused or bridged ring systems, and which is attached to the rest of the molecule by a single bond. Monocyclic cycloalkynyls include, for example, cycloheptynyl, cyclooctynyl, and the like. Unless otherwise stated specifically in the specification, a cycloalkynyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Heterocyclyl," "heterocyclic ring" or "heterocycle" as used interchangeably herein refers to a stable 3- to 20-membered aromatic or non-aromatic ring which consists of 2 to 12 carbon atoms and from one to six heteroatoms selected from the group consisting of nitrogen, oxygen and sulfur, and which is attached to the rest of the molecule by a single bond. Heterocyclycl or heterocyclic rings include heteroaryls as defined below. Unless stated otherwise specifically in the specification, the heterocyclyl can be a monocyclic, bicyclic, tricyclic or tetracyclic ring system, which can include fused, spirocyclic, or bridged ring systems (e.g., fused, or bridged ring systems); and the nitrogen, carbon or sulfur atoms in the heterocyclyl can be optionally oxidized; the nitrogen atom can be optionally quaternized; and the heterocyclyl can be partially or fully saturated. Examples of such heterocyclyls include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. For example, biotinyl, dihydrofuranyl, dihydroindolyl, dihydropyranyl, dihydrothienyl, dithiazolyl, homopiperidinyl, pyranyl, pyrazolinyl, thiopyranyl, pyrrolidin-2-only, or tetrahydroisoquinoly. Unless stated otherwise specifically in the specification, a heterocyclyl group can be optionally substituted.

"Heteroaryl" refers to a 5- to 20-membered ring system comprising hydrogen atoms, one to thirteen carbon atoms, one to six heteroatoms selected from the group consisting of nitrogen, oxygen and sulfur, and at least one aromatic ring, and which is attached to the rest of the molecule by a single bond. For purposes of this disclosure, the heteroaryl can be a monocyclic, bicyclic, tricyclic or tetracyclic ring system, which can include fused or bridged ring systems; the heteroaryl may contain one or more non-aromatic rings (e.g., cycloalkyl or heterocyclyl) fused to the aromatic ring. The nitrogen, carbon or sulfur atoms in the heteroaryl can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"Heteroarylalkyl" refers to a group of the formula —$R_b$—$R_f$ where $R_b$ is an alkylene chain as defined above and $R_f$ is a heteroaryl as defined above. Unless stated otherwise specifically in the specification, a heteroarylalkyl group can be optionally substituted.

The term "substituted" used herein means any of the above groups (i.e., alkyl, alkenyl, alkynyl, aryl, arylalkyl, carbocyclyl, cycloalkyl, cycloalkenyl, cycloalkynyl, heterocyclyl, N-heterocyclyl, heteroaryl, etc) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $NR_gR_h$, $NR_gC(=O)R_h$, $NR_gC(=O)NR_gR_h$, $NR_gC(=O)OR_h$, $NR_gSO_2R_h$, $OC(=O)NR_gR_h$, $OR_g$, $SR_g$, $SOR_g$, $SO_2R_g$, $OSO_2R_g$, $SO_2OR_g$, $=NSO_2R_g$, and $SO_2NR_gR_h$. "Substituted" also means any of the above groups in which one or more hydrogen atoms are replaced with $C(=O)R_g$, $C(=O)OR_g$, $C(=O)NR_gR_h$, $CH_2SO_2R_g$, $CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, "substituted" means any of the above groups in which two hydrogen atoms are each replaced by a bond to form a fused ring system containing the atoms to which the hydrogens were attached. Moreover, each of the foregoing substituents can also be optionally substituted with one or more of the above substituents. In some embodiments, any of the above groups (i.e., alkyl, alkenyl, alkynyl, aryl, arylalkyl, carbocyclyl, cycloalkyl, cycloalkenyl, cycloalkynyl, heterocyclyl, N-heterocyclyl, heteroaryl, etc) is substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide or thioketone.

The term "bond" is used herein to denote a direct coupling of the two adjacent groups, without any intervening atom or group. For example, when a group in Formula I is a bond, the group is effectively absent, and the moieties to which the group is depicted as being attached are bonded together.

The term "ring" may refer to a monocyclic, bicyclic, tricyclic or tetracyclic ring system, which can include fused or bridged ring systems.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers is designated "(±)" in nomenclature, but the skilled artisan will recognize that a structure may denote a chiral center implicitly. In some embodiments, an enantiomer or stereoisomer is provided substantially free of the corresponding enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by: (1) attachment of a mixture of enantiomers to a chiral auxiliary, separation of the resulting mixture of diastereomers by recrystallization or chromatography and liberation of the optically pure product from the auxiliary; (2) salt formation employing an optically active resolving agent; or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

Additionally, unless otherwise stated, structures described herein are also meant to include compounds that differ only in the presence of one or more isotopically enriched atoms. For example, compounds having the present structures except for the replacement of hydrogen by deuterium ($^{2}$H) or tritium ($^{3}$H), or the replacement of a carbon by a $^{13}$C- or $^{14}$C-carbon atom are within the scope of this disclosure. Such compounds is useful as, for example, analytical tools, probes in biological assays, or therapeutic agents.

As used herein, "cancer" refers to diseases, disorders, and conditions that involve abnormal cell growth with the potential to invade or spread to other parts of the body.

DETAILED DESCRIPTION

Described herein are pharmaceutical combinations comprising an estrogen receptor (ER) degrader and a cyclin-dependent kinase (CDK) inhibitor. Also described herein are methods of treating a patient with a form of cancer disclosed herein, or treating one or more of the symptoms of a a cancer disclosed herein, comprising administering an estrogen receptor (ER) degrader and a cyclin-dependent kinase (CDK) inhibitor. Suitable ER degraders include one or more ER degraders of the present disclosure, such as a compound of Formula (I), (I-A), (II-A), (I-B), (I-B*), (I-C), (III-C), compound(s) of Table 1A or compound(s) of Table 1). In some embodiments, the ER degrader is one or more compounds of Formula (I), (I-A), (II-A), (I-B), (I-B*), (I-C), (III-C), compound(s) of Table 1A or compound(s) of Table 1B) or a pharmaceutically acceptable salt, solvate, ester, or tautomer, thereof. In some embodiments, the ER degrader is one or more compounds of Formula (I), (I-A), (II-A), (I-B), (I-B*), (I-C), (III-C), compound(s) of Table 1A or compound(s) of Table 1B) or a tautomer, stereoisomer or a mixture of stereoisomers, or a pharmaceutically acceptable salt, or hydrate thereof. Suitable (CDK) inhibitors include one or more (CDK) inhibitors of the present disclosure, such as one or more compounds of Formula (II), or (III). In some embodiments, the CDK inhibitor is one or more compounds of Formula (II), or (III) or a pharmaceutically acceptable salt, solvate, ester, or tautomer, thereof. In some embodiments, the CDK inhibitor is one or more compounds of Formula (II), or (III) or a tautomer, stereoisomer or a mixture of stereoisomers, or a pharmaceutically acceptable salt, or hydrate thereof. In some embodiments, the CDK inhibitor is CDK4/6 inhibitor. In some embodiments, the CDK4/6 inhibitor is palbociclib, ribociclib, or abemaciclib, or a pharmaceutically acceptable salt.

Without being bound by theory, the administration of pharmaceutical combinations of one or more ER degraders and one or more CDK inhibitors of the present disclosure provide a greater therapeutic effect compared to each agent (e.g., ER degrader and, separately, CDK inhibitor) alone. In some embodiments, the use of combinations of the present disclosure provides more than an additive therapeutic effect compared to each agent alone. In some embodiments, the use of combinations of the present disclosure provides synergistic therapeutic effect compared to each agent alone. In some embodiments, the use of combinations of the present disclosure provides a therapeutic effect over a longer period of time compared to each agent alone.

The administration of a pharmaceutical combination of the present disclosure may result not only in a beneficial effect, e.g. a synergistic therapeutic effect, e.g. with regard to alleviating, delaying progression of or inhibiting the symptoms of a disease or disorder (e.g., cancer), but also result in further surprising beneficial effects, e.g. fewer side-effects, more durable response, an improved quality of life or a decreased morbidity, compared with a monotherapy comprising one of the one of the combination partners alone.

In some embodiments, a further benefit is that lower doses of the therapeutic agents of the pharmaceutical combination of the present disclosure may be used, for example, such that the dosages may not only often be smaller, but also may be applied less frequently, or can be used in order to diminish the incidence of side-effects observed with one of the combination partners alone.

As discussed herein, in some embodiments, the pharmaceutical combination or composition, or both, provided herein display a synergistic effect. The term "synergistic effect" as used herein, refers to action an ER degrader of the present disclosure, and a CDK inhibitor of the present disclosure, to produce an effect, for example, slowing the symptomatic progression of cancer or symptoms thereof, which is greater than the simple addition of the effects of each drug administered by themselves.

It can be shown by established test models that a pharmaceutical combination of the present disclosure results in the beneficial effects described herein. Relevant test models to prove such beneficial effects are known to those skilled in the art. The pharmacological activity of a combination of the disclosure may, for example, be demonstrated in a clinical study or in an animal model.

A synergistic effect can be calculated, for example, using suitable methods, such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. An additional method to show the synergistic effect is the highest single agent model (HSA) as null hypothesis (Berenbaum 1989). Excess over the HSA model predicts a functional connection between the inhibited targets (Lehar, Zimmermann et al. 2007, Lehar, Krueger et al. 2009). This method results in an indicator for the strength of the combination, z.sub.c.

In some embodiments, the present disclosure provides a synergistic combination (e.g., comprising an ER degrader and a CDK inhibitor disclosed herein) for administration to a subject in need thereof, where the dose range of each component corresponds to the synergistic ranges suggested in a suitable tumor model or clinical study.

ER Degrader

In some embodiments, the compound with ER degradation activity degrades ER alpha (aka an ER degrader).

Without being bound to any theory, it is believed that ERα degradation may occur when both ERα and a ubiquitin ligase are bound and brought into close proximity. Cereblon ("CRBN") E3 ubiquitin ligase is a ubiquitin ligase that CRBN forms an E3 ubiquitin ligase complex with damaged DNA binding protein 1 and Cullin 4. It functions as a substrate receptor by bringing the substrates to close proximity for ubiquitination and subsequent degradation by proteasomes. Recently, it has been discovered that small molecules drugs, e.g., thalidomide and its close analogs, lenalidomide and pomalidomide, can simultaneously interact with CRBN and some other proteins. In doing so, CRBN is exploited for target protein degradation, such as IKZF1 and IKZF3. This is thought to account for the anti-myeloma effects of thalidomide and related compounds.

In some embodiments, the ER degrader is described in U.S. Pat. No. 9,944,632 or 10,800,770, the contents of which are herein incorporated by reference in their entirety for all purposes.

In one aspect, the estrogen receptor (ER) degrader is a compound of formula (I):

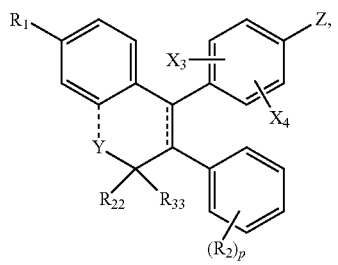

or a tautomer, stereoisomer or a mixture of stereoisomers, or a pharmaceutically acceptable salt, or hydrate thereof, wherein:

═ is a single or double bond;

--- is a single bond or absent;

Y is —CH$_3$, or —O—;

wherein, when Y is —CH$_3$, --- is absent, and ═ is a double bond; and when Y is —O—, --- and ═ are both single bonds;

Z is

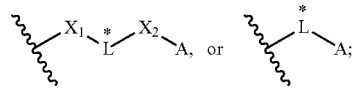

$X^3$ and $X^4$ are each independently selected from H or halo;

$X^1$ and $X^2$ are each independently selected from the group consisting of C(R$^3$)$_2$, NR$^4$, O, S, cycloalkyl, aryl, heterocycle, and heteroaryl, each of which is independently substituted with 0, 1, 2, or 3 R$^5$;

A is selected from:

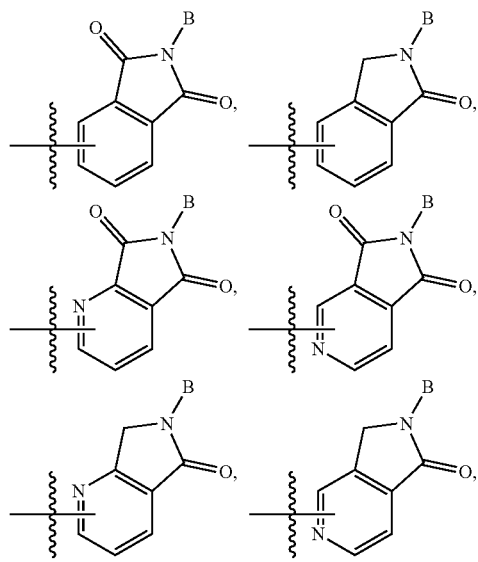

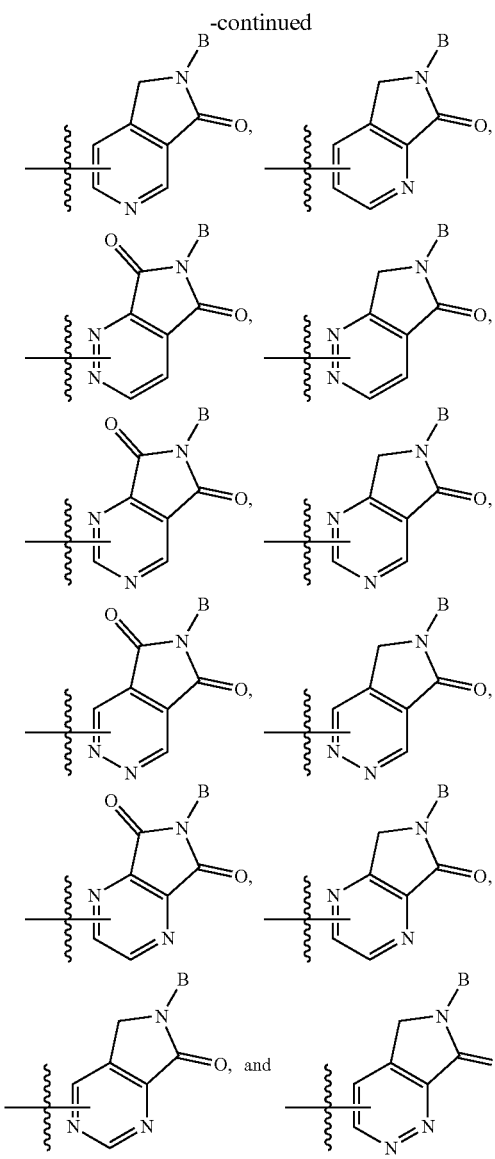

each of which is substituted with R$^{55}$ or 0, 1, 2, or 3 R$^5$;

B is selected from 5- to 6-membered cycloalkyl, 5- to 6-membered aryl, 5- to 6-membered heterocycle, and 5- to 6-membered heteroaryl, each of which is substituted with 0, 1, 2, or 3 R$^5$;

L* is a linker of 1 to 22 carbon atoms in length, wherein one or more carbon atoms are each optionally and independently replaced by a group selected from C(O), O, NR$^4$, S, C$_2$-alkenyl, C$_2$-alkynyl, cycloalkyl, aryl, heterocycle, and heteroaryl, each of which is substituted with 0, 1, 2, or 3 R$^5$;

R$^1$ and R$^2$ are each independently selected from the group consisting of H, C$_1$-C$_6$ acyl, cyano, C$_1$-C$_6$ alkyl, C$_1$-C$_6$ haloalkyl, halo, alkoxy, acyloxy, hydroxy, and sulfhydryl, each of which is substituted with 0, 1, 2, or 3 R$^5$;

each R$^3$ is independently selected from H, C$_1$-C$_6$ alkyl, halo, and hydroxy;

each R$^4$ is independently selected from H, C$_1$-C$_6$ alkyl, and acyl, each of which is substituted with 0, 1, 2, or 3 R$^5$;

each $R^{55}$ is independently selected from halogen, hydroxy, $C_1$-$C_3$ alkyl, $C_1$-$C_3$ alkoxy, $C_1$-$C_3$ haloalkyl, —N($R^7$)$_2$, and —CN, each of which is substituted with 0, 1, 2, or 3 $R^5$;

each $R^7$ is independently selected from hydrogen, $C_1$-$C_6$ alkyl, and acyl, each of which is substituted with 0, 1, 2, or 3 $R^6$, or two $R^7$ groups are taken together to form a 3- to 6-membered heterocycle or heteroaryl.

each $R^5$ is independently selected from $C_1$-$C_6$ alkyl, $C_1$-$C_6$ alkoxy, $C_1$-$C_6$ haloalkyl, halo, cyano, and hydroxy;

$R^{22}$ and $R^{33}$ are each independently selected from H, $C_1$-$C_3$ alkyl, or $C_1$-$C_3$ haloalkyl, each of which is substituted with 0, 1, 2, or 3 $R^5$;

wherein

represents the point of attachment of A to $X^2$; and p is 1, or 2.

In one aspect, the estrogen receptor (ER) degraders provided herein are compounds of Formula (I-A):

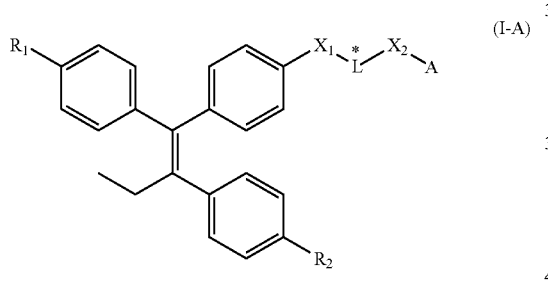

(I-A)

or a tautomer, stereoisomer or a mixture of stereoisomers, pharmaceutically acceptable salt, or hydrate thereof, wherein:

$X^1$ and $X^2$ are each independently selected from C($R^3$)$_2$, $NR^4$, O, S, cycloalkyl, aryl, heterocycle, and heteroaryl, each of which is independently substituted with 0, 1, 2, or 3 $R^5$;

A is selected from:

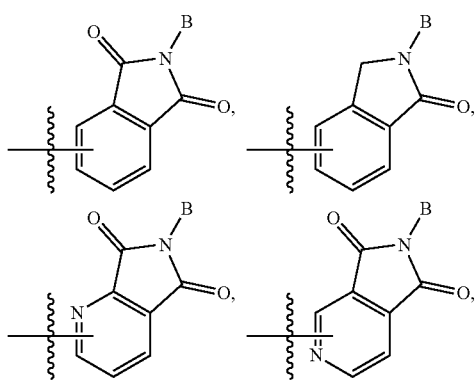

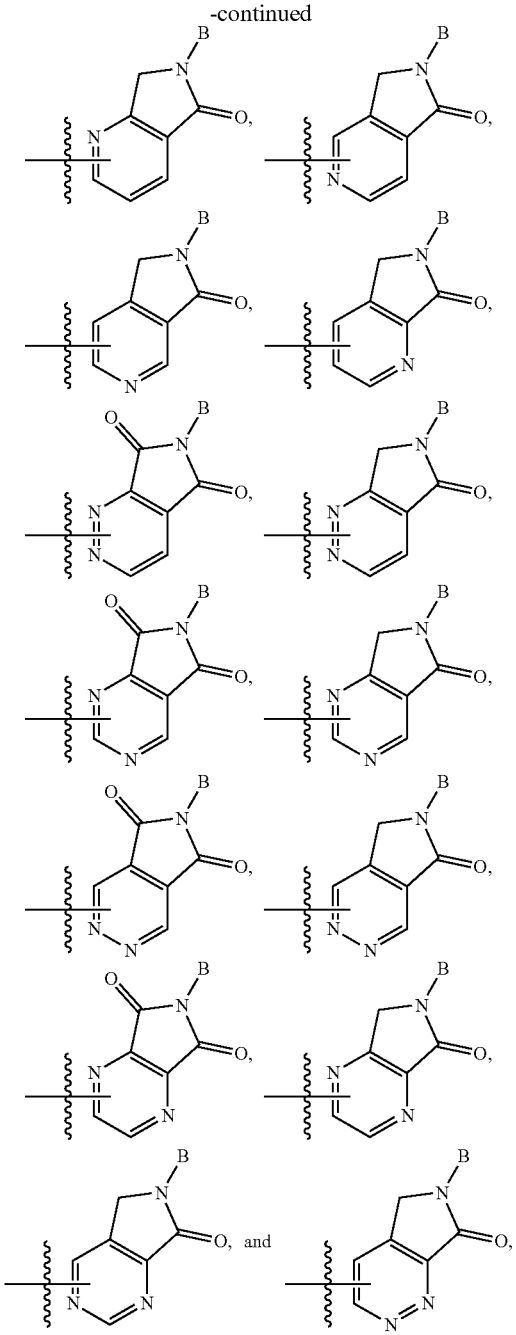

each of which is substituted with 0, 1, 2, or 3 $R^5$;

B is selected from 5- to 6-member cycloalkyl, 5- to 6-member aryl, 5- to 6-member heterocycle, and 5- to 6-member heteroaryl, each of which is substituted with 0, 1, 2, or 3 $R^5$;

L* is a linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$;

$R^1$ and $R^2$ are each independently selected from H, $C_1$-$C_6$ alkyl, halo, alkoxy, acyloxy, hydroxy, and sulfhydryl, each of which is substituted with 0, 1, 2, or 3 $R^5$;

each $R^3$ is independently selected from H, $C_1$-$C_6$ alkyl, halo, and hydroxy;

each $R^4$ is independently selected from H, $C_1$-$C_6$ alkyl, and acyl, each of which is substituted with 0, 1, 2, or 3 $R^5$; and each $R^5$ is independently selected from $C_1$-$C_6$ alkyl, halo, cyano, and hydroxy, wherein

represents the point of attachment of A to $X^2$.

In some embodiments, the compound of Formula (I) or Formula (I-A) may encompass both the E and Z isomers. In some embodiments, the compound of Formula (I) or Formula (I-A) is a mixture of trans- and -cis olefin.

In some embodiments of the compound of Formula (I) or Formula (I-A), A is

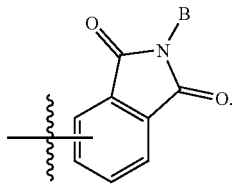

In some embodiments, A is

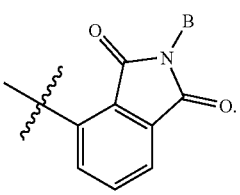

In some embodiments, A is

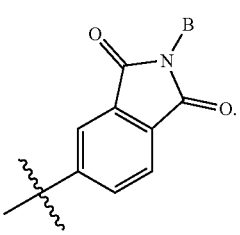

In some embodiments, A is

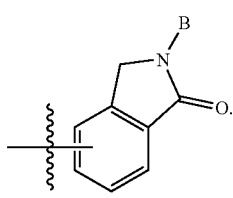

In some embodiments, A is

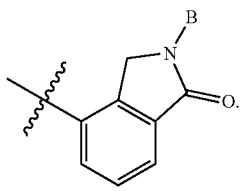

In some embodiments, A is

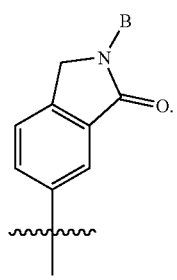

In some embodiments, A is

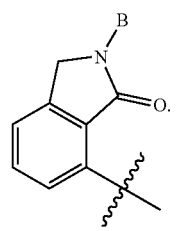

In some embodiments, A is

[structure]

In some embodiments, the estrogen receptor (ER) degrader is a compound of Formula (II-A), or a tautomer, stereoisomer, pharmaceutically salt, or hydrate thereof:

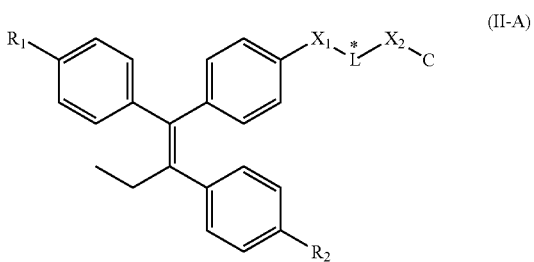

(II-A)

wherein:

X¹ and X² are each independently selected from $C(R^3)_2$, $NR^4$, O, S, cycloalkyl, aryl, heterocycle, and heteroaryl, each of which is independently substituted with 0, 1, 2, or 3 $R^5$;

B is selected from 5- to 6-member cycloalkyl, 5- to 6-member aryl, 5- to 6-member heterocycle, and 5- to 6-member heteroaryl, each of which is substituted with 0, 1, 2, or 3 $R^5$;

C is selected from:

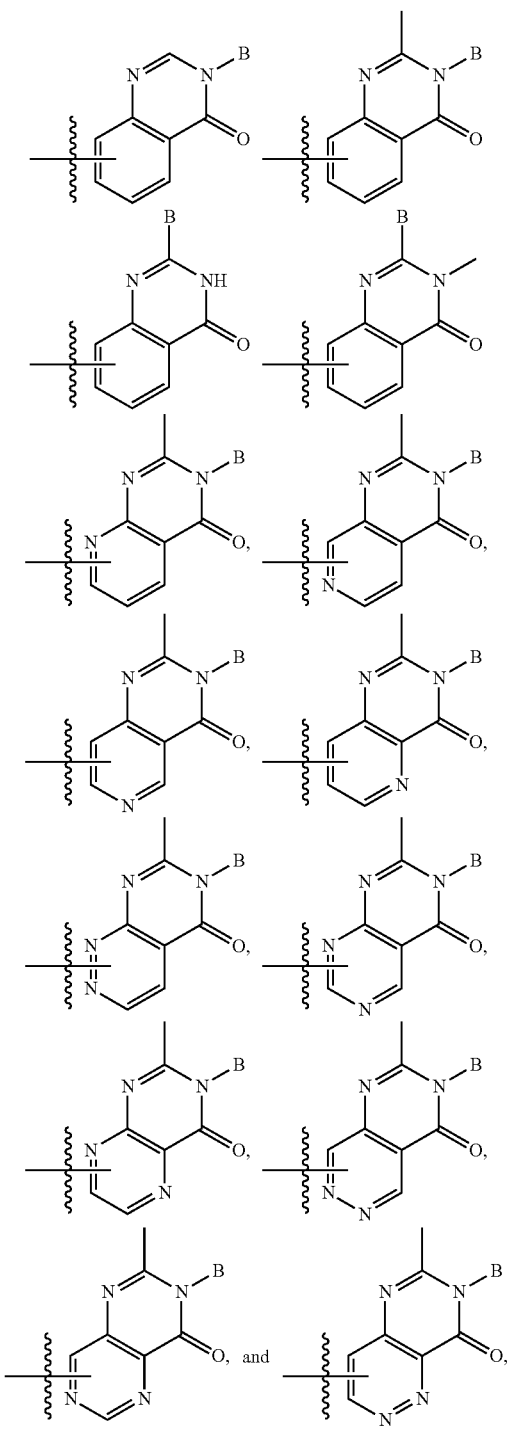

each of which is substituted with 0, 1, 2, or 3 $R^5$;

L* is a linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$;

$R^1$ and $R^2$ are each independently selected from H, $C_1$-$C_6$ alkyl, halo, alkoxy, acyloxy, hydroxy, and sulfhydryl, each of which is substituted with 0, 1, 2, or 3 $R^5$;

each $R^3$ is independently selected from H, $C_1$-$C_6$ alkyl, halo, and hydroxy;

each $R^4$ is independently selected from H, $C_1$-$C_6$ alkyl, and acyl, each of which is substituted with 0, 1, 2, or 3 $R^5$; and each $R^5$ is independently selected from $C_1$-$C_6$ alkyl, halo, cyano, and hydroxy, wherein

represents the point of attachment of C to X².

In some embodiments of the compound of Formula (II-A), C is

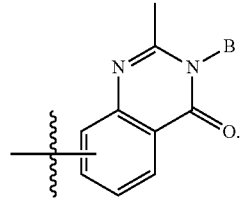

In some embodiments, C is

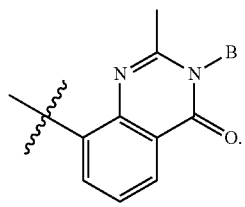

In some embodiments, C is

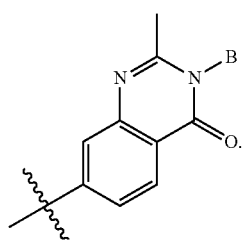

In some embodiments, C is

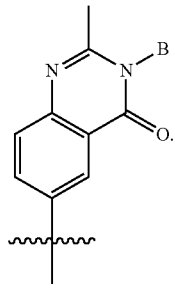

In some embodiments, C is

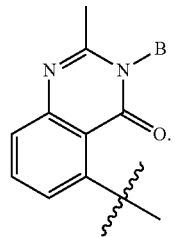

In some embodiments of the compound of Formulae (I), (I-A), and/or (II-A), B is be a 5-membered heterocycle substituted with 0, 1, 2, or 3 $R^5$. In some embodiments, B is a 5-membered heterocycle. In some embodiments, B is a 5-membered heterocycle substituted with 1 $R^5$. In some embodiments, $R^5$ is $C_1$ alkyl.

In some embodiments of the compound of Formulae (I), (I-A), and/or (II-A), B is a 6-membered heterocycle substituted with 0, 1, 2, or 3 $R^5$. In some embodiments, B is a 6-membered heterocycle. In some embodiments, B is a 6-membered heterocycle substituted with 1 $R^5$. In some embodiments, $R^5$ is $C_1$ alkyl.

In some embodiments of the compound of Formulae (I), (I-A), and/or (II-A), B is selected from the group consisting of:

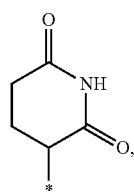 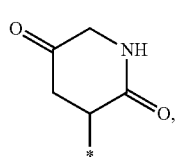 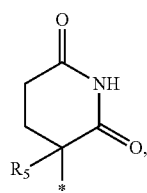

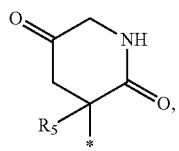 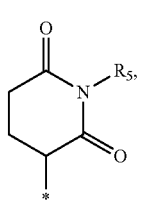 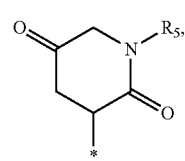

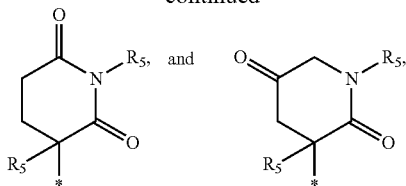

wherein * represents the point of attachment of B to A. In some embodiments, B is

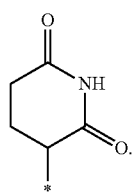

In some embodiments of the compound of Formulae (I), (I-A), and/or (II-A), $R^1$ and $R^2$ are each be independently selected from the group consisting of H, $C_1$-$C_3$ alkyl, halo, alkoxy, acyloxy, hydroxy, and sulfhydryl, each of which is substituted with 0, 1, 2, or 3 $R^5$. In some embodiments, $R^1$ and $R^2$ are each be independently selected from H, $C_1$ alkyl, halo, and hydroxy, each of which is substituted with 0, 1, 2, or 3 $R^5$. In some embodiments, $R^1$ and $R^2$ are each independently H or OH. In some embodiments, $R^1$ is H. In some embodiments, $R^1$ is OH. In some embodiments, $R^2$ is H. In some embodiments, $R^2$ is OH. In some embodiments, $R^1$ is OH and $R^2$ is H. In some embodiments, $R^1$ is H and $R^2$ is H. In some embodiments, $R^1$ is H and $R^2$ is OH. In some embodiments, $R^1$ is OH and $R^2$ is OH.

In some embodiments of the compound of Formulae (I), (I-A), and/or (II-A), $X^1$ and $X^2$ are each independently selected from the group consisting of $C(R^3)_2$, $NR^4$, O, S, 5 or 6-membered cycloalkyl, 5- or 6-membered aryl, 5- or 6-membered heterocycle, and 5- or 6-membered heteroaryl, each of which is independently substituted with 0, 1, 2, or 3 $R^5$. In some embodiments, wherein $X^1$ and $X^2$ are each independently selected from $CH_2$, $NR^4$, O, S, 5 or 6-membered cycloalkyl, 5- or 6-membered aryl, 5- or 6-membered heterocycle, and 5- or 6-membered heteroaryl, each of which is independently substituted with 0, 1, 2, or 3 $R^5$. In some embodiments, $X^1$ is O. In some embodiments, $X^1$ is $C(R^3)_2$. In some embodiments, $R^3$ is H or halo. In some embodiments, halo is fluoro. In some embodiments, $R^3$ is H. In some embodiments, $X^1$ is $NR^4$. In some embodiments, $R^4$ is selected from H, $C_1$-$C_3$ alkyl, and acyl, each of which is substituted with 0, 1, 2, or 3 $R^5$. In some embodiments, $R^4$ is H. In some embodiments, $R^4$ is $C_1$-$C_3$ alkyl substituted with 0, 1, 2, or 3 $R^5$. In some embodiments, $R^4$ is $C_1$ alkyl substituted with 0, 1, 2, or 3 $R^5$. In some embodiments, $R^4$ is $C_1$ alkyl. In some embodiments, $R^4$ is acyl substituted with 0, 1, 2, or 3 $R^5$.

In some embodiments of the compound of Formulae (I), (I-A), and/or (II-A), $X^1$ is a 5 or 6-member cycloalkyl. In some embodiments, $X^1$ is a 5- or 6-membered aryl. In some embodiments, $X^1$ is a 5- or 6-membered heterocycle. In some embodiments, $X^1$ is a 5- or 6-membered heteroaryl. In some embodiments, $X^1$ is a 5 or 6-membered cycloalkyl substituted with 0, 1, 2, or 3 $R^5$. In some embodiments, $X^1$ is a 5- or 6-membered aryl substituted with 0, 1, 2, or 3 $R^5$.

In some embodiments, $X^1$ is a 5- or 6-membered heterocycle substituted with 0, 1, 2, or 3 $R^5$. In some embodiments, $X^1$ is a 5- or 6-membered heteroaryl substituted with 0, 1, 2, or 3 $R^5$.

In some embodiments of the compound of Formulae (I), (I-A), and/or (II-A), $X^1$ is selected from the group consisting of aziridinyl, azetidinyl, pyrrolidinyl, piperidinyl, piperazinyl, pyrrolyl, pyridinyl, pyrimidinyl, oxiranyl, oxetanyl, tetrahydrofuranyl, furanyl, pyranyl, tetrahydropyranyl, dioxanyl, imidazolyl, pyrazolyl, oxazole, isoxazole, thiazole, isothiazole, triazole, tetrazole, indole, benzimidazole, benzofuran, benzoxazole, benzothiazole, quinoline, isoquinoline, and quinazoline, each of which is independently substituted with 0, 1, 2, or 3 $R^5$. In some embodiments, $X^1$ is selected from the group consisting of:

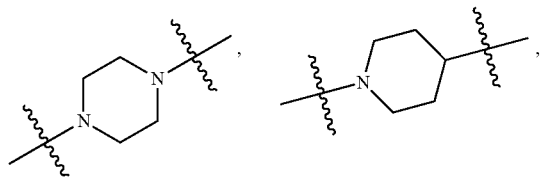

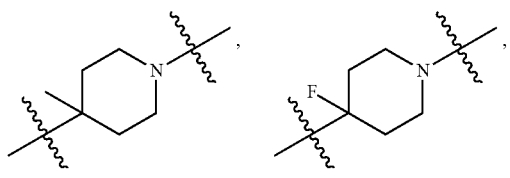

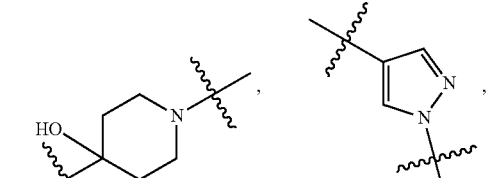

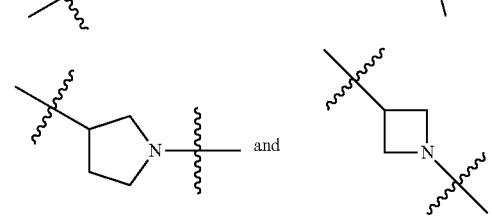

In some embodiments, $X^1$ is selected from the group consisting of:

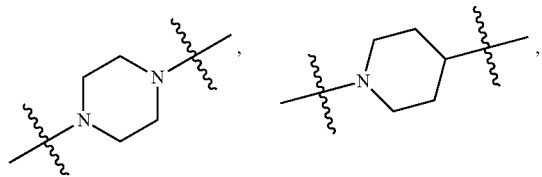

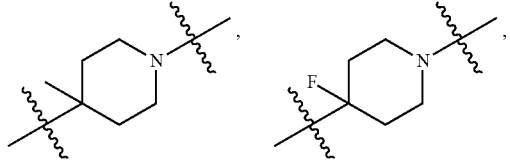

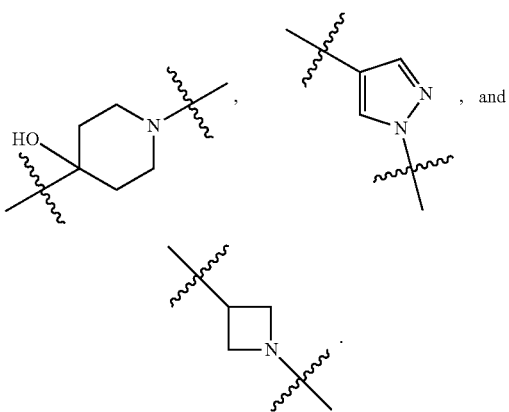

In some embodiments of the compound of Formulae (I), (I-A), and/or (II-A), $X^2$ is selected from the group consisting of:

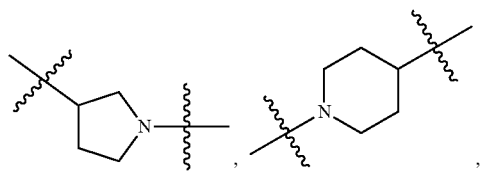

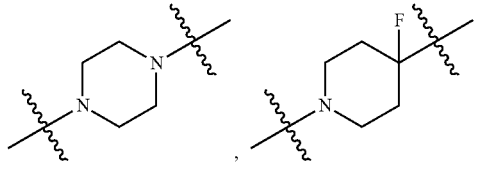

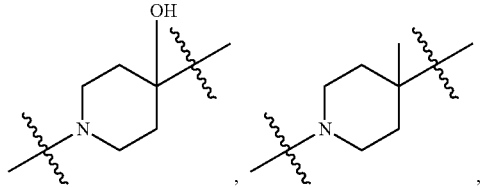

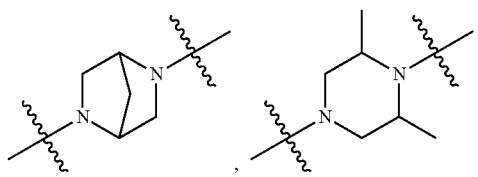

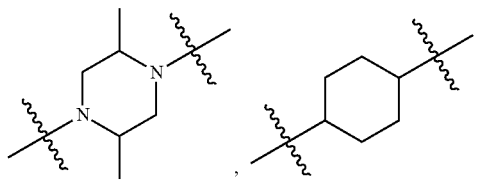

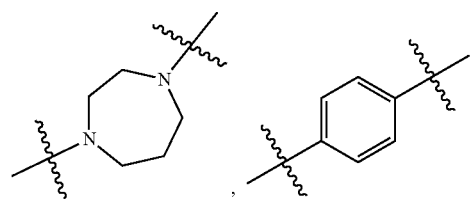

In some embodiments of the compound of Formulae (I), (I-A), and/or (II-A), L* is linker of 1 to 16 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵. In some embodiments, L* is a linker of 1 to 14 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵. In some embodiments, L* is a linker of 1 to 12 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵. In some embodiments, L* is a linker of 1 to 10 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵.

In some embodiments of the compound of Formulae (I), (I-A), and/or (II-A), L* is a linker of 1 to 8 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵. In some embodiments, L* is a linker of 1 to 6 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵.

In some embodiments of the compound of Formulae (I), (I-A), and/or (II-A), L* is a linker wherein two carbon atoms are each independently replaced by a heterocycle, each of which is independently substituted with 0, 1, 2, or 3 R⁵. In some embodiments, L* is a linker wherein one carbon atom is replaced by a heterocycle and one carbon atom is replaced by a cycloalkyl, each of which is independently substituted with 0, 1, 2, or 3 R⁵. In some embodiments, L* is a linker wherein more than one carbon atoms are each independently replaced by a group selected from C(O), O, NR⁴, S, C₂-alkenyl, C₂-alkynyl, cycloalkyl, aryl, heterocycle, and heteroaryl, each of which is substituted with 0, 1, 2, or 3 R⁵. In some embodiments, L* is a linker wherein more than one carbon atoms are each independently replaced by a group selected from C(O), O, and NR⁴, each of which is substituted with 0, 1, 2, or 3 R⁵.

In some embodiments of the compound of Formulae (I), (I-A), and/or (II-A), L* is In some embodiments, L* is In some embodiments, L* is
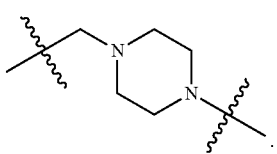 [SMILES: *CN1CCN(*)CC1]
In some embodiments, L* is
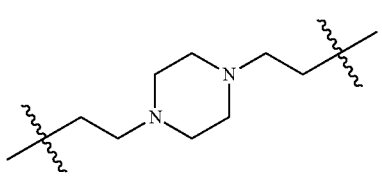
In some embodiments, L* is
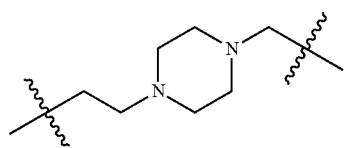
In some embodiments, L* is
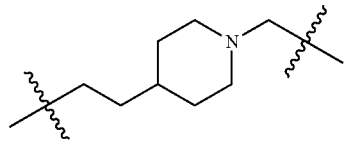
In some embodiments, L* is
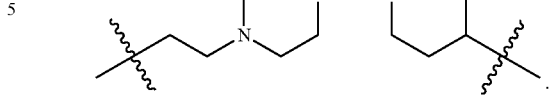
In some embodiments, L* is
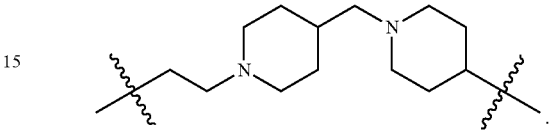
In some embodiments, L* is
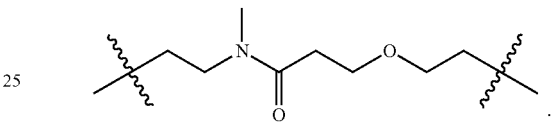
In some embodiments, L* is
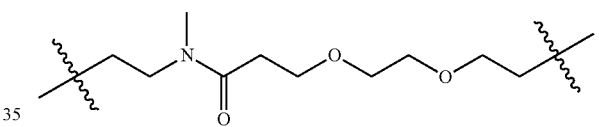
In some embodiments, L* is
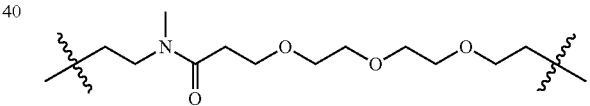
In some embodiments, L* is
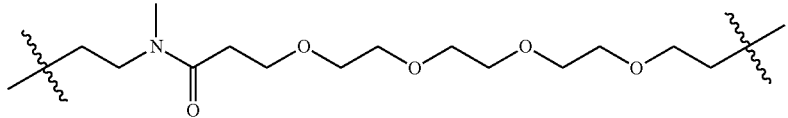
In some embodiments, L* is
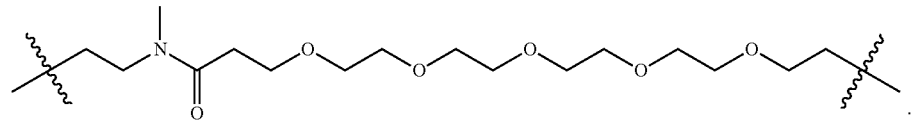 [SMILES: *CCOCCOCCOCCOCCOCCC(=O)N(C)CC*]

In some embodiments, L* is

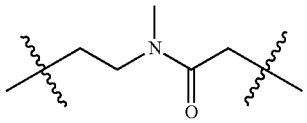

In some embodiments, L* is

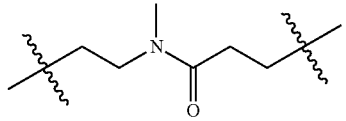

In some embodiments, L* is

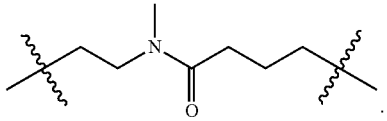 [SMILES: *CCCC(=O)N(C)CC*]

In some embodiments, L* is

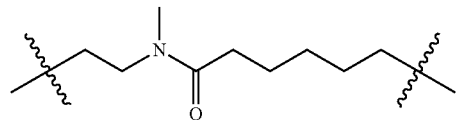

In some embodiments, L* is

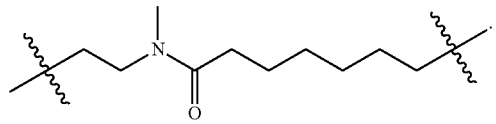

In some embodiments, L* is

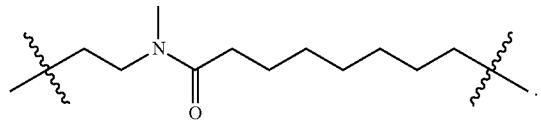 [SMILES: *CCCCCCCC(=O)N(C)CC*]

In some embodiments, L* is

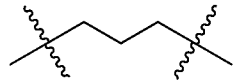

In some embodiments, L* is

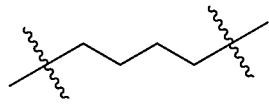

In some embodiments, L* is

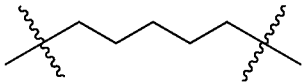

In some embodiments, L* is

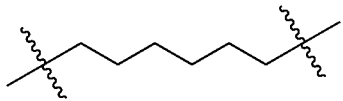

In some embodiments, the compound with ER degradation activity or tautomer, stereoisomer, pharmaceutically acceptable salt, or hydrate thereof provided herein, is selected from the group consisting of:

(Z)-3-(4-(3-(4-(2-(4-(1-(4-hydroxyphenyl)-2-phenylbut-1-en-1-yl)phenoxy)ethyl)piperazin-1-yl)propoxy)-1-oxoisoindolin-2-yl)piperidine-2,6-dione;

(Z)-3-(4-(2-(4-(2-(4-(1-(4-hydroxyphenyl)-2-phenylbut-1-en-1-yl)phenoxy)ethyl)piperazin-1-yl)ethoxy)-1-oxoisoindolin-2-yl)piperidine-2,6-dione;

(Z)-3-(5-(2-(4-(2-(4-(1-(4-hydroxyphenyl)-2-phenylbut-1-en-1-yl)phenoxy)ethyl)piperazin-1-yl)ethoxy)-1-oxoisoindolin-2-yl)piperidine-2,6-dione;

(Z)-3-(5-(2-(5-(2-(4-(1-(4-hydroxyphenyl)-2-phenylbut-1-en-1-yl)phenoxy)ethyl)-2,5-diazabicyclo[2.2.1]heptan-2-yl)ethoxy)-1-oxoisoindolin-2-yl)piperidine-2,6-dione;

(Z)-3-(5-((2-(4-(2-(4-(1-(4-hydroxyphenyl)-2-phenylbut-1-en-1-yl)phenoxy)ethyl)piperazin-1-yl)ethyl)amino)-1-oxoisoindolin-2-yl)piperidine-2,6-dione;

(Z)-3-(5-((3-(4-(2-(4-(1-(4-hydroxyphenyl)-2-phenylbut-1-en-1-yl)phenoxy)ethyl)piperazin-1-yl)propyl)amino)-1-oxoisoindolin-2-yl)piperidine-2,6-dione;

(Z)-3-(5-((3-(2-(2-(4-(1-(4-hydroxyphenyl)-2-phenylbut-1-en-1-yl)phenoxy)ethoxy)ethoxy)propyl)amino)-1-oxoisoindolin-2-yl)piperidine-2,6-dione;

(Z)-3-(2-((2-(2,6-dioxopiperidin-3-yl)-1,3-dioxoisoindolin-4-yl)amino)ethoxy)-N-(2-(4-(1,2-diphenylbut-1-en-1-yl)phenoxy)ethyl)-N-methylpropanamide;

(Z)-3-(4-(2-(6-(2-(4-(1-(4-hydroxyphenyl)-2-phenylbut-1-en-1-yl)phenoxy)ethyl)-2,6-diazaspiro[3.3]heptan-2-yl)ethoxy)-1-oxoisoindolin-2-yl)piperidine-2,6-dione;

(Z)-3-(5-(5-(4-(2-(4-(1-(4-hydroxyphenyl)-2-phenylbut-1-en-1-yl)phenoxy)ethyl)piperazin-1-yl)-5-oxopentyl)-1-oxoisoindolin-2-yl)piperidine-2,6-dione;

(Z)-2-(2,6-dioxopiperidin-3-yl)-5-(4-(2-(4-(1-(4-hydroxyphenyl)-2-phenylbut-1-en-1-yl)phenoxy)ethyl)piperazin-1-yl)isoindoline-1,3-dione;

(Z)-3-(5-((4-(4-(2-(4-(1-(4-hydroxyphenyl)-2-phenylbut-1-en-1-yl)phenoxy)ethyl)piperazin-1-yl)butyl)amino)-1-oxoisoindolin-2-yl)piperidine-2,6-dione;

(Z)-3-(5-(3-(4-(2-(4-(1-(4-hydroxyphenyl)-2-phenylbut-1-en-1-yl)phenoxy)ethyl)piperazin-1-yl)-3-oxopropyl)-1-oxoisoindolin-2-yl)piperidine-2,6-dione;

(Z)-3-(5-((3-(3-(4-(1-(4-hydroxyphenyl)-2-phenylbut-1-en-1-yl)phenoxy)propoxy)propyl)amino)-1-oxoisoindolin-2-yl)piperidine-2,6-dione;

(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;

(E)/(Z)-2-(2,6-dioxopiperidin-3-yl)-5-(4-(4-(4-(1-(4-hydroxyphenyl)-2-phenylbut-1-en-1-yl)phenoxy)butyl)piperazin-1-yl)isoindoline-1,3-dione;

(Z)-2-(2,6-dioxopiperidin-3-yl)-5-(4-(4-(4-(1-(4-hydroxyphenyl)-2-phenylbut-1-en-1-yl)phenoxy)butyl)piperazin-1-yl)isoindoline-1,3-dione;

(E)/(Z)—(S)-3-(5-(4-(4-(4-(1-(4-hydroxyphenyl)-2-phenylbut-1-en-1-yl)phenoxy)butyl)piperazin-1-yl)-1-oxoisoindolin-2-yl)piperidine-2,6-dione;

(Z)-3-(5-(4-(4-(4-(1-(4-hydroxyphenyl)-2-phenylbut-1-en-1-yl)phenoxy)butyl)piperazin-1-yl)-1-oxoisoindolin-2-yl)piperidine-2,6-dione;

(Z)-3-(5-(4-(2-(4-(1-(4-hydroxyphenyl)-2-phenylbut-1-en-1-yl)phenoxy)ethyl)piperazin-1-yl)-1-oxoisoindolin-2-yl)piperidine-2,6-dione;

(Z)-2-(2,6-dioxopiperidin-3-yl)-5-((2-(1-(2-(4-(1-(4-hydroxyphenyl)-2-phenylbut-1-en-1-yl)phenoxy)ethyl)piperidin-4-yl)ethyl)amino)isoindoline-1,3-dione;

(Z)-3-(5-((2-(1-(2-(4-(1-(4-hydroxyphenyl)-2-phenylbut-1-en-1-yl)phenoxy)ethyl)piperidin-4-yl)ethyl)amino)-1-oxoisoindolin-2-yl)piperidine-2,6-dione;

(Z)-2-(2,6-dioxopiperidin-3-yl)-5-((3-(1-(2-(4-(1-(4-hydroxyphenyl)-2-phenylbut-1-en-1-yl)phenoxy)ethyl)piperidin-4-yl)propyl)amino)isoindoline-1,3-dione;

(Z)-3-(5-((3-(1-(2-(4-(1-(4-hydroxyphenyl)-2-phenylbut-1-en-1-yl)phenoxy)ethyl)piperidin-4-yl)propyl)amino)-1-oxoisoindolin-2-yl)piperidine-2,6-dione;

(Z)-2-(2,6-dioxopiperidin-3-yl)-5-(((1-(2-(4-(1-(4-hydroxyphenyl)-2-phenylbut-1-en-1-yl)phenoxy)ethyl)piperidin-4-yl)methyl)amino)isoindoline-1,3-dione;

(Z)-3-(5-((1-(2-(4-(1-(4-hydroxyphenyl)-2-phenylbut-1-en-1-yl)phenoxy)ethyl)piperidin-4-yl)amino)-1-oxoisoindolin-2-yl)piperidine-2,6-dione;

(Z)-2-(2,6-dioxopiperidin-3-yl)-5-((1-(2-(4-(1-(4-hydroxyphenyl)-2-phenylbut-1-en-1-yl)phenoxy)ethyl)piperidin-4-yl)amino)isoindoline-1,3-dione;

(Z)-3-(5-(3-((1-(2-(4-(1-(4-hydroxyphenyl)-2-phenylbut-1-en-1-yl)phenoxy)ethyl)piperidin-4-yl)oxy)propyl)-1-oxoisoindolin-2-yl)piperidine-2,6-dione;

(Z)-2-(2,6-dioxopiperidin-3-yl)-5-(3-((1-(2-(4-(1-(4-hydroxyphenyl)-2-phenylbut-1-en-1-yl)phenoxy)ethyl)piperidin-4-yl)oxy)propyl)isoindoline-1,3-dione;

(E)/(Z)-2-(2,6-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione;

(Z)-2-(2,6-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione;

(E)/(Z)-2-(2,6-dioxopiperidin-3-yl)-5-(4-(6-(4-(1-(4-hydroxyphenyl)-2-phenylbut-1-en-1-yl)phenoxy)hexyl)piperazin-1-yl)isoindoline-1,3-dione;

(Z)-2-(2,6-dioxopiperidin-3-yl)-5-(4-(6-(4-(1-(4-hydroxyphenyl)-2-phenylbut-1-en-1-yl)phenoxy)hexyl)piperazin-1-yl)isoindoline-1,3-dione;

(Z)-3-(5-(3-(3-(4-(1-(4-hydroxyphenyl)-2-phenylbut-1-en-1-yl)phenoxy)propoxy)propoxy)-1-oxoisoindolin-2-yl)piperidine-2,6-dione;

(E)/(Z)—(S)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(E)/(Z)—(S)-3-(5-(4-(6-(4-(1-(4-hydroxyphenyl)-2-phenylbut-1-en-1-yl)phenoxy)hexyl)piperazin-1-yl)-1-oxoisoindolin-2-yl)piperidine-2,6-dione;

(Z)-3-(5-(4-(6-(4-(1-(4-hydroxyphenyl)-2-phenylbut-1-en-1-yl)phenoxy)hexyl)piperazin-1-yl)-1-oxoisoindolin-2-yl)piperidine-2,6-dione;

(Z)-3-(5-(4-(3-(4-(1-(4-hydroxyphenyl)-2-phenylbut-1-en-1-yl)phenoxy)propoxy)butoxy)-1-oxoisoindolin-2-yl)piperidine-2,6-dione;

(Z)-3-(2-(2-(2-((2-(2,6-dioxopiperidin-3-yl)-1,3-dioxoisoindolin-4-yl)amino)ethoxy)ethoxy)ethoxy)-N-(2-(4-(1,2-diphenylbut-1-en-1-yl)phenoxy)ethyl)-N-methylpropanamide;

(Z)-3-(5-((6-(4-(1-(4-hydroxyphenyl)-2-phenylbut-1-en-1-yl)phenoxy)hexa-2,4-diyn-1-yl)oxy)-1-oxoisoindolin-2-yl)piperidine-2,6-dione;

(Z)-3-(5-(4-(3-(4-(1-(4-hydroxyphenyl)-2-phenylbut-1-en-1-yl)phenoxy)propyl)piperazin-1-yl)-1-oxoisoindolin-2-yl)piperidine-2,6-dione;

(Z)-2-(2,6-dioxopiperidin-3-yl)-5-(4-(3-(4-(1-(4-hydroxyphenyl)-2-phenylbut-1-en-1-yl)phenoxy)propyl)piperazin-1-yl)isoindoline-1,3-dione;

(Z)-3-(5-(2-(4-(2-(4-(1-(4-hydroxyphenyl)-2-phenylbut-1-en-1-yl)phenoxy)ethyl)-1,4-diazepan-1-yl)ethoxy)-1-oxoisoindolin-2-yl)piperidine-2,6-dione;

(E)-2-(2,6-dioxopiperidin-3-yl)-5-((5-(4-(4-(1-(4-hydroxyphenyl)-2-phenylbut-1-en-1-yl)phenyl)piperazin-1-yl)pentyl)oxy)isoindoline-1,3-dione;

(E)-3-(5-((5-(4-(4-(1-(4-hydroxyphenyl)-2-phenylbut-1-en-1-yl)phenyl)piperazin-1-yl)pentyl)oxy)-1-oxoisoindolin-2-yl)piperidine-2,6-dione;

(E)-2-(2,6-dioxopiperidin-3-yl)-5-(4-(4-(4-(1-(4-hydroxyphenyl)-2-phenylbut-1-en-1-yl)phenyl)piperazin-1-yl)butoxy)isoindoline-1,3-dione;

(E)-3-(5-(4-(4-(4-(1-(4-hydroxyphenyl)-2-phenylbut-1-en-1-yl)phenyl)piperazin-1-yl)butoxy)-1-oxoisoindolin-2-yl)piperidine-2,6-dione;

(E)-2-(2,6-dioxopiperidin-3-yl)-5-((5-(4-(4-(1-(4-hydroxyphenyl)-2-phenylbut-1-en-1-yl)phenyl)piperazin-1-yl)pentyl)amino)isoindoline-1,3-dione;

(E)-2-(2,6-dioxopiperidin-3-yl)-5-((4-(4-(4-(1-(4-hydroxyphenyl)-2-phenylbut-1-en-1-yl)phenyl)piperazin-1-yl)butyl)amino)isoindoline-1,3-dione;

(Z)—N-((2-(2,6-dioxopiperidin-3-yl)-1-oxoisoindolin-5-yl)methyl)-2-(4-(2-(4-(1-(4-hydroxyphenyl)-2-phenylbut-1-en-1-yl)phenoxy)ethyl)piperazin-1-yl)acetamide;

(Z)-3-(5-(3-(3-(3-(4-(1-(4-hydroxyphenyl)-2-phenylbut-1-en-1-yl)phenoxy)propoxy)propoxy)propoxy)-1-oxoisoindolin-2-yl)piperidine-2,6-dione;

(Z)-3-(5-(2-(2-(2-(4-(1-(4-hydroxyphenyl)-2-phenylbut-1-en-1-yl)phenoxy)ethoxy)ethoxy)ethoxy)-1-oxoisoindolin-2-yl)piperidine-2,6-dione;

(Z)-3-(5-(3-(2-(2-(4-(1-(4-hydroxyphenyl)-2-phenylbut-1-en-1-yl)phenoxy)ethoxy)ethoxy)propoxy)-1-oxoisoindolin-2-yl)piperidine-2,6-dione;

(Z)-3-(5-(2-(1-(2-(4-(1-(4-hydroxyphenyl)-2-phenylbut-1-en-1-yl)phenoxy)ethyl)piperidin-3-yl)ethoxy)-1-oxoisoindolin-2-yl)piperidine-2,6-dione;

(Z)-3-(5-(4-((4-(4-(1-(4-hydroxyphenyl)-2-phenylbut-1-en-1-yl)phenoxy)butyl)amino)phenyl)-1-oxoisoindolin-2-yl)piperidine-2,6-dione;

(Z)-3-(5-(2-(2-(4-(1-(4-hydroxyphenyl)-2-phenylbut-1-en-1-yl)phenoxy)ethoxy)ethoxy)-1-oxoisoindolin-2-yl)piperidine-2,6-dione;

(Z)-2-(2,6-dioxopiperidin-3-yl)-5-(2-(2-(4-(1-(4-hydroxyphenyl)-2-phenylbut-1-en-1-yl)phenoxy)ethoxy)ethoxy)isoindoline-1,3-dione;

(Z)-3-(5-(4-(5-(4-(1-(4-hydroxyphenyl)-2-phenylbut-1-en-1-yl)phenoxy)pentyl)-2,5-dimethylpiperazin-1-yl)-1-oxoisoindolin-2-yl)piperidine-2,5-dione;

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12-tetraoxapentadecan-15-amide;

(Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,5-dione;

(Z)-2-(2,5-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione;

(Z)-2-(2,6-dioxopiperidin-3-yl)-5-(4-((4-(4-(1-(4-hydroxyphenyl)-2-phenylbut-1-en-1-yl)phenoxy)cyclohexyl)methyl)piperazin-1-yl)isoindoline-1,3-dione;

(Z)-3-(5-(4-((4-(4-(1-(4-hydroxyphenyl)-2-phenylbut-1-en-1-yl)phenoxy)cyclohexyl)methyl)piperazin-1-yl)-1-oxoisoindolin-2-yl)piperidine-2,6-dione;

(Z)-2-(2,6-dioxopiperidin-3-yl)-5-(4-(2-((4-(4-(1-(4-hydroxyphenyl)-2-phenylbut-1-en-1-yl)phenoxy)cyclohexyl)oxy)ethyl)piperazin-1-yl)isoindoline-1,3-dione;

(Z)-3-(5-(4-(2-((4-(4-(1-(4-hydroxyphenyl)-2-phenylbut-1-en-1-yl)phenoxy)cyclohexyl)oxy)ethyl)piperazin-1-yl)-1-oxoisoindolin-2-yl)piperidine-2,6-dione;

(Z)-3-(5-(2-((2-(2-(4-(1-(4-hydroxyphenyl)-2-phenylbut-1-en-1-yl)phenoxy)ethyl)-2-azaspiro[3.3]heptan-6-yl)oxy)ethoxy)-1-oxoisoindolin-2-yl)piperidine-2,6-dione;

(E)-3-(6-((4-(4-(4-(1-(4-hydroxyphenyl)-2-phenylbut-1-en-1-yl)phenyl)piperazin-1-yl)butyl)amino)-1-oxoisoindolin-2-yl)piperidine-2,6-dione;

(Z)-3-(5-((2-(2-(4-(1-(4-hydroxyphenyl)-2-phenylbut-1-en-1-yl)phenoxy)ethoxy)ethyl)amino)-1-oxoisoindolin-2-yl)piperidine-2,6-dione;

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide;

(Z)-2-(2,6-dioxopiperidin-3-yl)-5-((2-(2-(4-(1-(4-hydroxyphenyl)-2-phenylbut-1-en-1-yl)phenoxy)ethoxy)ethyl)amino)isoindoline-1,3-dione;

(Z)—N-((2-(2,6-dioxopiperidin-3-yl)-1-oxoisoindolin-5-yl)methyl)-2-(4-(1-(4-(1-(4-hydroxyphenyl)-2-phenylbut-1-en-1-yl)phenoxy)propan-2-yl)piperazin-1-yl)acetamide;

(Z)-3-(5-(3-(4-(3-(4-(1-(4-hydroxyphenyl)-2-phenylbut-1-en-1-yl)phenoxy)propyl)-1,4-diazepan-1-yl)propyl)-1-oxoisoindolin-2-yl)piperidine-2,6-dione;

(E)-3-(5-((5-(4-(4-(1-(4-hydroxyphenyl)-2-phenylbut-1-en-1-yl)phenyl)piperazin-1-yl)pentyl)amino)-1-oxoisoindolin-2-yl)piperidine-2,6-dione;

(Z)-3-(5-(3-(2-(4-(1-(4-hydroxyphenyl)-2-phenylbut-1-en-1-yl)phenoxy)ethoxy)propoxy)-1-oxoisoindolin-2-yl)piperidine-2,6-dione;

(Z)-2-(2,6-dioxopiperidin-3-yl)-5-(3-(2-(4-(1-(4-hydroxyphenyl)-2-phenylbut-1-en-1-yl)phenoxy)ethoxy)propoxy)isoindoline-1,3-dione;

(Z)-3-(5-(3-(3-(2-(4-(1-(4-hydroxyphenyl)-2-phenylbut-1-en-1-yl)phenoxy)ethoxy)propoxy)propoxy)-1-oxoisoindolin-2-yl)piperidine-2,6-dione;

(Z)-3-(5-(2-(4-(4-(4-(1-(4-hydroxyphenyl)-2-phenylbut-1-en-1-yl)phenoxy)butyl)-1,4-diazepan-1-yl)ethyl)-1-oxoisoindolin-2-yl)piperidine-2,6-dione;

(Z)-3-(5-(4-amino-3-((5-(4-(1-(4-hydroxyphenyl)-2-phenylbut-1-en-1-yl)phenoxy)pentyl)oxy)phenyl)-1-oxoisoindolin-2-yl)piperidine-2,6-dione;

(Z)-3-(5-(4-amino-3-(4-(4-(1-(4-hydroxyphenyl)-2-phenylbut-1-en-1-yl)phenoxy)butoxy)phenyl)-1-oxoisoindolin-2-yl)piperidine-2,6-dione;

(Z)-3-(5-((3-(2-(4-(1-(4-hydroxyphenyl)-2-phenylbut-1-en-1-yl)phenoxy)ethoxy)propyl)amino)-1-oxoisoindolin-2-yl)piperidine-2,6-dione;

(Z)-2-(2,6-dioxopiperidin-3-yl)-5-((3-(2-(4-(1-(4-hydroxyphenyl)-2-phenylbut-1-en-1-yl)phenoxy)ethoxy)propyl)amino)isoindoline-1,3-dione;

(Z)-3-(5-(3-(3-(4-(4-(1-(4-hydroxyphenyl)-2-phenylbut-1-en-1-yl)phenoxy)butoxy)propoxy)propoxy)-1-oxoisoindolin-2-yl)piperidine-2,6-dione;

(Z)-3-(5-(3-(1-(2-(4-(1-(4-hydroxyphenyl)-2-phenylbut-1-en-1-yl)phenoxy)ethyl)piperidin-3-yl)propyl)-1-oxoisoindolin-2-yl)piperidine-2,6-dione;

(Z)-3-(5-(2-(4-(2-(4-(1-(4-hydroxyphenyl)-2-phenylbut-1-en-1-yl)phenoxy)ethyl)-1,4-diazepan-1-yl)ethyl)-1-oxoisoindolin-2-yl)piperidine-2,6-dione;

(Z)-3-(5-(2-(3-(4-(1-(4-hydroxyphenyl)-2-phenylbut-1-en-1-yl)phenoxy)propyl)-1H-indol-5-yl)-1-oxoisoindolin-2-yl)piperidine-2,6-dione;

(Z)-3-(5-(2-(4-(4-(1-(4-hydroxyphenyl)-2-phenylbut-1-en-1-yl)phenoxy)butyl)-1H-indol-5-yl)-1-oxoisoindolin-2-yl)piperidine-2,6-dione;

(Z)-3-(5-(2-(5-(4-(1-(4-hydroxyphenyl)-2-phenylbut-1-en-1-yl)phenoxy)pentyl)-1H-indol-5-yl)-1-oxoisoindolin-2-yl)piperidine-2,6-dione;

(Z)-3-(5-(2-((1-(3-(4-(1-(4-hydroxyphenyl)-2-phenylbut-1-en-1-yl)phenoxy)propyl)piperidin-3-yl)oxy)ethyl)-1-oxoisoindolin-2-yl)piperidine-2,6-dione;

(Z)-3-(5-(2-((1-(2-(4-(1-(4-hydroxyphenyl)-2-phenylbut-1-en-1-yl)phenoxy)ethyl)piperidin-3-yl)oxy)ethyl)-1-oxoisoindolin-2-yl)piperidine-2,6-dione;

(E)-3-(5-(4-((2-((4-(1-(4-hydroxyphenyl)-2-phenylbut-1-en-1-yl)benzyl)oxy)ethyl)(methyl)amino)cyclohexyl)-1-oxoisoindolin-2-yl)piperidine-2,6-dione;

(Z)-3-(5-(4-(5-(4-(1-(4-hydroxyphenyl)-2-phenylbut-1-en-1-yl)phenoxy)pentyl)-1,4-diazepan-1-yl)-1-oxoisoindolin-2-yl)piperidine-2,6-dione;

(Z)-2-(2,6-dioxopiperidin-3-yl)-5-(4-(5-(4-(1-(4-hydroxyphenyl)-2-phenylbut-1-en-1-yl)phenoxy)pentyl)-1,4-diazepan-1-yl)isoindoline-1,3-dione;

(Z)-2-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylacetamide;

(Z)-3-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylpropanamide;

(Z)-3-(5-(4-(4-(4-(1-(4-hydroxyphenyl)-2-phenylbut-1-en-1-yl)phenoxy)butyl)-1,4-diazepan-1-yl)-1-oxoisoindolin-2-yl)piperidine-2,6-dione;

(Z)-2-(2,6-dioxopiperidin-3-yl)-5-(4-(4-(4-(1-(4-hydroxyphenyl)-2-phenylbut-1-en-1-yl)phenoxy)butyl)-1,4-diazepan-1-yl)isoindoline-1,3-dione;

(Z)-3-(5-(4-(2-(2-((4-(1-(4-hydroxyphenyl)-2-phenylbut-1-en-1-yl)phenoxy)methyl)cyclopropyl)ethyl)piperazin-1-yl)-1-oxoisoindolin-2-yl)piperidine-2,6-dione;

(Z)-2-(2,6-dioxopiperidin-3-yl)-5-(4-(2-(2-((4-(1-(4-hydroxyphenyl)-2-phenylbut-1-en-1-yl)phenoxy)methyl)cyclopropyl)ethyl)piperazin-1-yl)isoindoline-1,3-dione;

(Z)-2-(2,6-dioxopiperidin-3-yl)-5-(4-((4-(4-(1-(4-hydroxyphenyl)-2-phenylbut-1-en-1-yl)phenoxy)piperidin-1-yl)methyl)piperidin-1-yl)isoindoline-1,3-dione;

(Z)-2-(2,6-dioxopiperidin-3-yl)-5-(4-(1-(2-(4-(1-(4-hydroxyphenyl)-2-phenylbut-1-en-1-yl)phenoxy)ethyl)piperidin-4-yl)piperazin-1-yl)isoindoline-1,3-dione;

(Z)-2-(2,6-dioxopiperidin-3-yl)-5-(4-((1-(2-(4-(1-(4-hydroxyphenyl)-2-phenylbut-1-en-1-yl)phenoxy)ethyl)piperidin-4-yl)methyl)piperazin-1-yl)isoindoline-1,3-dione;

(Z)-2-(2,6-dioxopiperidin-3-yl)-5-(4-((1-(2-(4-(1-(4-hydroxyphenyl)-2-phenylbut-1-en-1-yl)phenoxy)ethyl)azetidin-3-yl)methyl)piperazin-1-yl)isoindoline-1,3-dione;

(Z)-3-(5-(4-(4,4-difluoro-5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-2-(2,6-dioxopiperidin-3-yl)-5-(4-(2-(1-(2-(4-(1-(4-hydroxyphenyl)-2-phenylbut-1-en-1-yl)phenoxy)ethyl)azetidin-3-yl)ethyl)piperazin-1-yl)isoindoline-1,3-dione;

(Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)-1-methylpiperidine-2,6-dione;

(Z)-3-(5-(6-((1-(2-(4-(1-(4-hydroxyphenyl)-2-phenylbut-1-en-1-yl)phenoxy)ethyl)pyrrolidin-3-yl)oxy)pyridin-3-yl)-1-oxoisoindolin-2-yl)piperidine-2,6-dione;

(Z)-2-(2,6-dioxopiperidin-3-yl)-5-(4-((1-(2-(4-(1-(4-hydroxyphenyl)-2-phenylbut-1-en-1-yl)phenoxy)ethyl)pyrrolidin-3-yl)methyl)piperazin-1-yl)isoindoline-1,3-dione;

(Z)-2-(2,6-dioxopiperidin-3-yl)-5-(4-((4-(2-(4-(1-(4-hydroxyphenyl)-2-phenylbut-1-en-1-yl)phenoxy)ethyl)piperazin-1-yl)methyl)piperidin-1-yl)isoindoline-1,3-dione;

(Z)-2-(2,6-dioxopiperidin-3-yl)-5-(5-(1-(2-(4-(1-(4-hydroxyphenyl)-2-phenylbut-1-en-1-yl)phenoxy)ethyl)piperidin-4-yl)-2,5-diazabicyclo[2.2.1]heptan-2-yl)isoindoline-1,3-dione;

(Z)-2-(2,6-dioxopiperidin-3-yl)-5-(5-((1-(2-(4-(1-(4-hydroxyphenyl)-2-phenylbut-1-en-1-yl)phenoxy)ethyl)piperidin-4-yl)methyl)-2,5-diazabicyclo[2.2.1]heptan-2-yl)isoindoline-1,3-dione;

(Z)-3-(5-(4-(5-(4-(1-(4-hydroxyphenyl)-2-phenylbut-1-en-1-yl)phenoxy)pentyl)-3,5-dimethylpiperazin-1-yl)-1-oxoisoindolin-2-yl)piperidine-2,6-dione;

(Z)-3-(5-(4-((4-(4-(1-(4-hydroxyphenyl)-2-phenylbut-1-en-1-yl)phenoxy)piperidin-1-yl)methyl)piperidin-1-yl)-1-oxoisoindolin-2-yl)piperidine-2,6-dione;

(Z)-4-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylbutanamide;

(Z)-2-(2,6-dioxopiperidin-3-yl)-5-(7-(4-(4-(1-(4-hydroxyphenyl)-2-phenylbut-1-en-1-yl)phenoxy)butyl)-2,7-diazaspiro[3.5]nonan-2-yl)isoindoline-1,3-dione;

(Z)-2-(2,6-dioxopiperidin-3-yl)-6-(4-(5-(4-(1-(4-hydroxyphenyl)-2-phenylbut-1-en-1-yl)phenoxy)pentyl)piperazin-1-yl)-1H-pyrrolo[3,4-c]pyridine-1,3(2H)-dione;

(Z)-3-(5-(7-(4-(4-(1-(4-hydroxyphenyl)-2-phenylbut-1-en-1-yl)phenoxy)butyl)-2,7-diazaspiro[3.5]nonan-2-yl)-1-oxoisoindolin-2-yl)piperidine-2,6-dione;

(Z)-3-(5-(4-((1-(2-(4-(1-(4-hydroxyphenyl)-2-phenylbut-1-en-1-yl)phenoxy)ethyl)pyrrolidin-3-yl)methyl)piperazin-1-yl)-1-oxoisoindolin-2-yl)piperidine-2,6-dione;

(Z)-2-(2,6-dioxopiperidin-3-yl)-5-(6-(4-(4-(1-(4-hydroxyphenyl)-2-phenylbut-1-en-1-yl)phenoxy)butyl)-2,6-diazaspiro[3.3]heptan-2-yl)isoindoline-1,3-dione;

(Z)-3-(5-(2-(4-(6-(4-(1-(4-hydroxyphenyl)-2-phenylbut-1-en-1-yl)phenoxy)pyridin-3-yl)piperazin-1-yl)ethoxy)-1-oxoisoindolin-2-yl)piperidine-2,6-dione;

(Z)-2-(2,6-dioxopiperidin-3-yl)-5-(2-(4-(6-(4-(1-(4-hydroxyphenyl)-2-phenylbut-1-en-1-yl)phenoxy)pyridin-3-yl)piperazin-1-yl)ethoxy)isoindoline-1,3-dione;

(Z)-2-(2,6-dioxopiperidin-3-yl)-5-(3-(4-(6-(4-(1-(4-hydroxyphenyl)-2-phenylbut-1-en-1-yl)phenoxy)pyridin-3-yl)piperazin-1-yl)propoxy)isoindoline-1,3-dione;

(Z)-3-(5-(3-(4-(6-(4-(1-(4-hydroxyphenyl)-2-phenylbut-1-en-1-yl)phenoxy)pyridin-3-yl)piperazin-1-yl)propoxy)-1-oxoisoindolin-2-yl)piperidine-2,6-dione;

(Z)-2-(2,6-dioxopiperidin-3-yl)-5-(4-(3-(4-(1-(4-hydroxyphenyl)-2-phenylbut-1-en-1-yl)phenoxy)propyl)-1-oxa-4,9-diazaspiro[5.5]undecan-9-yl)isoindoline-1,3-dione;

(Z)-3-(5-(4-(5-(4-(1-(4-hydroxyphenyl)-2-phenylbut-1-en-1-yl)phenoxy)pentyl)-2,5-dimethylpiperazin-1-yl)-1-oxoisoindolin-2-yl)piperidine-2,6-dione;

(Z)-6-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylhexanamide;

(Z)-2-(2,6-dioxopiperidin-3-yl)-5-(5-((1-(2-(4-(1-(4-hydroxyphenyl)-2-phenylbut-1-en-1-yl)phenoxy)ethyl)pyrrolidin-3-yl)oxy)pyrazin-2-yl)isoindoline-1,3-dione;

(Z)-2-(2,6-dioxopiperidin-3-yl)-5-(5-(4-(2-(4-(1-(4-hydroxyphenyl)-2-phenylbut-1-en-1-yl)phenoxy)ethyl)piperazin-1-yl)pyrazin-2-yl)isoindoline-1,3-dione;

(Z)-2-(2,6-dioxopiperidin-3-yl)-5-(5-((1-(2-(4-(1-(4-hydroxyphenyl)-2-phenylbut-1-en-1-yl)phenoxy)ethyl)azetidin-3-yl)methoxy)pyrazin-2-yl)isoindoline-1,3-dione;

(Z)-2-(2,6-dioxopiperidin-3-yl)-5-((2-(4-(2-(4-(1-(4-hydroxyphenyl)-2-phenylbut-1-en-1-yl)phenoxy)ethyl)piperazin-1-yl)pyrimidin-5-yl)oxy)isoindoline-1,3-dione;

(Z)-6-(2,6-dioxopiperidin-3-yl)-2-(4-(5-(4-(1-(4-hydroxyphenyl)-2-phenylbut-1-en-1-yl)phenoxy)pentyl)piperazin-1-yl)-5H-pyrrolo[3,4-b]pyrazine-5,7(6H)-dione;

(Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide;

(Z)-2-(2,6-dioxopiperidin-3-yl)-5-(1'-(2-(4-(1-(4-hydroxyphenyl)-2-phenylbut-1-en-1-yl)phenoxy)ethyl)-[1,4'-bipiperidin]-4-yl)isoindoline-1,3-dione;

(Z)-2-(2,6-dioxopiperidin-3-yl)-5-((6-(4-(2-(4-(1-(4-hydroxyphenyl)-2-phenylbut-1-en-1-yl)phenoxy)ethyl)piperazin-1-yl)pyridin-3-yl)oxy)isoindoline-1,3-dione;

(E)-3-(5-(4-(3-(4-(4-(1-(4-hydroxyphenyl)-2-phenylbut-1-en-1-yl)phenyl)-1H-pyrazol-1-yl)propyl)piperazin-1-yl)-1-oxoisoindolin-2-yl)piperidine-2,6-dione;

(Z)-6-(2,6-dioxopiperidin-3-yl)-2-(4-(5-(4-(1-(4-hydroxyphenyl)-2-phenylbut-1-en-1-yl)phenoxy)pentyl)piperazin-1-yl)-5H-pyrrolo[3,4-d]pyrimidine-5,7(6H)-dione;

(Z)-3-(5-(1'-(2-(4-(1-(4-hydroxyphenyl)-2-phenylbut-1-en-1-yl)phenoxy)ethyl)-[1,4'-bipiperidin]-4-yl)-1-oxoisoindolin-2-yl)piperidine-2,6-dione;

(Z)-2-(2,6-dioxopiperidin-3-yl)-5-(4-(2-(4-(4-(1-(4-hydroxyphenyl)-2-phenylbut-1-en-1-yl)phenoxy)piperidin-1-yl)ethyl)piperazin-1-yl)isoindoline-1,3-dione;

(E)-3-(5-(4-(1-(3-(4-(1-(4-hydroxyphenyl)-2-phenylbut-1-en-1-yl)phenyl)propyl)pyrrolidin-3-yl)piperazin-1-yl)-1-oxoisoindolin-2-yl)piperidine-2,6-dione;

(E)-2-(2,6-dioxopiperidin-3-yl)-5-(4-((1-(3-(4-(1-(4-hydroxyphenyl)-2-phenylbut-1-en-1-yl)phenyl)propyl)azetidin-3-yl)methyl)piperazin-1-yl)isoindoline-1,3-dione;

(E)-3-(5-(4-((1-(3-(4-(1-(4-hydroxyphenyl)-2-phenylbut-1-en-1-yl)phenyl)propyl)azetidin-3-yl)methyl)piperazin-1-yl)-1-oxoisoindolin-2-yl)piperidine-2,6-dione;

(Z)-3-(5-((6-(4-(2-(4-(1-(4-hydroxyphenyl)-2-phenylbut-1-en-1-yl)phenoxy)ethyl)piperazin-1-yl)pyridin-3-yl)oxy)-1-oxoisoindolin-2-yl)piperidine-2,6-dione;

(E)-3-(5-(4-(2-(4-(4-(1-(4-hydroxyphenyl)-2-phenylbut-1-en-1-yl)phenyl)piperazin-1-yl)ethyl)piperazin-1-yl)-1-oxoisoindolin-2-yl)piperidine-2,6-dione;

(E)-3-(5-(4-(2-(4-(4-(1-(4-hydroxyphenyl)-2-phenylbut-1-en-1-yl)phenyl)piperidin-1-yl)ethyl)piperazin-1-yl)-1-oxoisoindolin-2-yl)piperidine-2,6-dione;

(E)-2-(2,6-dioxopiperidin-3-yl)-5-(4-(2-(4-(4-(1-(4-hydroxyphenyl)-2-phenylbut-1-en-1-yl)phenyl)piperidin-1-yl)ethyl)piperazin-1-yl)isoindoline-1,3-dione;

(Z)-3-(5-(4-(2-(2-(4-(1-(4-hydroxyphenyl)-2-phenylbut-1-en-1-yl)phenoxy)ethyl)-2-azaspiro[3.3]heptan-6-yl)piperazin-1-yl)-1-oxoisoindolin-2-yl)piperidine-2,6-dione;

(E)-2-(2,6-dioxopiperidin-3-yl)-5-(4-(3-(4-(4-(1-(4-hydroxyphenyl)-2-phenylbut-1-en-1-yl)phenyl)-1H-pyrazol-1-yl)propyl)piperazin-1-yl)isoindoline-1,3-dione;

(E)-2-(2,6-dioxopiperidin-3-yl)-5-(4-(3-(5-(4-(1-(4-hydroxyphenyl)-2-phenylbut-1-en-1-yl)phenyl)-2H-tetrazol-2-yl)propyl)piperazin-1-yl)isoindoline-1,3-dione;

(Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide;

(Z)-3-(5-(4-(3-(4-(1-(4-hydroxyphenyl)-2-phenylbut-1-en-1-yl)phenoxy)propyl)-1-oxa-4,9-diazaspiro[5.5]undecan-9-yl)-1-oxoisoindolin-2-yl)piperidine-2,6-dione;

(E)-3-(5-(4-((1-(3-(4-(1-(4-hydroxyphenyl)-2-phenylbut-1-en-1-yl)phenyl)propyl)piperidin-4-yl)methyl)piperazin-1-yl)-1-oxoisoindolin-2-yl)piperidine-2,6-dione;

(E)-2-(2,6-dioxopiperidin-3-yl)-5-(4-((1-(3-(4-(1-(4-hydroxyphenyl)-2-phenylbut-1-en-1-yl)phenyl)propyl)piperidin-4-yl)methyl)piperazin-1-yl)isoindoline-1,3-dione;

(E)-3-(5-(4-(1-(3-(4-(1-(4-hydroxyphenyl)-2-phenylbut-1-en-1-yl)phenyl)propyl)piperidin-4-yl)piperazin-1-yl)-1-oxoisoindolin-2-yl)piperidine-2,6-dione;

(E)-2-(2,6-dioxopiperidin-3-yl)-5-(4-(1-(3-(4-(1-(4-hydroxyphenyl)-2-phenylbut-1-en-1-yl)phenyl)propyl)piperidin-4-yl)piperazin-1-yl)isoindoline-1,3-dione;

(E)-3-(5-(4-(3-(4-(4-(1-(4-hydroxyphenyl)-2-phenylbut-1-en-1-yl)phenyl)piperidin-1-yl)propyl)piperazin-1-yl)-1-oxoisoindolin-2-yl)piperidine-2,6-dione;

(E)-2-(2,6-dioxopiperidin-3-yl)-5-(4-(3-(4-(4-(1-(4-hydroxyphenyl)-2-phenylbut-1-en-1-yl)phenyl)piperidin-1-yl)propyl)piperazin-1-yl)isoindoline-1,3-dione;

(Z)-2-(2,6-dioxopiperidin-3-yl)-4-((1-((4-(2-(4-(1-(4-hydroxyphenyl)-2-phenylbut-1-en-1-yl)phenoxy)ethyl)piperazin-1-yl)methyl)piperidin-4-yl)amino)isoindoline-1,3-dione;

(Z)-2-(2,6-dioxopiperidin-3-yl)-4-((1-((1-(2-(4-(1-(4-hydroxyphenyl)-2-phenylbut-1-en-1-yl)phenoxy)ethyl)piperidin-4-yl)methyl)piperidin-4-yl)amino)isoindoline-1,3-dione;

(Z)-3-(4-((1-((1-(2-(4-(1-(4-hydroxyphenyl)-2-phenylbut-1-en-1-yl)phenoxy)ethyl)piperidin-4-yl)methyl)piperidin-4-yl)amino)-1-oxoisoindolin-2-yl)piperidine-2,6-dione;

(Z)-3-(4-((1-((4-(2-(4-(1-(4-hydroxyphenyl)-2-phenylbut-1-en-1-yl)phenoxy)ethyl)piperazin-1-yl)methyl)piperidin-4-yl)amino)-1-oxoisoindolin-2-yl)piperidine-2,6-dione;

(Z)-3-(2-(2-((2-(2,6-dioxopiperidin-3-yl)-1,3-dioxoisoindolin-4-yl)amino)ethoxy)ethoxy)-N-(2-(4-(1-(4-hydroxyphenyl)-2-phenylbut-1-en-1-yl)phenoxy)ethyl)-N-methylpropanamide;

(Z)-1-((2-(2,6-dioxopiperidin-3-yl)-1-oxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide;

(Z)-1-((2-(2,6-dioxopiperidin-3-yl)-1,3-dioxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide;

(Z)-3-(5-((2-(4-(2-(4-(1-(4-hydroxyphenyl)-2-phenylbut-1-en-1-yl)phenoxy)ethyl)piperazin-1-yl)pyrimidin-5-yl)oxy)-1-oxoisoindolin-2-yl)piperidine-2,6-dione;

(Z)-3-(7-chloro-5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(E)/(Z)—(S)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-(S)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)/(Z)—(S)-3-(5-(4-(2-(1-(4-(1-(4-hydroxyphenyl)-2-phenylbut-1-en-1-yl)phenyl)piperidin-4-yl)ethyl)piperazin-1-yl)-1-oxoisoindolin-2-yl)piperidine-2,6-dione;

(E)-3-(5-(4-(2-(1-(4-(1-(4-hydroxyphenyl)-2-phenylbut-1-en-1-yl)phenyl)piperidin-4-yl)ethyl)piperazin-1-yl)-1-oxoisoindolin-2-yl)piperidine-2,6-dione;

(Z)-3-(5-fluoro-6-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(4-fluoro-5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(E)-3-(5-(2-(4-((1-(4-(1-(4-hydroxyphenyl)-2-phenylbut-1-en-1-yl)phenyl)piperidin-4-yl)methyl)-1,4-diazepan-1-yl)ethyl)-1-oxoisoindolin-2-yl)piperidine-2,6-dione;

(Z)-3-(5-(6-(4-(4-(1-(4-hydroxyphenyl)-2-phenylbut-1-en-1-yl)phenoxy)butyl)-2,6-diazaspiro[3.3]heptan-2-yl)-1-oxoisoindolin-2-yl)piperidine-2,6-dione;

(Z)-3-(5-(8-(4-(4-(1-(4-hydroxyphenyl)-2-phenylbut-1-en-1-yl)phenoxy)butyl)octahydro-2H-pyrazino[1,2-a]pyrazin-2-yl)-1-oxoisoindolin-2-yl)piperidine-2,6-dione;

(Z)-3-(5-(4-(2-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(7-fluoro-5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(5-(4-(3-hydroxy-5-(4-(1-(4-hydroxyphenyl)-2-phenylbut-1-en-1-yl)phenoxy)-3-methylpentyl)piperazin-1-yl)-1-oxoisoindolin-2-yl)piperidine-2,6-dione;

(Z)-3-(5-(4-(5-(4-(1-(4-hydroxyphenyl)-2-phenylbut-1-en-1-yl)phenoxy)-2-oxopentyl)piperazin-1-yl)-1-oxoisoindolin-2-yl)piperidine-2,6-dione;

(Z)-3-(4-fluoro-5-(4-(2-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(4,6-difluoro-5-(4-(2-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-2-(2,6-dioxopiperidin-3-yl)-5-(5-(4-(4-(1-(4-hydroxyphenyl)-2-phenylbut-1-en-1-yl)phenoxy)butyl)hexahydropyrrolo[3,4-c]pyrrol-2(1H)-yl)isoindoline-1,3-dione;

(Z)-2-(2,6-dioxopiperidin-3-yl)-5-(5-(3-(4-(1-(4-hydroxyphenyl)-2-phenylbut-1-en-1-yl)phenoxy)propyl)hexahydropyrrolo[3,4-c]pyrrol-2(1H)-yl)isoindoline-1,3-dione;

(Z)-3-(5-(4-(2-(2-(4-(1-(4-hydroxyphenyl)-2-phenylbut-1-en-1-yl)phenoxy)ethoxy)ethyl)piperazin-1-yl)-1-oxoisoindolin-2-yl)piperidine-2,6-dione;

(Z)-3-(5-(4-(2-(3-(4-(1-(4-hydroxyphenyl)-2-phenylbut-1-en-1-yl)phenoxy)cyclobutoxy)ethyl)piperazin-1-yl)-1-oxoisoindolin-2-yl)piperidine-2,6-dione;

(Z)-5-(4-(4,4-difluoro-5-(4-(1-(4-hydroxyphenyl)-2-phenylbut-1-en-1-yl)phenoxy)pentyl)piperazin-1-yl)-2-(2,6-dioxopiperidin-3-yl)isoindoline-1,3-dione;

(Z)-3-(5-(4-(3-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(5-(5-(4-(4-(1-(4-hydroxyphenyl)-2-phenylbut-1-en-1-yl)phenoxy)butyl)hexahydropyrrolo[3,4-c]pyrrol-2(1H)-yl)-1-oxoisoindolin-2-yl)piperidine-2,6-dione;

(Z)-3-(5-(5-(3-(4-(1-(4-hydroxyphenyl)-2-phenylbut-1-en-1-yl)phenoxy)propyl)hexahydropyrrolo[3,4-c]pyrrol-2(1H)-yl)-1-oxoisoindolin-2-yl)piperidine-2,6-dione;

(Z)-3-(5-(4-(5-((4-(1-(4-hydroxyphenyl)-2-phenylbut-1-en-1-yl)phenyl)sulfonyl)pentyl)piperazin-1-yl)-1-oxoisoindolin-2-yl)piperidine-2,6-dione;

(E)-3-(5-(2-(4-((1-(4-(1-(4-hydroxyphenyl)-2-phenylbut-1-en-1-yl)phenyl)azetidin-3-yl)methyl)-1,4-diazepan-1-yl)ethyl)-1-oxoisoindolin-2-yl)piperidine-2,6-dione;

(Z)-3-(5-(4-(2-((2-(4-(1-(4-hydroxyphenyl)-2-phenylbut-1-en-1-yl)phenoxy)ethyl)amino)ethyl)piperazin-1-yl)-1-oxoisoindolin-2-yl)piperidine-2,6-dione;

(E)/(Z)-2-(2,6-dioxopiperidin-3-yl)-5-(4-((1-(4-(1-(4-hydroxyphenyl)-2-phenylbut-1-en-1-yl)phenyl)piperidin-4-yl)methyl)piperazin-1-yl)isoindoline-1,3-dione;

(E)-2-(2,6-dioxopiperidin-3-yl)-5-(4-((1-(4-(1-(4-hydroxyphenyl)-2-phenylbut-1-en-1-yl)phenyl)piperidin-4-yl)methyl)piperazin-1-yl)isoindoline-1,3-dione;

(E)/(Z)-2-(2,6-dioxopiperidin-3-yl)-5-(4-(2-(1-(4-(1-(4-hydroxyphenyl)-2-phenylbut-1-en-1-yl)phenyl)piperidin-4-yl)ethyl)piperazin-1-yl)isoindoline-1,3-dione;

(E)-2-(2,6-dioxopiperidin-3-yl)-5-(4-(2-(1-(4-(1-(4-hydroxyphenyl)-2-phenylbut-1-en-1-yl)phenyl)piperidin-4-yl)ethyl)piperazin-1-yl)isoindoline-1,3-dione;

(Z)-3-(5-(4-(5-((4-(1-(4-hydroxyphenyl)-2-phenylbut-1-en-1-yl)phenyl)thio)pentyl)piperazin-1-yl)-1-oxoisoindolin-2-yl)piperidine-2,6-dione;

(Z)-3-(5-(4-((5-((4-(1-(4-hydroxyphenyl)-2-phenylbut-1-en-1-yl)phenoxy)methyl)tetrahydrofuran-2-yl)methyl)piperazin-1-yl)-1-oxoisoindolin-2-yl)piperidine-2,6-dione;

(Z)-3-(5-(4-(2-(3-(4-(1-(4-hydroxyphenyl)-2-phenylbut-1-en-1-yl)phenoxy)cyclobutyl)ethyl)piperazin-1-yl)-1-oxoisoindolin-2-yl)piperidine-2,6-dione;

(Z)-3-(6-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione;

(Z)-3-(2-(4-(5-(4-(1-(4-hydroxyphenyl)-2-phenylbut-1-en-1-yl)phenoxy)pentyl)piperazin-1-yl)-5-oxo-5,7-dihydro-6H-pyrrolo[3,4-b]pyridin-6-yl)piperidine-2,6-dione;

(Z)-3-(2-(4-(4,4-difluoro-5-(4-(1-(4-hydroxyphenyl)-2-phenylbut-1-en-1-yl)phenoxy)pentyl)piperazin-1-yl)-5-oxo-5,7-dihydro-6H-pyrrolo[3,4-b]pyridin-6-yl)piperidine-2,6-dione;

(Z)-3-(6-(4-(5-(4-(1-(4-hydroxyphenyl)-2-phenylbut-1-en-1-yl)phenoxy)pentyl)piperazin-1-yl)-3-oxo-1,3-dihydro-2H-pyrrolo[3,4-c]pyridin-2-yl)piperidine-2,6-dione;

(Z)-2-(2,6-dioxopiperidin-3-yl)-5-(4-(1-(2-(4-(1-(4-hydroxyphenyl)-2-phenylbut-1-en-1-yl)phenoxy)ethyl)pyrrolidin-3-yl)butyl)isoindoline-1,3-dione;

(Z)-3-(5-(4-((3-((4-(1-(4-hydroxyphenyl)-2-phenylbut-1-en-1-yl)phenoxy)methyl)cyclobutyl)methyl)piperazin-1-yl)-1-oxoisoindolin-2-yl)piperidine-2,6-dione;

(Z)-3-(2-(4-(1-(2-(4-(1-(4-hydroxyphenyl)-2-phenylbut-1-en-1-yl)phenoxy)ethyl)pyrrolidin-3-yl)butyl)-5-oxo-5,7-dihydro-6H-pyrrolo[3,4-b]pyridin-6-yl)piperidine-2,6-dione;

(E)-3-(5-((1-((1-(4-(1-(4-hydroxyphenyl)-2-phenylbut-1-en-1-yl)phenyl)piperidin-4-yl)methyl)piperidin-4-yl)methoxy)-1-oxoisoindolin-2-yl)piperidine-2,6-dione;

(Z)-2-(2,6-dioxopiperidin-3-yl)-4-(4-(1-(2-(4-(1-(4-hydroxyphenyl)-2-phenylbut-1-en-1-yl)phenoxy)ethyl)pyrrolidin-3-yl)butyl)isoindoline-1,3-dione;

(E)-3-(2-(4-((1-(4-(1-(4-hydroxyphenyl)-2-phenylbut-1-en-1-yl)phenyl)piperidin-4-yl)methyl)piperazin-1-yl)-5-oxo-5,7-dihydro-6H-pyrrolo[3,4-b]pyridin-6-yl)piperidine-2,6-dione;

(E)-3-(2-(4-(2-(1-(4-(1-(4-hydroxyphenyl)-2-phenylbut-1-en-1-yl)phenyl)piperidin-4-yl)ethyl)piperazin-1-yl)-5-oxo-5,7-dihydro-6H-pyrrolo[3,4-b]pyridin-6-yl)piperidine-2,6-dione;

(E)-2-(2,6-dioxopiperidin-3-yl)-5-((1-((1-(4-(1-(4-hydroxyphenyl)-2-phenylbut-1-en-1-yl)phenyl)piperidin-4-yl)methyl)piperidin-4-yl)methoxy)isoindoline-1,3-dione;

(Z)-3-(5-(4-((6-((4-(1-(4-hydroxyphenyl)-2-phenylbut-1-en-1-yl)phenoxy)methyl)pyridazin-3-yl)methyl)piperazin-1-yl)-1-oxoisoindolin-2-yl)piperidine-2,6-dione;

(E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)-3-methylpiperidine-2,6-dione;

(E)-3-(5-(7-((1-(4-(1-(4-hydroxyphenyl)-2-phenylbut-1-en-1-yl)phenyl)piperidin-4-yl)methyl)-2,7-diazaspiro[3.5]nonan-2-yl)-1-oxoisoindolin-2-yl)piperidine-2,6-dione;

(Z)-3-(6-(2-(4-(3-(4-(1-(4-hydroxyphenyl)-2-phenylbut-1-en-1-yl)phenoxy)cyclobutoxy)piperidin-1-yl)ethoxy)-1-oxoisoindolin-2-yl)piperidine-2,6-dione;

(Z)-2-(2,6-dioxopiperidin-3-yl)-5-(4-(6,6,6-trifluoro-5-(4-(1-(4-hydroxyphenyl)-2-phenylbut-1-en-1-yl)phenoxy)hexyl)piperazin-1-yl)isoindoline-1,3-dione;

(Z)-3-(1-oxo-5-(4-(6,6,6-trifluoro-5-(4-(1-(4-hydroxyphenyl)-2-phenylbut-1-en-1-yl)phenoxy)hexyl)piperazin-1-yl)isoindolin-2-yl)piperidine-2,6-dione;

(Z)-3-(5-(4-((5-((4-(1-(4-hydroxyphenyl)-2-phenylbut-1-en-1-yl)phenoxy)methyl)pyridin-2-yl)methyl)piperazin-1-yl)-1-oxoisoindolin-2-yl)piperidine-2,6-dione;

(E)-3-(6-(4-((1-(4-(1-(4-hydroxyphenyl)-2-phenylbut-1-en-1-yl)phenyl)piperidin-4-yl)methyl)piperazin-1-yl)-3-oxo-1,3-dihydro-2H-pyrrolo[3,4-c]pyridin-2-yl)piperidine-2,6-dione;

(E)-3-(5-(4-(7-(4-(1-(4-hydroxyphenyl)-2-phenylbut-1-en-1-yl)phenyl)-7-azaspiro[3.5]nonan-2-yl)piperazin-1-yl)-1-oxoisoindolin-2-yl)piperidine-2,6-dione;

(E)-3-(2-(4-(7-(4-(1-(4-hydroxyphenyl)-2-phenylbut-1-en-1-yl)phenyl)-7-azaspiro[3.5]nonan-2-yl)piperazin-1-yl)-5-oxo-5,7-dihydro-6H-pyrrolo[3,4-b]pyridin-6-yl)piperidine-2,6-dione;

(E)-3-(6-(4-(2-(1-(4-(1-(4-hydroxyphenyl)-2-phenylbut-1-en-1-yl)phenyl)piperidin-4-yl)ethyl)piperazin-1-yl)-3-oxo-1,3-dihydro-2H-pyrrolo[3,4-c]pyridin-2-yl)piperidine-2,6-dione;

(E)-3-(5-(4-((1-(4-(1-(4-hydroxyphenyl)-2-phenylbut-1-en-1-yl)phenyl)-4-methylpiperidin-4-yl)methyl)piperazin-1-yl)-1-oxoisoindolin-2-yl)piperidine-2,6-dione;

(E)-3-(4,6-difluoro-5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(5-((1-((1-(4-(1-(4-hydroxyphenyl)-2-phenylbut-1-en-1-yl)phenyl)piperidin-4-yl)methyl)piperidin-4-yl)oxy)-1-oxoisoindolin-2-yl)piperidine-2,6-dione;

(E)-3-(2-(3-(((1-(4-(1-(4-hydroxyphenyl)-2-phenylbut-1-en-1-yl)phenyl)piperidin-4-yl)methyl)amino)pyrrolidin-1-yl)-5-oxo-5,7-dihydro-6H-pyrrolo[3,4-b]pyridin-6-yl)piperidine-2,6-dione;

(E)-3-(4-fluoro-5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(6-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(5-(3-(((1-(4-(1-(4-hydroxyphenyl)-2-phenylbut-1-en-1-yl)phenyl)piperidin-4-yl)methyl)amino)pyrrolidin-1-yl)-1-oxoisoindolin-2-yl)piperidine-2,6-dione;

(E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)-1-methylpiperidine-2,6-dione;

(E)-3-(5-(4-((4-hydroxy-1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(E)-3-(5-(4-(((1-(4-(1-(4-hydroxyphenyl)-2-phenylbut-1-en-1-yl)phenyl)piperidin-4-yl)methyl)amino)piperidin-1-yl)-1-oxoisoindolin-2-yl)piperidine-2,6-dione;

(E)-3-(5-(4-((1-(4-(1-(4-hydroxyphenyl)-2-phenylbut-1-en-1-yl)phenyl)piperidin-4-yl)amino)piperidin-1-yl)-1-oxoisoindolin-2-yl)piperidine-2,6-dione;

(E)-3-(5-(4-((4-fluoro-1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione;

(Z)-3-(4-((2-(4-(2-(4-(1-(4-hydroxyphenyl)-2-phenylbut-1-en-1-yl)phenoxy)ethyl)piperazin-1-yl)ethyl)amino)-1-oxoisoindolin-2-yl)piperidine-2,6-dione;

(Z)-2-(2,6-dioxopiperidin-3-yl)-4-((2-(4-(2-(4-(1-(4-hydroxyphenyl)-2-phenylbut-1-en-1-yl)phenoxy)ethyl)piperazin-1-yl)ethyl)amino)isoindoline-1,3-dione;

(Z)-3-(5-(2-(4-(2-(4-(1-(4-hydroxyphenyl)-2-phenylbut-1-en-1-yl)phenoxy)ethyl)piperazin-1-yl)-2-oxoethoxy)-1-oxoisoindolin-2-yl)piperidine-2,6-dione;

(Z)-3-(4-((6-((4-(2-(4-(1-(4-hydroxyphenyl)-2-phenylbut-1-en-1-yl)phenoxy)ethyl)piperazin-1-yl)methyl)pyridin-3-yl)methoxy)-1-oxoisoindolin-2-yl)piperidine-2,6-dione;

(Z)-3-(4-(2-(4-(1-(4-(1-(4-hydroxyphenyl)-2-phenylbut-1-en-1-yl)phenoxy)propan-2-yl)piperazin-1-yl)ethoxy)-1-oxoisoindolin-2-yl)piperidine-2,6-dione;

(Z)-3-(4-(2-(2-(4-(1-(4-hydroxyphenyl)-2-phenylbut-1-en-1-yl)phenoxy)ethoxy)ethoxy)-1-oxoisoindolin-2-yl)piperidine-2,6-dione;

(Z)-3-(4-((14-(4-(1-(4-hydroxyphenyl)-2-phenylbut-1-en-1-yl)phenoxy)-3,6,9,12-tetraoxatetradecyl)amino)-1-oxoisoindolin-2-yl)piperidine-2,6-dione;

(Z)-3-(4-(2-(2-(2-(4-(1-(4-hydroxyphenyl)-2-phenylbut-1-en-1-yl)phenoxy)ethoxy)ethoxy)ethoxy)-1-oxoisoindolin-2-yl)piperidine-2,6-dione;

(Z)-2-(2,6-dioxopiperidin-3-yl)-4-((14-(4-(1-(4-hydroxyphenyl)-2-phenylbut-1-en-1-yl)phenoxy)-3,6,9,12-tetraoxatetradecyl)amino)isoindoline-1,3-dione;

(Z)-3-(4-(2-(2-(2-(2-(4-(1-(4-hydroxyphenyl)-2-phenylbut-1-en-1-yl)phenoxy)ethoxy)ethoxy)ethoxy)ethoxy)-1-oxoisoindolin-2-yl)piperidine-2,6-dione;

(Z)-3-(4-((2-(2-(2-(2-(4-(1-(4-hydroxyphenyl)-2-phenylbut-1-en-1-yl)phenoxy)ethoxy)ethoxy)ethoxy)ethyl)amino)-1-oxoisoindolin-2-yl)piperidine-2,6-dione;

(Z)-2-(2,6-dioxopiperidin-3-yl)-4-((2-(2-(2-(4-(1-(4-hydroxyphenyl)-2-phenylbut-1-en-1-yl)phenoxy)ethoxy)ethoxy)ethyl)amino)isoindoline-1,3-dione;

(Z)-3-(4-(2-(2-(2-(4-(1-(4-hydroxyphenyl)-2-phenylbut-1-en-1-yl)phenoxy)ethoxy)ethoxy)ethyl)amino)-1-oxoisoindolin-2-yl)piperidine-2,6-dione;

(Z)-3-(4-((14-(4-(1-(4-hydroxyphenyl)-2-phenylbut-1-en-1-yl)phenoxy)-3,6,9,12-tetraoxatetradecyl)oxy)-1-oxoisoindolin-2-yl)piperidine-2,6-dione;

(Z)-2-(2,6-dioxopiperidin-3-yl)-4-((2-(2-(2-(4-(1-(4-hydroxyphenyl)-2-phenylbut-1-en-1-yl)phenoxy)ethoxy)ethoxy)ethyl)amino)isoindoline-1,3-dione;

(Z)-3-(4-((2-(2-(4-(1-(4-hydroxyphenyl)-2-phenylbut-1-en-1-yl)phenoxy)ethoxy)ethyl)amino)-1-oxoisoindolin-2-yl)piperidine-2,6-dione;

(Z)-3-(4-(2-(4-(1-(4-hydroxyphenyl)-2-phenylbut-1-en-1-yl)phenoxy)ethoxy)-1-oxoisoindolin-2-yl)piperidine-2,6-dione;

(Z)-2-(2,6-dioxopiperidin-3-yl)-4-((2-(2-(4-(1-(4-hydroxyphenyl)-2-phenylbut-1-en-1-yl)phenoxy)ethoxy)ethyl)amino)isoindoline-1,3-dione;

(Z)-2-(2,6-dioxopiperidin-3-yl)-4-((2-(4-(1-(4-hydroxyphenyl)-2-phenylbut-1-en-1-yl)phenoxy)ethyl)amino)isoindoline-1,3-dione;

(Z)-3-(4-((2-(4-(1-(4-hydroxyphenyl)-2-phenylbut-1-en-1-yl)phenoxy)ethyl)amino)-1-oxoisoindolin-2-yl)piperidine-2,6-dione;

(Z)-3-(4-(3-(3-(4-(1-(4-hydroxyphenyl)-2-phenylbut-1-en-1-yl)phenoxy)propoxy)propoxy)-1-oxoisoindolin-2-yl)piperidine-2,6-dione;

(Z)-3-(4-(3-(3-(3-(4-(1-(4-hydroxyphenyl)-2-phenylbut-1-en-1-yl)phenoxy)propoxy)propoxy)propoxy)-1-oxoisoindolin-2-yl)piperidine-2,6-dione;

(Z)-3-(4-(2-(5-(2-(4-(1-(4-hydroxyphenyl)-2-phenylbut-1-en-1-yl)phenoxy)ethyl)-2,5-diazabicyclo[2.2.1]heptan-2-yl)ethoxy)-1-oxoisoindolin-2-yl)piperidine-2,6-dione;

(Z)-3-(5-(2-(6-(2-(4-(1-(4-hydroxyphenyl)-2-phenylbut-1-en-1-yl)phenoxy)ethyl)-2,6-diazaspiro[3.3]heptan-2-yl)ethoxy)-1-oxoisoindolin-2-yl)piperidine-2,6-dione;

(Z)-3-(5-(2-((1-(2-(4-(1-(4-hydroxyphenyl)-2-phenylbut-1-en-1-yl)phenoxy)ethyl)piperidin-4-yl)oxy)ethoxy)-1-oxoisoindolin-2-yl)piperidine-2,6-dione;

(Z)-3-(5-((7-(2-(4-(1-(4-hydroxyphenyl)-2-phenylbut-1-en-1-yl)phenoxy)ethyl)-7-azaspiro[3.5]nonan-2-yl)oxy)-1-oxoisoindolin-2-yl)piperidine-2,6-dione;

(Z)-3-(5-(4-(4-(1-(4-(1-(4-hydroxyphenyl)-2-phenylbut-1-en-1-yl)phenoxy)propan-2-yl)piperazin-1-yl)butyl)-1-oxoisoindolin-2-yl)piperidine-2,6-dione;

(Z)—N-((2-(2,6-dioxopiperidin-3-yl)-1-oxoisoindolin-5-yl)methyl)-1-(2-(4-(1-(4-hydroxyphenyl)-2-phenylbut-1-en-1-yl)phenoxy)ethyl)piperidine-4-carboxamide;

(Z)—N-((2-(2,6-dioxopiperidin-3-yl)-1-oxoisoindolin-5-yl)methyl)-2-(1-(2-(4-(1-(4-hydroxyphenyl)-2-phenylbut-1-en-1-yl)phenoxy)ethyl)piperidin-4-yl)acetamide;

(Z)-2-(2,6-dioxopiperidin-3-yl)-5-((2-(2-(2-(4-(1-(4-hydroxyphenyl)-2-phenylbut-1-en-1-yl)phenoxy)ethoxy)ethoxy)ethyl)amino)isoindoline-1,3-dione;

(Z)-2-(2,6-dioxopiperidin-3-yl)-5-(4-(7-(4-(1-(4-hydroxyphenyl)-2-phenylbut-1-en-1-yl)phenoxy)heptyl)piperazin-1-yl)isoindoline-1,3-dione;

(Z)-3-(5-((3-(4-(2-(4-(1-(4-hydroxyphenyl)-2-phenylbut-1-en-1-yl)phenoxy)ethyl)-1,4-diazepan-1-yl)propyl)amino)-1-oxoisoindolin-2-yl)piperidine-2,6-dione;

(Z)-2-(2,6-dioxopiperidin-3-yl)-5-(3-(3-(4-(1-(4-hydroxyphenyl)-2-phenylbut-1-en-1-yl)phenoxy)propoxy)propoxy)isoindoline-1,3-dione;

(Z)-2-(2,6-dioxopiperidin-3-yl)-5-(2-(2-(2-(4-(1-(4-hydroxyphenyl)-2-phenylbut-1-en-1-yl)phenoxy)ethoxy)ethoxy)ethoxy)isoindoline-1,3-dione;

(Z)-2-(2,6-dioxopiperidin-3-yl)-5-(3-(2-(2-(4-(1-(4-hydroxyphenyl)-2-phenylbut-1-en-1-yl)phenoxy)ethoxy)ethoxy)propoxy)isoindoline-1,3-dione;

(Z)-2-(2,6-dioxopiperidin-3-yl)-5-(3-(3-(3-(4-(1-(4-hydroxyphenyl)-2-phenylbut-1-en-1-yl)phenoxy)propoxy)propoxy)propoxy)isoindoline-1,3-dione;

(Z)-2-(2,6-dioxopiperidin-3-yl)-5-((3-(3-(4-(1-(4-hydroxyphenyl)-2-phenylbut-1-en-1-yl)phenoxy)propoxy)propyl)amino)isoindoline-1,3-dione;

(Z)-2-(2,6-dioxopiperidin-3-yl)-5-((3-(2-(2-(4-(1-(4-hydroxyphenyl)-2-phenylbut-1-en-1-yl)phenoxy)ethoxy)ethoxy)propyl)amino)isoindoline-1,3-dione;

(Z)-2-(2,6-dioxopiperidin-3-yl)-5-((3-(3-(3-(4-(1-(4-hydroxyphenyl)-2-phenylbut-1-en-1-yl)phenoxy)propoxy)propoxy)propyl)amino)isoindoline-1,3-dione;

(Z)-3-(5-((2-(2-(2-(4-(1-(4-hydroxyphenyl)-2-phenylbut-1-en-1-yl)phenoxy)ethoxy)ethoxy)ethyl)amino)-1-oxoisoindolin-2-yl)piperidine-2,6-dione;

(Z)-2-(2,6-dioxopiperidin-3-yl)-5-(3-(3-(2-(4-(1-(4-hydroxyphenyl)-2-phenylbut-1-en-1-yl)phenoxy)ethoxy)propoxy)propoxy)isoindoline-1,3-dione;

(Z)-3-(5-((3-(3-(2-(4-(1-(4-hydroxyphenyl)-2-phenylbut-1-en-1-yl)phenoxy)ethoxy)propoxy)propyl)amino)-1-oxoisoindolin-2-yl)piperidine-2,6-dione;

(Z)-2-(2,6-dioxopiperidin-3-yl)-5-(3-(3-(4-(4-(1-(4-hydroxyphenyl)-2-phenylbut-1-en-1-yl)phenoxy)butoxy)propoxy)propoxy)isoindoline-1,3-dione;

(Z)-2-(2,6-dioxopiperidin-3-yl)-5-((3-(3-(2-(4-(1-(4-hydroxyphenyl)-2-phenylbut-1-en-1-yl)phenoxy)ethoxy)propoxy)propyl)amino)isoindoline-1,3-dione;

(Z)-2-(2,6-dioxopiperidin-3-yl)-5-((3-(3-(4-(4-(1-(4-hydroxyphenyl)-2-phenylbut-1-en-1-yl)phenoxy)butoxy)propoxy)propyl)amino)isoindoline-1,3-dione;

(Z)-3-(5-((3-(3-(4-(4-(1-(4-hydroxyphenyl)-2-phenylbut-1-en-1-yl)phenoxy)butoxy)propoxy)propyl)amino)-1-oxoisoindolin-2-yl)piperidine-2,6-dione;

(Z)-3-(5-((3-(3-(3-(4-(1-(4-hydroxyphenyl)-2-phenylbut-1-en-1-yl)phenoxy)propoxy)propoxy)propyl)amino)-1-oxoisoindolin-2-yl)piperidine-2,6-dione;

(Z)-2-(2,6-dioxopiperidin-3-yl)-5-((3-(4-(2-(4-(1-(4-hydroxyphenyl)-2-phenylbut-1-en-1-yl)phenoxy)ethyl)piperazin-1-yl)propyl)amino)isoindoline-1,3-dione;

(Z)-2-(2,6-dioxopiperidin-3-yl)-5-((3-(4-(2-(4-(1-(4-hydroxyphenyl)-2-phenylbut-1-en-1-yl)phenoxy)ethyl)-1,4-diazepan-1-yl)propyl)amino)isoindoline-1,3-dione;

(E)-2-(2,6-dioxopiperidin-3-yl)-5-((3-(4-(3-(4-(1-(4-hydroxyphenyl)-2-phenylbut-1-en-1-yl)phenyl)propyl)piperazin-1-yl)propyl)amino)isoindoline-1,3-dione;

(E)-2-(2,6-dioxopiperidin-3-yl)-5-((3-(4-(3-(4-(1-(4-hydroxyphenyl)-2-phenylbut-1-en-1-yl)phenyl)propyl)-1,4-diazepan-1-yl)propyl)amino)isoindoline-1,3-dione;

(E)-2-(2,6-dioxopiperidin-3-yl)-5-((3-(4-(4-(1-(4-hydroxyphenyl)-2-phenylbut-1-en-1-yl)phenyl)piperidin-1-yl)propyl)amino)isoindoline-1,3-dione;

(E)-2-(2,6-dioxopiperidin-3-yl)-5-((4-(4-(4-(1-(4-hydroxyphenyl)-2-phenylbut-1-en-1-yl)phenyl)piperidin-1-yl)butyl)amino)isoindoline-1,3-dione;

(E)-3-(5-((3-(4-(3-(4-(1-(4-hydroxyphenyl)-2-phenylbut-1-en-1-yl)phenyl)propyl)piperazin-1-yl)propyl)amino)-1-oxoisoindolin-2-yl)piperidine-2,6-dione;

(E)-3-(5-((3-(4-(3-(4-(1-(4-hydroxyphenyl)-2-phenylbut-1-en-1-yl)phenyl)propyl)-1,4-diazepan-1-yl)propyl)amino)-1-oxoisoindolin-2-yl)piperidine-2,6-dione;

(E)-3-(5-((3-(4-(4-(1-(4-hydroxyphenyl)-2-phenylbut-1-en-1-yl)phenyl)piperidin-1-yl)propyl)amino)-1-oxoisoindolin-2-yl)piperidine-2,6-dione;

(E)-3-(5-((5-(4-(4-(1-(4-hydroxyphenyl)-2-phenylbut-1-en-1-yl)phenyl)piperidin-1-yl)pentyl)amino)-1-oxoisoindolin-2-yl)piperidine-2,6-dione; and (E)-3-(5-(2-(4-(5-(4-(1-(4-hydroxyphenyl)-2-phenylbut-1-en-1-yl)phenyl)pentyl)-1,4-diazepan-1-yl)ethyl)-1-oxoisoindolin-2-yl)piperidine-2,6-dione.

In some embodiments, the compound with ER degradation activity or tautomer, stereoisomer, pharmaceutically acceptable salt, or hydrate thereof provided herein, is selected from the group consisting of:

(Z)-3-(2-((2-(2,6-dioxopiperidin-3-yl)-1,3-dioxoisoindolin-4-yl)amino)ethoxy)-N-(2-(4-(1,2-diphenylbut-1-en-1-yl)phenoxy)ethyl)-N-methylpropanamide;

(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;

(Z)-3-(2-(2-(2-((2-(2,6-dioxopiperidin-3-yl)-1,3-dioxoisoindolin-4-yl)amino)ethoxy)ethoxy)ethoxy)-N-(2-(4-(1,2-diphenylbut-1-en-1-yl)phenoxy)ethyl)-N-methylpropanamide;

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12-tetraoxapentadecan-15-amide;

(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide;

(Z)-2-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylacetamide;

(Z)-3-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylpropanamide;

(Z)-4-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylbutanamide;

(Z)-6-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylhexanamide;

(Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide;

(Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide;

(Z)-2-(2,6-dioxopiperidin-3-yl)-4-((1-((4-(2-(4-(1-(4-hydroxyphenyl)-2-phenylbut-1-en-1-yl)phenoxy)ethyl)piperazin-1-yl)methyl)piperidin-4-yl)amino)isoindoline-1,3-dione;

(Z)-2-(2,6-dioxopiperidin-3-yl)-4-((1-((1-(2-(4-(1-(4-hydroxyphenyl)-2-phenylbut-1-en-1-yl)phenoxy)ethyl)piperidin-4-yl)methyl)piperidin-4-yl)amino)isoindoline-1,3-dione;

(Z)-3-(4-((1-((1-(2-(4-(1-(4-hydroxyphenyl)-2-phenylbut-1-en-1-yl)phenoxy)ethyl)piperidin-4-yl)methyl)piperidin-4-yl)amino)-1-oxoisoindolin-2-yl)piperidine-2,6-dione;

(Z)-3-(4-((1-((4-(2-(4-(1-(4-hydroxyphenyl)-2-phenylbut-1-en-1-yl)phenoxy)ethyl)piperazin-1-yl)methyl)piperidin-4-yl)amino)-1-oxoisoindolin-2-yl)piperidine-2,6-dione;

(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;

(Z)-3-(2-(2-((2-(2,6-dioxopiperidin-3-yl)-1,3-dioxoisoindolin-4-yl)amino)ethoxy)ethoxy)-N-(2-(4-(1-(4-hydroxyphenyl)-2-phenylbut-1-en-1-yl)phenoxy)ethyl)-N-methylpropanamide;

(Z)-1-((2-(2,6-dioxopiperidin-3-yl)-1-oxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide;

(Z)-1-((2-(2,6-dioxopiperidin-3-yl)-1,3-dioxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide; and (Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide.

In some embodiments the compound with ER degradation activity or tautomer, stereoisomer, pharmaceutically acceptable salt, or hydrate thereof provided herein, is selected from the group consisting of:
(Z)-3-(2-((2-(2,6-dioxopiperidin-3-yl)-1,3-dioxoisoindolin-4-yl)amino)ethoxy)-N-(2-(4-(1,2-diphenylbut-1-en-1-yl)phenoxy)ethyl)-N-methylpropanamide;
(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;
(Z)-3-(2-(2-(2-((2-(2,6-dioxopiperidin-3-yl)-1,3-dioxoisoindolin-4-yl)amino)ethoxy)ethoxy)ethoxy)-N-(2-(4-(1,2-diphenylbut-1-en-1-yl)phenoxy)ethyl)-N-methylpropanamide;
(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12-tetraoxapentadecan-15-amide;
(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide;
(Z)-2-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylacetamide;
(Z)-3-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylpropanamide;
(Z)-4-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylbutanamide;
(Z)-6-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylhexanamide;
(Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide; and
(Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide.

In some embodiments, provided herein is a compound, or tautomer, stereoisomer, pharmaceutically acceptable salt, or hydrate thereof, chosen from:
(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;
(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12-tetraoxapentadecan-15-amide;
(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide;
(Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide; and
(Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide.

In some embodiments, the compound with ER degradation activity or tautomer, stereoisomer, pharmaceutically acceptable salt, or hydrate thereof provided herein, is selected from the group consisting of:
(Z)-2-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylacetamide;
(Z)-3-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylpropanamide;
(Z)-4-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylbutanamide;
(Z)-6-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylhexanamide;
(Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide; and
(Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide.

In some embodiments, the compound with ER degradation activity or tautomer, stereoisomer, pharmaceutically acceptable salt, or hydrate thereof provided herein, is selected from the group consisting of:
(Z)-2-(2,6-dioxopiperidin-3-yl)-4-((1-((4-(2-(4-(1-(4-hydroxyphenyl)-2-phenylbut-1-en-1-yl)phenoxy)ethyl)piperazin-1-yl)methyl)piperidin-4-yl)amino)isoindoline-1,3-dione;
(Z)-2-(2,6-dioxopiperidin-3-yl)-4-((1-((1-(2-(4-(1-(4-hydroxyphenyl)-2-phenylbut-1-en-1-yl)phenoxy)ethyl)piperidin-4-yl)methyl)piperidin-4-yl)amino)isoindoline-1,3-dione;
(Z)-3-(4-((1-((1-(2-(4-(1-(4-hydroxyphenyl)-2-phenylbut-1-en-1-yl)phenoxy)ethyl)piperidin-4-yl)methyl)piperidin-4-yl)amino)-1-oxoisoindolin-2-yl)piperidine-2,6-dione; and
(Z)-3-(4-((1-((4-(2-(4-(1-(4-hydroxyphenyl)-2-phenylbut-1-en-1-yl)phenoxy)ethyl)piperazin-1-yl)methyl)piperidin-4-yl)amino)-1-oxoisoindolin-2-yl)piperidine-2,6-dione.

In some embodiments, the compound with ER degradation activity or tautomer, stereoisomer, pharmaceutically acceptable salt, or hydrate thereof provided herein, is selected from the group consisting of:
(Z)-3-(2-((2-(2,6-dioxopiperidin-3-yl)-1,3-dioxoisoindolin-4-yl)amino)ethoxy)-N-(2-(4-(1,2-diphenylbut-1-en-1-yl)phenoxy)ethyl)-N-methylpropanamide;
(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;
(Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide;
(Z)-3-(2-(2-((2-(2,6-dioxopiperidin-3-yl)-1,3-dioxoisoindolin-4-yl)amino)ethoxy)ethoxy)-N-(2-(4-(1-(4-hydroxyphenyl)-2-phenylbut-1-en-1-yl)phenoxy)ethyl)-N-methylpropanamide;
(Z)-1-((2-(2,6-dioxopiperidin-3-yl)-1-oxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide;
(Z)-1-((2-(2,6-dioxopiperidin-3-yl)-1,3-dioxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide; and
(Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-pentaoxaoctadecan-18-amide.

In some embodiments, the compound with ER degradation activity or tautomer, stereoisomer, pharmaceutically acceptable salt, or hydrate thereof provided herein, is selected from the group consisting of:

(Z)-3-(8-((2-(4-(2-(4-(1-(4-hydroxyphenyl)-2-phenylbut-1-en-1-yl)phenoxy)ethyl)piperazin-1-yl)ethyl)amino)-2-methyl-4-oxoquinazolin-3(4H)-yl)piperidine-2,6-dione; and (Z)-3-(8-(2-(4-(2-(4-(1-(4-hydroxyphenyl)-2-phenylbut-1-en-1-yl)phenoxy)ethyl)piperazin-1-yl)ethoxy)-2-methyl-4-oxoquinazolin-3(4H)-yl)piperidine-2,6-dione.

In some embodiments, the compound with ER degradation activity or tautomer, stereoisomer, pharmaceutically acceptable salt, or hydrate thereof provided herein, is selected from the group consisting of:

3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione (S)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione (S,E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione (E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione.

In a particular embodiment, the compound with ER degradation activity is (S,E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione In some embodiments the compound with ER degradation activity or tautomer, stereoisomer, pharmaceutically acceptable salt, or hydrate thereof provided herein, is a pharmaceutically acceptable salt of a compound of Formula (I), Formula (I-A) or Formula (I-A).

In some embodiments, the compound with ER degradation activity or tautomer, stereoisomer, pharmaceutically acceptable salt, or hydrate thereof provided herein, is one or more compounds selected from Table 1A.

TABLE 1A
Exemplary Compound of the Present Disclosure
| # | Structure | IUPAC Name |
|---|---|---|
| 1 | 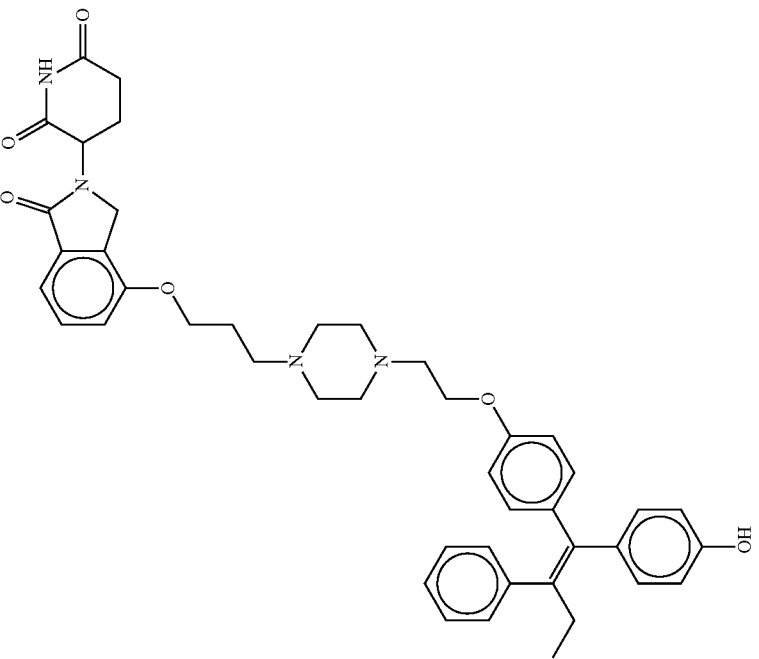 | (Z)-3-(4-(3-(4-(2-(4-(1-(4-hydroxyphenyl)-2-phenylbut-1-en-1-yl)phenoxy)ethyl)piperazin-1-yl)propoxy)-1-oxoisoindolin-2-yl)piperidine-2,6-dione |

TABLE 1A-continued

Exemplary Compound of the Present Disclosure

| # | Structure | IUPAC Name |
|---|---|---|
| 2 | 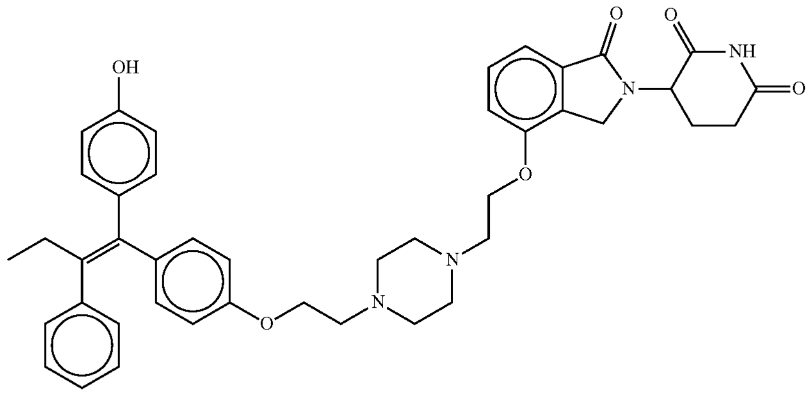 | (Z)-3-(4-(2-(4-(2-(4-(1-(4-hydroxyphenyl)-2-phenylbut-1-en-1-yl)phenoxy)ethyl)piperazin-1-yl)ethoxy)-1-oxoisoindolin-2-yl)piperidine-2,6-dione |
| 3 | 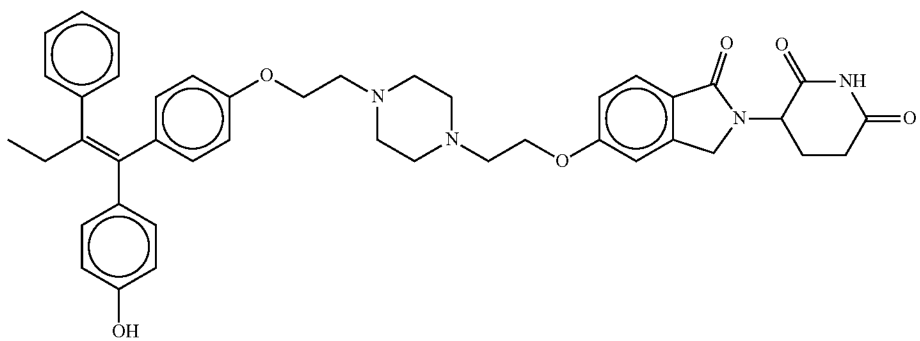 | (Z)-3-(5-(2-(4-(2-(4-(1-(4-hydroxyphenyl)-2-phenylbut-1-en-1-yl)phenoxy)ethyl)piperazin-1-yl)ethoxy)-1-oxoisoindolin-2-yl)piperidine-2,6-dione |

TABLE 1A-continued

Exemplary Compound of the Present Disclosure

| # | Structure | IUPAC Name |
|---|---|---|
| 4 | 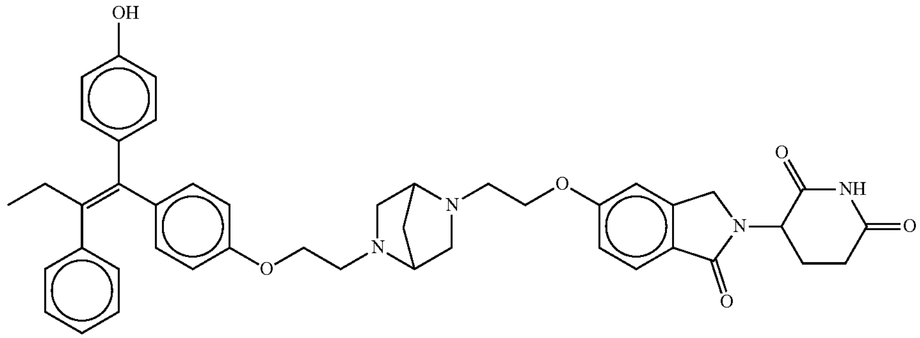 | (Z)-3-(5-(2-(5-(2-(4-(1-(4-hydroxyphenyl)-2-phenylbut-1-en-1-yl)phenoxy)ethyl)-2,5-diazabicyclo[2.2.1]heptan-2-yl)ethoxy)-1-oxoisoindolin-2-yl)piperidine-2,6-dione |
| 5 | 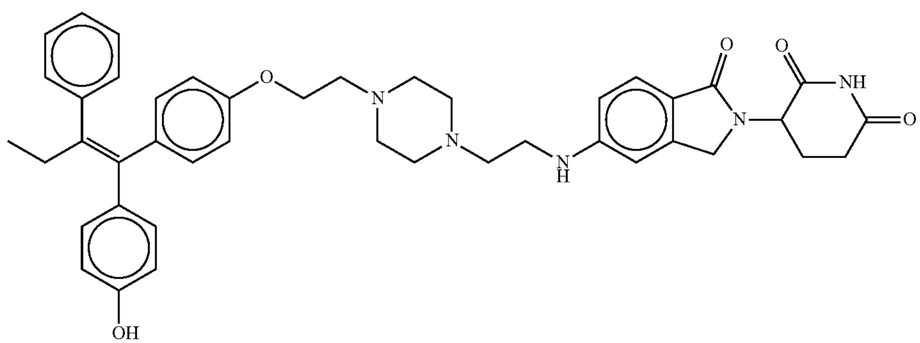 | (Z)-3-(5-((2-(4-(2-(4-(1-(4-hydroxyphenyl)-2-phenylbut-1-en-1-yl)phenoxy)ethyl)piperazin-1-yl)ethyl)amino)-1-oxoisoindolin-2-yl)piperidine-2,6-dione |
| 6 | 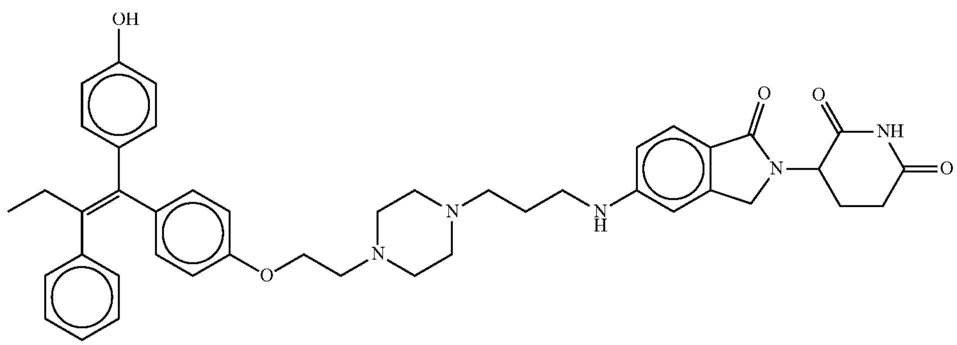 | (Z)-3-(5-((3-(4-(2-(4-(4-hydroxyphenyl)-2-phenylbut-1-en-1-yl)phenoxy)ethyl)piperazin-1-yl)propyl)amino)-1-oxoisoindolin-2-yl)piperidine-2,6-dione |

TABLE 1A-continued

Exemplary Compound of the Present Disclosure

| # | Structure | IUPAC Name |
|---|---|---|
| 7 | 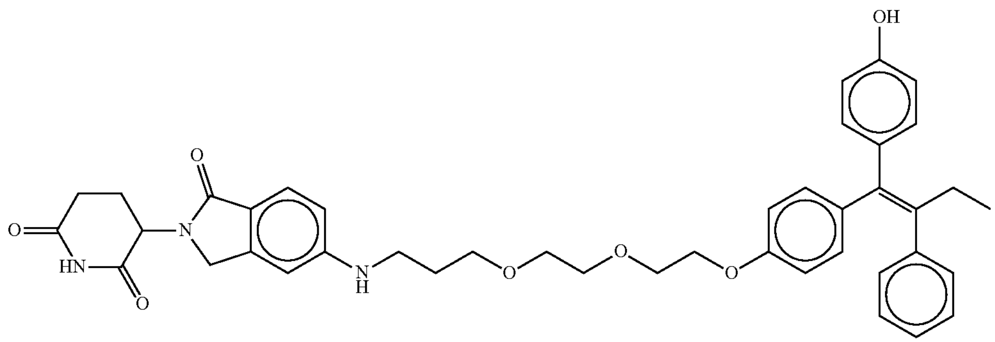 | (Z)-3-(5-((3-(2-(4-(1-(4-hydroxyphenyl)-2-phenylbut-1-en-1-yl)phenoxy)ethoxy)ethoxy)propyl)amino)-1-oxoisoindolin-2-yl)piperidine-2,6-dione |
| 8 | 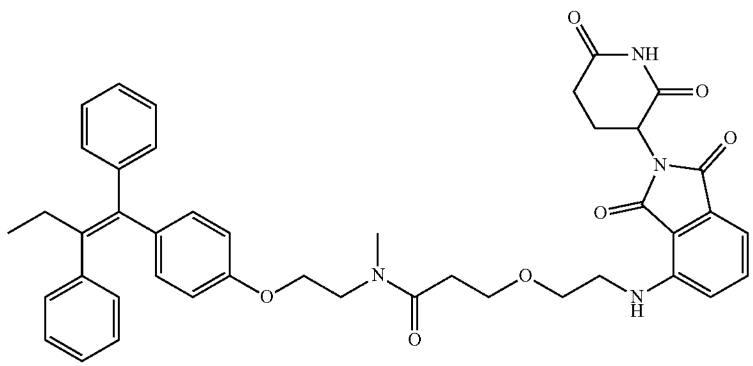 [SMILES: CC/C(=C(\c1ccccc1)c1ccc(OCCN(C)C(=O)CCOCCNc2cccc3c2C(=O)N(C2CCC(=O)NC2=O)C3=O)cc1)c1ccccc1] | (Z)-3-(2-((2-(2,6-dioxopiperidin-3-yl)-1,3-dioxoisoindolin-4-yl)amino)ethoxy)-N-(2-(4-(1,2-diphenylbut-1-en-1-yl)phenoxy)ethyl)-N-methylpropanamide |

TABLE 1A-continued

Exemplary Compound of the Present Disclosure

| # | Structure | IUPAC Name |
|---|-----------|------------|
| 9 | 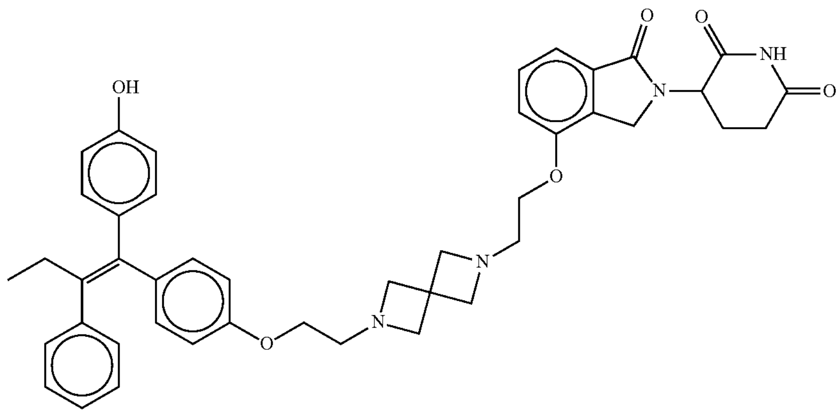 | (Z)-3-(4-(2-(6-(2-(4-(1-(4-hydroxyphenyl)-2-phenylbut-1-en-1-yl)phenoxy)ethyl)-2,6-diazaspiro[3.3]heptan-2-yl)ethoxy)-1-oxoisoindolin-2-yl)piperidine-2,6-dione |
| 10 | 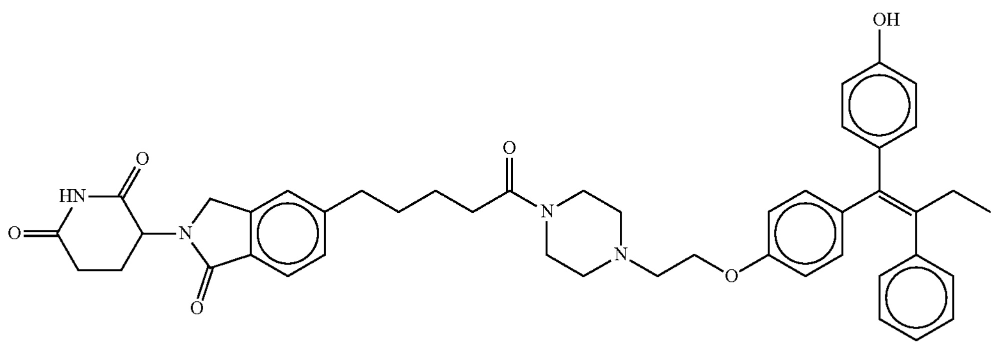 | (Z)-3-(5-(5-(4-(2-(4-(1-(4-hydroxyphenyl)-2-phenylbut-1-en-1-yl)phenoxy)ethyl)piperazin-1-yl)-5-oxopentyl)-1-oxoisoindolin-2-yl)piperidine-2,6-dione |

TABLE 1A-continued

Exemplary Compound of the Present Disclosure

| # | Structure | IUPAC Name |
|---|---|---|
| 11 | 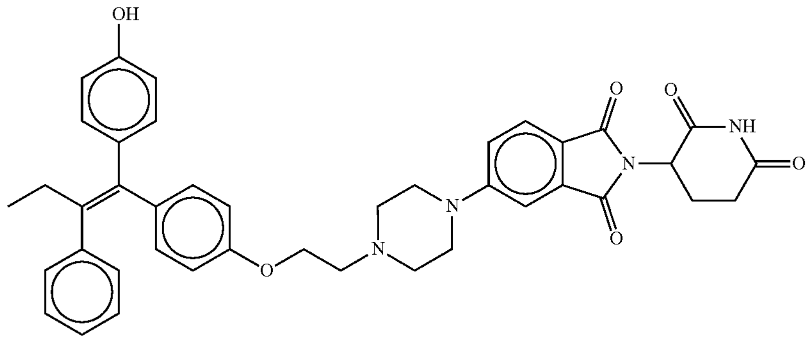 | (Z)-2-(2,6-dioxopiperidin-3-yl)-5-(4-(2-(4-(1-(4-hydroxyphenyl)-2-phenylbut-1-en-1-yl)phenoxy)ethyl)piperazin-1-yl)isoindoline-1,3-dione |
| 12 | 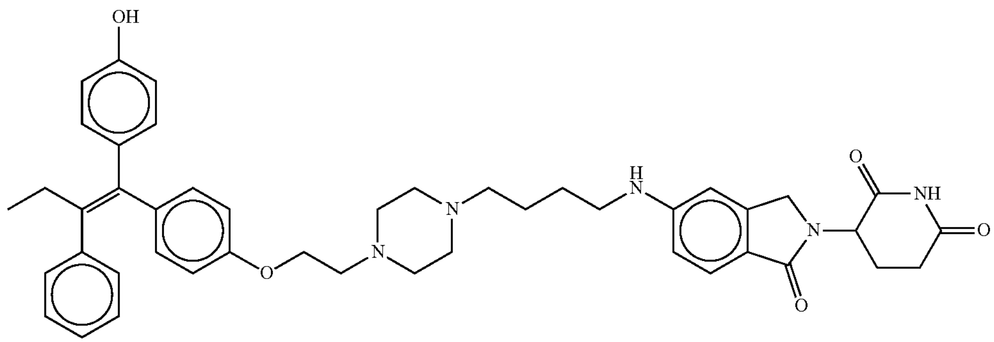 | (Z)-3-(5-((4-(4-(2-(4-(1-(4-hydroxyphenyl)-2-phenylbut-1-en-1-yl)phenoxy)ethyl)piperazin-1-yl)butyl)amino)-1-oxoisoindolin-2-yl)piperidine-2,6-dione |
| 13 | 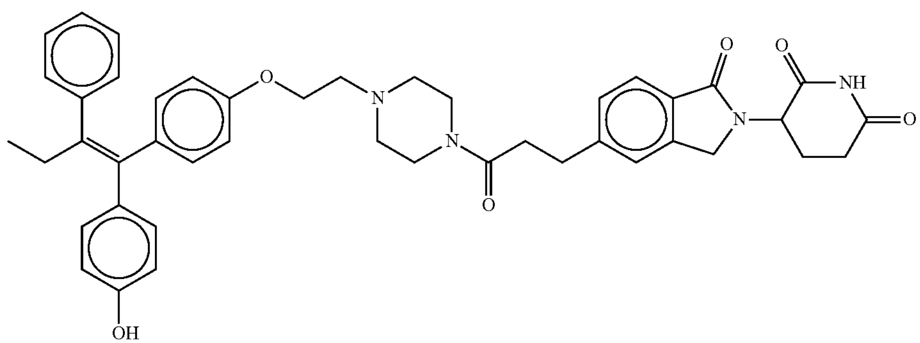 | (Z)-3-(5-(3-(4-(2-(4-(1-(4-hydroxyphenyl)-2-phenylbut-1-en-1-yl)phenoxy)ethyl)piperazin-1-yl)-3-oxopropyl)-1-oxoisoindolin-2-yl)piperidine-2,6-dione |

TABLE 1A-continued

Exemplary Compound of the Present Disclosure

| # | Structure | IUPAC Name |
|---|---|---|
| 14 | 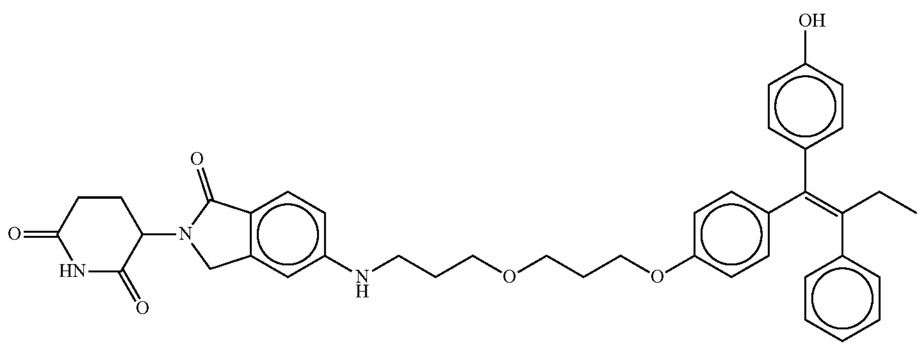 | (Z)-3-(5-((3-(4-(1-(4-hydroxyphenyl)-2-phenylbut-1-en-1-yl)phenoxy)propoxy)propyl)amino)-1-oxoisoindolin-2-yl)piperidine-2,6-dione |
| 15 | 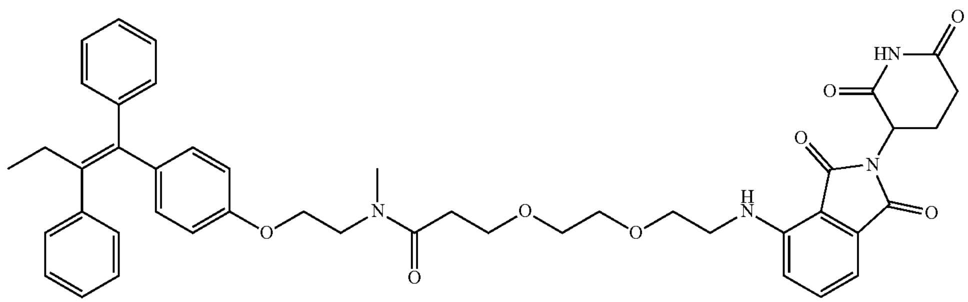 [SMILES: CC/C(=C(\c1ccccc1)c1ccc(OCCN(C)C(=O)CCOCCOCCNc2cccc3c2C(=O)N(C2CCC(=O)NC2=O)C3=O)cc1)c1ccccc1] | (Z)-3-(2-(2-((2-(2,6-dioxopiperidin-3-yl)-1,3-dioxoisoindolin-4-yl)amino)ethoxy)ethoxy)-N-(2-(4-(1,2-diphenylbut-1-en-1-yl)phenoxy)ethyl)-N-methylpropanamide |
| 16a | 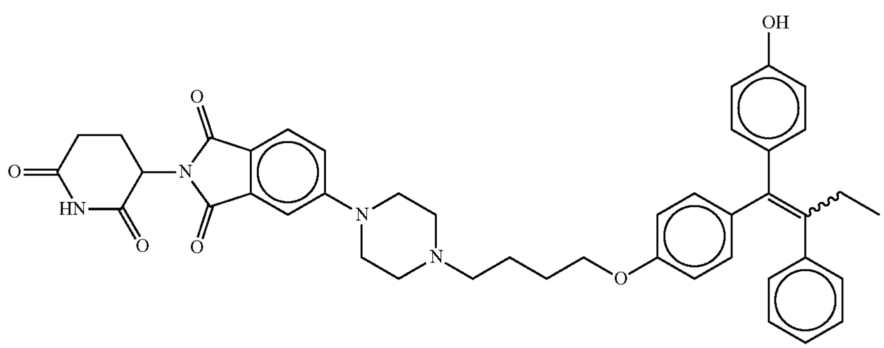 | (E)/(Z)-2-(2,6-dioxopiperidin-3-yl)-5-(4-(4-(1-(4-hydroxyphenyl)-2-phenylbut-1-en-1-yl)phenoxy)butyl)piperazin-1-yl)isoindoline-1,3-dione |

TABLE 1A-continued

Exemplary Compound of the Present Disclosure

| # | Structure | IUPAC Name |
|---|---|---|
| 16 | 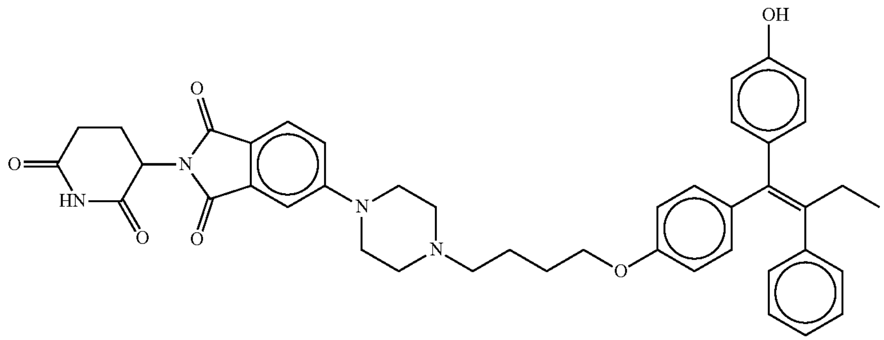 | (Z)-2-(2,6-dioxopiperidin-3-yl)-5-(4-(4-(1-(4-hydroxyphenyl)-2-phenylbut-1-en-1-yl)phenoxy)butyl)piperazin-1-yl)isoindoline-1,3-dione |
| 17a | 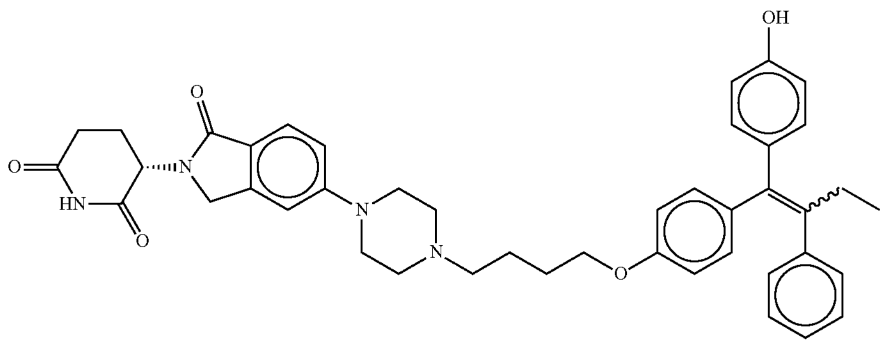 | (E)/(Z)-(S)-3-(5-(4-(4-(1-(4-hydroxyphenyl)-2-phenyl but-1-en-1-yl)phenoxy)butyl)piperazin-1-yl)-1-oxoisoindolin-2-yl)piperidine-2,6-dione |
| 17 | 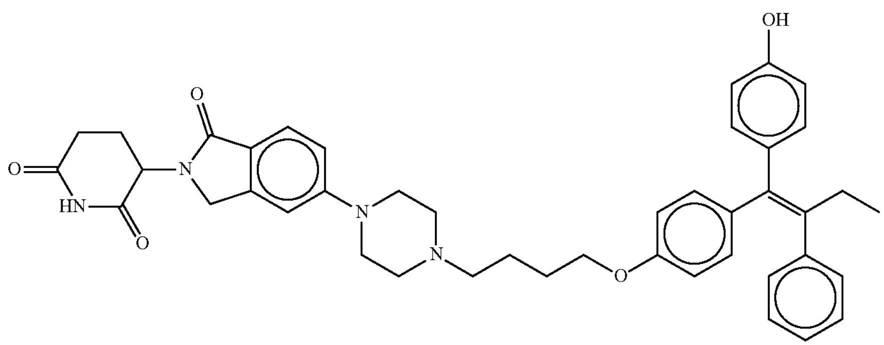 | (Z)-3-(5-(4-(4-(1-(4-hydroxyphenyl)-2-phenylbut-1-en-1-yl)phenoxy)butyl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|-----------|------------|
| 18 | 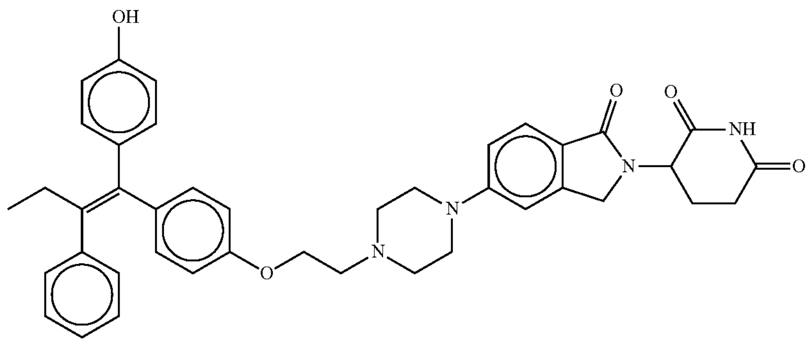 | (Z)-3-(5-(4-(2-(4-(1-(4-hydroxyphenyl)-2-phenylbut-1-en-1-yl)phenoxy)ethyl)piperazin-1-yl)-1-oxoisoindolin-2-yl)piperidine-2,6-dione |
| 19 | 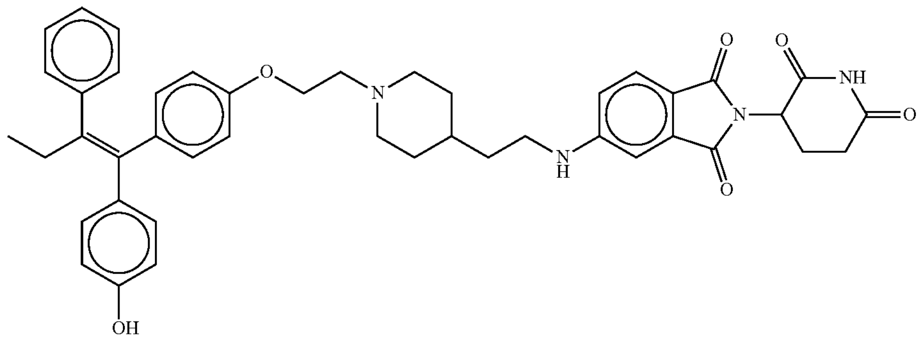 | (Z)-2-(2,6-dioxopiperidin-3-yl)-5-((2-(1-(2-(4-(1-(4-hydroxyphenyl)-2-phenylbut-1-en-1-yl)phenoxy)ethyl)piperidin-4-yl)ethyl)amino)isoindoline-1,3-dione |

TABLE 1A-continued

Exemplary Compound of the Present Disclosure

| # | Structure | IUPAC Name |
|---|---|---|
| 20 | 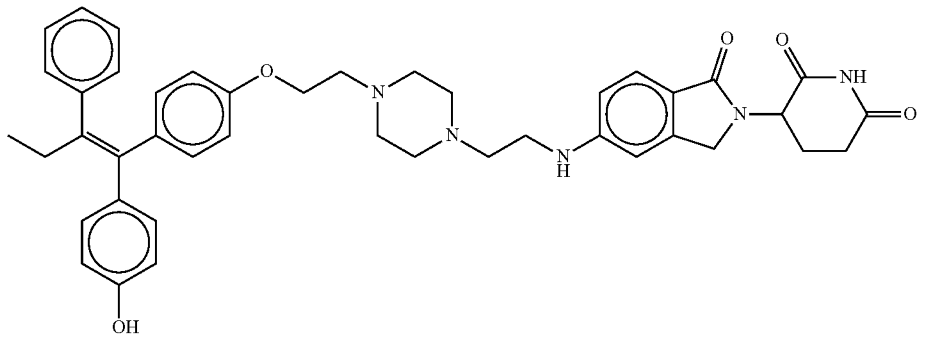 | (Z)-3-(5-((2-(4-(2-(4-(1-(4-hydroxyphenyl)-2-phenylbut-1-en-1-yl)phenoxy)ethyl)piperazin-1-yl)ethyl)amino)-1-oxoisoindolin-2-yl)piperidine-2,6-dione |
| 21 | 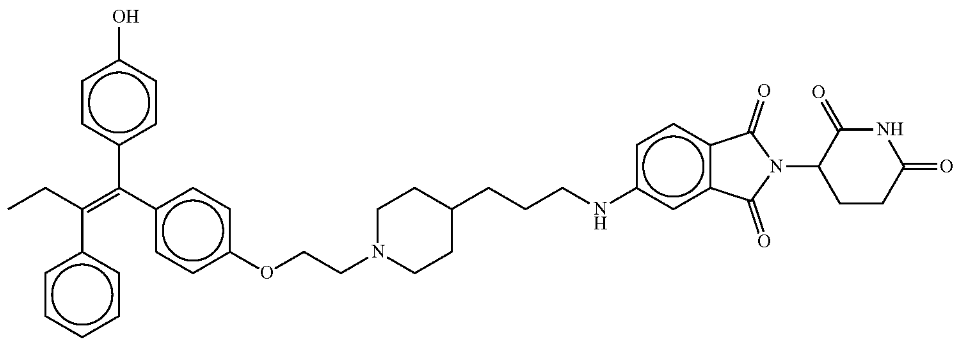 | (Z)-2-(2,6-dioxopiperidin-3-yl)-5-((3-(1-(2-(4-(1-(4-hydroxyphenyl)-2-phenylbut-1-en-1-yl)phenoxy)ethyl)piperidin-4-yl)propyl)amino)isoindoline-1,3-dione |
| 22 | 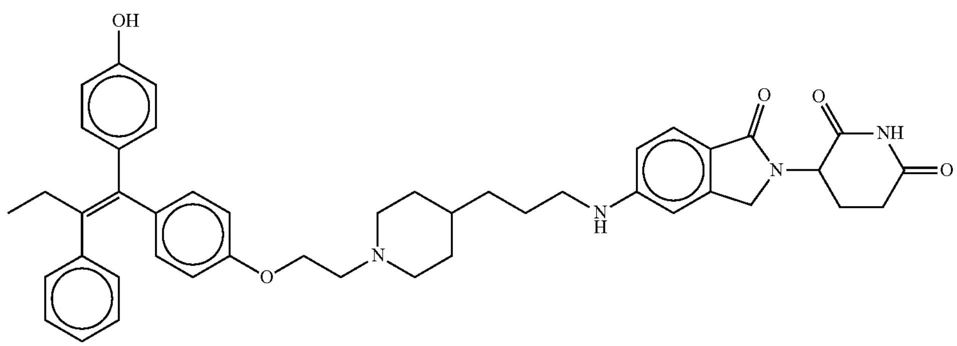 | (Z)-3-(5-((3-(1-(2-(4-(1-(4-hydroxyphenyl)-2-phenylbut-1-en-1-yl)phenoxy)ethyl)piperidin-4-yl)propyl)amino)-1-oxoisoindolin-2-yl)piperidine-2,6-dione |

TABLE 1A-continued

Exemplary Compound of the Present Disclosure

| # | Structure | IUPAC Name |
|---|-----------|------------|
| 23 | 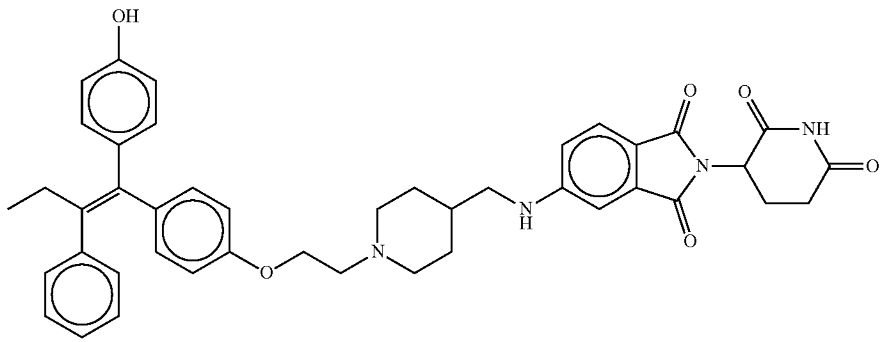 | (Z)-2-(2,6-dioxopiperidin-3-yl)-5-((1-(2-(4-(1-(4-hydroxyphenyl)-2-phenylbut-1-en-1-yl)phenoxy)ethyl)piperidin-4-yl)methyl)amino)isoindoline-1,3-dione |
| 24 | 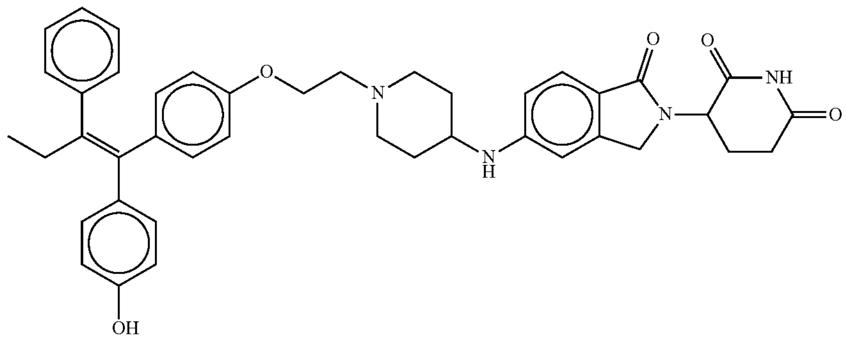 | (Z)-3-(5-((1-(2-(4-(1-(4-hydroxyphenyl)-2-phenylbut-1-en-1-yl)phenoxy)ethyl)piperidin-4-yl)amino)-1-oxoisoindolin-2-yl)piperidine-2,6-dione |

TABLE 1A-continued

Exemplary Compound of the Present Disclosure

| # | Structure | IUPAC Name |
|---|---|---|
| 25 | 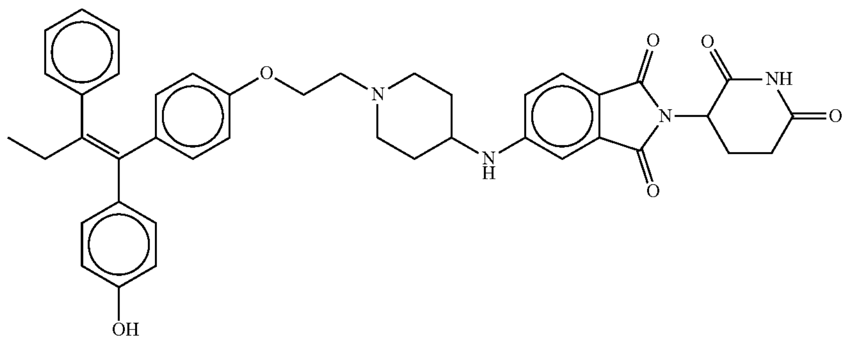 | (Z)-2-(2,6-dioxopiperidin-3-yl)-5-((1-(2-(4-(1-(4-hydroxyphenyl)-2-phenylbut-1-en-1-yl)phenoxy)ethyl)piperidin-4-yl)amino)isoindoline-1,3-dione |
| 26 | 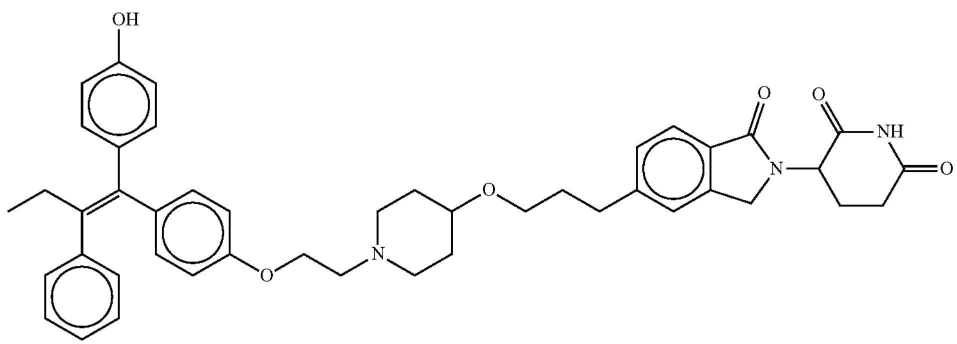 | (Z)-3-(5-(3-((1-(2-(4-(1-(4-hydroxyphenyl)-2-phenylbut-1-en-1-yl)phenoxy)ethyl)piperidin-4-yl)oxy)propyl)-1-oxoisoindolin-2-yl)piperidine-2,6-dione |
| 27 | 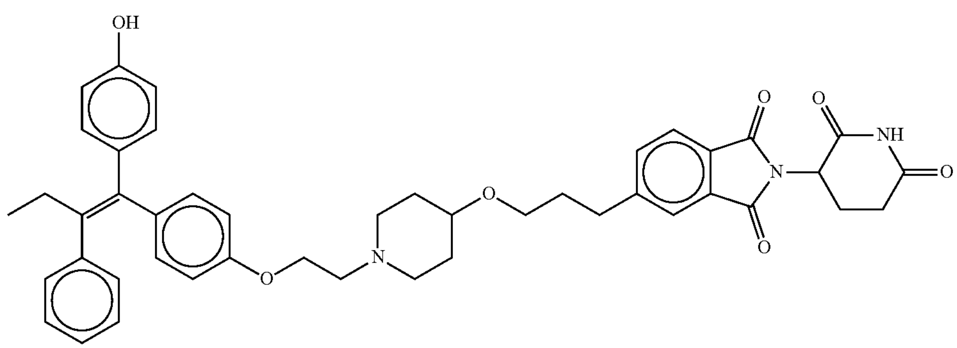 | (Z)-2-(2,6-dioxopiperidin-3-yl)-5-(3-((1-(2-(4-(1-(4-hydroxyphenyl)-2-phenylbut-1-en-1-yl)phenoxy)ethyl)piperidin-4-yl)oxy)propyl)isoindoline-1,3-dione |

TABLE 1A-continued
Exemplary Compound of the Present Disclosure
| # | Structure | IUPAC Name |
|---|---|---|
| 28a | 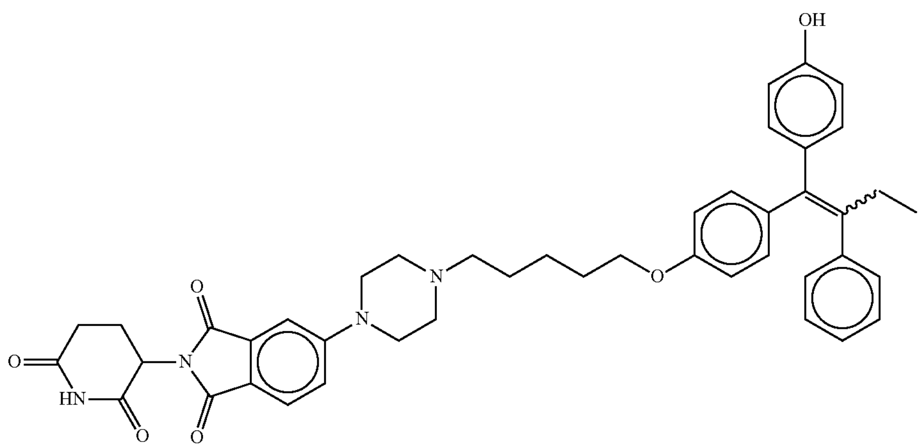 | (E)/(Z)-2-(2,6-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione |
| 28 | 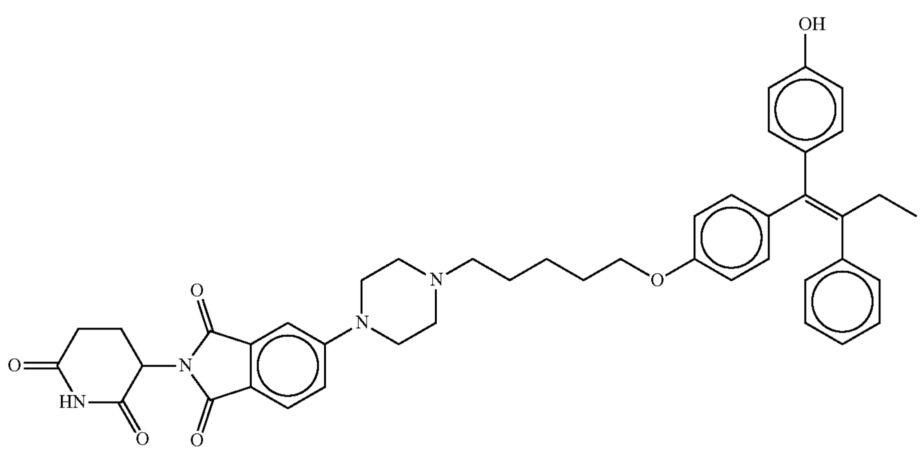 | (Z)-2-(2,6-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione |

TABLE 1A-continued

Exemplary Compound of the Present Disclosure

| # | Structure | IUPAC Name |
|---|---|---|
| 29a | 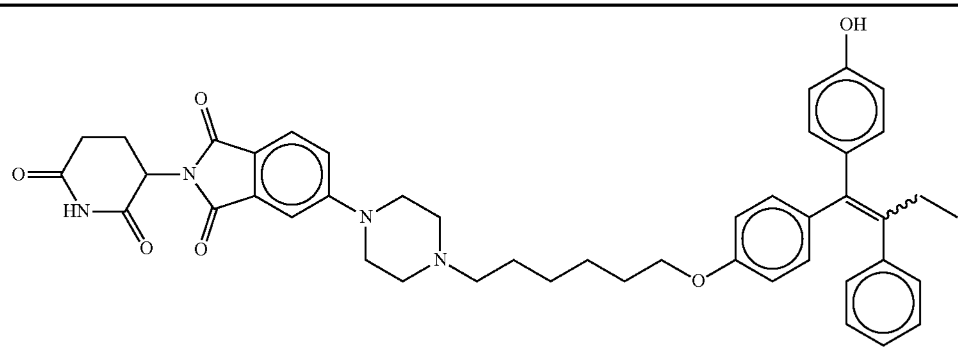 | (E)(Z)-2-(2,6-dioxopiperidin-3-yl)-5-(4-(6-(4-(1-(4-hydroxyphenyl)-2-phenylbut-1-en-1-yl)phenoxy)hexyl)piperazin-1-yl)isoindoline-1,3-dione |
| 29 | 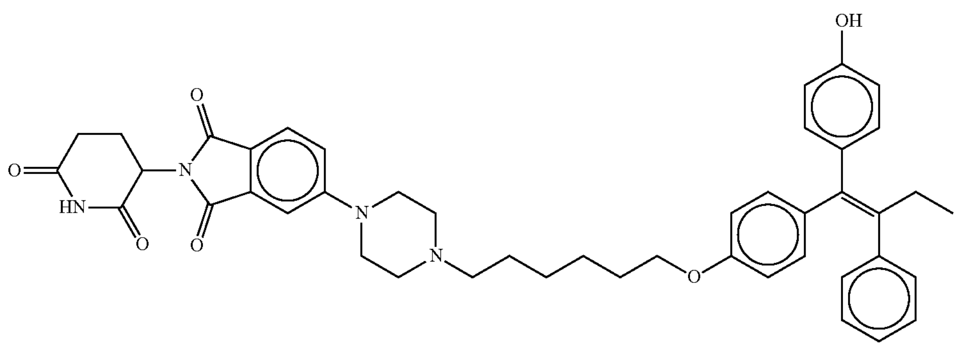 | (Z)-2-(2,6-dioxopiperidin-3-yl)-5-(4-(6-(4-(1-(4-hydroxyphenyl)-2-phenylbut-1-en-1-yl)phenoxy)hexyl)piperazin-1-yl)isoindoline-1,3-dione |
| 30 | 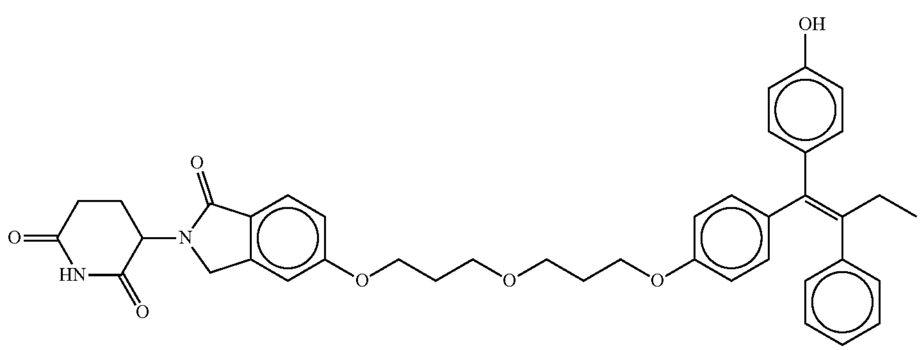 | (Z)-3-(5-(3-(4-(1-(4-hydroxyphenyl)-2-phenylbut-1-en-1-yl)phenoxy)propoxy)-1-oxoisoindolin-2-yl)piperidine-2,6-dione |

TABLE 1A-continued
Exemplary Compound of the Present Disclosure
| # | Structure | IUPAC Name |
|---|---|---|
| 31a | 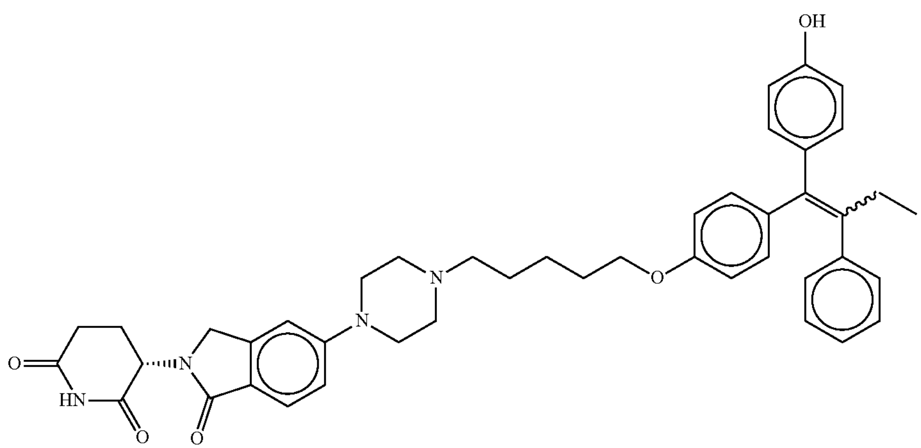 | (E)(Z)-3-(S)-3-(4-(5-(4-(4-(5-(4-1-(4-hydroxyphenyl)-2-phenylbut-1-en-1-yl)phenoxy)pentyl)piperazin-1-yl)-1-oxoisoindolin-2-yl)piperidine-2,6-dione |
| 31 | 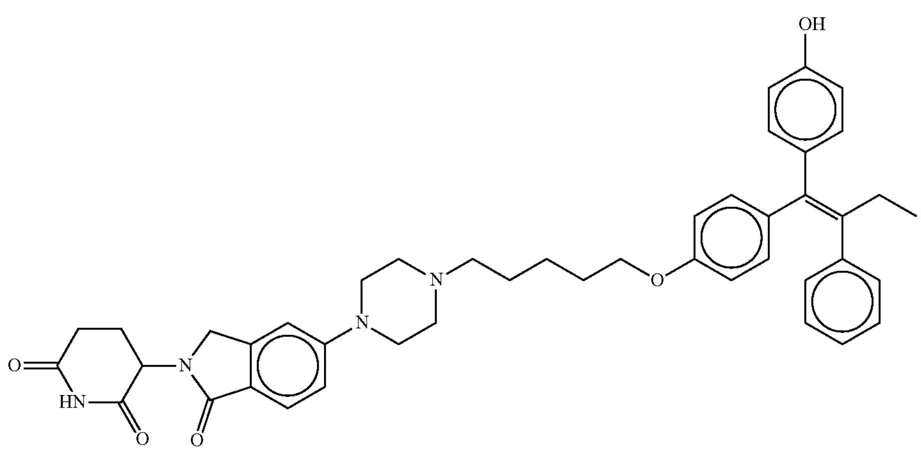 | (Z)-3-(5-(4-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 32a | 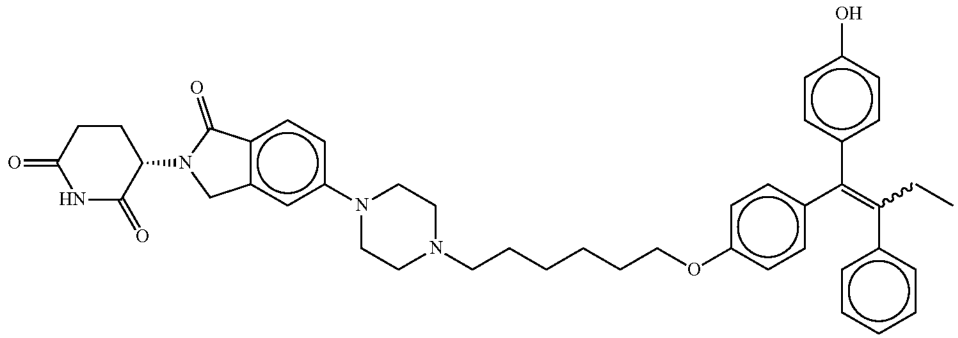 | (E)/(Z)-(S)-3-(5-(4-(6-(4-(1-(4-hydroxyphenyl)-2-phenylbut-1-en-1-yl)phenoxy)hexyl)piperazin-1-yl)-1-oxoisoindolin-2-yl)piperidine-2,6-dione |
| 32 | 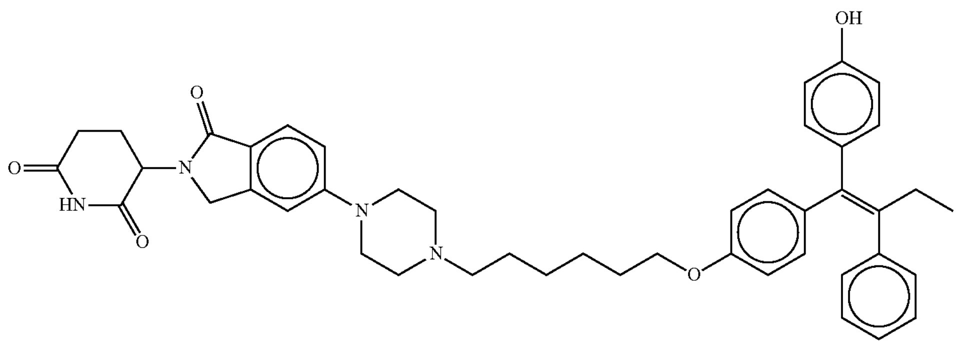 | (Z)-3-(5-(4-(6-(4-(1-(4-hydroxyphenyl)-2-phenylbut-1-en-1-yl)phenoxy)hexyl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 33 | 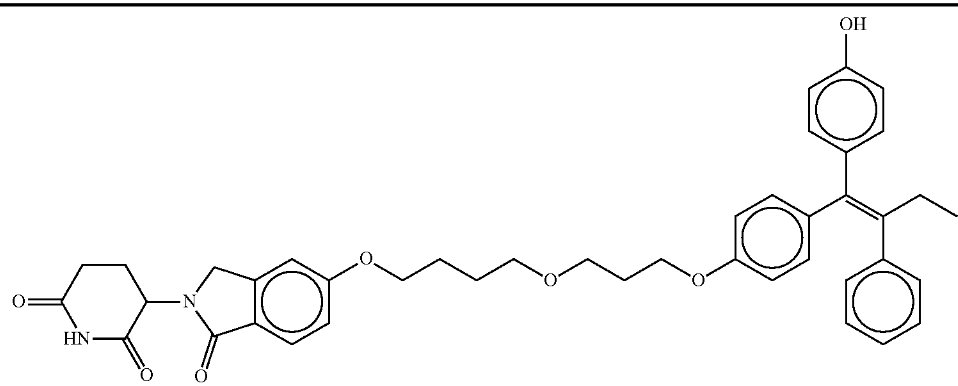 | (Z)-3-(5-(4-(3-(4-(1-(4-hydroxyphenyl)-2-phenylbut-1-en-1-yl)phenoxy)propoxy)butoxy)-1-oxoisoindolin-2-yl)piperidine-2,6-dione |
| 34 | 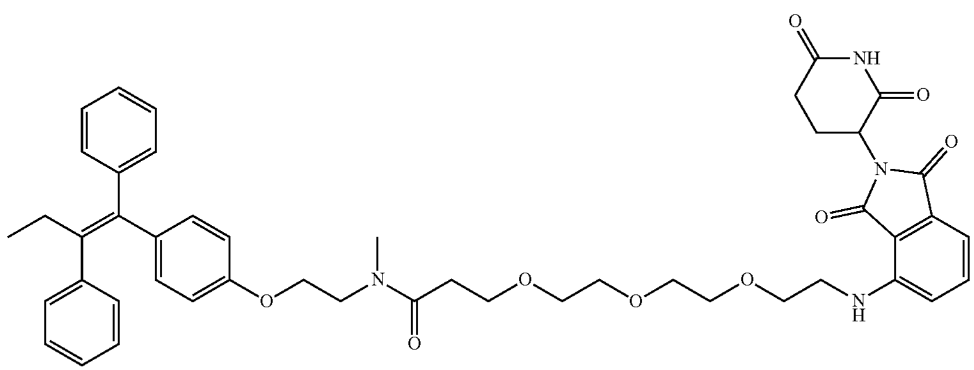 [SMILES: CC/C(=C(\c1ccccc1)c1ccc(OCCN(C)C(=O)CCOCCOCCOCCNc2cccc3c2C(=O)N(C2CCC(=O)NC2=O)C3=O)cc1)c1ccccc1] | (Z)-3-(2-(2-(2-(2-(2,6-dioxopiperidin-3-yl)-1,3-dioxoisoindolin-4-yl)amino)ethoxy)ethoxy)ethoxy)-N-(2-(4-(1,2-diphenylbut-1-en-1-yl)phenoxy)ethyl)-N-methylpropanamide |

TABLE 1A-continued
Exemplary Compound of the Present Disclosure
| # | Structure | IUPAC Name |
|---|---|---|
| 35 | 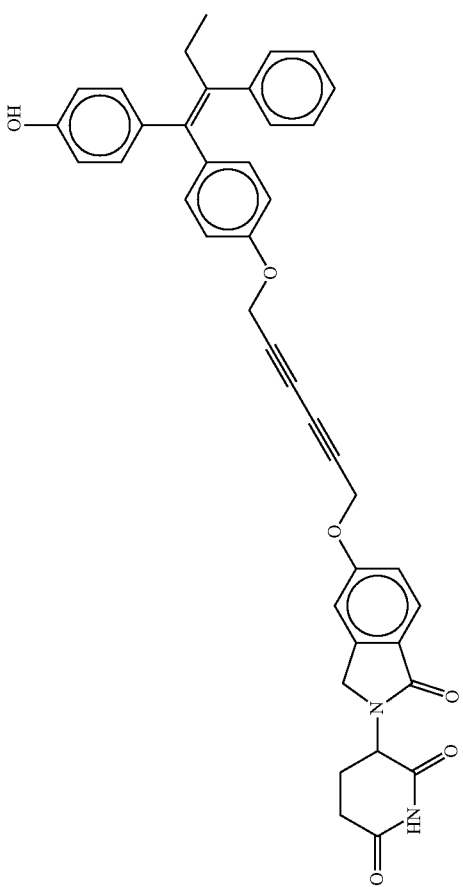 | (Z)-3-(5-((6-(4-(1-(4-hydroxyphenyl)-2-phenylbut-1-en-1-yl)phenoxy)hexa-2,4-diyn-1-yl)oxy)-1-oxoisoindolin-2-yl)piperidine-2,6-dione |
| 36 | 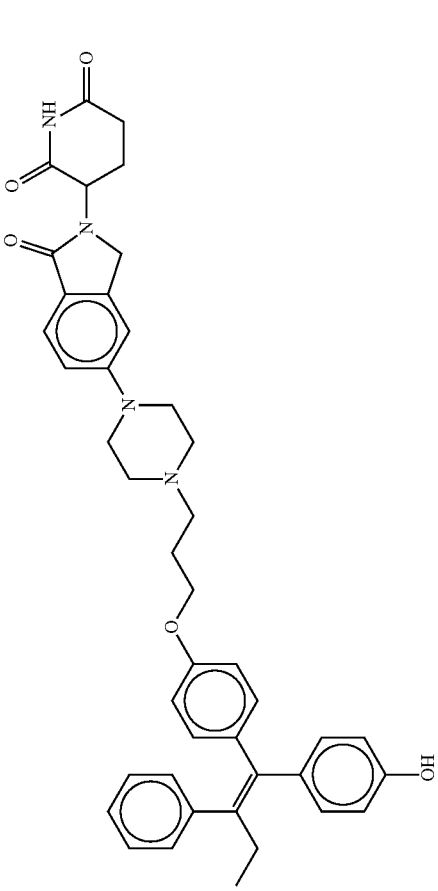 | (Z)-3-(5-(4-(3-(4-(1-(4-hydroxyphenyl)-2-phenylbut-1-en-1-yl)phenoxy)propyl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 37 | 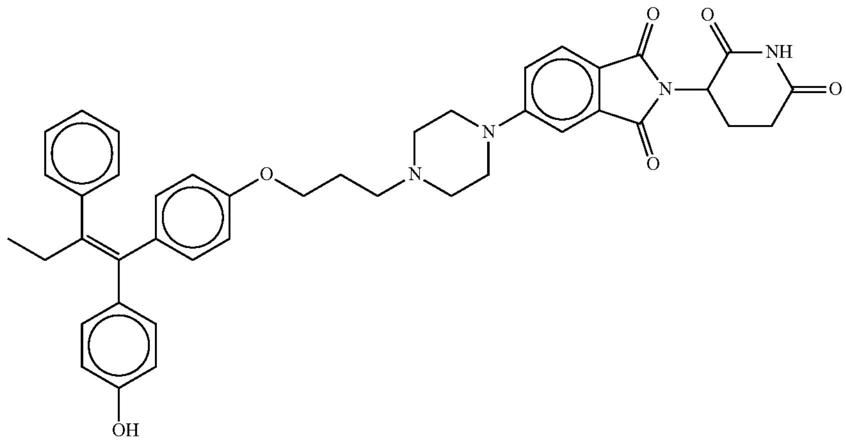 | (Z)-2-(2,6-dioxopiperidin-3-yl)-5-(4-(3-(4-(1-(4-hydroxyphenyl)-2-phenylbut-1-en-1-yl)phenoxy)propyl)piperazin-1-yl)isoindoline-1,3-dione |
| 38 | 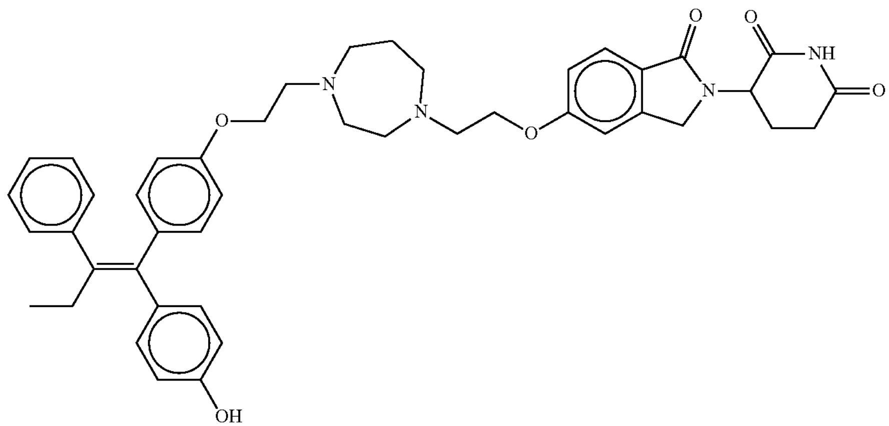 | (Z)-3-(5-(2-(4-(2-(4-(1-(4-hydroxyphenyl)-2-phenylbut-1-en-1-yl)phenoxy)ethyl)-1,4-diazepan-1-yl)ethoxy)-1-oxoisoindolin-2-yl)piperidine-2,6-dione |

TABLE 1A-continued
Exemplary Compound of the Present Disclosure
| # | Structure | IUPAC Name |
|---|---|---|
| 39 | 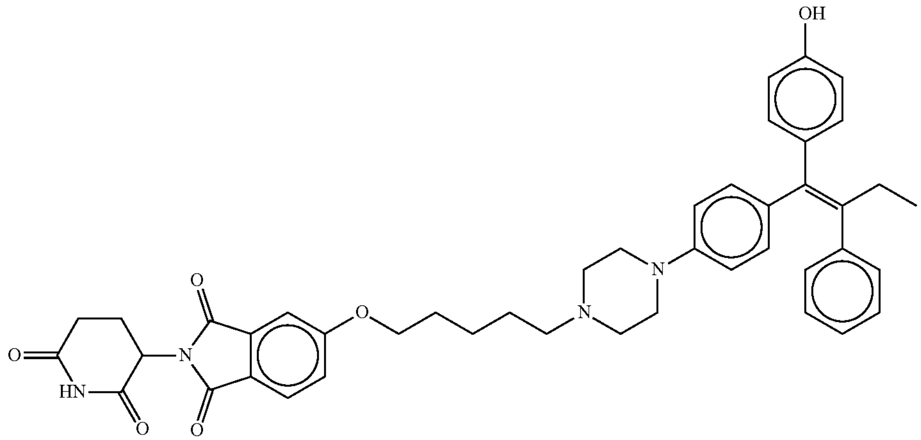 | (E)-2-(2,6-dioxopiperidin-3-yl)-5-((5-(4-(4-(1-(4-hydroxyphenyl)-2-phenylbut-1-en-1-yl)phenyl)piperazin-1-yl)pentyl)oxy)isoindoline-1,3-dione |
| 40 | 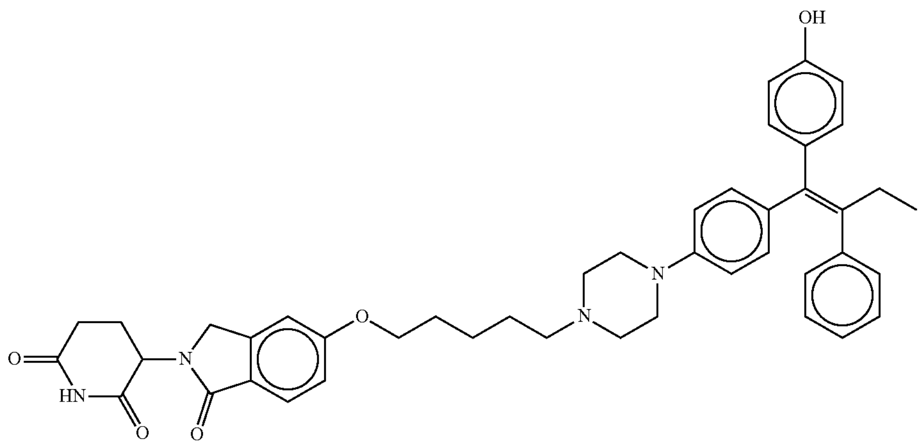 | (E)-3-(5-((5-(4-(4-(1-(4-hydroxyphenyl)-2-phenylbut-1-en-1-yl)phenyl)piperazin-1-yl)pentyl)oxy)-1-oxoisoindolin-2-yl)piperidine-2,6-dione |

TABLE 1A-continued
Exemplary Compound of the Present Disclosure
| # | Structure | IUPAC Name |
|---|---|---|
| 41 | 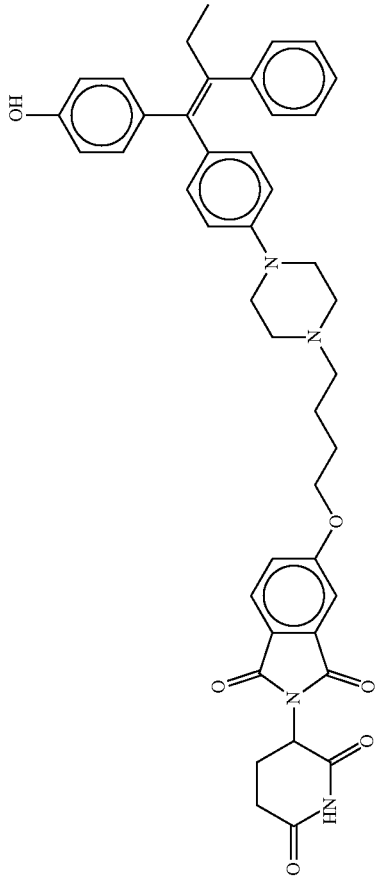 | (E)-2-(2,6-dioxopiperidin-3-yl)-5-(4-(4-(4-(1-(4-hydroxyphenyl)-2-phenylbut-1-en-1-yl)phenyl)piperazin-1-yl)butoxy)isoindoline-1,3-dione |
| 42 | 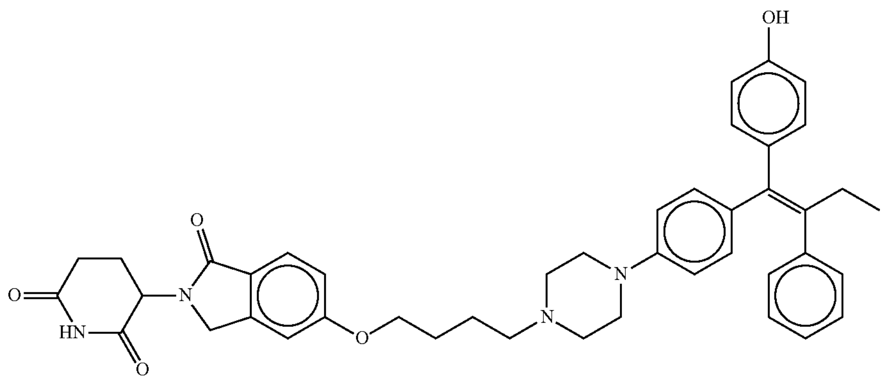 | (E)-3-(5-(4-(4-(4-(1-(4-hydroxyphenyl)-2-phenylbut-1-en-1-yl)phenyl)piperazin-1-yl)butoxy)-1-oxoisoindolin-2-yl)piperidine-2,6-dione |

TABLE 1A-continued
Exemplary Compound of the Present Disclosure
| # | Structure | IUPAC Name |
|---|---|---|
| 43 | 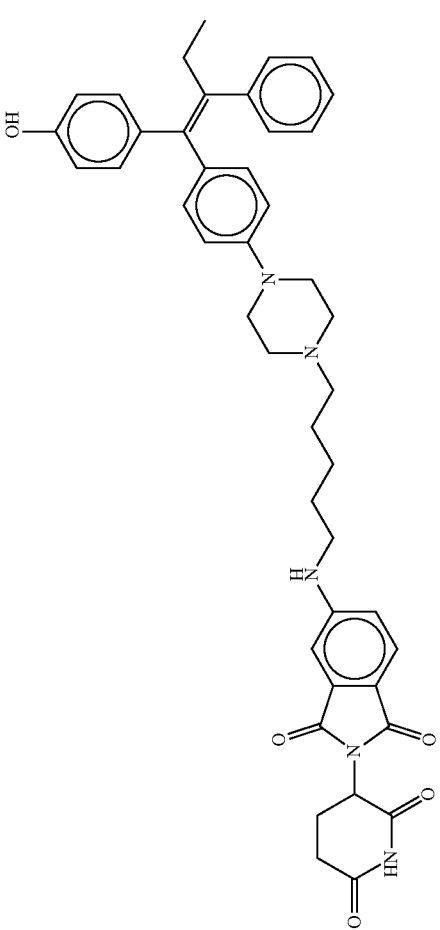 | (E)-2-(2,6-dioxopiperidin-3-yl)-5-((5-(4-(4-(1-(4-hydroxyphenyl)-2-phenylbut-1-en-1-yl)phenyl)piperazin-1-yl)pentyl)amino)isoindoline-1,3-dione |
| 44 | | (E)-2-(2,6-dioxopiperidin-3-yl)-5-((4-(4-(1-(4-hydroxyphenyl)-2-phenylbut-1-en-1-yl)phenyl)piperazin-1-yl)butyl)amino)isoindoline-1,3-dione |

TABLE 1A-continued
Exemplary Compound of the Present Disclosure
| # | Structure | IUPAC Name |
|---|---|---|
| 45 | 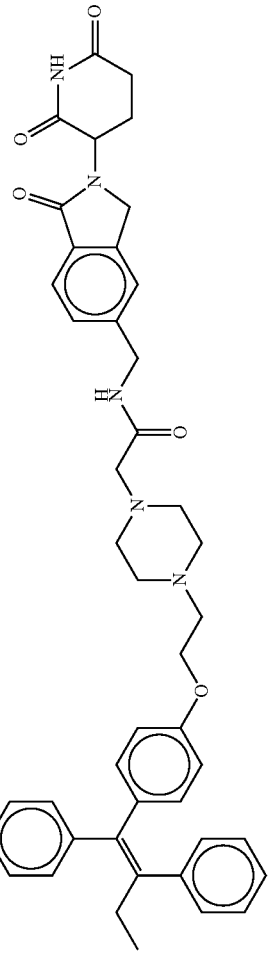 | (Z)-N-((2-(2,6-dioxopiperidin-3-yl)-1-oxoisoindolin-5-yl)methyl)-2-(4-(2-(4-(1-(4-hydroxyphenyl)-2-phenylbut-1-en-1-yl)phenoxy)ethyl)piperazin-1-yl)acetamide |
| 46 | 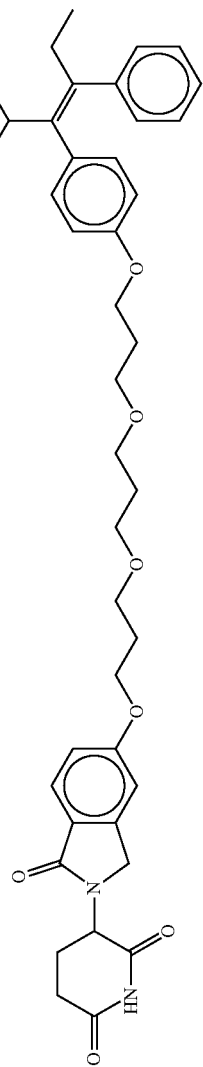 | (Z)-3-(5-(3-(3-(4-(1-(4-hydroxyphenyl)-2-phenylbut-1-en-1-yl)phenoxy)propoxy)propoxy)-1-oxoisoindolin-2-yl)piperidine-2,6-dione |

TABLE 1A-continued
Exemplary Compound of the Present Disclosure
| # | Structure | IUPAC Name |
|---|---|---|
| 47 | 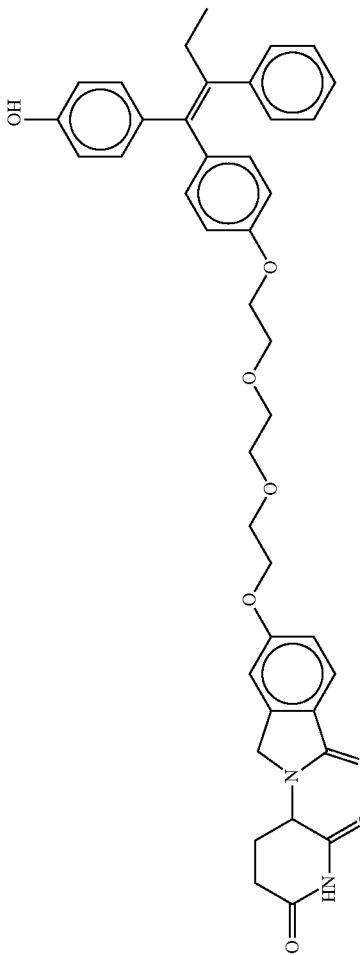 | (Z)-3-(5-(2-(2-(2-(4-(1-(4-hydroxyphenyl)-2-phenylbut-1-en-1-yl)phenoxy)ethoxy)ethoxy)ethoxy)-1-oxoisoindolin-2-yl)piperidine-2,6-dione |
| 48 | 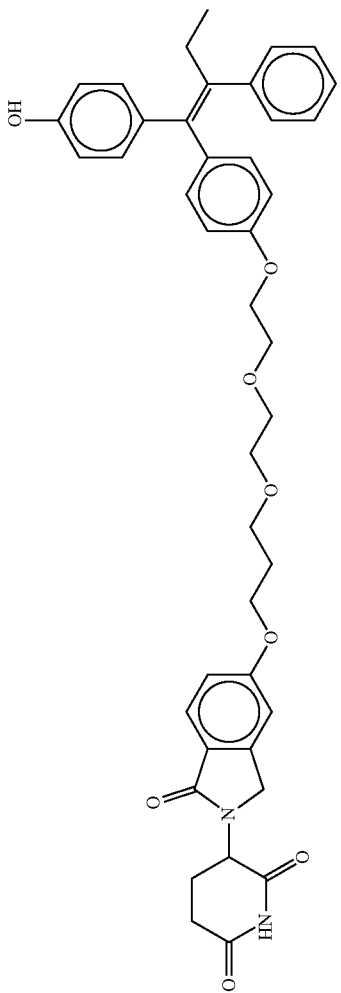 | (Z)-3-(5-(3-(2-(2-(4-(1-(4-hydroxyphenyl)-2-phenylbut-1-en-1-yl)phenoxy)ethoxy)ethoxy)propoxy)-1-oxoisoindolin-2-yl)piperidine-2,6-dione |

TABLE 1A-continued

Exemplary Compound of the Present Disclosure

| # | Structure | IUPAC Name |
|---|---|---|
| 49 | 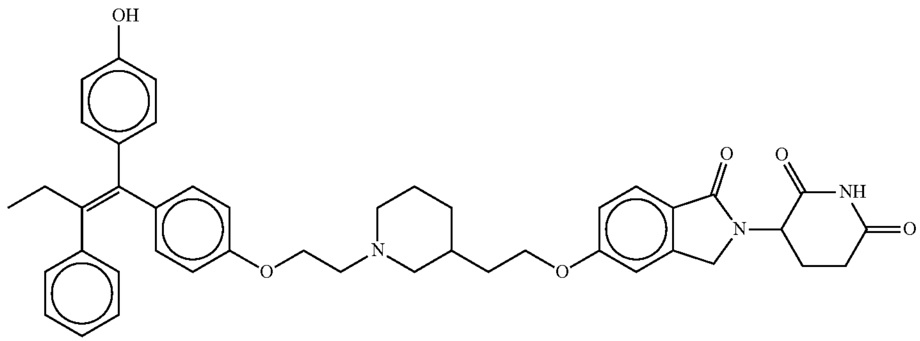 | (Z)-3-(5-(2-(1-(2-(4-(1-(4-hydroxyphenyl)-2-phenylbut-1-en-1-yl)phenoxy)ethyl)piperidin-3-yl)ethoxy)-1-oxoisoindolin-2-yl)piperidine-2,6-dione |
| 50 | 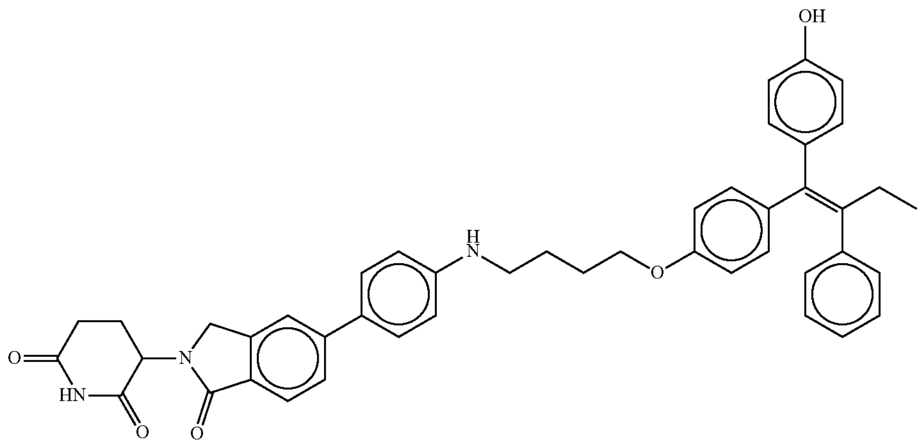 | (Z)-3-(5-((4-(4-(1-(4-hydroxyphenyl)-2-phenylbut-1-en-1-yl)phenoxy)butyl)amino)phenyl)-1-oxoisoindolin-2-yl)piperidine-2,6-dione |

TABLE 1A-continued
Exemplary Compound of the Present Disclosure
| # | Structure | IUPAC Name |
|---|---|---|
| 51 | 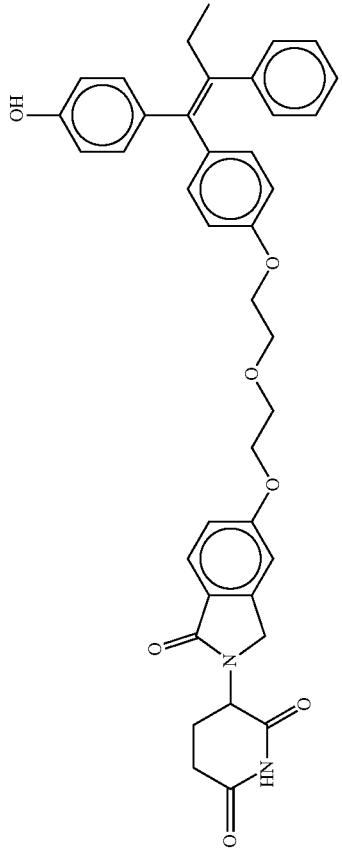 | (Z)-3-(5-(2-(2-(4-(1-(4-hydroxyphenyl)-2-phenylbut-1-en-1-yl)phenoxy)ethoxy)ethoxy)-1-oxoisoindolin-2-yl)piperidine-2,6-dione |
| 52 | 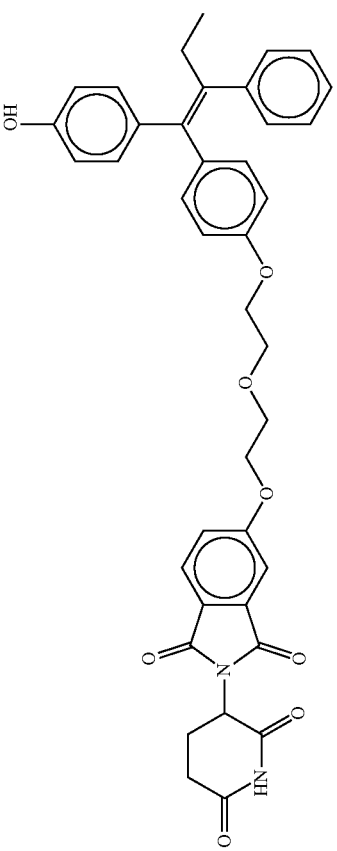 | (Z)-2-(2,6-dioxopiperidin-3-yl)-5-(2-(2-(4-(1-(4-hydroxyphenyl)-2-phenylbut-1-en-1-yl)phenoxy)ethoxy)ethoxy)isoindoline-1,3-dione |

TABLE 1A-continued
Exemplary Compound of the Present Disclosure
| # | Structure | IUPAC Name |
|---|---|---|
| 53 | 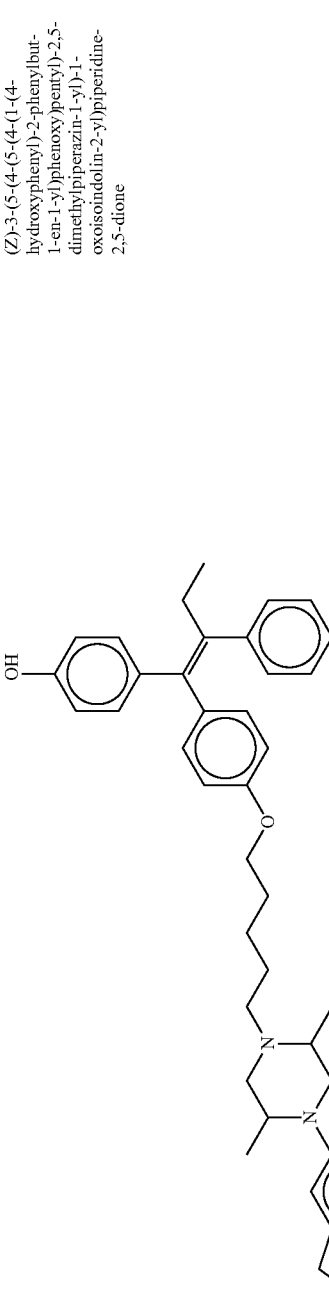 | (Z)-3-(5-(4-(5-(4-(1-(4-hydroxyphenyl)-2-phenylbut-1-en-1-yl)phenoxy)pentyl)-2,5-dimethylpiperazin-1-yl)-1-oxoisoindolin-2-yl)piperidine-2,5-dione |
| 54 | 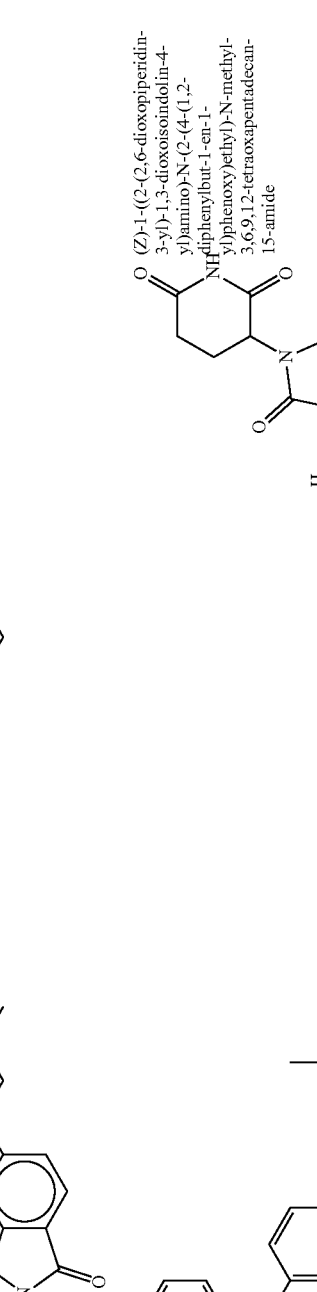 | (Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12-tetraoxapentadecan-15-amide |

TABLE 1A-continued
Exemplary Compound of the Present Disclosure
| # | Structure | IUPAC Name |
|---|---|---|
| 55 | 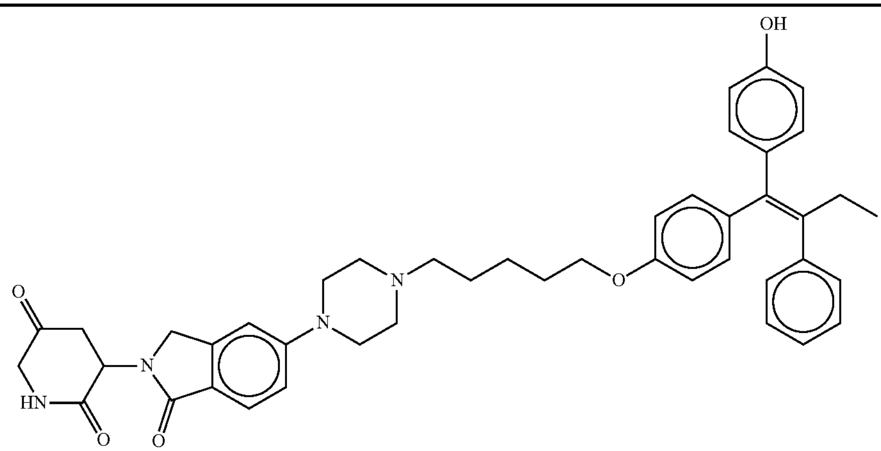 | (Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,5-dione |
| 56 | 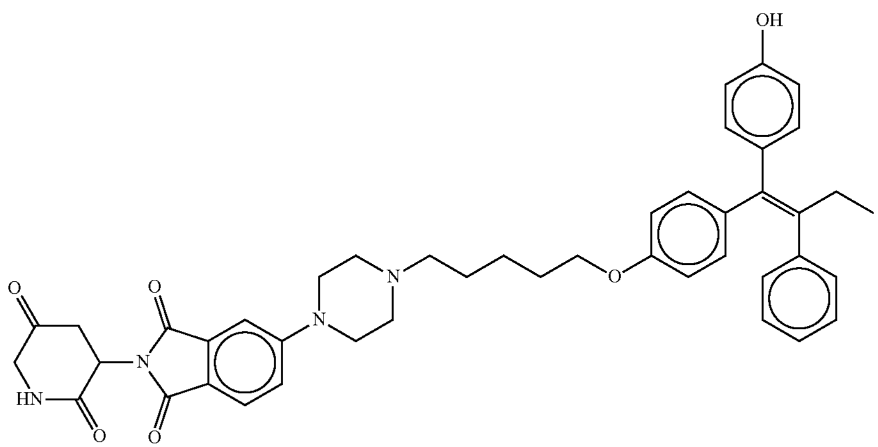 | (Z)-2-(2,5-dioxopiperidin-3-yl)-5-(4-(5-(4-(1-(4-hydroxyphenyl)-2-phenylbut-1-en-1-yl)phenoxy)pentyl)piperazin-1-yl)isoindoline-1,3-dione |

TABLE 1A-continued

Exemplary Compound of the Present Disclosure

| # | Structure | IUPAC Name |
|---|---|---|
| 57 | 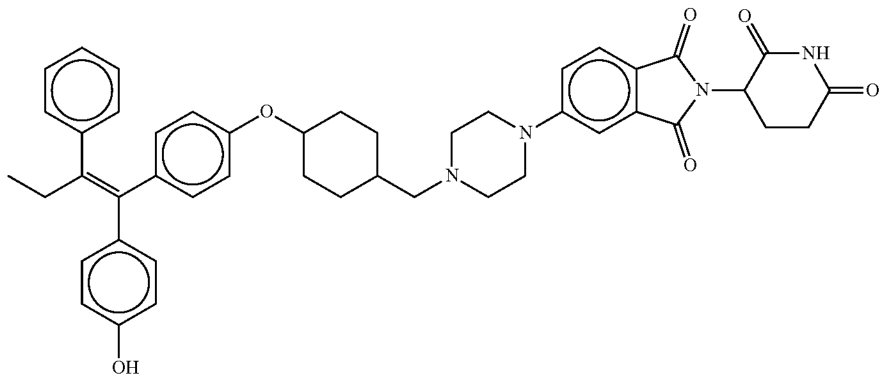 | (Z)-2-(2,6-dioxopiperidin-3-yl)-5-(4-((4-(4-(1-(4-hydroxyphenyl)-2-phenylbut-1-en-1-yl)phenoxy)cyclohexyl)methyl)piperazin-1-yl)isoindoline-1,3-dione |
| 58 | 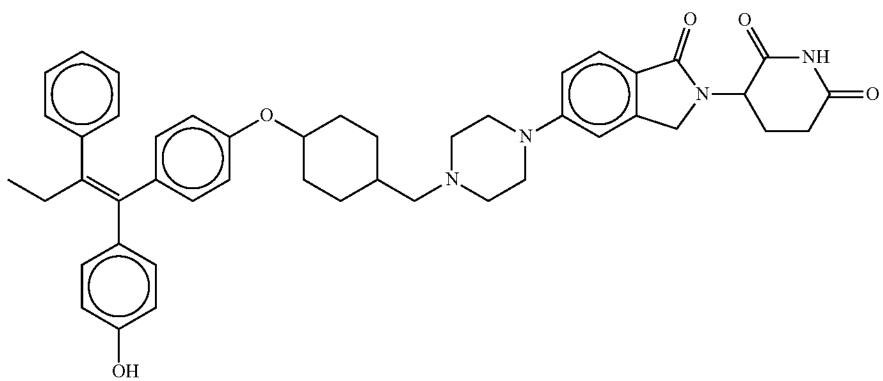 | (Z)-3-(5-(4-((4-(4-(1-(4-hydroxyphenyl)-2-phenylbut-1-en-1-yl)phenoxy)cyclohexyl)methyl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 59 | 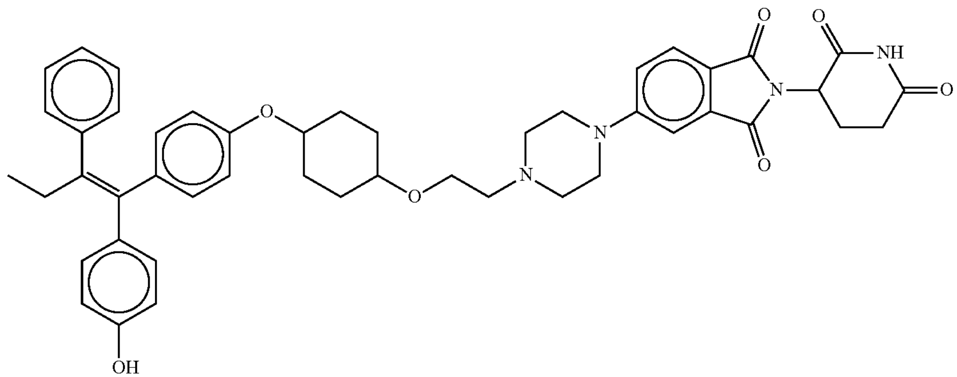 | (Z)-2-(2,6-dioxopiperidin-3-yl)-5-(4-(2-((4-(4-(1-(4-hydroxyphenyl)-2-phenylbut-1-en-1-yl)phenoxy)cyclohexyl)oxy)ethyl)piperazin-1-yl)isoindoline-1,3-dione |
| 60 | 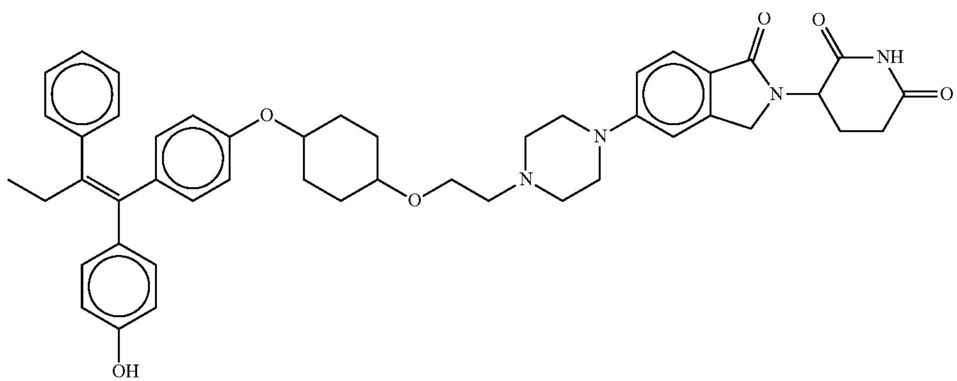 | (Z)-3-(5-(4-(2-((4-(4-(1-(4-hydroxyphenyl)-2-phenylbut-1-en-1-yl)phenoxy)cyclohexyl)oxy)ethyl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 61 | 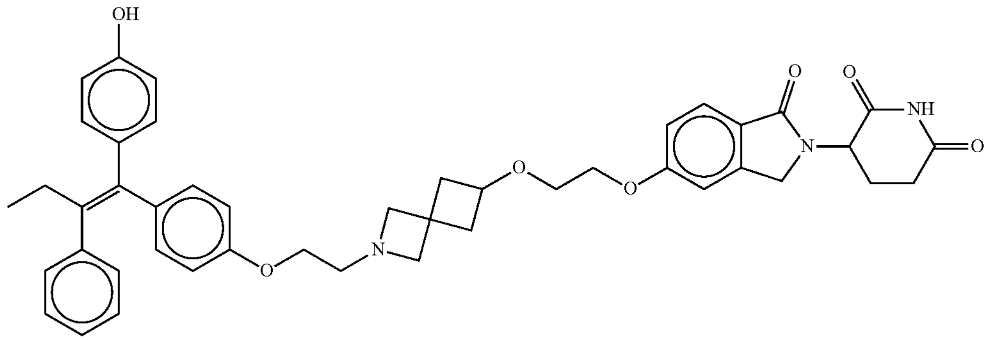 | (Z)-3-(5-(2-((2-(2-(4-(1-(4-hydroxyphenyl)-2-phenylbut-1-en-1-yl)phenoxy)ethyl)-2-azaspiro[3.3]heptan-6-yl)oxy)ethoxy)-1-oxoisoindolin-2-yl)piperidine-2,6-dione |
| 62 | 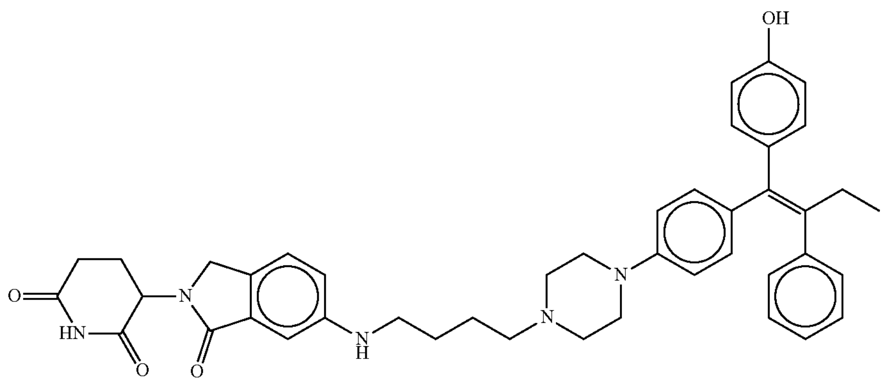 | (E)-3-(6-((4-(4-(1-(4-hydroxyphenyl)-2-phenylbut-1-en-1-yl)phenyl)piperazin-1-yl)butyl)amino)-1-oxoisoindolin-2-yl)piperidine-2,6-dione |

TABLE 1A-continued
Exemplary Compound of the Present Disclosure
| # | Structure | IUPAC Name |
|---|---|---|
| 63 | 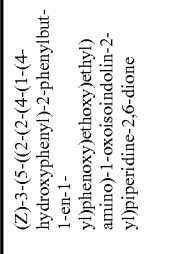 | (Z)-3-(5-((2-(4-(1-(4-hydroxyphenyl)-2-phenylbut-1-en-1-yl)phenoxy)ethoxy)ethyl)amino)-1-oxoisoindolin-2-yl)piperidine-2,6-dione |
| 64 | 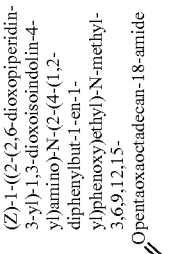 | (Z)-1-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyl-3,6,9,12,15-Opentaoxaoctadecan-18-amide |

TABLE 1A-continued

Exemplary Compound of the Present Disclosure

| # | Structure | IUPAC Name |
|---|---|---|
| 65 | 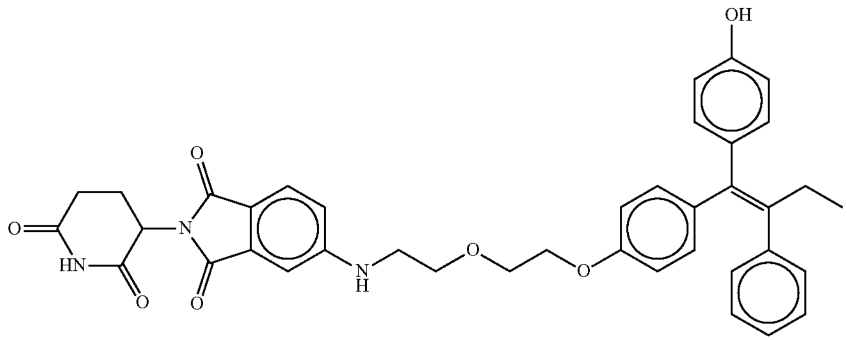 | (Z)-2-(2,6-dioxopiperidin-3-yl)-5-((2-(2-(4-(1-(4-hydroxyphenyl)-2-phenylbut-1-en-1-yl)phenoxy)ethoxy)ethyl)amino)isoindoline-1,3-dione |
| 66 | 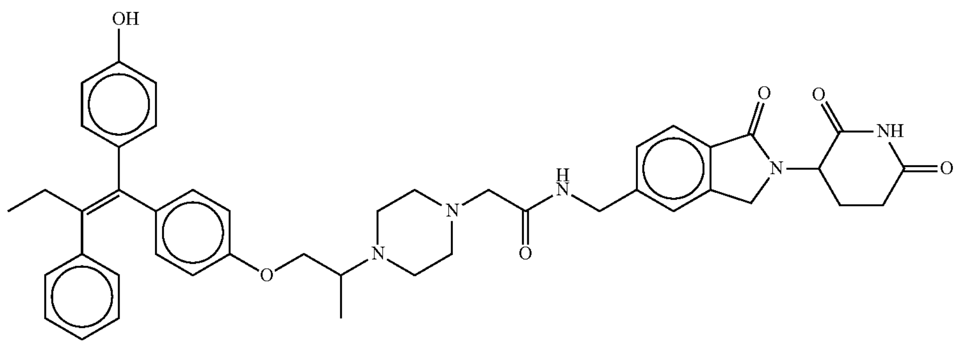 | (Z)-N-(2-(2,6-dioxopiperidin-3-yl)-1-oxoisoindolin-5-yl)methyl)-2-(4-(1-(4-hydroxyphenyl)-2-phenylbut-1-en-1-yl)phenoxy)propan-2-yl)piperazin-1-yl)acetamide |
| 67 | 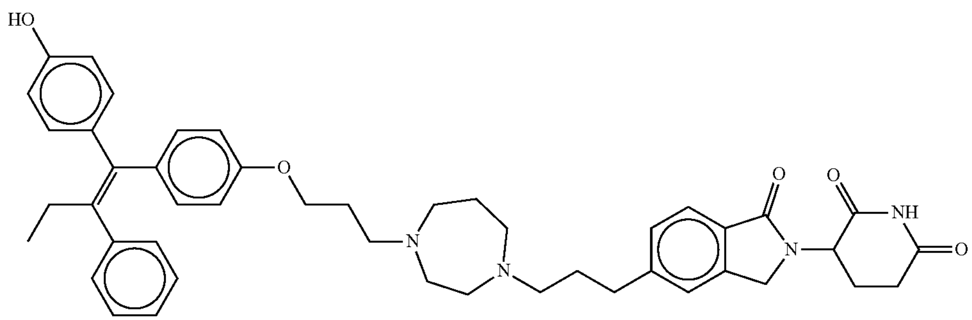 | (Z)-3-(5-(3-(4-(4-(1-(4-hydroxyphenyl)-2-phenylbut-1-en-1-yl)phenoxy)propyl)-1,4-diazepan-1-yl)propyl)-1-oxoisoindolin-2-yl)piperidine-2,6-dione |

TABLE 1A-continued
Exemplary Compound of the Present Disclosure
| # | Structure | IUPAC Name |
|---|---|---|
| 68 | 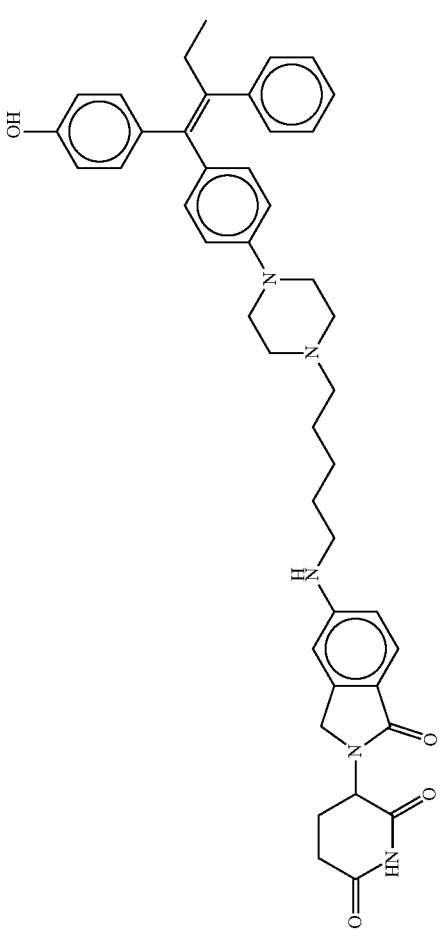 | (E)-3-((5-(4-(4-(1-(4-hydroxyphenyl)-2-phenylbut-1-en-1-yl)phenyl)piperazin-1-yl)pentyl)amino)-1-oxoisoindolin-2-yl)piperidine-2,6-dione |
| 69 | 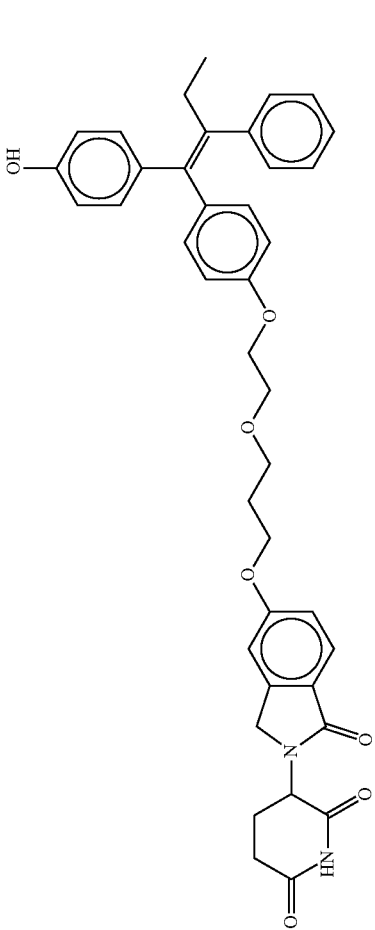 | (Z)-3-(5-(3-(2-(4-(1-(4-hydroxyphenyl)-2-phenylbut-1-en-1-yl)phenoxy)ethoxy)propoxy)-1-oxoisoindolin-2-yl)piperidine-2,6-dione |

TABLE 1A-continued
Exemplary Compound of the Present Disclosure
| # | Structure | IUPAC Name |
|---|---|---|
| 70 | 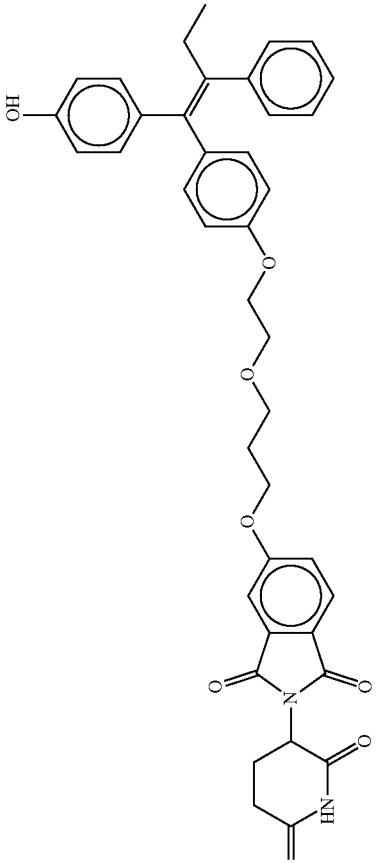 | (Z)-2-(2,6-dioxopiperidin-3-yl)-5-(3-(2-(4-(1-(4-hydroxyphenyl)-2-phenylbut-1-en-1-yl)phenoxy)ethoxy)propoxy)isoindoline-1,3-dione |
| 71 | 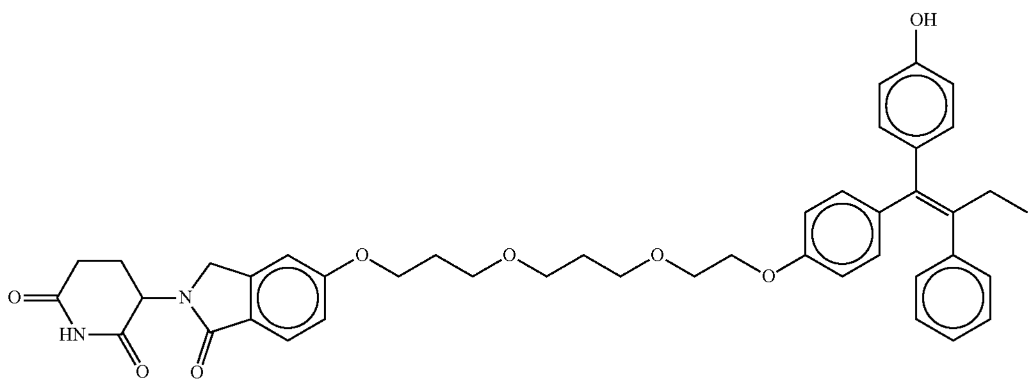 | (Z)-3-(5-(3-(3-(2-(4-(1-(4-hydroxyphenyl)-2-phenylbut-1-en-1-yl)phenoxy)ethoxy)propoxy)propoxy)-1-oxoisoindolin-2-yl)piperidine-2,6-dione |

TABLE 1A-continued

Exemplary Compound of the Present Disclosure

| # | Structure | IUPAC Name |
|---|---|---|
| 72 | 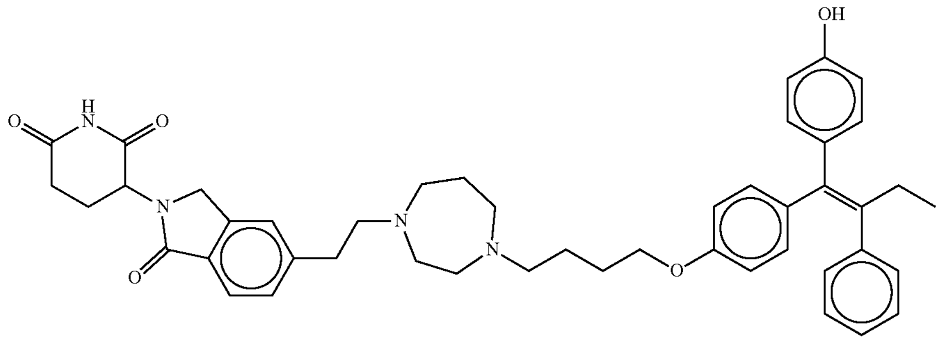 | (Z)-3-(5-(2-(4-(4-(4-(1-(4-hydroxyphenyl)-2-phenylbut-1-en-1-yl)phenoxy)butyl)-1,4-diazepan-1-yl)ethyl)-1-oxoisoindolin-2-yl)piperidine-2,6-dione |
| 73 | 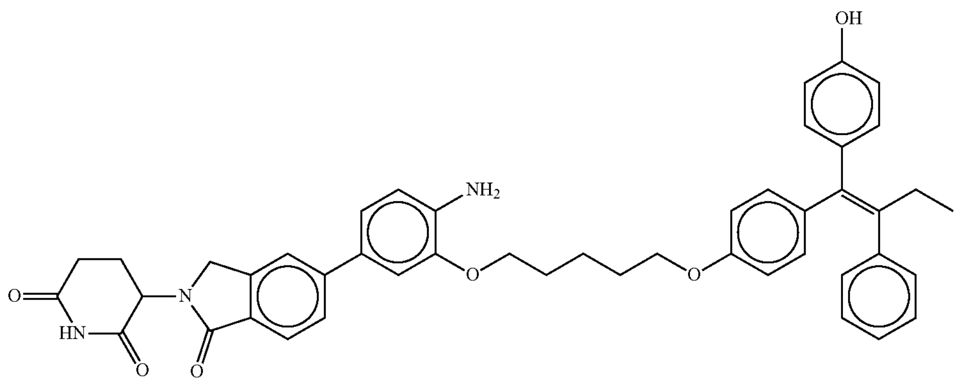 | (Z)-3-(5-(4-amino-3-((5-(4-(1-(4-hydroxyphenyl)-2-phenylbut-1-en-1-yl)phenoxy)pentyl)oxy)phenyl)-1-oxoisoindolin-2-yl)piperidine-2,6-dione |

TABLE 1A-continued
Exemplary Compound of the Present Disclosure
| # | Structure | IUPAC Name |
|---|---|---|
| 74 | 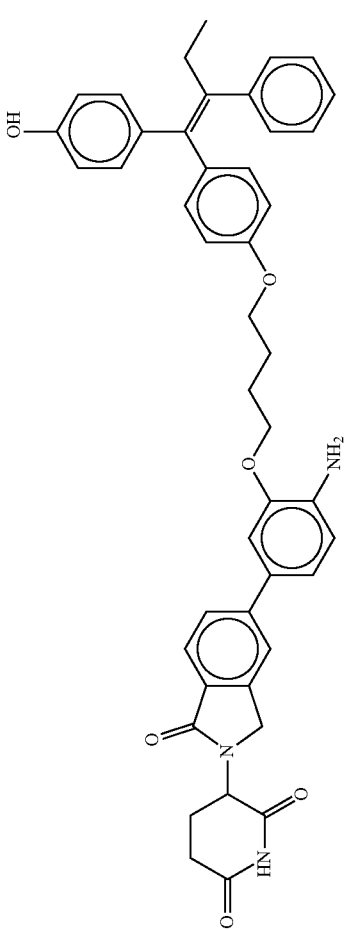 | (Z)-3-(5-(4-amino-3-(4-(4-(1-(4-hydroxyphenyl)-2-phenylbut-1-en-1-yl)phenoxy)butoxy)phenyl)-1-oxoisoindolin-2-yl)piperidine-2,6-dione |
| 75 | 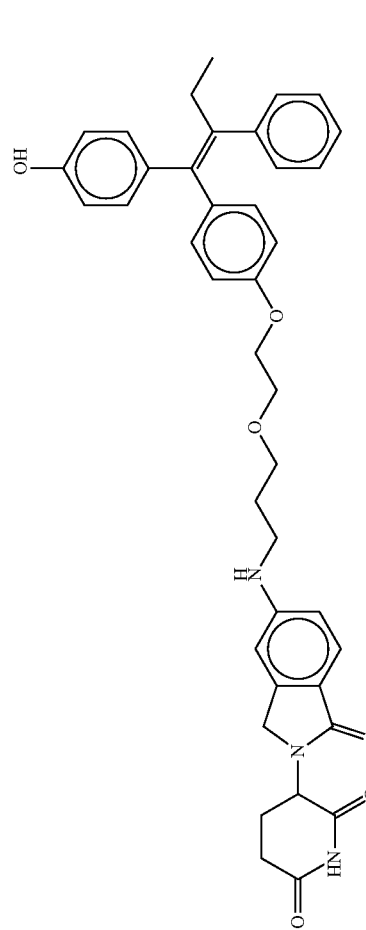 | (Z)-3-(5-((3-(2-(4-(1-(4-hydroxyphenyl)-2-phenylbut-1-en-1-yl)phenoxy)ethoxy)propyl)amino)-1-oxoisoindolin-2-yl)piperidine-2,6-dione |

TABLE 1A-continued
Exemplary Compound of the Present Disclosure
| # | Structure | IUPAC Name |
|---|---|---|
| 76 | 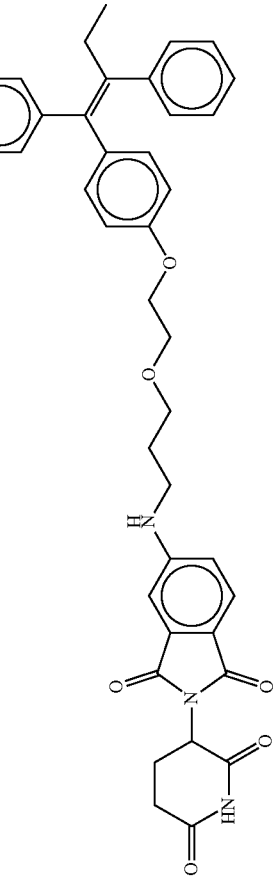 | (Z)-2-(2,6-dioxopiperidin-3-yl)-5-((3-(2-(4-(1-(4-hydroxyphenyl)-2-phenylbut-1-en-1-yl)phenoxy)ethoxy)propyl)amino)isoindoline-1,3-dione |
| 77 | 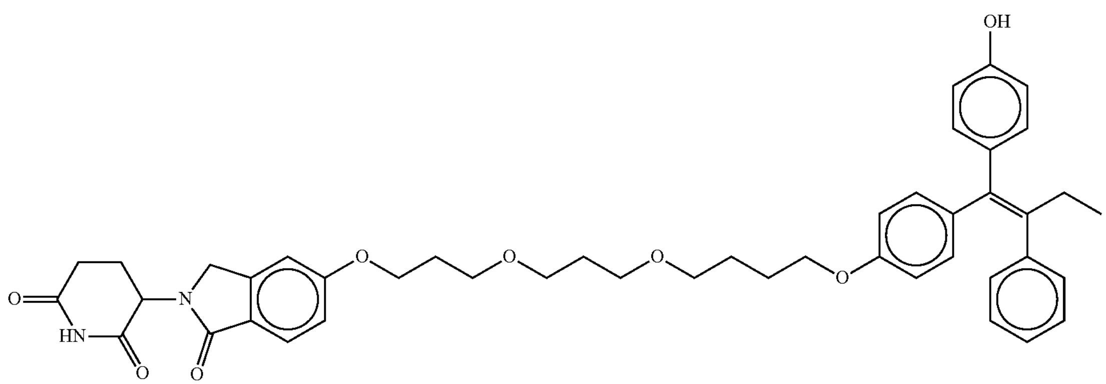 | (Z)-3-(5-(3-(3-(4-(1-(4-hydroxyphenyl)-2-phenylbut-1-en-1-yl)phenoxy)butoxy)propoxy)-1-oxoisoindolin-2-yl)piperidine-2,6-dione |

TABLE 1A-continued
Exemplary Compound of the Present Disclosure
| # | Structure | IUPAC Name |
|---|-----------|------------|
| 78 | 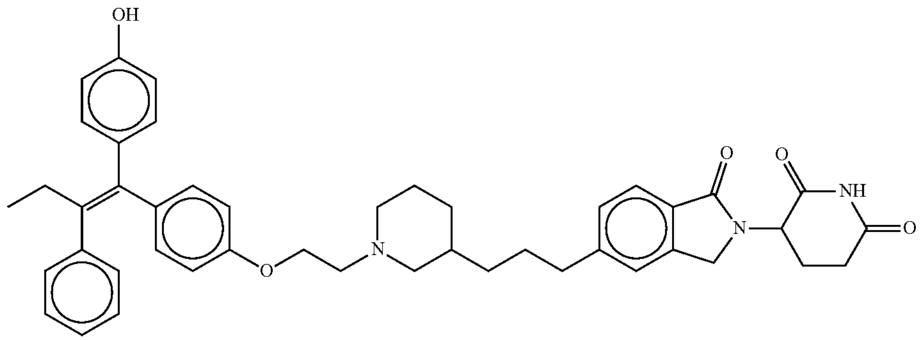 | (Z)-3-(5-(3-(1-(2-(4-(1-(4-hydroxyphenyl)-2-phenylbut-1-en-1-yl)phenoxy)ethyl)piperidin-3-yl)propyl)-1-oxoisoindolin-2-yl)piperidine-2,6-dione |
| 79 | 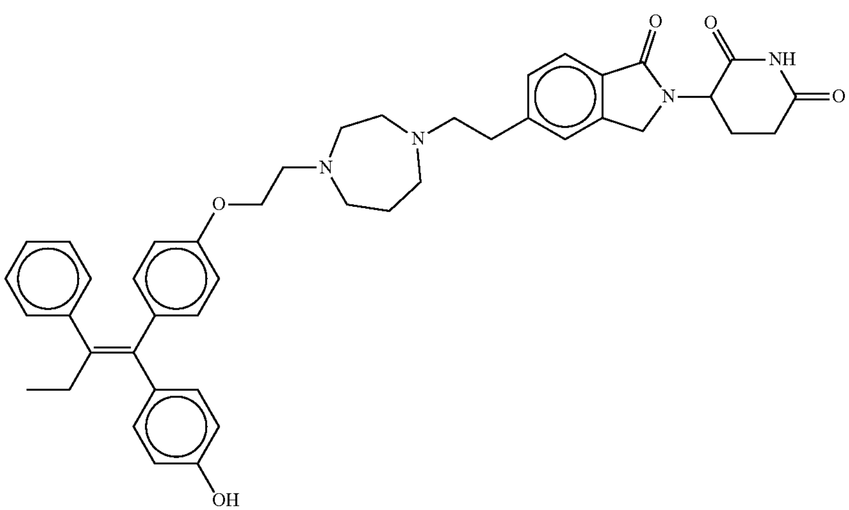 | (Z)-3-(5-(2-(4-(2-(4-(1-(4-hydroxyphenyl)-2-phenylbut-1-en-1-yl)phenoxy)ethyl)-1,4-diazepan-1-yl)ethyl)-1-oxoisoindolin-2-yl)piperidine-2,6-dione |

TABLE 1A-continued

Exemplary Compound of the Present Disclosure

| # | Structure | IUPAC Name |
|---|---|---|
| 80 | 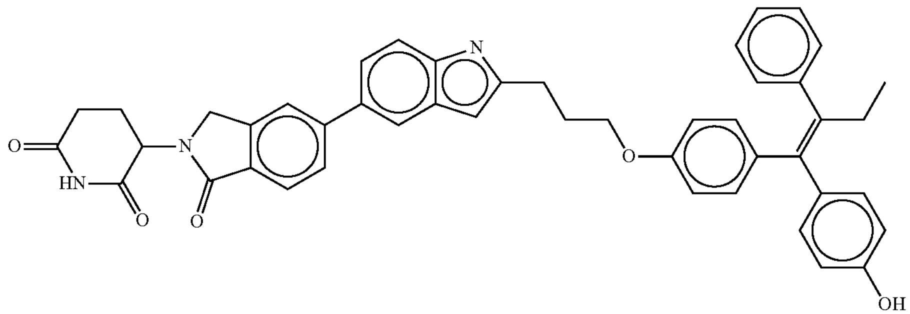 | (Z)-3-(5-(2-(3-(4-(1-(4-hydroxyphenyl)-2-phenylbut-1-en-1-yl)phenoxy)propyl)-1H-indol-5-yl)-1-oxoisoindolin-2-yl)piperidine-2,6-dione |
| 81 | 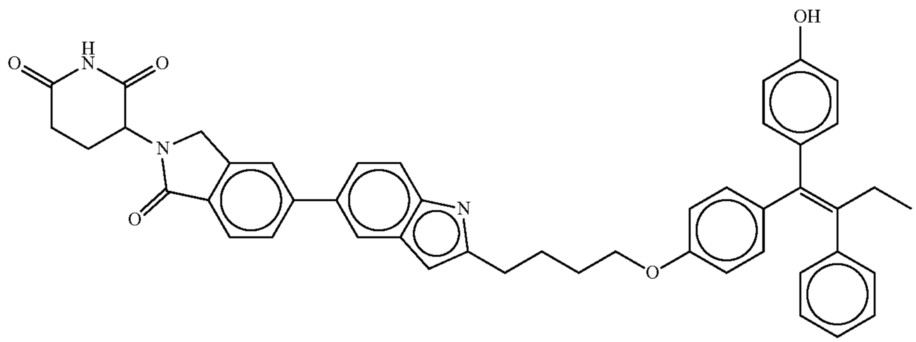 | (Z)-3-(5-(2-(4-(1-(4-hydroxyphenyl)-2-phenylbut-1-en-1-yl)phenoxy)butyl)-1H-indol-5-yl)-1-oxoisoindolin-2-yl)piperidine-2,6-dione |
| 82 | 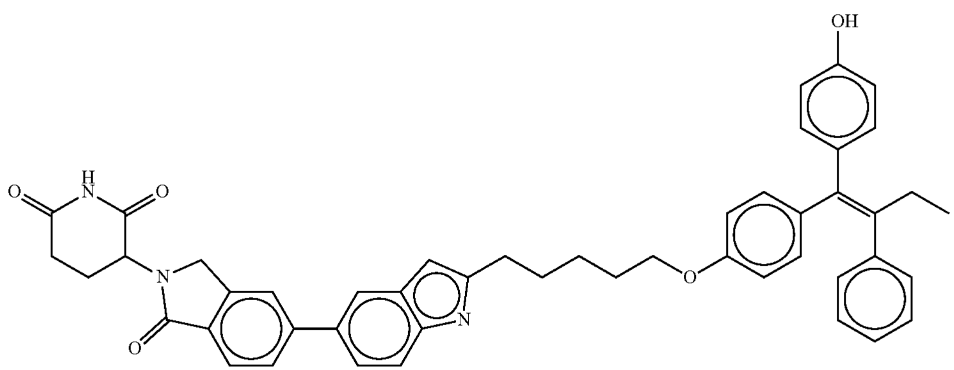 | (Z)-3-(5-(2-(5-(4-(1-(4-hydroxyphenyl)-2-phenylbut-1-en-1-yl)phenoxy)pentyl)-1H-indol-5-yl)-1-oxoisoindolin-2-yl)piperidine-2,6-dione |

TABLE 1A-continued
Exemplary Compound of the Present Disclosure
| # | Structure | IUPAC Name |
|---|---|---|
| 83 | 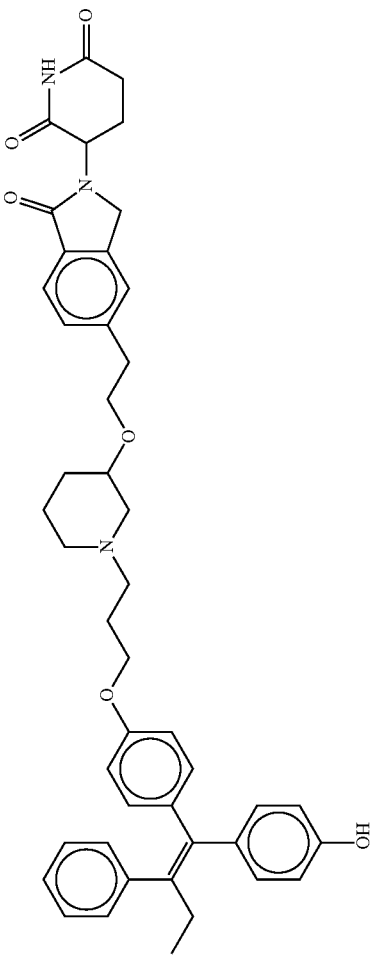 | (Z)-3-(5-(2-((1-(3-(4-(1-(4-hydroxyphenyl)-2-phenylbut-1-en-1-yl)phenoxy)propyl)piperidin-3-yl)oxy)ethyl)-1-oxoisoindolin-2-yl)piperidine-2,6-dione |
| 84 | 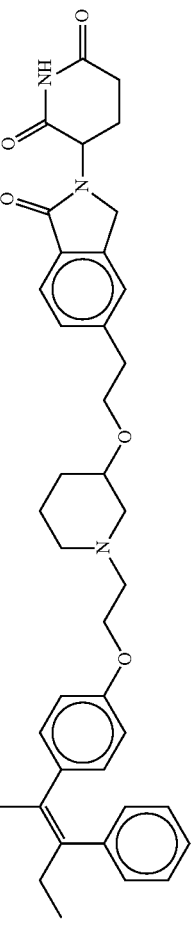 | (Z)-3-(5-(2-((1-(2-(4-(1-(4-hydroxyphenyl)-2-phenylbut-1-en-1-yl)phenoxy)ethyl)piperidin-3-yl)oxy)ethyl)-1-oxoisoindolin-2-yl)piperidine-2,6-dione |

TABLE 1A-continued
Exemplary Compound of the Present Disclosure
| # | Structure | IUPAC Name |
|---|---|---|
| 85 | 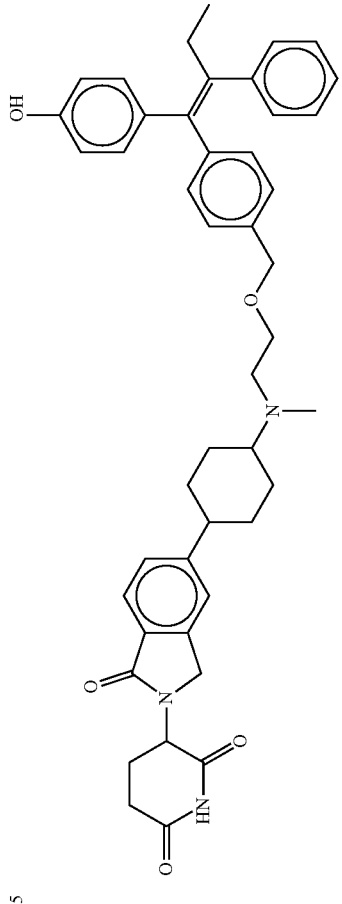 | (E)-3-(5-(4-((2-((4-(1-(4-hydroxyphenyl)-2-phenylbut-1-en-1-yl)benzyl)oxy)ethyl)(methyl)amino)cyclohexyl)-1-oxoisoindolin-2-yl)piperidine-2,6-dione |
| 86 | 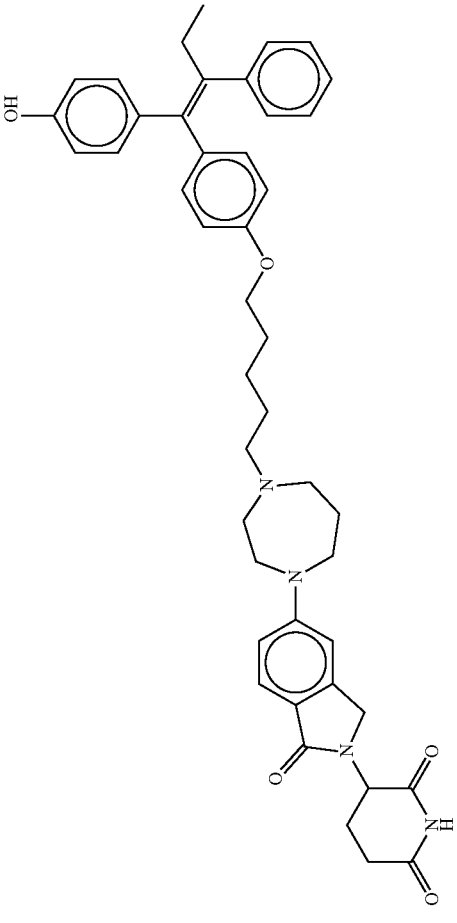 | (Z)-3-(5-(4-(5-(4-(1-(4-hydroxyphenyl)-2-phenylbut-1-en-1-yl)phenoxy)pentyl)-1,4-diazepan-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 87 | 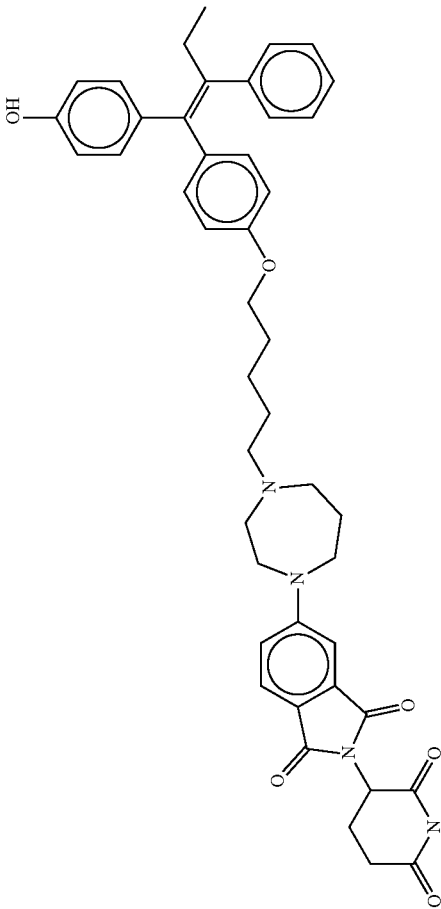 | (Z)-2-(2,6-dioxopiperidin-3-yl)-5-(4-(5-(4-(1-(4-hydroxyphenyl)-2-phenylbut-1-en-1-yl)phenoxy)pentyl)-1,4-diazepan-1-yl)isoindoline-1,3-dione |
| 88 | 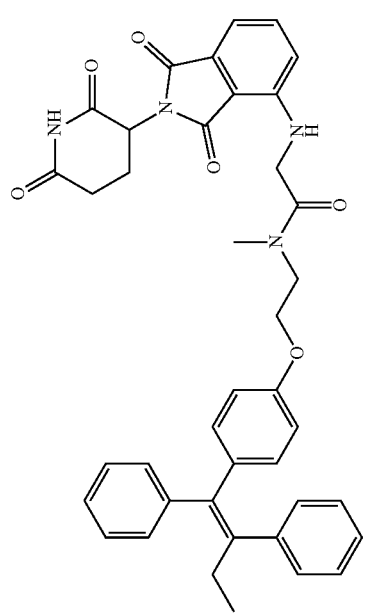 | (Z)-2-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylacetamide |

TABLE 1A-continued
Exemplary Compound of the Present Disclosure
| # | Structure | IUPAC Name |
|---|-----------|------------|
| 89 | 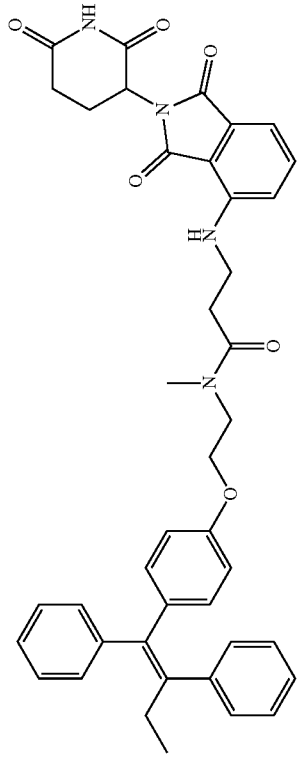 | (Z)-3-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylpropanamide |
| 90 | 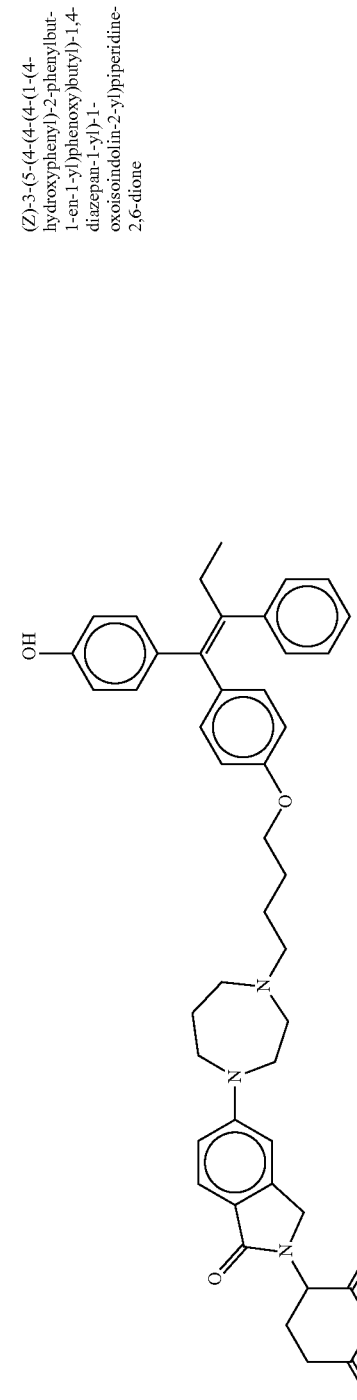 | (Z)-3-(5-(4-(4-(1-(4-hydroxyphenyl)-2-phenylbut-1-en-1-yl)phenoxy)butyl)-1,4-diazepan-1-yl)-1-oxoisoindolin-2-yl)piperidine-2,6-dione |

TABLE 1A-continued

Exemplary Compound of the Present Disclosure

| # | Structure | IUPAC Name |
|---|-----------|------------|
| 91 | 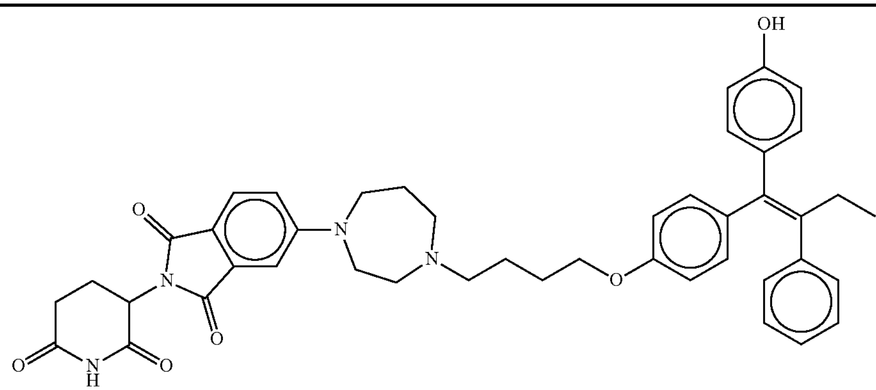 | (Z)-2-(2,6-dioxopiperidin-3-yl)-5-(4-(4-(1-(4-hydroxyphenyl)-2-phenylbut-1-en-1-yl)phenoxy)butyl)-1,4-diazepan-1-yl)isoindoline-1,3-dione |
| 92 | 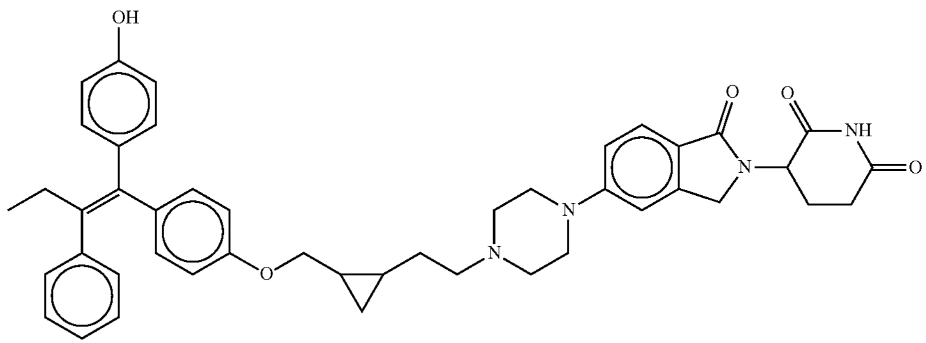 | (Z)-3-(5-(4-(2-(2-((4-(1-(4-hydroxyphenyl)-2-phenylbut-1-en-1-yl)phenoxy)methyl)cyclopropyl)ethyl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 93 | 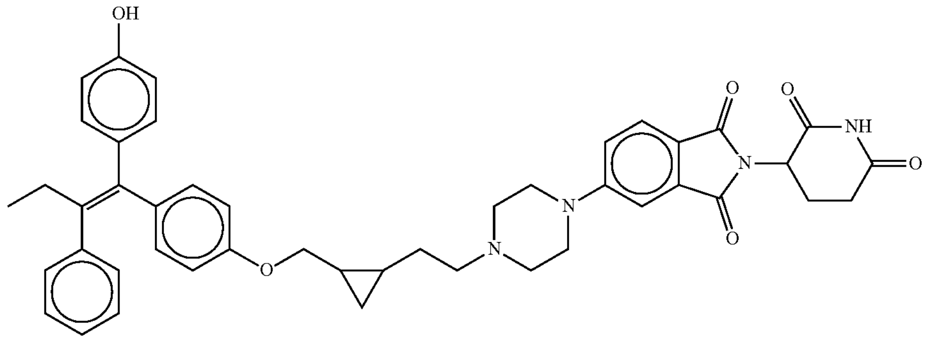 | (Z)-2-(2,6-dioxopiperidin-3-yl)-5-(4-(2-(2-((4-(1-(4-hydroxyphenyl)-2-phenylbut-1-en-1-yl)phenoxy)methyl)cyclopropyl)ethyl)piperazin-1-yl)isoindoline-1,3-dione |
| 94 | 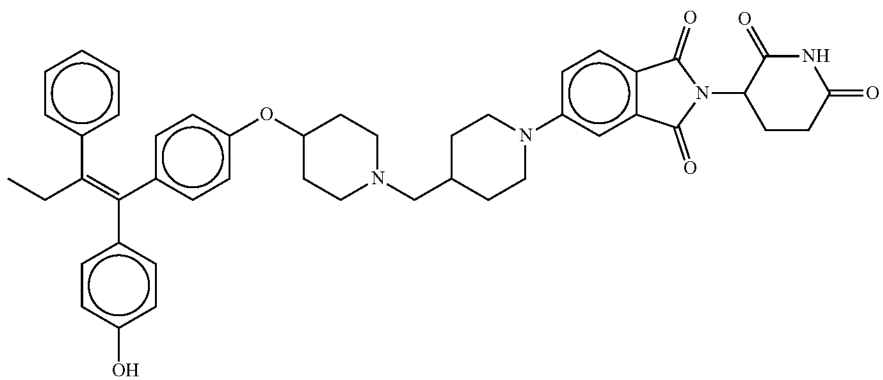 | (Z)-2-(2,6-dioxopiperidin-3-yl)-5-(4-((4-(4-(1-(4-hydroxyphenyl)-2-phenylbut-1-en-1-yl)phenoxy)piperidin-1-yl)methyl)piperidin-1-yl)isoindoline-1,3-dione |

TABLE 1A-continued
Exemplary Compound of the Present Disclosure
| # | Structure | IUPAC Name |
|---|---|---|
| 95 | 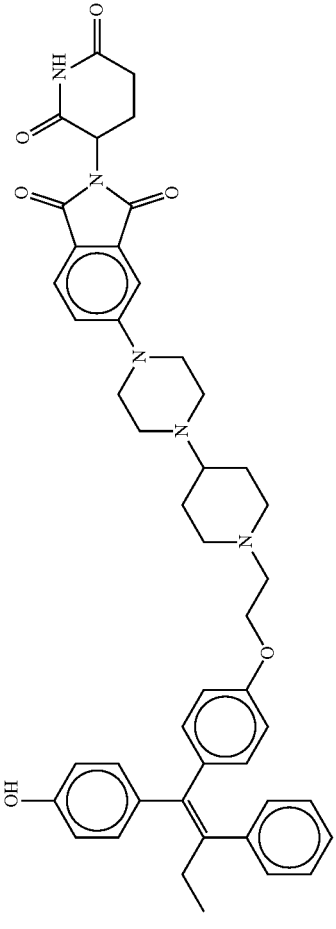 | (Z)-2-(2,6-dioxopiperidin-3-yl)-5-(4-(1-(2-(4-(1-(4-hydroxyphenyl)-2-phenylbut-1-en-1-yl)phenoxy)ethyl)piperidin-4-yl)piperazin-1-yl)isoindoline-1,3-dione |
| 96 | 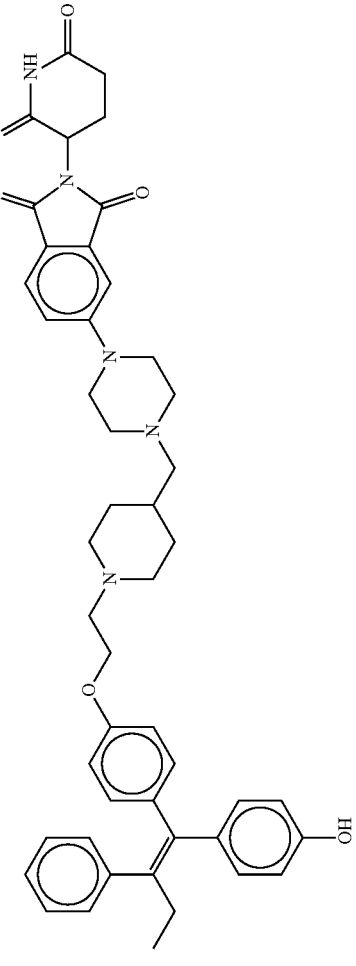 | (Z)-2-(2,6-dioxopiperidin-3-yl)-5-(4-((1-(2-(4-(1-(4-hydroxyphenyl)-2-phenylbut-1-en-1-yl)phenoxy)ethyl)piperidin-4-yl)methyl)piperazin-1-yl)isoindoline-1,3-dione |

TABLE 1A-continued
Exemplary Compound of the Present Disclosure
| # | Structure | IUPAC Name |
|---|---|---|
| 97 | 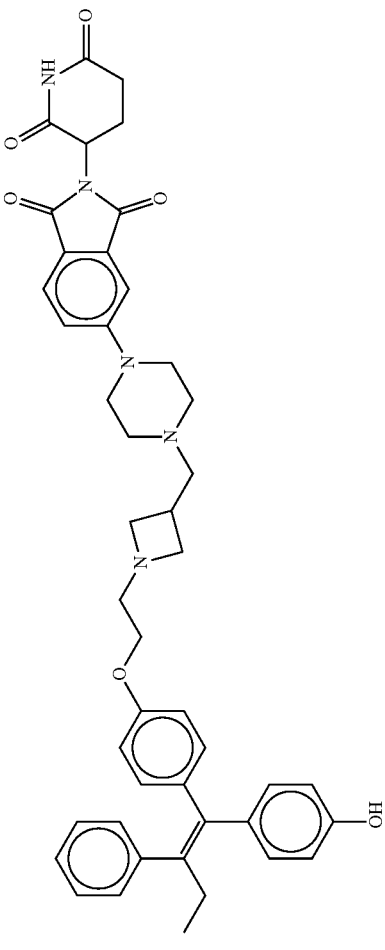 | (Z)-2-(2,6-dioxopiperidin-3-yl)-5-(4-((1-(2-(4-(1-(4-hydroxyphenyl)-2-phenylbut-1-en-1-yl)phenoxy)ethyl)azetidin-3-yl)methyl)piperazin-1-yl)isoindoline-1,3-dione |
| 98 | 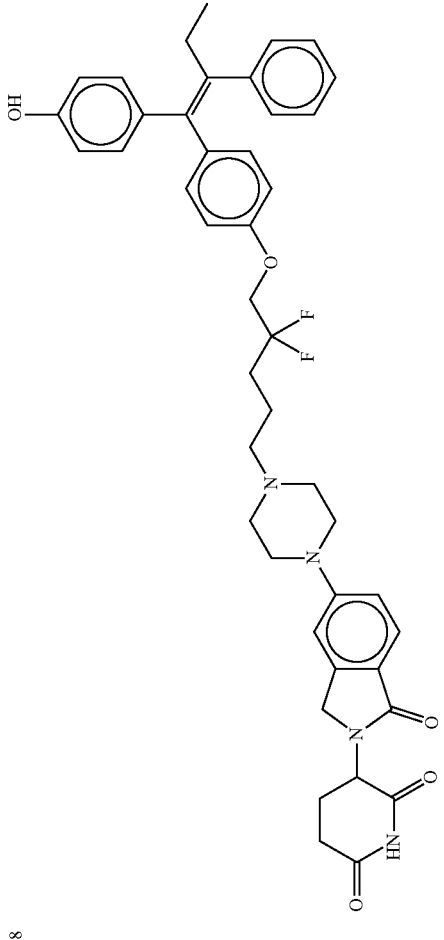 | (Z)-3-(5-(4-(4,4-difluoro-5-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 99 | 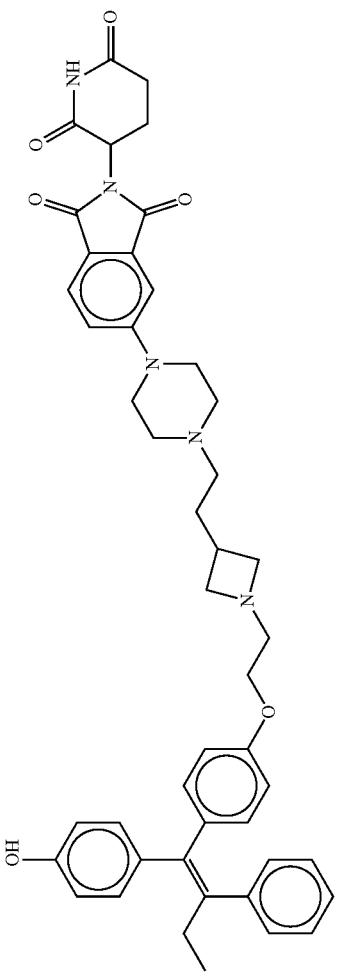 | (Z)-2-(2,6-dioxopiperidin-3-yl)-5-(4-(2-(1-(2-(4-(1-(4-hydroxyphenyl)-2-phenylbut-1-en-1-yl)phenoxy)ethyl)azetidin-3-yl)ethyl)piperazin-1-yl)isoindoline-1,3-dione |
| 100 | 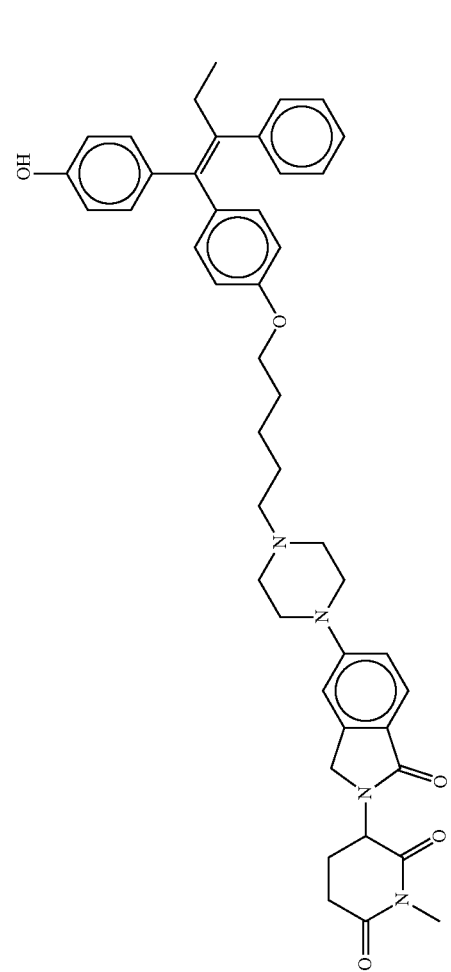 | (Z)-3-(5-(4-(5-(4-(1-(4-hydroxyphenyl)-2-phenylbut-1-en-1-yl)phenoxy)pentyl)piperazin-1-yl)-1-oxoisoindolin-2-yl)-1-methylpiperidine-2,6-dione |

TABLE 1A-continued
Exemplary Compound of the Present Disclosure
| # | Structure | IUPAC Name |
|---|---|---|
| 101 | 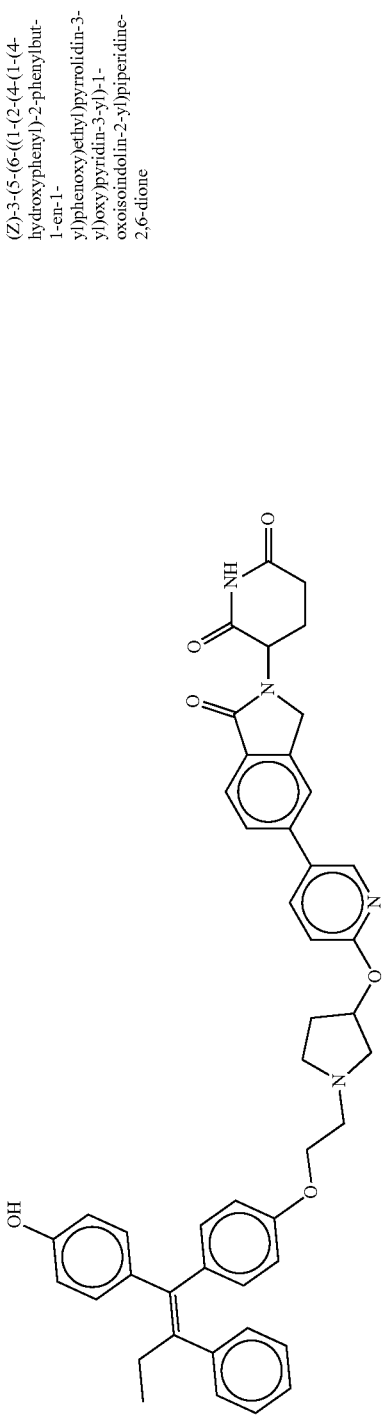 | (Z)-3-(5-(6-((1-(2-(4-(1-(4-hydroxyphenyl)-2-phenylbut-1-en-1-yl)phenoxy)ethyl)pyrrolidin-3-yl)oxy)pyridin-3-yl)-1-oxoisoindolin-2-yl)piperidine-2,6-dione |
| 102 | 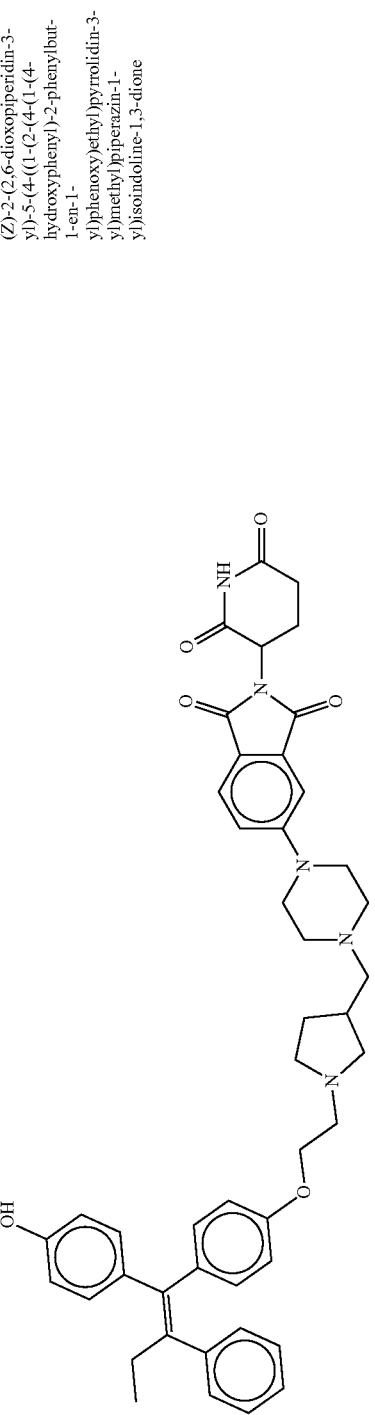 | (Z)-2-(2,6-dioxopiperidin-3-yl)-5-(4-((1-(2-(4-(1-(4-hydroxyphenyl)-2-phenylbut-1-en-1-yl)phenoxy)ethyl)pyrrolidin-3-yl)methyl)piperazin-1-yl)isoindoline-1,3-dione |

TABLE 1A-continued

Exemplary Compound of the Present Disclosure

| # | Structure | IUPAC Name |
|---|---|---|
| 103 | 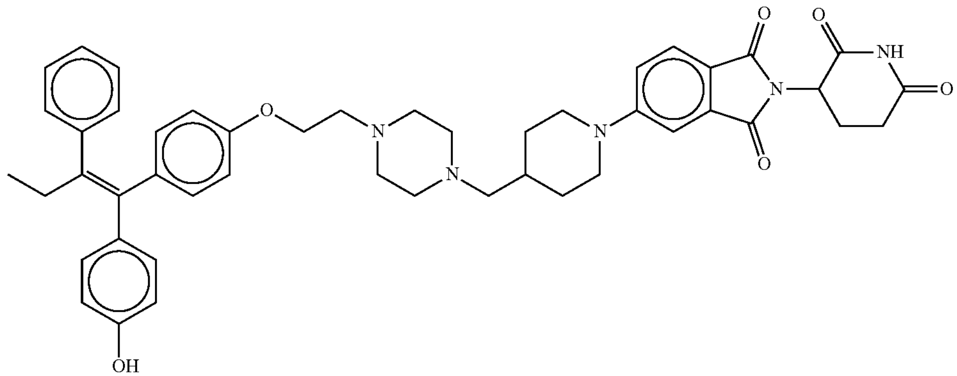 | (Z)-2-(2,6-dioxopiperidin-3-yl)-5-(4-((4-(2-(4-(1-(4-hydroxyphenyl)-2-phenylbut-1-en-1-yl)phenoxy)ethyl)piperazin-1-yl)methyl)piperidin-1-yl)isoindoline-1,3-dione |
| 104 | 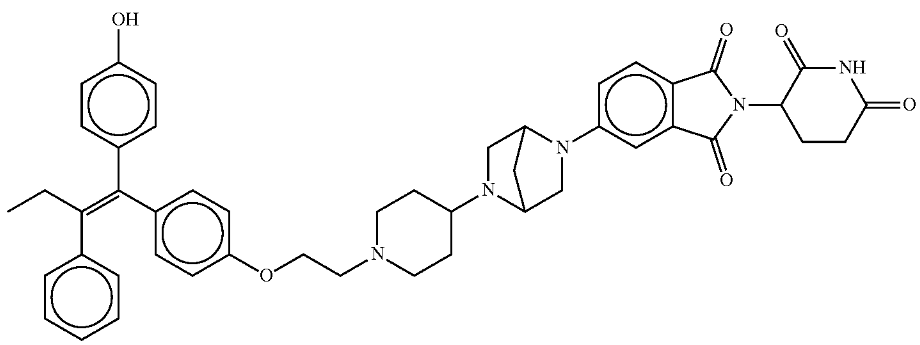 | (Z)-2-(2,6-dioxopiperidin-3-yl)-5-(1-(2-(4-(1-(4-hydroxyphenyl)-2-phenylbut-1-en-1-yl)phenoxy)ethyl)piperidin-4-yl)-2,5-diazabicyclo[2.2.1]heptan-2-yl)isoindoline-1,3-dione |

TABLE 1A-continued
Exemplary Compound of the Present Disclosure
| # | Structure | IUPAC Name |
|---|---|---|
| 105 | 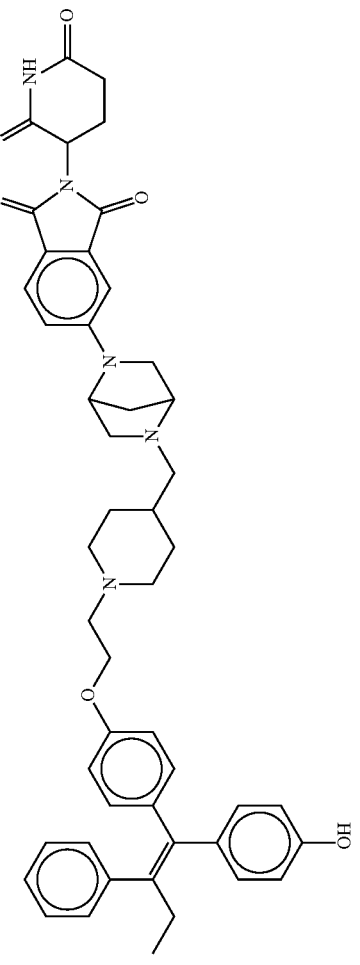 | (Z)-2-(2,6-dioxopiperidin-3-yl)-5-((1-(2-(4-(1-(4-hydroxyphenyl)-2-phenylbut-1-en-1-yl)phenoxy)ethyl)piperidin-4-yl)methyl)-2,5-diazabicyclo[2.2.1]heptan-2-yl)isoindoline-1,3-dione |
| 106 | 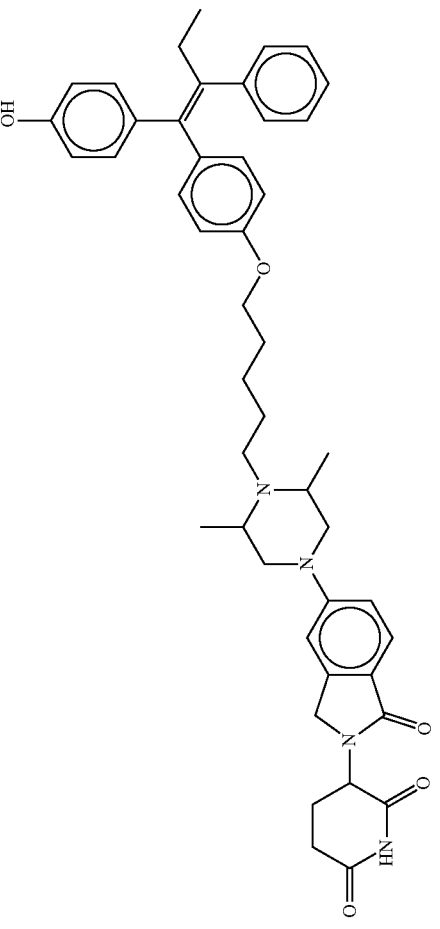 | (Z)-3-(5-(4-(5-(4-(1-(4-hydroxyphenyl)-2-phenylbut-1-en-1-yl)phenoxy)pentyl)-3,5-dimethylpiperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 107 | 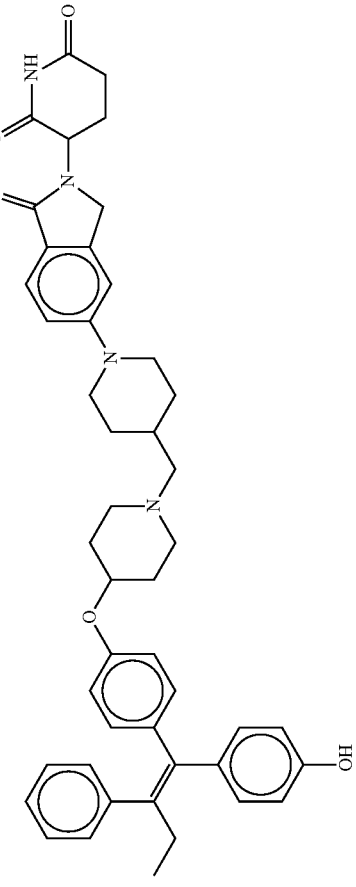 | (Z)-3-(5-(4-((4-(4-(1-(4-hydroxyphenyl)-2-phenylbut-1-en-1-yl)phenoxy)piperidin-1-yl)methyl)piperidin-1-yl)-1-oxoisoindolin-2-yl)piperidine-2,6-dione |
| 108 | 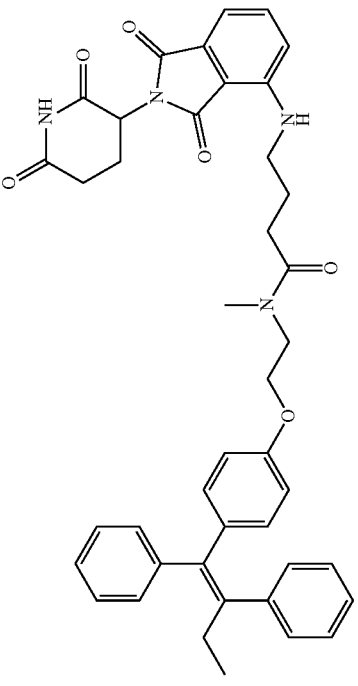 | (Z)-4-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylbutanamide |

TABLE 1A-continued
Exemplary Compound of the Present Disclosure
| # | Structure | IUPAC Name |
|---|---|---|
| 109 | 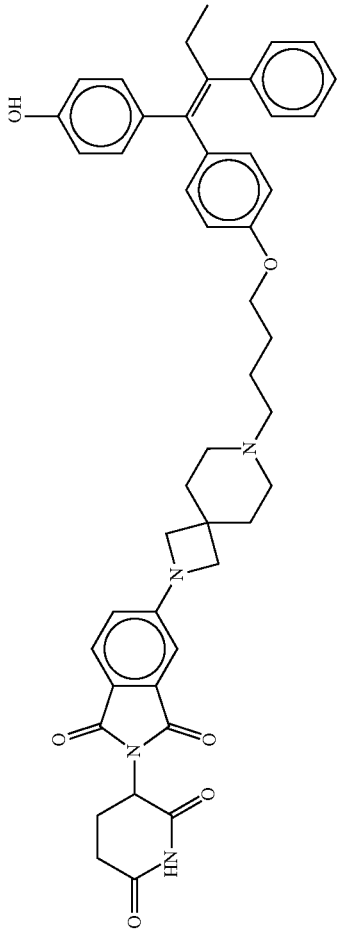 | (Z)-2-(2,6-dioxopiperidin-3-yl)-5-(7-(4-(4-(1-(4-hydroxyphenyl)-2-phenylbut-1-en-1-yl)phenoxy)butyl)-2,7-diazaspiro[3.5]nonan-2-yl)isoindoline-1,3-dione |
| 110 | 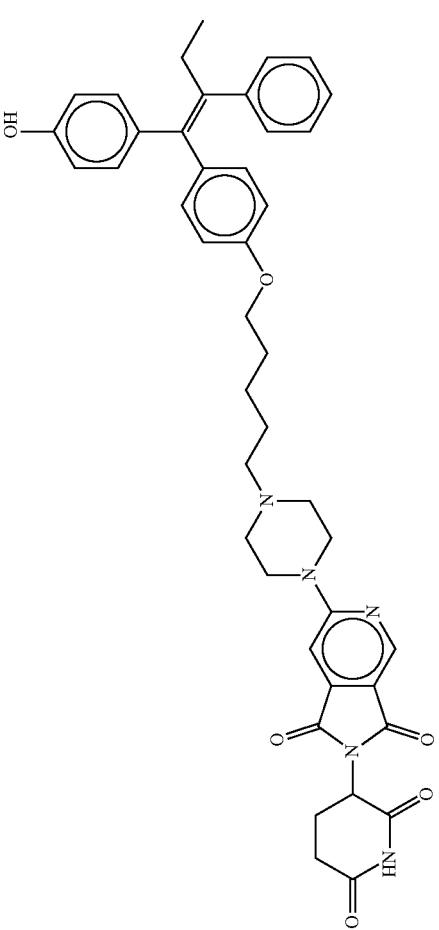 | (Z)-2-(2,6-dioxopiperidin-3-yl)-6-(4-(5-(4-(1-(4-hydroxyphenyl)-2-phenylbut-1-en-1-yl)phenoxy)pentyl)piperazin-1-yl)-1H-pyrrolo[3,4-c]pyridine-1,3(2H)-dione |

TABLE 1A-continued
Exemplary Compound of the Present Disclosure
| # | Structure | IUPAC Name |
|---|-----------|------------|
| 111 | 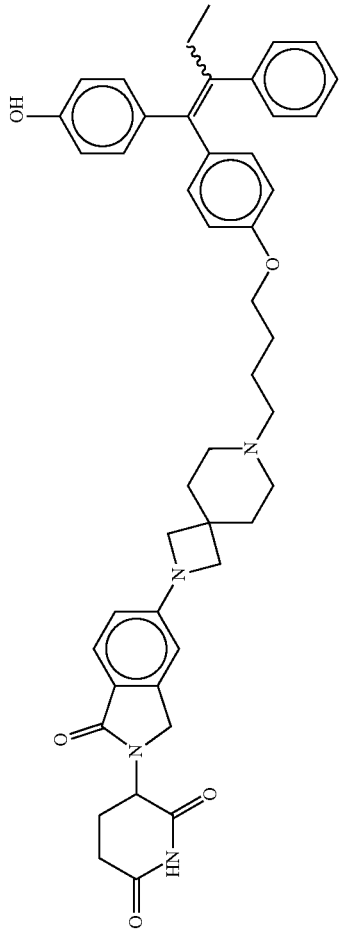 | (Z)/(E)-3-(5-(7-(4-(4-(1-(4-hydroxyphenyl)-2-phenylbut-1-en-1-yl)phenoxy)butyl)-2,7-diazaspiro[3.5]nonan-2-yl)-1-oxoisoindolin-2-yl)piperidine-2,6-dione |
| 112 | 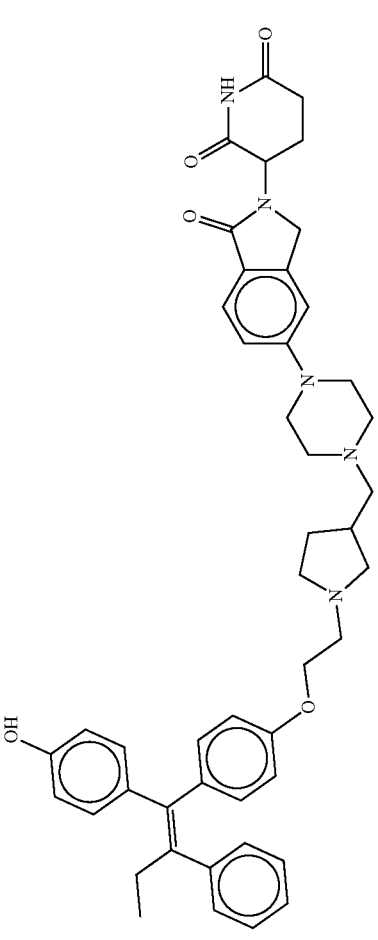 | (Z)-3-(5-(4-((1-(2-(4-(1-(4-hydroxyphenyl)-2-phenylbut-1-en-1-yl)phenoxy)ethyl)pyrrolidin-3-yl)methyl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 113 | 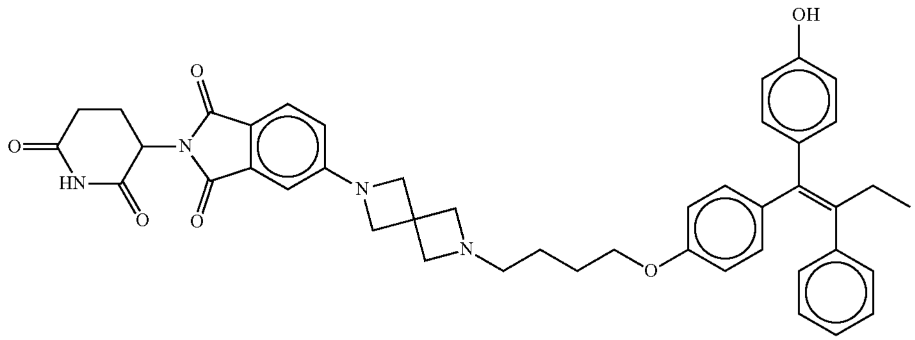 | (Z)-2-(2,6-dioxopiperidin-3-yl)-5-(6-(4-(1-(4-hydroxyphenyl)-2-phenylbut-1-en-1-yl)phenoxy)butyl)-2,6-diazaspiro[3.3]heptan-2-yl)isoindoline-1,3-dione |
| 114 | 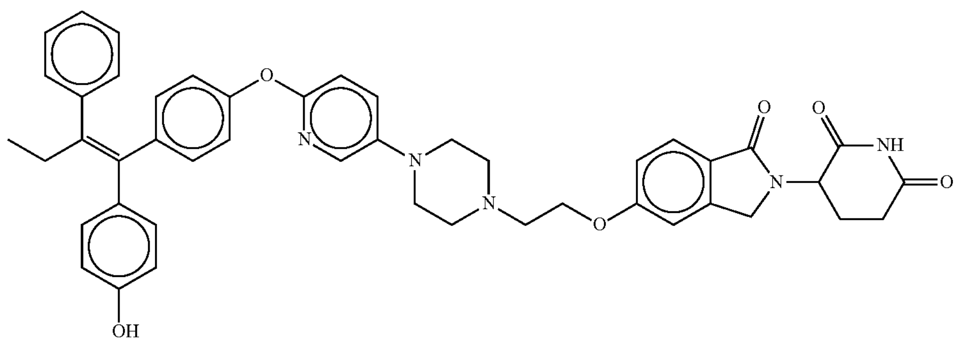 | (Z)-3-(5-(2-(4-(6-(4-(1-(4-hydroxyphenyl)-2-phenylbut-1-en-1-yl)phenoxy)pyridin-3-yl)piperazin-1-yl)ethoxy)-1-oxoisoindolin-2-yl)piperidine-2,6-dione |
| 115 | 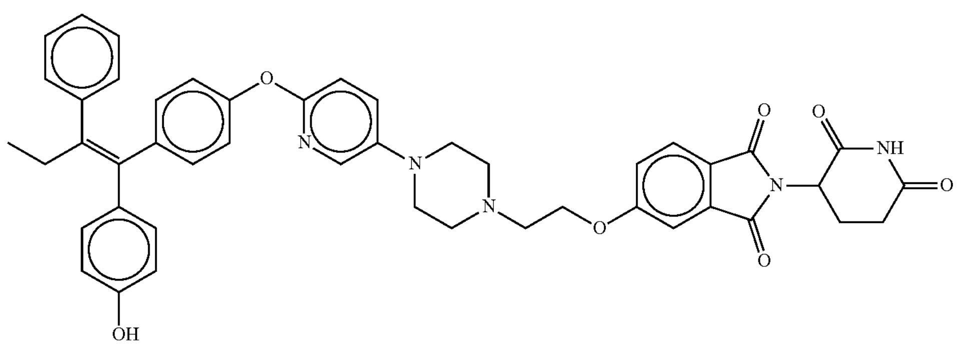 | (Z)-2-(2,6-dioxopiperidin-3-yl)-5-(2-(4-(6-(4-(1-(4-hydroxyphenyl)-2-phenylbut-1-en-1-yl)phenoxy)pyridin-3-yl)piperazin-1-yl)ethoxy)isoindoline-1,3-dione |

TABLE 1A-continued

Exemplary Compound of the Present Disclosure

| # | Structure | IUPAC Name |
|---|---|---|
| 116 | 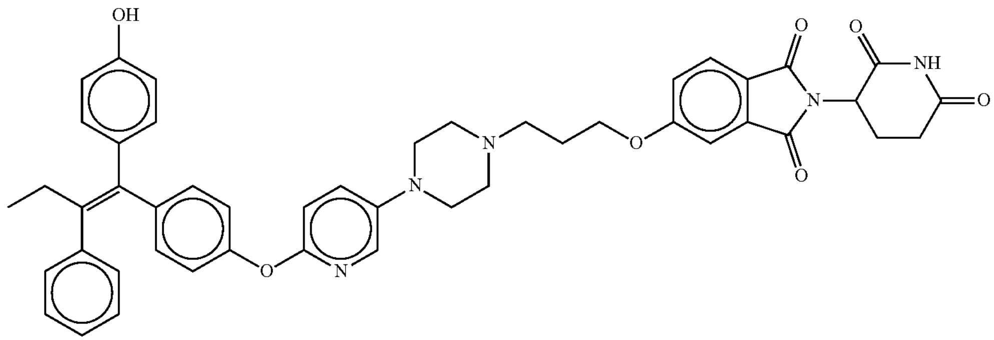 | (Z)-2-(2,6-dioxopiperidin-3-yl)-5-(3-(4-(6-(4-(1-(4-hydroxyphenyl)-2-phenylbut-1-en-1-yl)phenoxy)pyridin-3-yl)piperazin-1-yl)propoxy)isoindoline-1,3-dione |
| 117 | 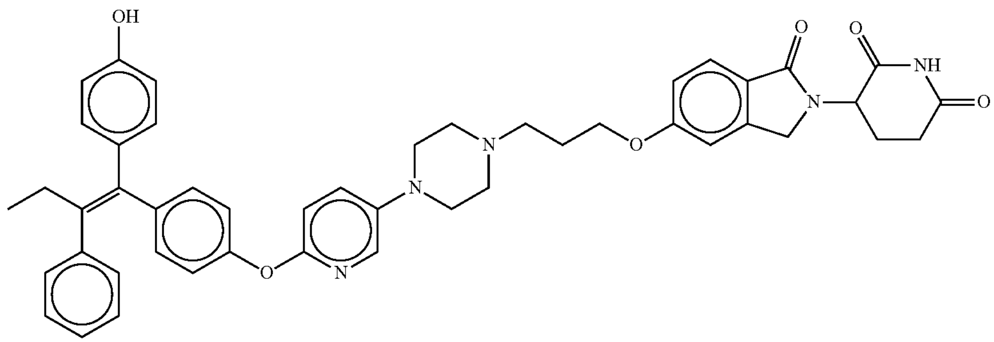 | (Z)-3-(5-(3-(4-(6-(4-(1-(4-hydroxyphenyl)-2-phenylbut-1-en-1-yl)phenoxy)pyridin-3-yl)piperazin-1-yl)propoxy)-1-oxoisoindolin-2-yl)piperidine-2,6-dione |

TABLE 1A-continued
Exemplary Compound of the Present Disclosure
| # | Structure | IUPAC Name |
|---|---|---|
| 118 | 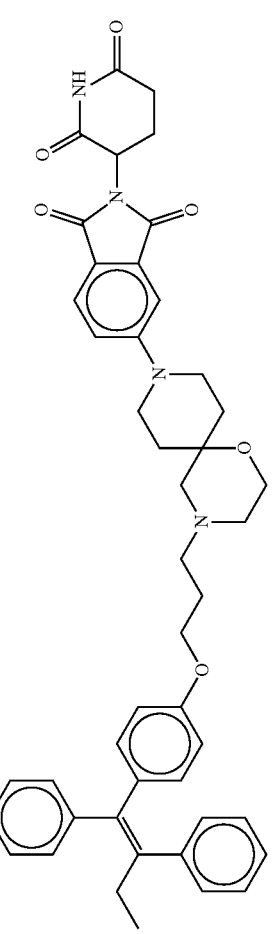 | (Z)-2-(2,6-dioxopiperidin-3-yl)-5-(4-(3-(4-(1-(4-hydroxyphenyl)-2-phenylbut-1-en-1-yl)phenoxy)propyl)-1-oxa-4,9-diazaspiro[5.5]undecan-9-yl)isoindoline-1,3-dione |
| 119 | 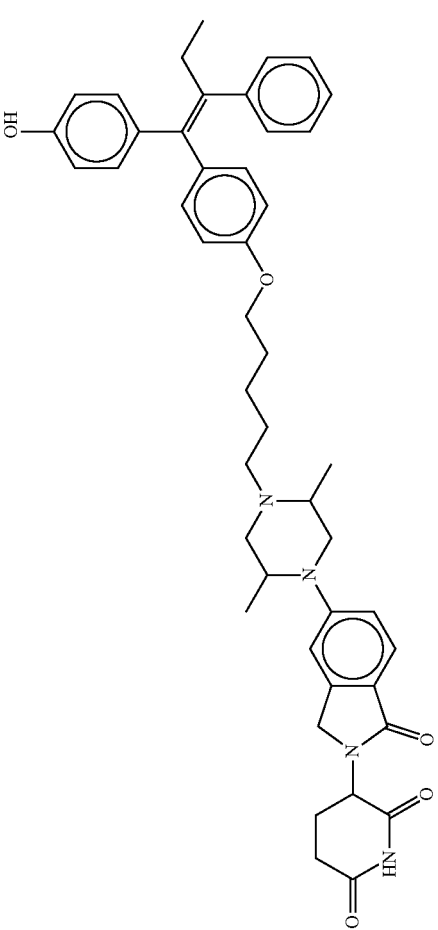 | (Z)-3-(5-(4-(5-(4-(1-(4-hydroxyphenyl)-2-phenylbut-1-en-1-yl)phenoxy)pentyl)-2,5-dimethylpiperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 120 | 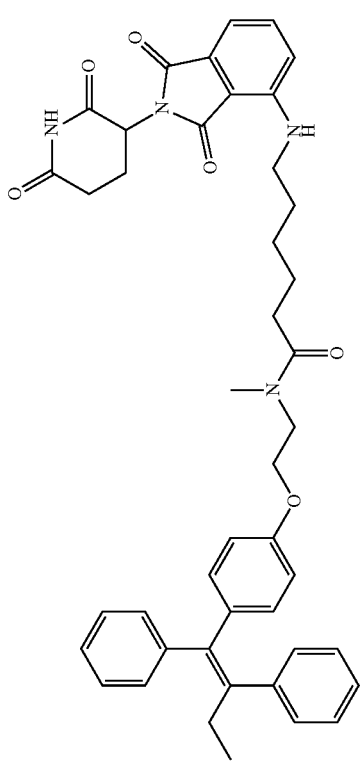 | (Z)-6-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylhexanamide |
| 121 | 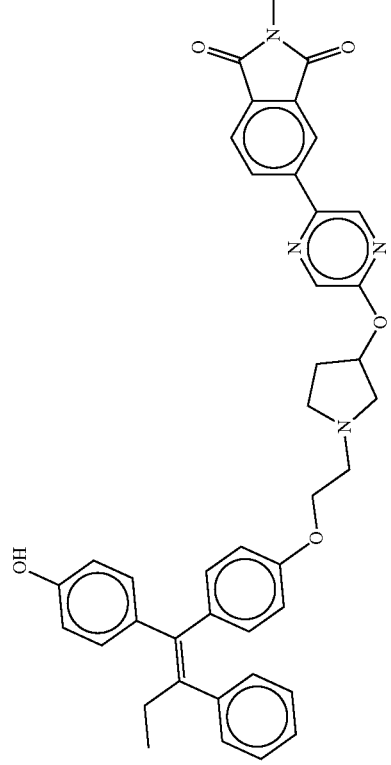 | (Z)-2-(2,6-dioxopiperidin-3-yl)-5-(5-((1-(2-(4-(1-(4-hydroxyphenyl)-2-phenylbut-1-en-1-yl)phenoxy)ethyl)pyrrolidin-3-yl)oxy)pyrazin-2-yl)isoindoline-1,3-dione |

TABLE 1A-continued

Exemplary Compound of the Present Disclosure

| # | Structure | IUPAC Name |
|---|---|---|
| 122 | 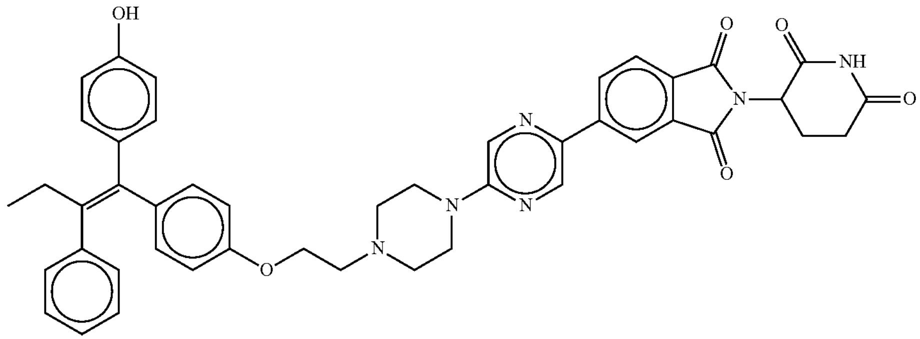 | (Z)-5-(4-(2-(4-(1-(4-hydroxyphenyl)-2-phenylbut-1-en-1-yl)phenoxy)ethyl)piperazin-1-yl)pyrazin-2-yl)isoindoline-1,3-dione |
| 123 | 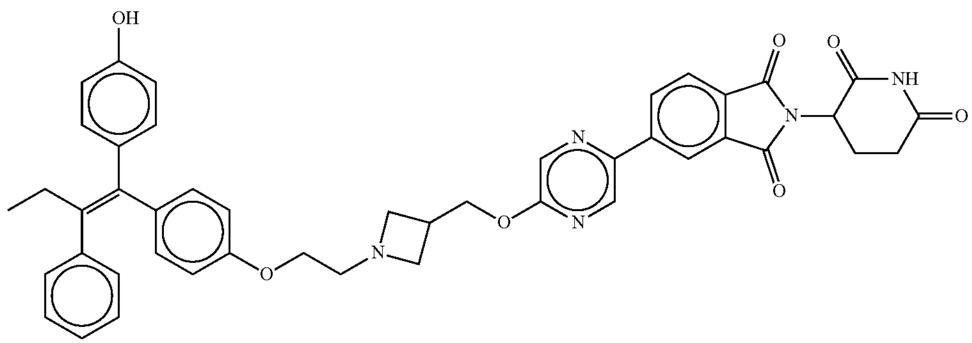 | (Z)-2-(2,6-dioxopiperidin-3-yl)-5-((1-(2-(4-(1-(4-hydroxyphenyl)-2-phenylbut-1-en-1-yl)phenoxy)ethyl)azetidin-3-yl)methoxy)pyrazin-2-yl)isoindoline-1,3-dione |
| 124 | 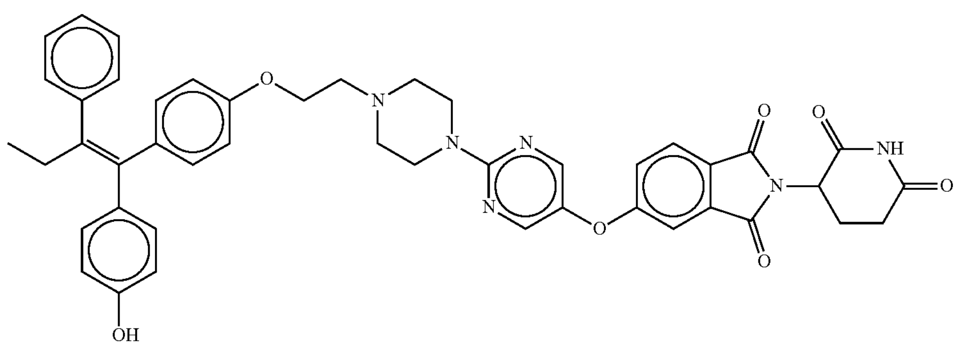 | (Z)-2-(2,6-dioxopiperidin-3-yl)-5-((2-(4-(2-(4-(1-(4-hydroxyphenyl)-2-phenylbut-1-en-1-yl)phenoxy)ethyl)piperazin-1-yl)pyrimidin-5-yl)oxy)isoindoline-1,3-dione |

TABLE 1A-continued
Exemplary Compound of the Present Disclosure
| # | Structure | IUPAC Name |
|---|---|---|
| 125 | 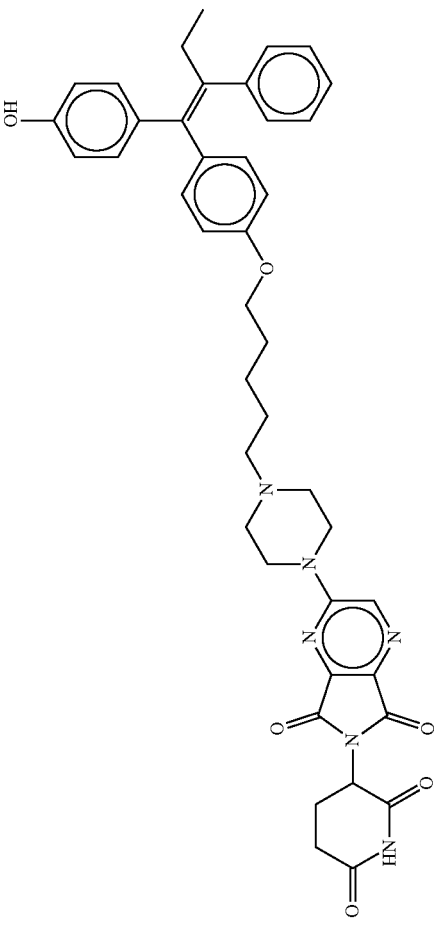 | (Z)-6-(2,6-dioxopiperidin-3-yl)-2-(4-(5-(4-(1-(4-hydroxyphenyl)-2-phenylbut-1-en-1-yl)phenoxy)pentyl)piperazin-1-yl)-5H-pyrrolo[3,4-b]pyrazine-5,7(6H)-dione |
| 126 | 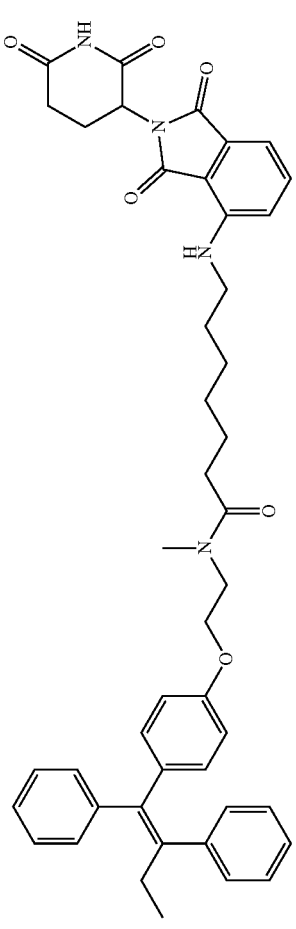 | (Z)-7-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methylheptanamide |

TABLE 1A-continued

Exemplary Compound of the Present Disclosure

| # | Structure | IUPAC Name |
|---|---|---|
| 127 | 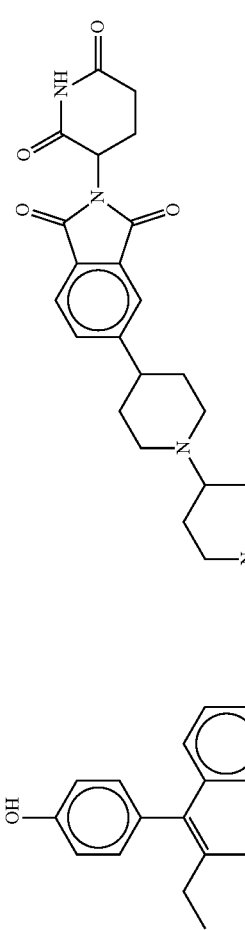 | (Z)-2-(2,6-dioxopiperidin-3-yl)-5-(1'-(2-(4-(1-(4-hydroxyphenyl)-2-phenylbut-1-en-1-yl)phenoxy)ethyl)-[1,4'-bipiperidin]-4-yl)isoindoline-1,3-dione |
| 128 | 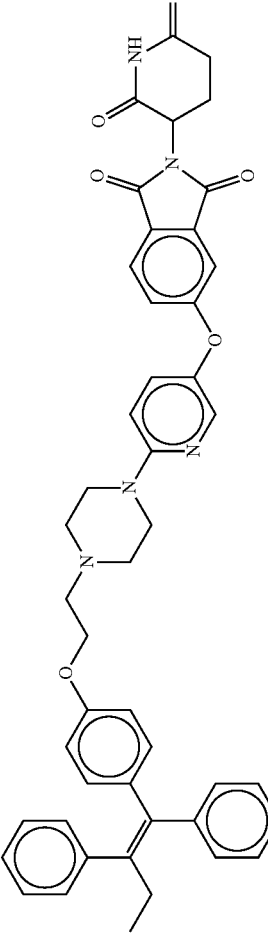 | (Z)-2-(2,6-dioxopiperidin-3-yl)-5-((6-(4-(2-(4-(1-(4-hydroxyphenyl)-2-phenylbut-1-en-1-yl)phenoxy)ethyl)piperazin-1-yl)pyridin-3-yl)oxy)isoindoline-1,3-dione |
| 129 | 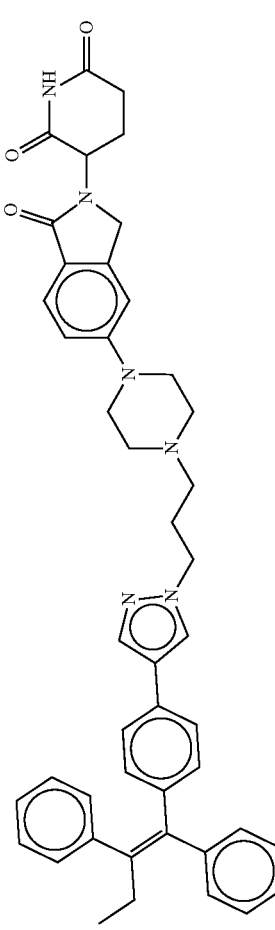 | (E)-3-(5-(4-(3-(4-(4-(1-(4-hydroxyphenyl)-2-phenylbut-1-en-1-yl)phenyl)-1H-pyrazol-1-yl)propyl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 130 | 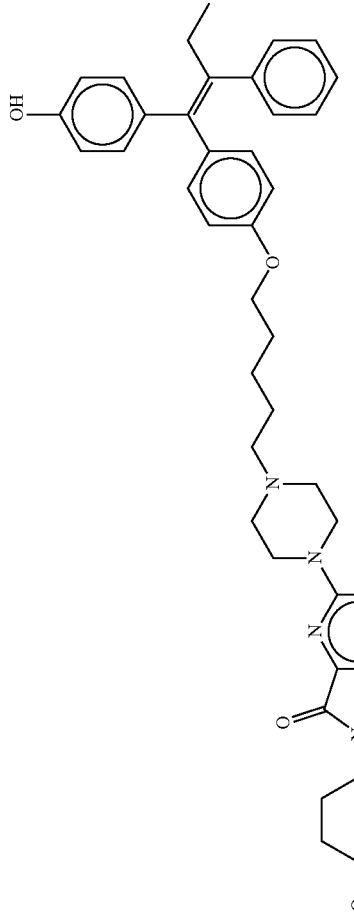 | (Z)-6-(2,6-dioxopiperidin-3-yl)-2-(4-(5-(4-(1-(4-hydroxyphenyl)-2-phenylbut-1-en-1-yl)phenoxy)pentyl)piperazin-1-yl)-5H-pyrrolo[3,4-d]pyrimidine-5,7(6H)-dione |
| 131 | 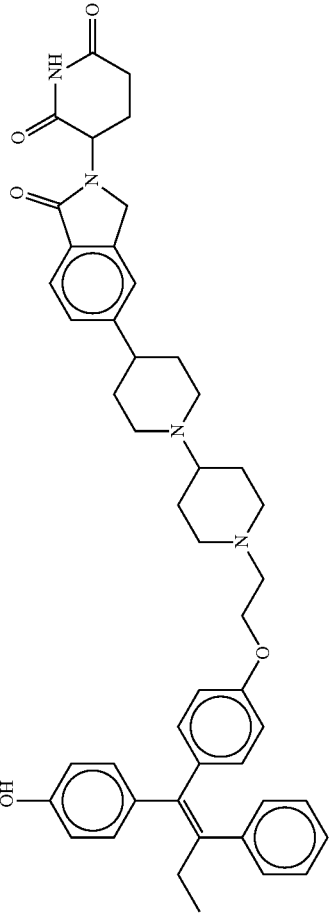 | (Z)-3-(5-(1'-(2-(4-(1-(4-hydroxyphenyl)-2-phenylbut-1-en-1-yl)phenoxy)ethyl)-[1,4'-bipiperidin]-4-yl)-1-oxoisoindolin-2-yl)piperidine-2,6-dione |

TABLE 1A-continued

Exemplary Compound of the Present Disclosure

| # | Structure | IUPAC Name |
|---|---|---|
| 132 | 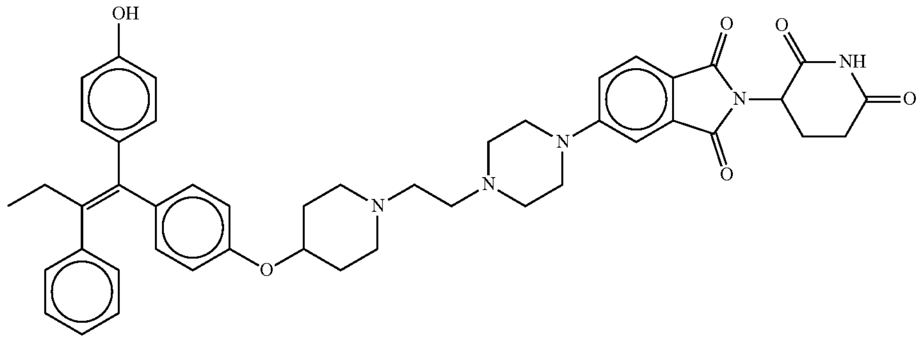 | (Z)-2-(2,6-dioxopiperidin-3-yl)-5-(4-(2-(4-(4-(1-(4-hydroxyphenyl)-2-phenylbut-1-en-1-yl)phenoxy)piperidin-1-yl)ethyl)piperazin-1-yl)isoindoline-1,3-dione |
| 133 | 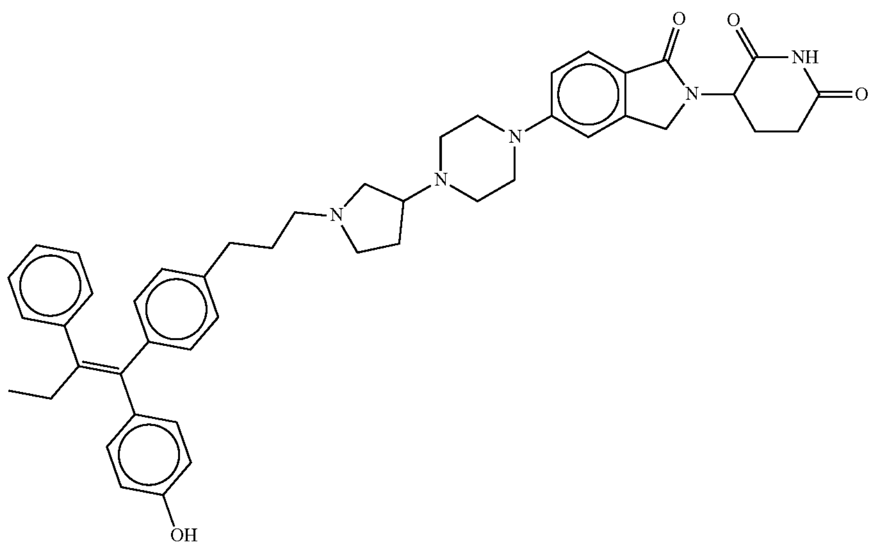 | (E)-3-(5-(4-(1-(3-(4-(1-(4-hydroxyphenyl)-2-phenylbut-1-en-1-yl)phenyl)propyl)pyrrolidin-3-yl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 134 | 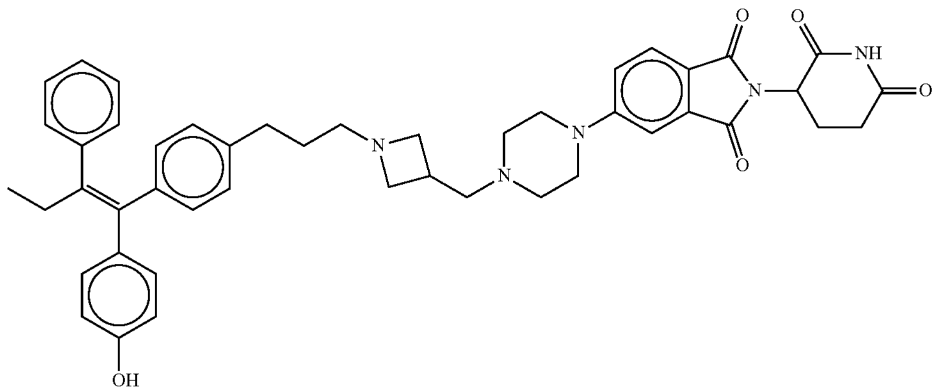 | (E)-2-(2,6-dioxopiperidin-3-yl)-5-(4-((1-(3-(4-(1-(4-hydroxyphenyl)-2-phenylbut-1-en-1-yl)phenyl)propyl)azetidin-3-yl)methyl)piperazin-1-yl)isoindoline-1,3-dione |
| 135 | 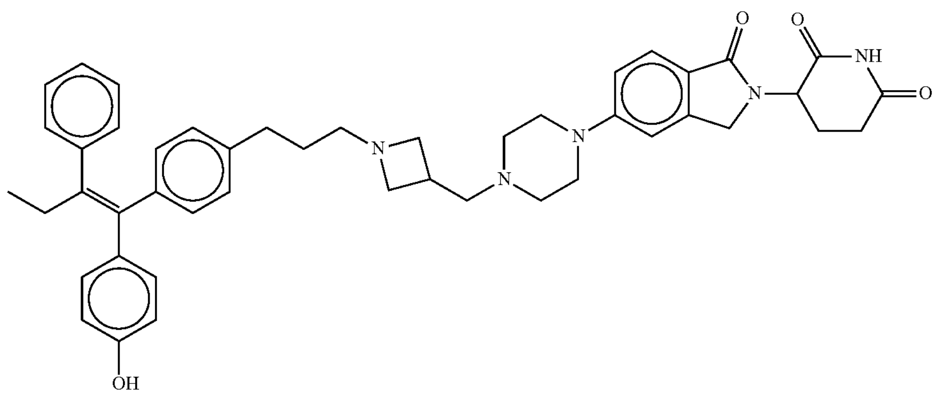 | (E)-3-(5-(4-((1-(3-(4-(1-(4-hydroxyphenyl)-2-phenylbut-1-en-1-yl)phenyl)propyl)azetidin-3-yl)methyl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 136 | 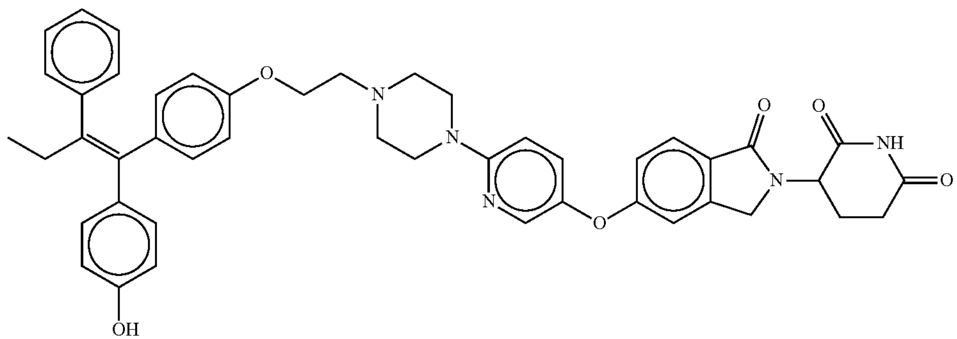 | (Z)-3-(5-((6-(4-(2-(4-(1-(4-hydroxyphenyl)-2-phenylbut-1-en-1-yl)phenoxy)ethyl)piperazin-1-yl)pyridin-3-yl)oxy)-1-oxoisoindolin-2-yl)piperidine-2,6-dione |
| 137 | 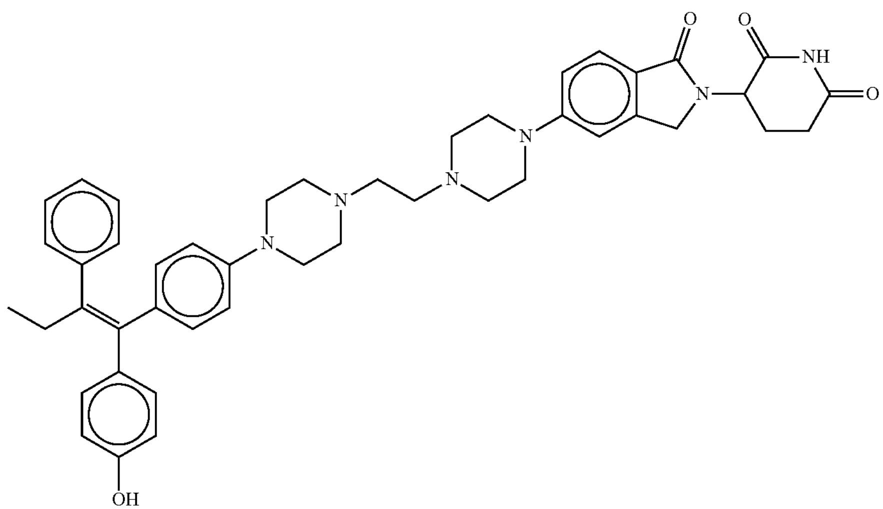 | (E)-3-(5-(4-(2-(4-(1-(4-hydroxyphenyl)-2-phenylbut-1-en-1-yl)phenyl)piperazin-1-yl)ethyl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 138 | 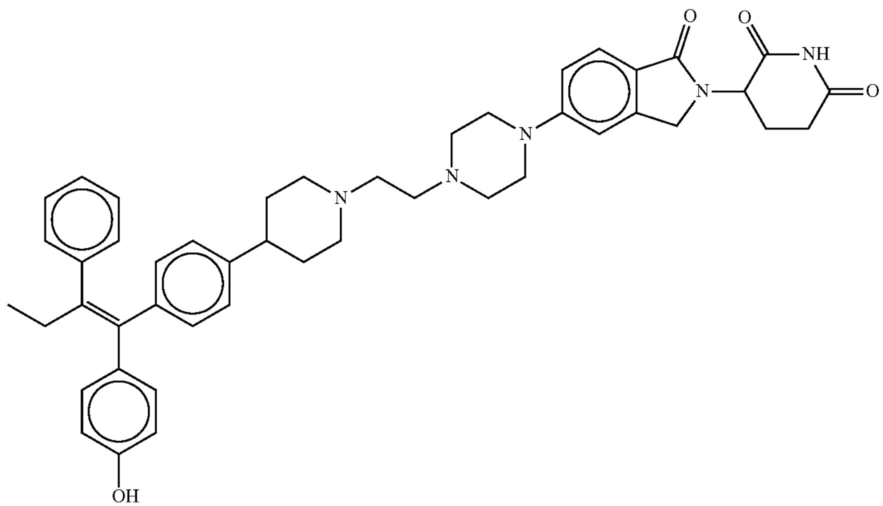 | (E)-3-(5-(4-(2-(4-(4-(1-(4-hydroxyphenyl)-2-phenylbut-1-en-1-yl)phenyl)piperidin-1-yl)ethyl)piperazin-1-yl)-1-oxoisoindolin-2-yl)piperidine-2,6-dione |
| 139 | 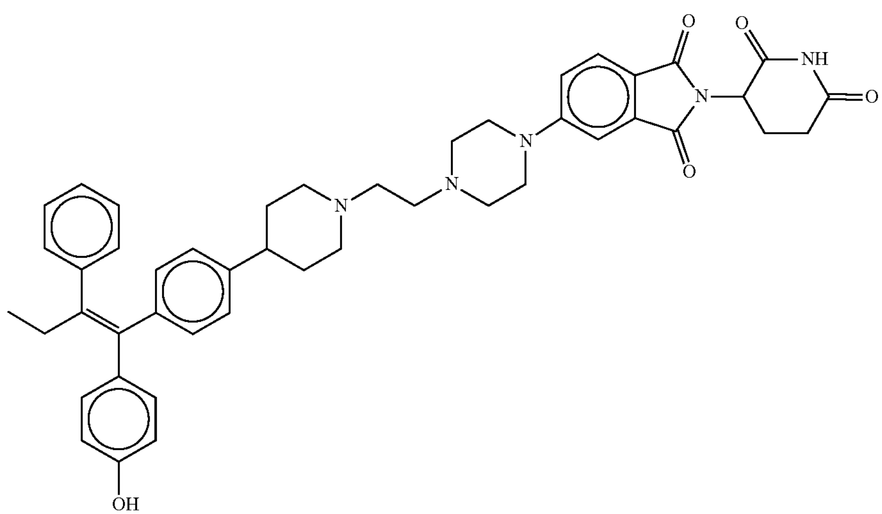 | (E)-2-(2,6-dioxopiperidin-3-yl)-5-(4-(2-(4-(4-(1-(4-hydroxyphenyl)-2-phenylbut-1-en-1-yl)phenyl)piperidin-1-yl)ethyl)piperazin-1-yl)isoindoline-1,3-dione |

TABLE 1A-continued
Exemplary Compound of the Present Disclosure
| # | Structure | IUPAC Name |
|---|---|---|
| 140 | 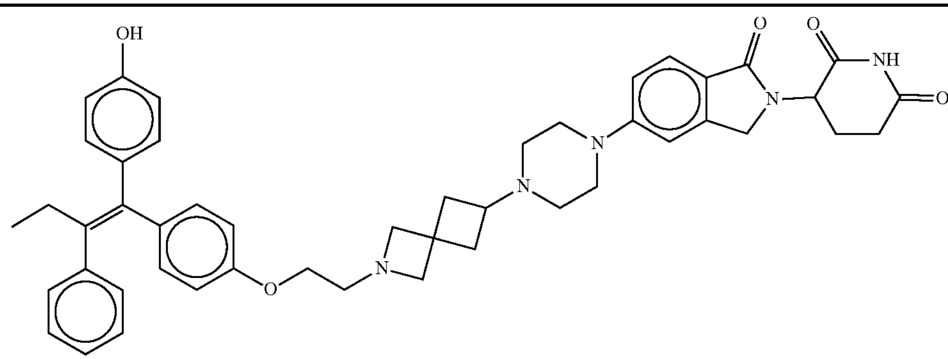 | (Z)-3-(5-(4-(2-(2-(4-(1-(4-hydroxyphenyl)-2-phenylbut-1-en-1-yl)phenoxy)ethyl)-2-azaspiro[3.3]heptan-6-yl)piperazin-1-yl)-1-oxoisoindolin-2-yl)piperidine-2,6-dione |
| 141 | 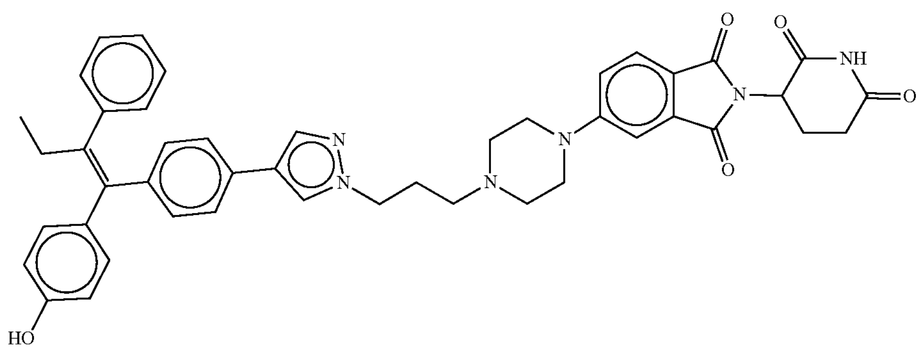 | (E)-2-(2,6-dioxopiperidin-3-yl)-5-(4-(3-(4-(1-(4-hydroxyphenyl)-2-phenylbut-1-en-1-yl)-1H-pyrazol-1-yl)propyl)piperazin-1-yl)isoindoline-1,3-dione |

TABLE 1A-continued
Exemplary Compound of the Present Disclosure
| # | Structure | IUPAC Name |
|---|---|---|
| 142 | 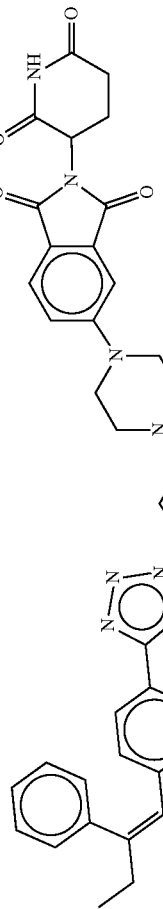 | (E)-2-(2,6-dioxopiperidin-3-yl)-5-(4-(3-(5-(4-(1-(4-hydroxyphenyl)-2-phenylbut-1-en-1-yl)phenyl)-2H-tetrazol-2-yl)propyl)piperazin-1-yl)isoindoline-1,3-dione |
| 143 | 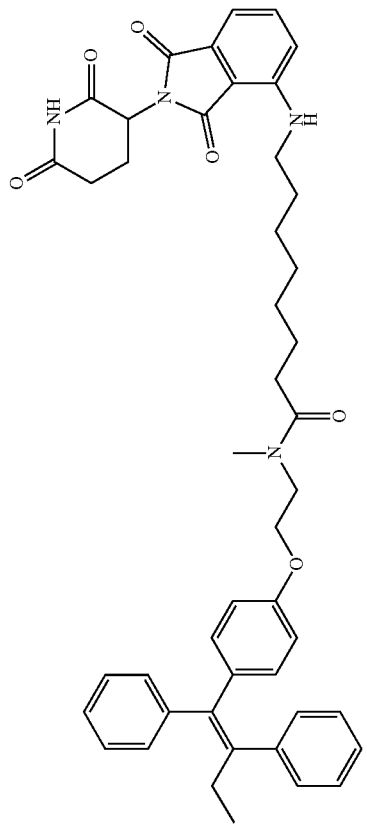 | (Z)-8-((2-(2,6-dioxopiperidin-3-yl)-1,3-dioxoisoindolin-4-yl)amino)-N-(2-(4-(1,2-diphenylbut-1-en-1-yl)phenoxy)ethyl)-N-methyloctanamide |

TABLE 1A-continued

Exemplary Compound of the Present Disclosure

| # | Structure | IUPAC Name |
|---|---|---|
| 144 | 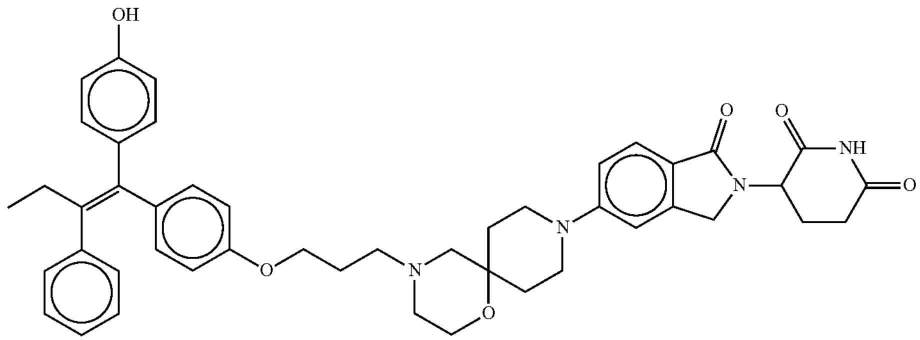 | (Z)-3-(5-(4-(3-(4-(1-(4-hydroxyphenyl)-2-phenylbut-1-en-1-yl)phenoxy)propyl)-1-oxa-4,9-diazaspiro[5.5]undecan-9-yl)-1-oxoisoindolin-2-yl)piperidine-2,6-dione |
| 145 | 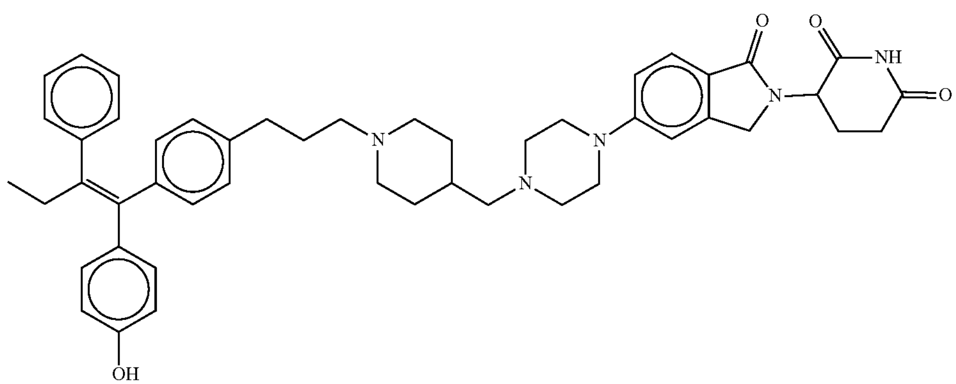 | (E)-3-(5-(4-((1-(3-(4-(1-(4-hydroxyphenyl)-2-phenylbut-1-en-1-yl)phenyl)propyl)piperidin-4-yl)methyl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 146 | 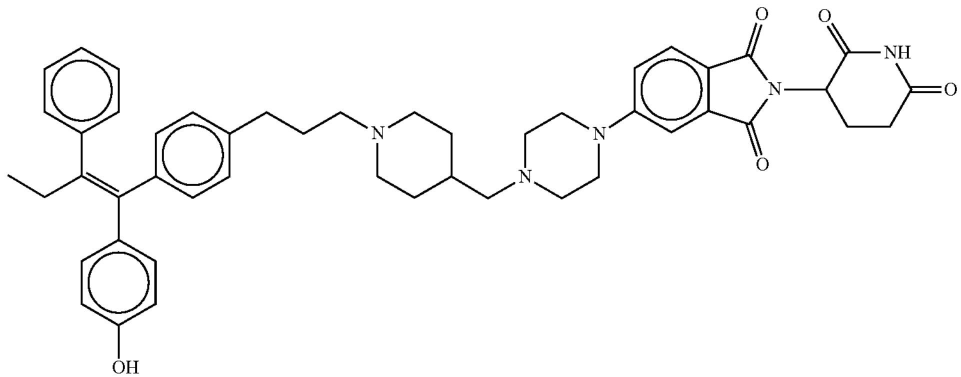 | (E)-2-(2,6-dioxopiperidin-3-yl)-5-(4-((1-(3-(4-(1-(4-hydroxyphenyl)-2-phenylbut-1-en-1-yl)phenyl)propyl)piperidin-4-yl)methyl)piperazin-1-yl)isoindoline-1,3-dione |
| 147 | 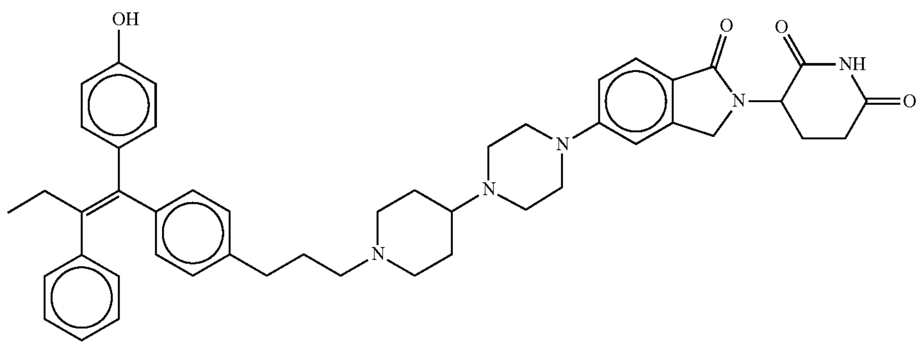 | (E)-3-(5-(4-(1-(3-(4-(1-(4-hydroxyphenyl)-2-phenylbut-1-en-1-yl)phenyl)propyl)piperidin-4-yl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 148 | 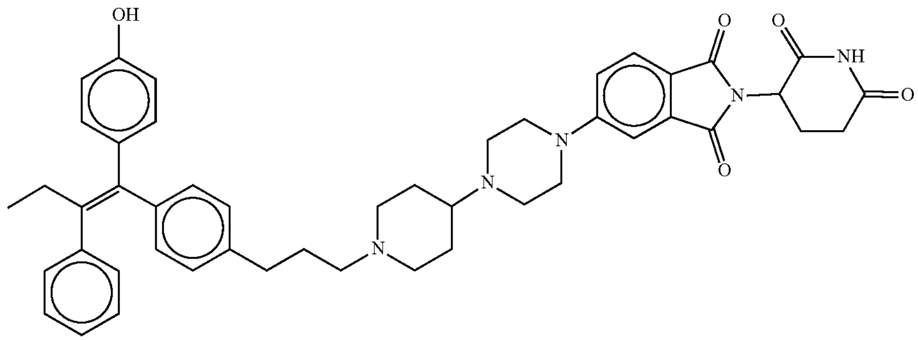 | (E)-2-(2,6-dioxopiperidin-3-yl)-5-(4-(1-(3-(4-(1-(4-hydroxyphenyl)-2-phenylbut-1-en-1-yl)phenyl)propyl)piperidin-4-yl)piperazin-1-yl)isoindoline-1,3-dione |
| 149 | 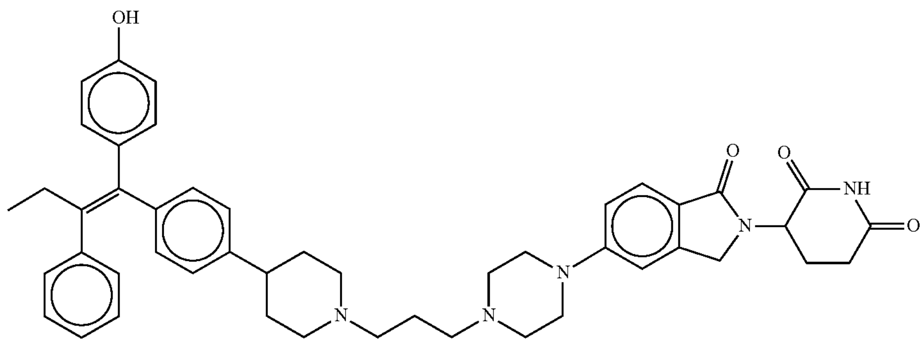 | (E)-3-(5-(4-(3-(4-(1-(4-hydroxyphenyl)-2-phenylbut-1-en-1-yl)phenyl)piperidin-1-yl)propyl)piperazin-1-yl)-1-oxoisoindolin-2-yl)piperidine-2,6-dione |
| 150 | 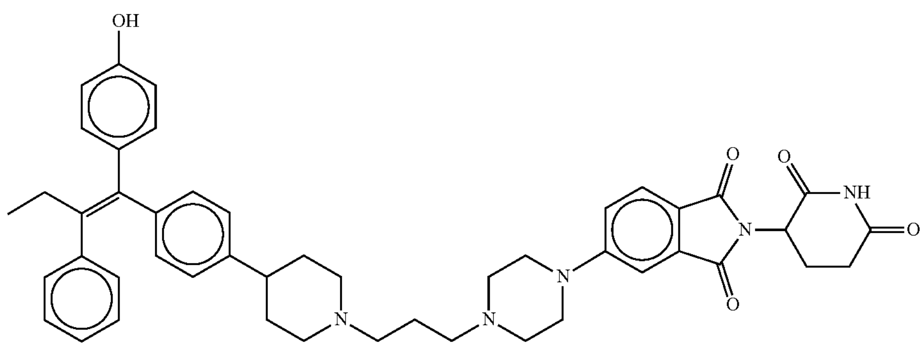 | (E)-2-(2,6-dioxopiperidin-3-yl)-5-(4-(3-(4-(1-(4-hydroxyphenyl)-2-phenylbut-1-en-1-yl)phenyl)piperidin-1-yl)propyl)piperazin-1-yl)isoindoline-1,3-dione |

TABLE 1A-continued
Exemplary Compound of the Present Disclosure
| # | Structure | IUPAC Name |
|---|---|---|
| 151 | 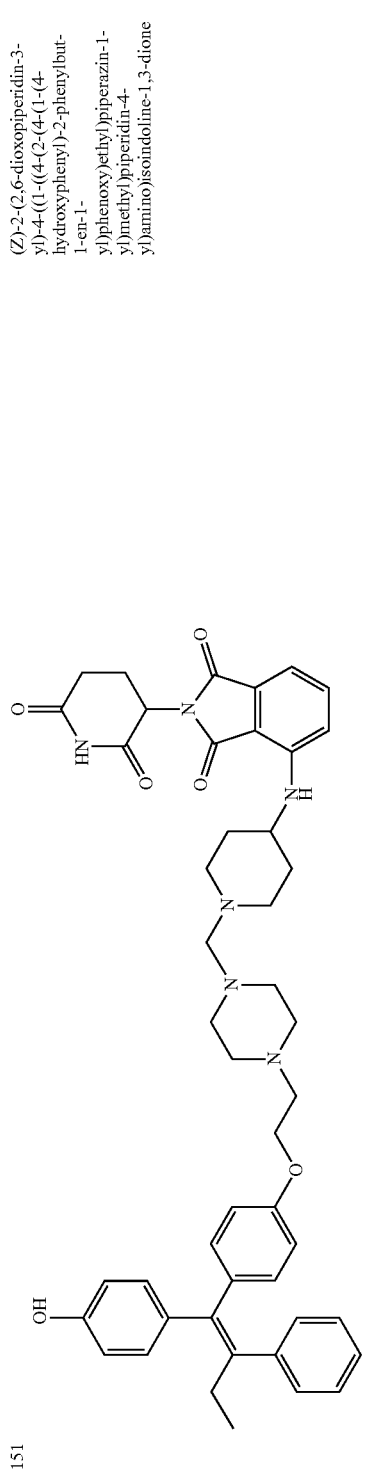 | (Z)-2-(2,6-dioxopiperidin-3-yl)-4-((1-((4-(2-(4-(1-(4-hydroxyphenyl)-2-phenylbut-1-en-1-yl)phenoxy)ethyl)piperazin-1-yl)methyl)piperidin-4-yl)amino)isoindoline-1,3-dione |
| 152 | 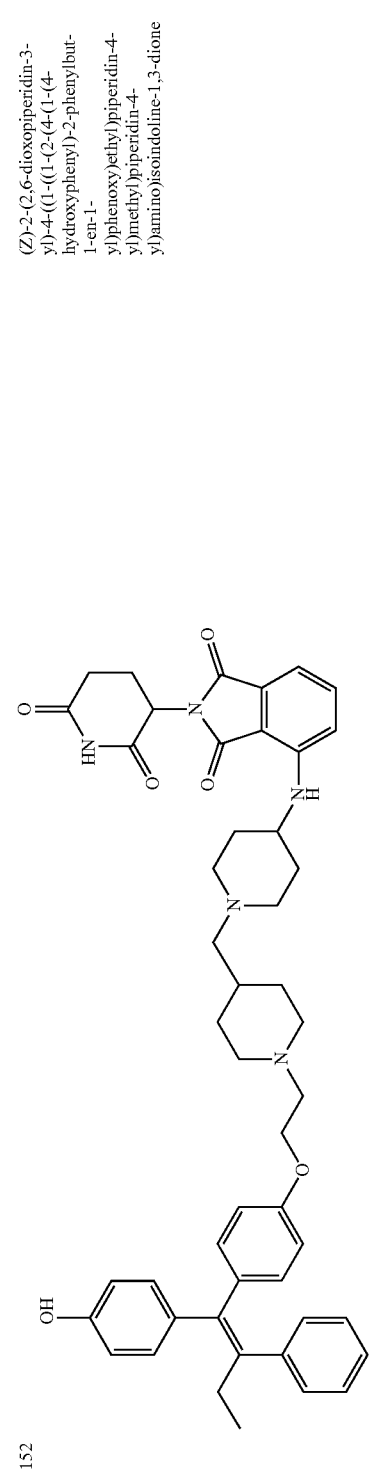 | (Z)-2-(2,6-dioxopiperidin-3-yl)-4-((1-(2-(4-(1-(4-hydroxyphenyl)-2-phenylbut-1-en-1-yl)phenoxy)ethyl)piperidin-4-yl)methyl)piperidin-4-yl)amino)isoindoline-1,3-dione |

TABLE 1A-continued
Exemplary Compound of the Present Disclosure
| # | Structure | IUPAC Name |
|---|---|---|
| 153 | 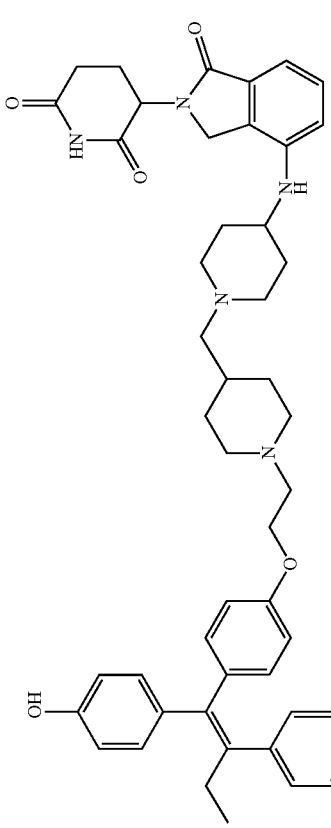 | (Z)-3-(4-((1-((1-(2-(4-(1-(4-hydroxyphenyl)-2-phenylbut-1-en-1-yl)phenoxy)ethyl)piperidin-4-yl)methyl)piperidin-4-yl)amino)-1-oxoisoindolin-2-yl)piperidine-2,6-dione |
| 154 | 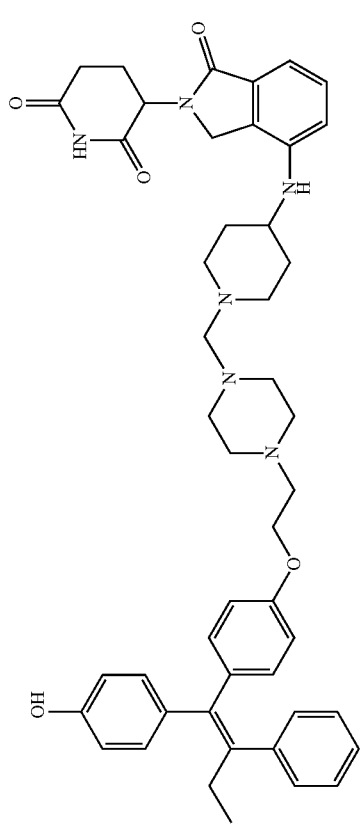 | (Z)-3-(4-((1-((4-(2-(4-(1-(4-hydroxyphenyl)-2-phenylbut-1-en-1-yl)phenoxy)ethyl)piperazin-1-yl)methyl)piperidin-4-yl)amino)-1-oxoisoindolin-2-yl)piperidine-2,6-dione |

TABLE 1A-continued

Exemplary Compound of the Present Disclosure

| # | Structure | IUPAC Name |
|---|---|---|
| 155 | 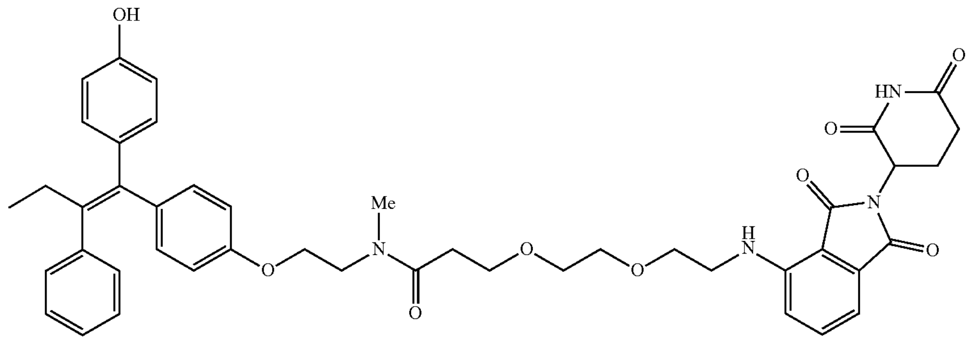 [SMILES: CC/C(=C(\c1ccc(O)cc1)c1ccc(OCCN(C)C(=O)CCOCCOCCNc2cccc3c2C(=O)N(C2CCC(=O)NC2=O)C3=O)cc1)c1ccccc1] | (Z)-3-(2-(2-((2-(2,6-dioxopiperidin-3-yl)-1,3-dioxoisoindolin-4-yl)amino)ethoxy)ethoxy)-N-(2-(4-(1-(4-hydroxyphenyl)-2-phenylbut-1-en-1-yl)phenoxy)ethyl)-N-methylpropanamide |
| 156 | 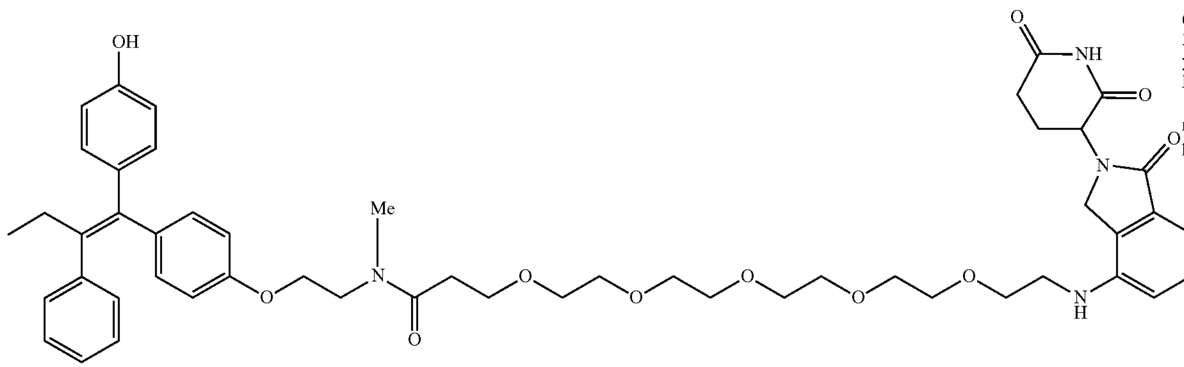 [SMILES: CC/C(=C(\c1ccc(O)cc1)c1ccc(OCCN(C)C(=O)CCOCCOCCOCCOCCOCCNc2cccc3c2CN(C2CCC(=O)NC2=O)C3=O)cc1)c1ccccc1] | (Z)-1-((2-(2,6-dioxopiperidin-3-yl)-1-oxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide |

TABLE 1A-continued
Exemplary Compound of the Present Disclosure
| # | Structure | IUPAC Name |
|---|---|---|
| 157 | 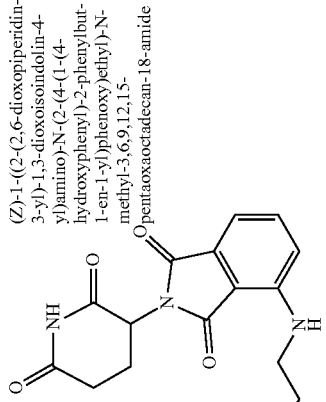 | (Z)-1-((2-(2,6-dioxopiperidin-3-yl)-1,3-dioxoisoindolin-4-yl)amino)-N-(2-(4-(1-(4-hydroxyphenyl)-2-phenylbut-1-en-1-yl)phenoxy)ethyl)-N-methyl-3,6,9,12,15-pentaoxaoctadecan-18-amide |
| 158 | 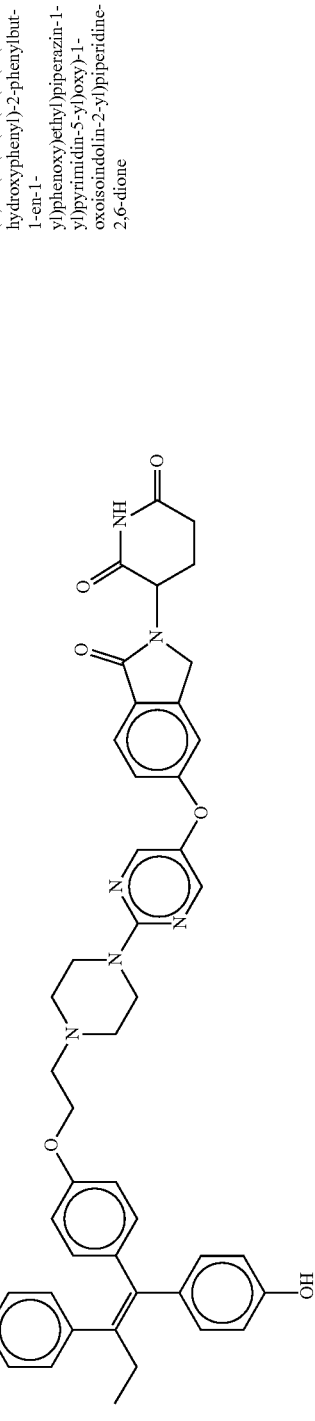 | (Z)-3-(5-(2-(4-(2-(4-(1-(4-hydroxyphenyl)-2-phenylbut-1-en-1-yl)phenoxy)ethyl)piperazin-1-yl)pyrimidin-5-yl)oxy)-1-oxoisoindolin-2-yl)piperidine-2,6-dione |

TABLE 1A-continued
Exemplary Compound of the Present Disclosure
| # | Structure | IUPAC Name |
|---|---|---|
| 159 | 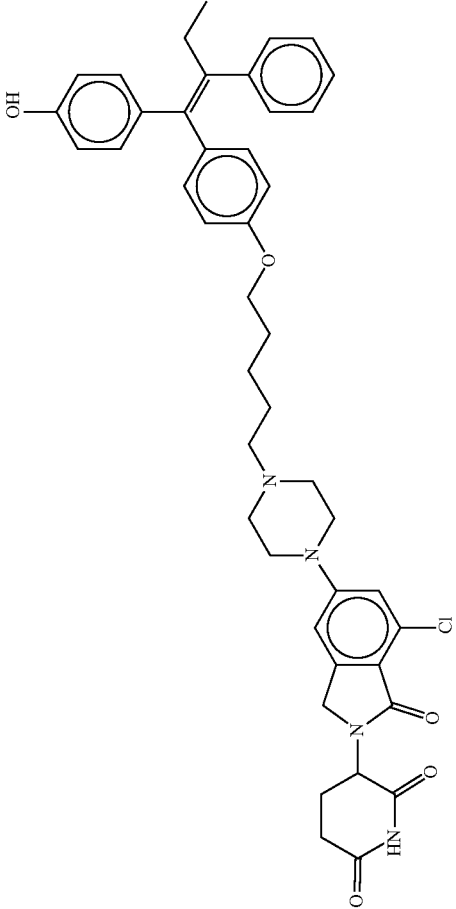 | (Z)-3-(7-chloro-5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione |
| 160a | 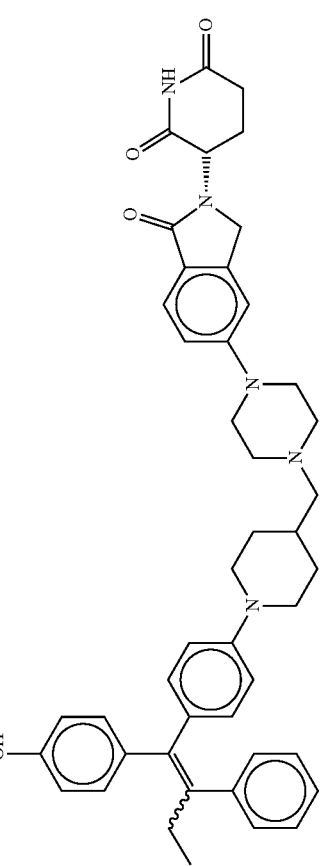 | (E)/(Z)-(S)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 160 | 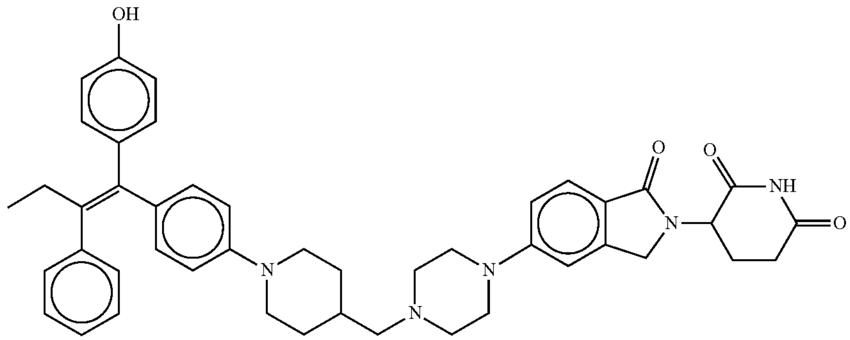 | (E)-3-(5-(4-((1-(4-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |
| 160b | 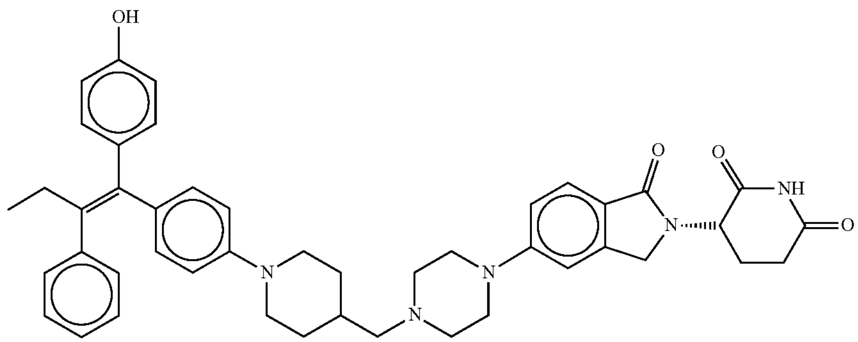 | (E)-(S)-3-(5-(4-((1-(4-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |

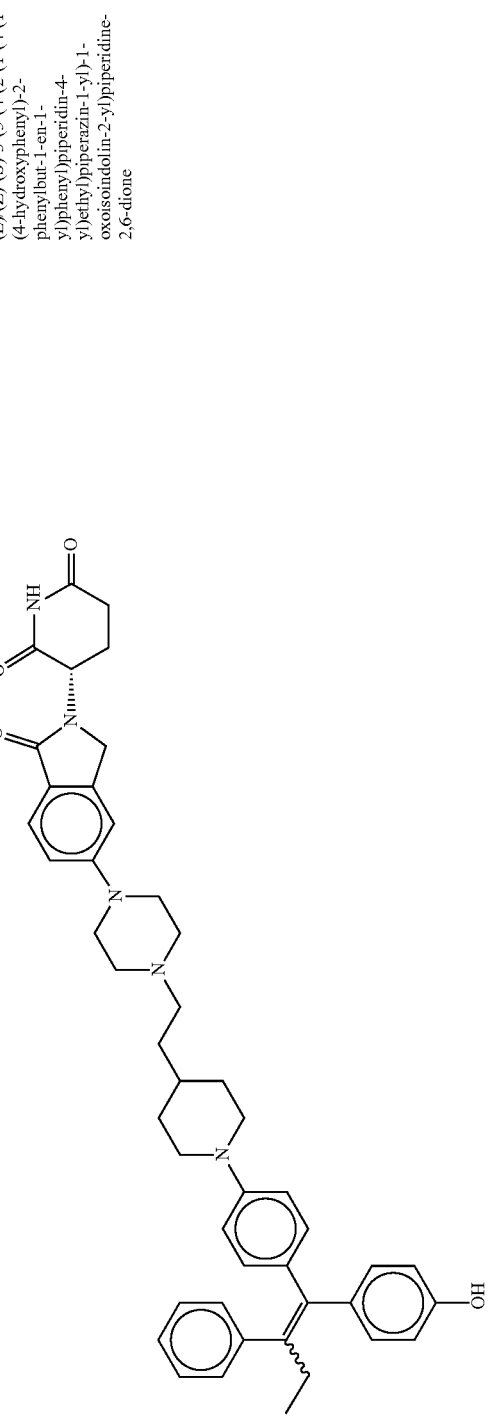

TABLE 1A-continued
Exemplary Compound of the Present Disclosure
| # | Structure | IUPAC Name |
|---|---|---|
| 162 | 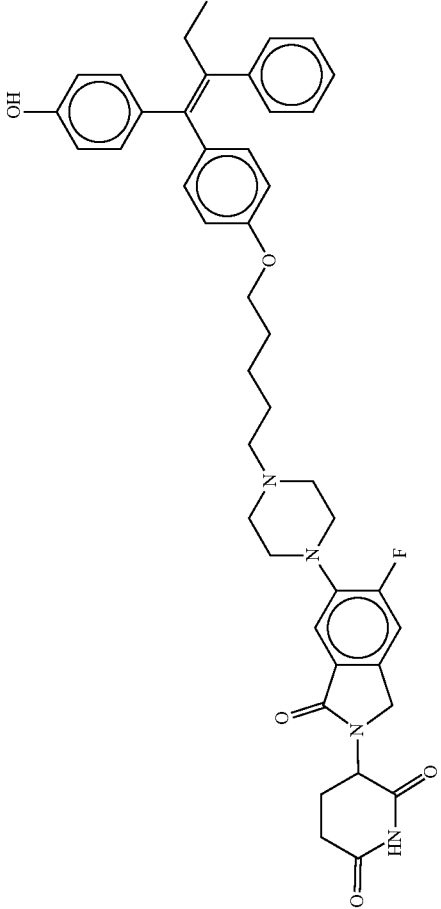 | (Z)-3-(5-fluoro-6-(4-(5-(4-(1-(4-hydroxyphenyl)-2-phenylbut-1-en-1-yl)phenoxy)pentyl)piperazin-1-yl)-1-oxoi soindolin-2-yl)piperidine-2,6-dione |
| 163 | 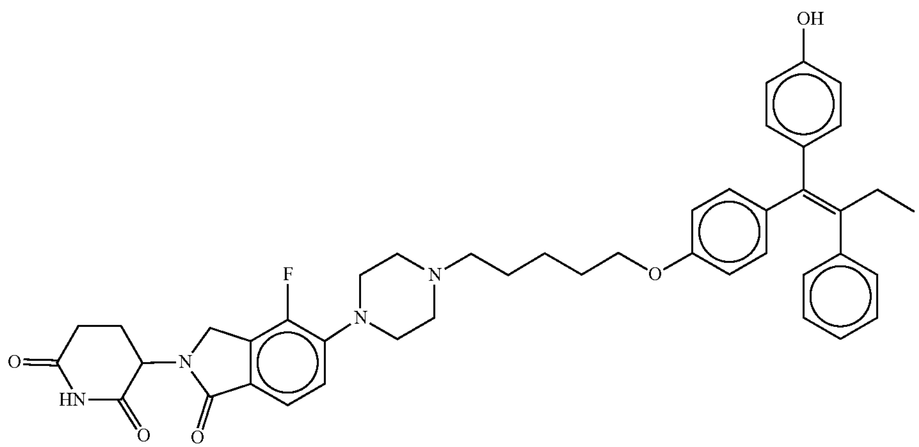 | (Z)-3-(4-fluoro-5-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 164 | 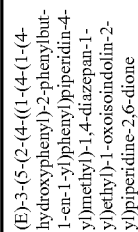 | (E)-3-(5-(2-(4-((1-(4-(1-(4-hydroxyphenyl)-2-phenylbut-1-en-1-yl)phenyl)piperidin-4-yl)methyl)-1,4-diazepan-1-yl)ethyl)-1-oxoisoindolin-2-yl)piperidine-2,6-dione |
| 165 | 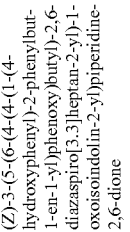 | (Z)-3-(5-(6-(4-(4-(1-(4-hydroxyphenyl)-2-phenylbut-1-en-1-yl)phenoxy)butyl)-2,6-diazaspiro[3.3]heptan-2-yl)-1-oxoisoindolin-2-yl)piperidine-2,6-dione |

TABLE 1A-continued
Exemplary Compound of the Present Disclosure
| # | Structure | IUPAC Name |
|---|---|---|
| 166 | 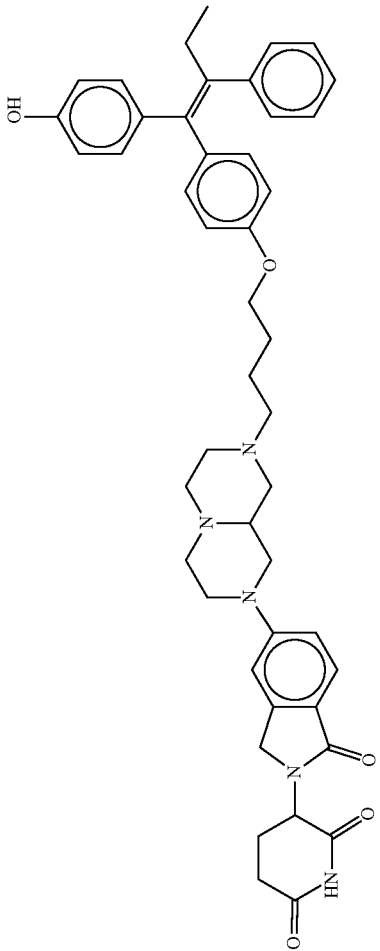 | (Z)-3-(5-(8-(4-(4-(1-(4-hydroxyphenyl)-2-phenylbut-1-en-1-yl)phenoxy)butyl)octahydro-2H-pyrazino[1,2-a]pyrazin-2-yl)-1-oxoisoindolin-2-yl)piperidine-2,6-dione |
| 167 | 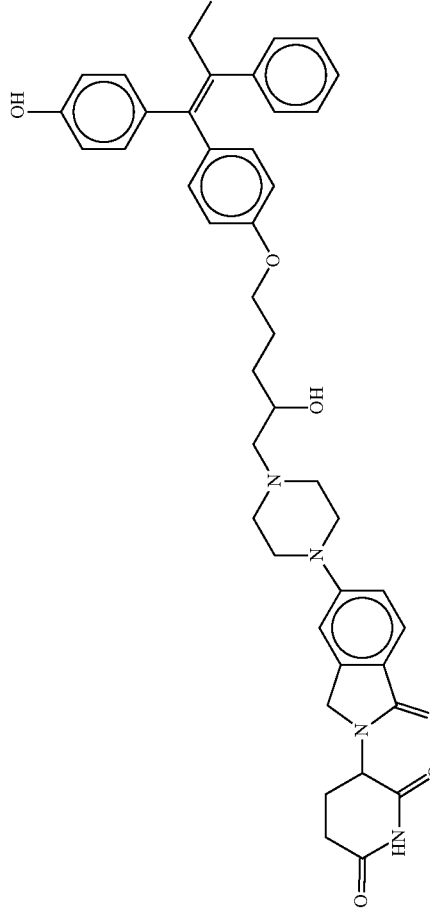 | (Z)-3-(5-(4-(2-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 168 | 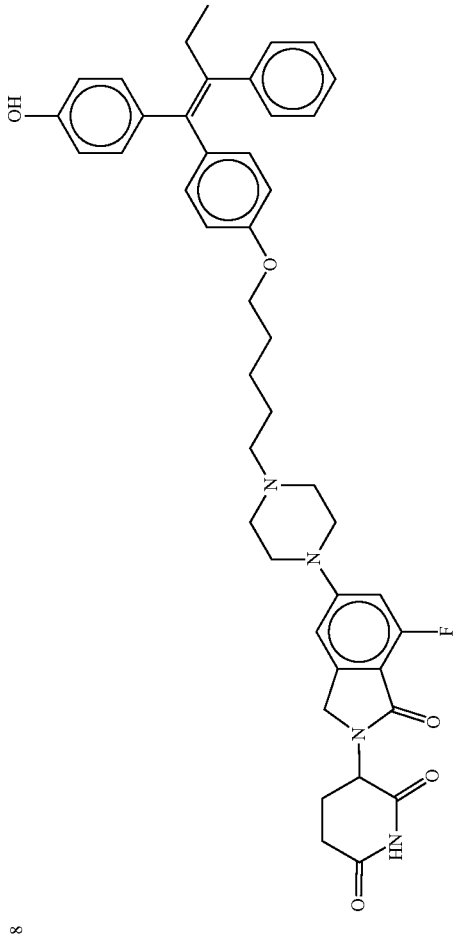 | (Z)-3-(7-fluoro-5-(4-(5-(4-(1-(4-hydroxyphenyl)-2-phenylbut-1-en-1-yl)-1-oxoisoindolin-2-yl)phenoxy)pentyl)piperazin-1-yl)piperidine-2,6-dione |
| 169 | 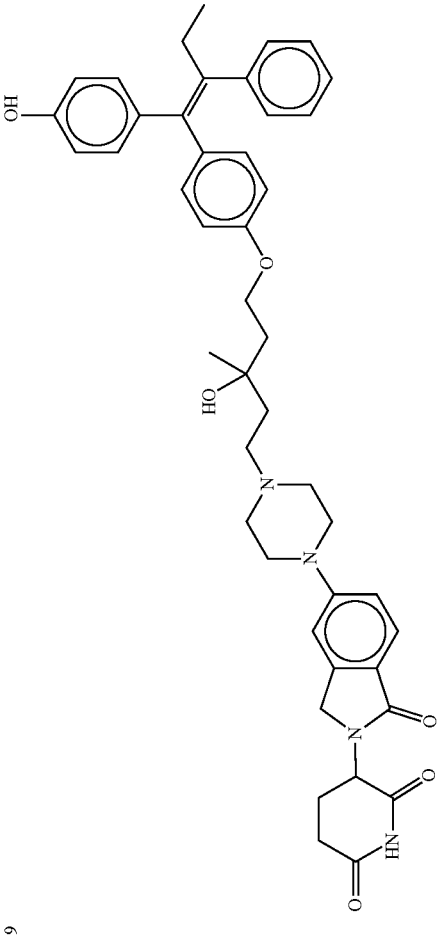 | (Z)-3-(5-(4-(3-hydroxy-5-(4-(1-(4-hydroxyphenyl)-2-phenylbut-1-en-1-yl)phenoxy)-3-methylpentyl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 170 | 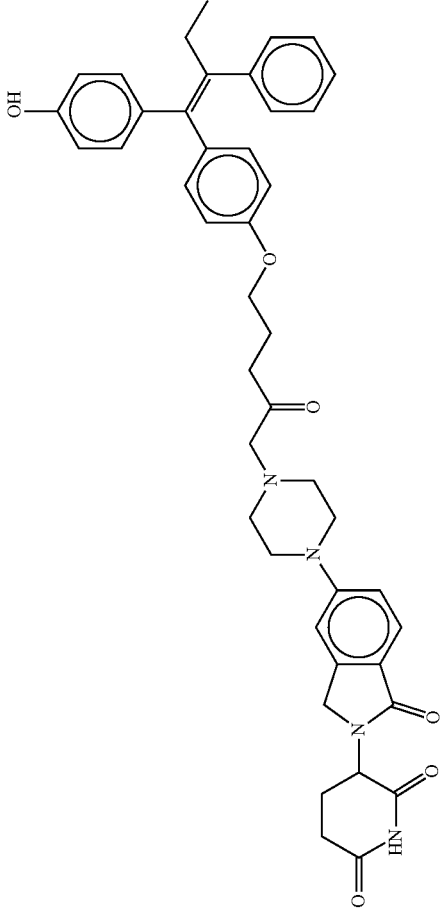 | (Z)-3-(5-(4-(5-(4-(1-(4-hydroxyphenyl)-2-phenylbut-1-en-1-yl)phenoxy)-2-oxopentyl)piperazin-1-yl)-1-oxoisoindolin-2-yl)piperidine-2,6-dione |
| 171 | 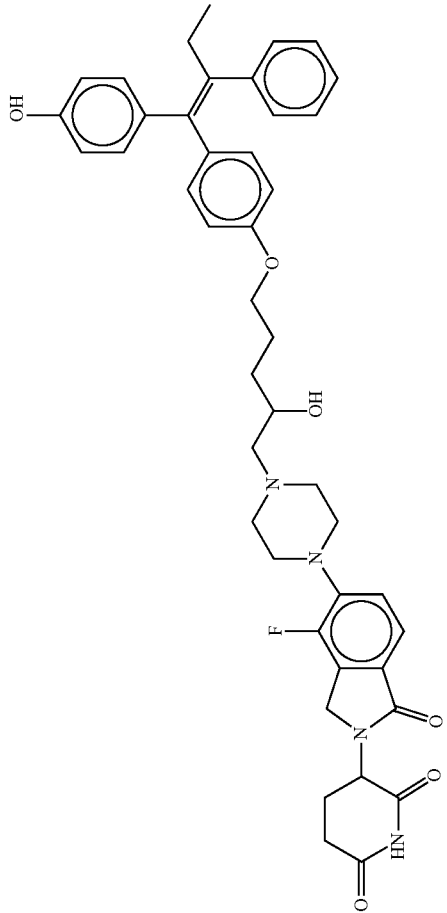 | (Z)-3-(4-fluoro-5-(4-(2-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 172 | 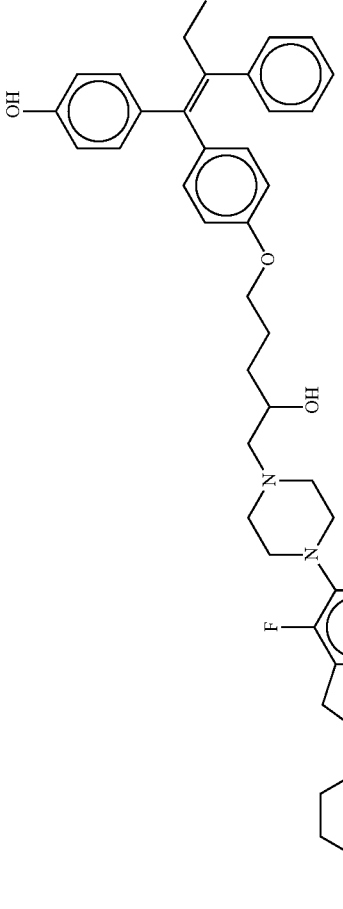 | (Z)-3-(4,6-difluoro-5-(4-(2-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione |
| 173 | 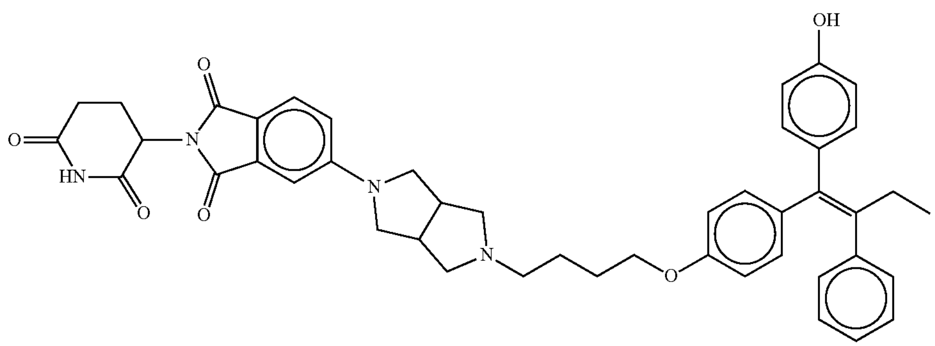 | (Z)-2-(2,6-dioxopiperidin-3-yl)-5-(5-(4-(1-(4-hydroxyphenyl)-2-phenylbut-1-en-1-yl)phenoxy)butyl)hexahydropyrrolo[3,4-c]pyrrol-2(1H)-yl)isoindoline-1,3-dione |

TABLE 1A-continued
Exemplary Compound of the Present Disclosure
| # | Structure | IUPAC Name |
|---|---|---|
| 174 | 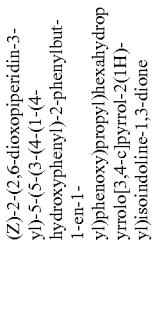 | (Z)-2-(2,6-dioxopiperidin-3-yl)-5-(3-(4-(1-(4-hydroxyphenyl)-2-phenylbut-1-en-1-yl)phenoxy)propyl)hexahydropyrrolo[3,4-c]pyrrol-2(1H)-yl)isoindoline-1,3-dione |
| 175 | 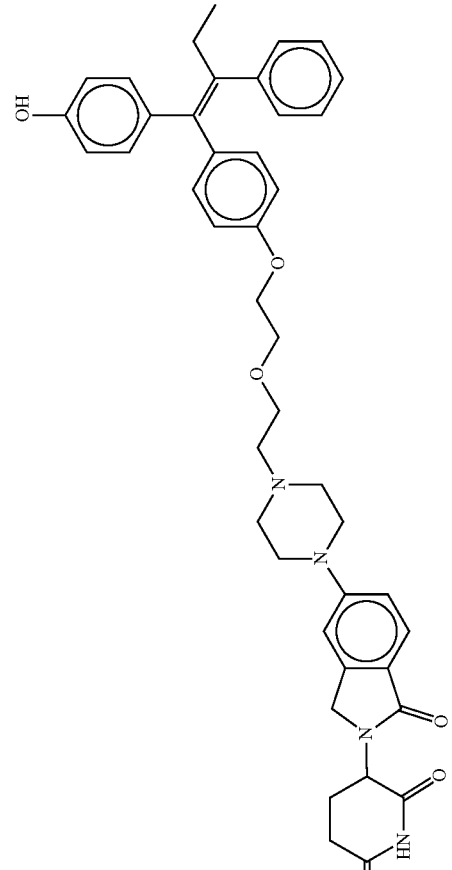 | (Z)-3-(5-(4-(2-(4-(1-(4-hydroxyphenyl)-2-phenylbut-1-en-1-yl)phenoxy)ethoxy)ethyl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 176 | 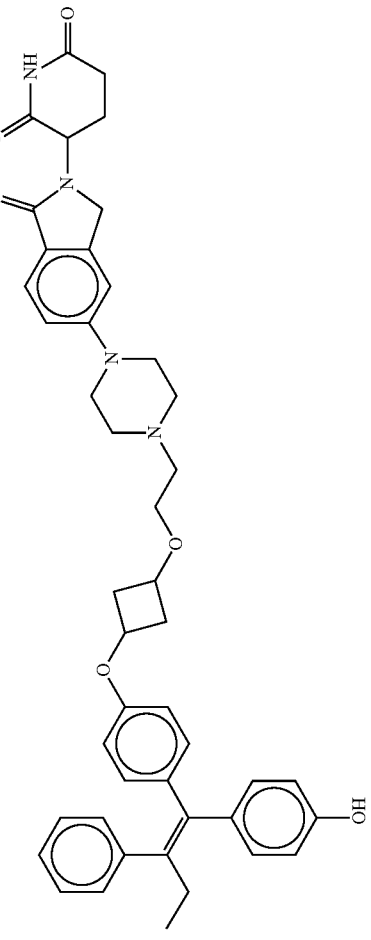 | (Z)-3-(5-(4-(2-(3-(4-(1-(4-hydroxyphenyl)-2-phenylbut-1-en-1-yl)phenoxy)cyclobutoxy)ethyl)piperazin-1-yl)-1-oxoisoindolin-2-yl)piperidine-2,6-dione |
| 177 | 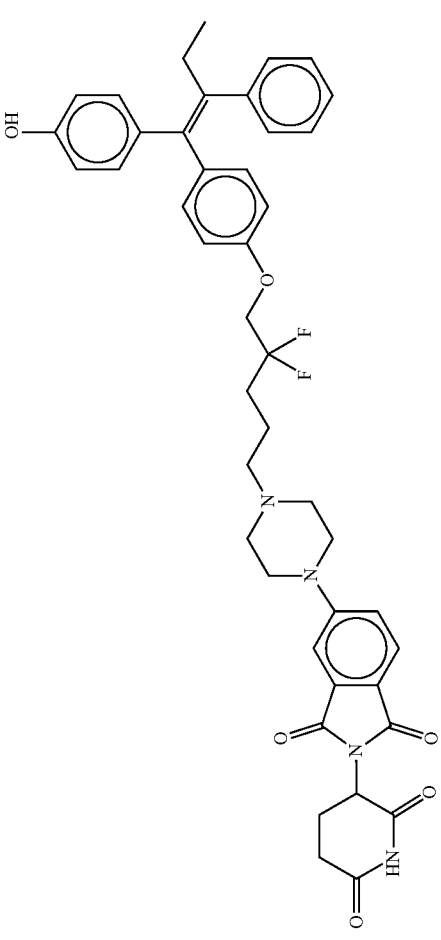 | (Z)-5-(4-(4,4-difluoro-5-(4-(1-(4-hydroxyphenyl)-2-phenylbut-1-en-1-yl)phenoxy)pentyl)piperazin-1-yl)-2-(2,6-dioxopiperidin-3-yl)isoindoline-1,3-dione |

TABLE 1A-continued
Exemplary Compound of the Present Disclosure
| # | Structure | IUPAC Name |
|---|---|---|
| 178 | 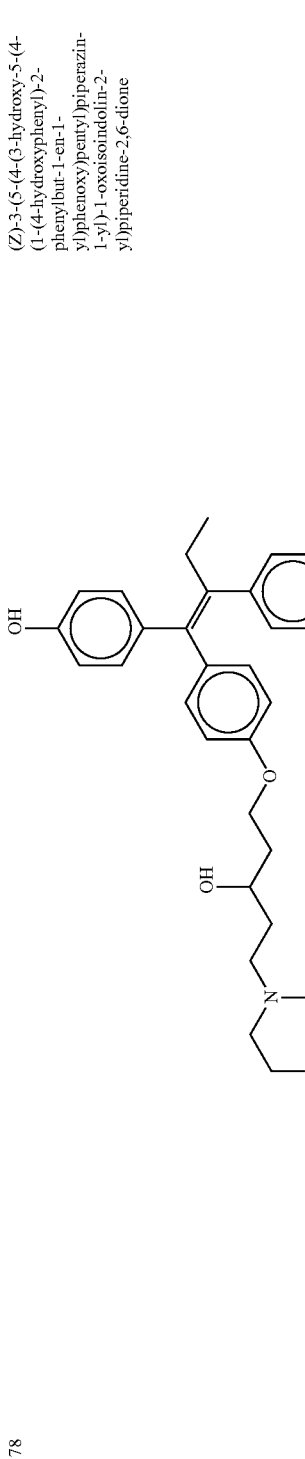 | (Z)-3-(5-(4-(3-hydroxy-5-(4-(1-(4-hydroxyphenyl)-2-phenylbut-1-en-1-yl)phenoxy)pentyl)piperazin-1-yl)-1-oxoisoindolin-2-yl)piperidine-2,6-dione |
| 179 | 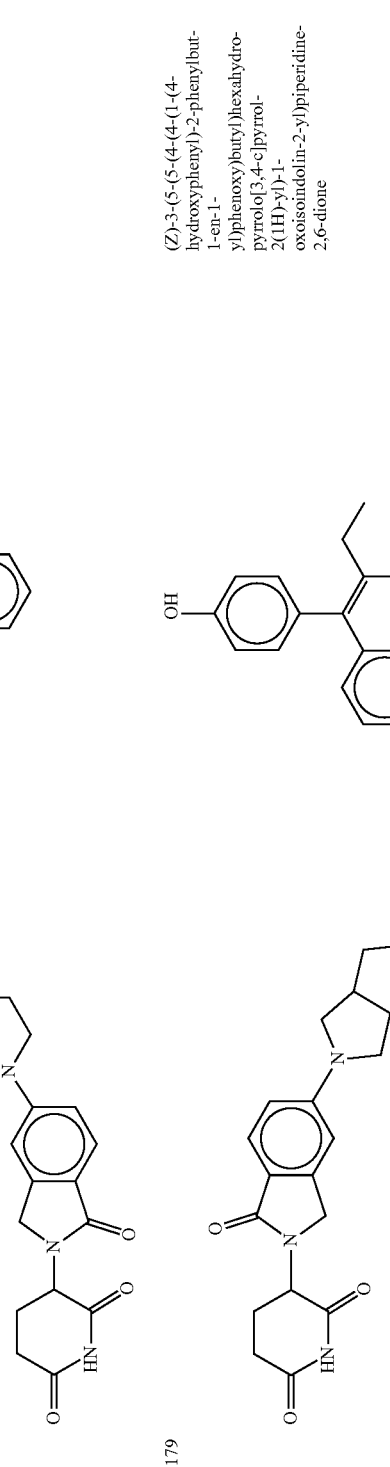 | (Z)-3-(5-(5-(4-(1-(4-hydroxyphenyl)-2-phenylbut-1-en-1-yl)phenoxy)butyl)hexahydropyrrolo[3,4-c]pyrrol-2(1H)-yl)-1-oxoisoindolin-2-yl)piperidine-2,6-dione |

TABLE 1A-continued

Exemplary Compound of the Present Disclosure

| # | Structure | IUPAC Name |
|---|---|---|
| 180 | 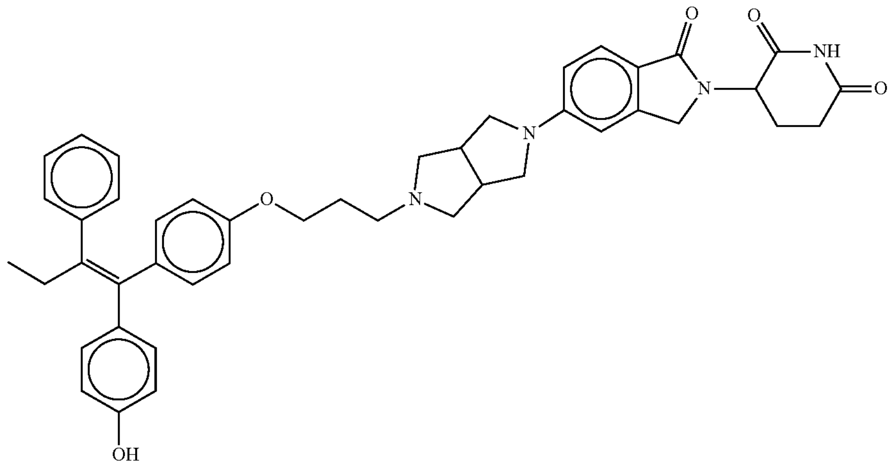 | (Z)-3-(5-(3-(4-(1-(4-hydroxyphenyl)-2-phenylbut-1-en-1-yl)phenoxy)propyl)hexahydropyrrolo[3,4-c]pyrrol-2(1H)-yl)-1-oxoisoindolin-2-yl)piperidine-2,6-dione |
| 181 | 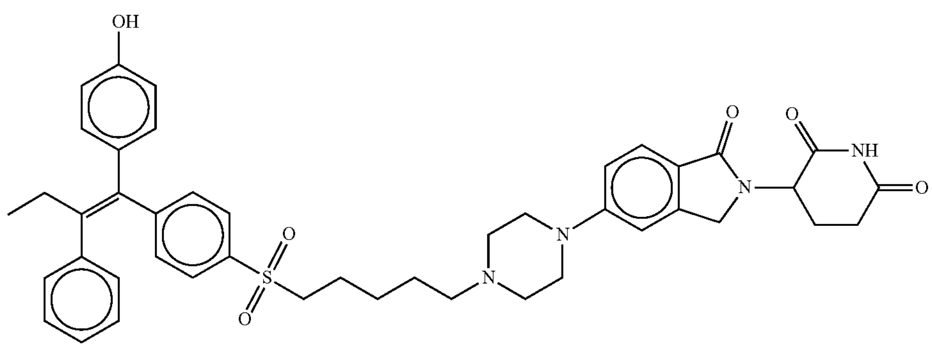 | (Z)-3-(5-(4-(5-((4-(1-(4-hydroxyphenyl)-2-phenylbut-1-en-1-yl)phenyl)sulfonyl)pentyl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 182 | 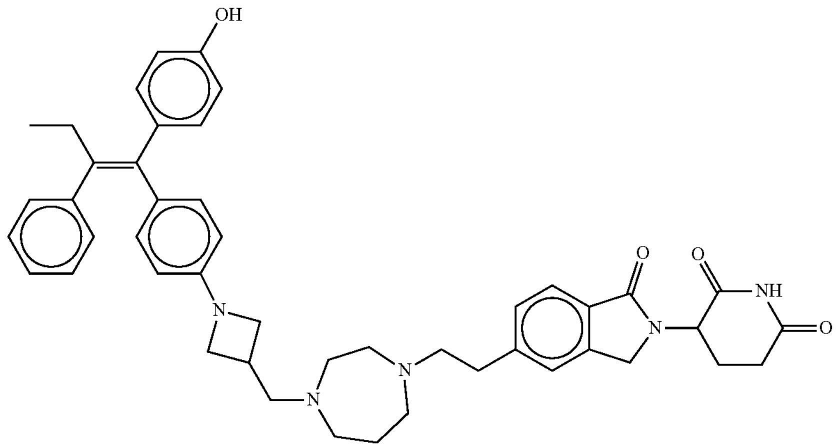 | (E)-3-(5-(2-(4-((1-(4-(1-(4-hydroxyphenyl)-2-phenylbut-1-en-1-yl)phenyl)azetidin-3-yl)methyl)-1,4-diazepan-1-yl)ethyl)-1-oxoisoindolin-2-yl)piperidine-2,6-dione |
| 183 | 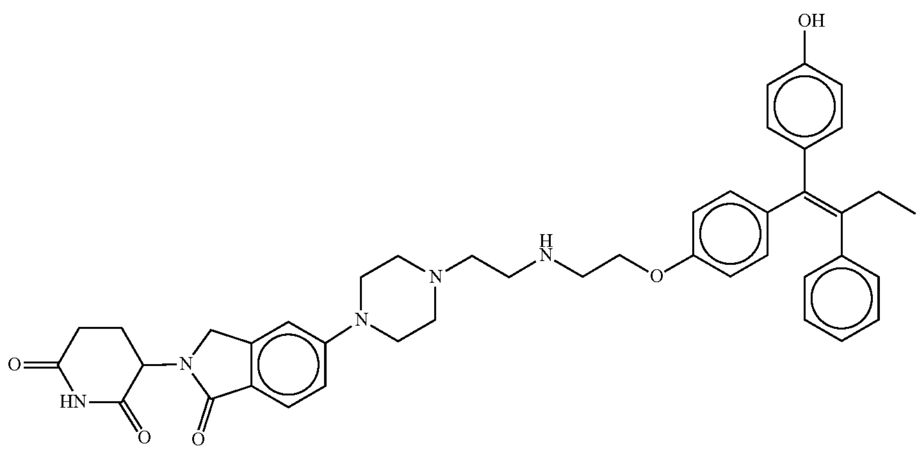 | (Z)-3-(5-(4-(2-(4-(1-(4-hydroxyphenyl)-2-phenylbut-1-en-1-yl)phenoxy)ethyl)amino)ethyl)piperazin-1-yl)-1-oxoisoindolin-2-yl)piperidine-2,6-dione |
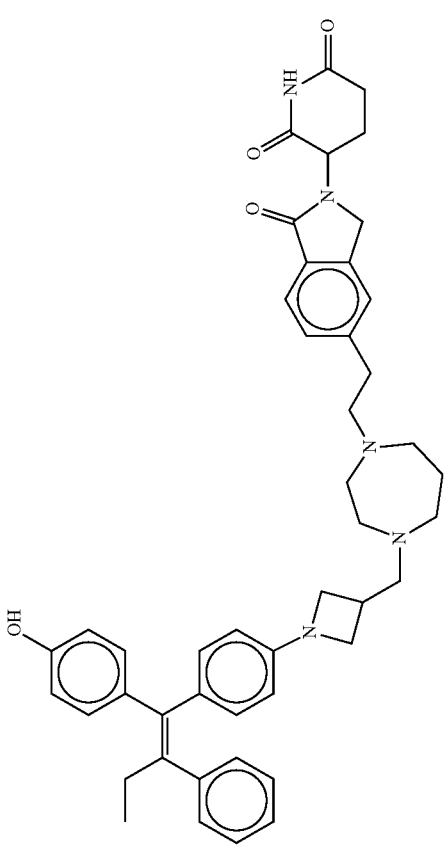

TABLE 1A-continued

Exemplary Compound of the Present Disclosure

| # | Structure | IUPAC Name |
|---|---|---|
| 184a | 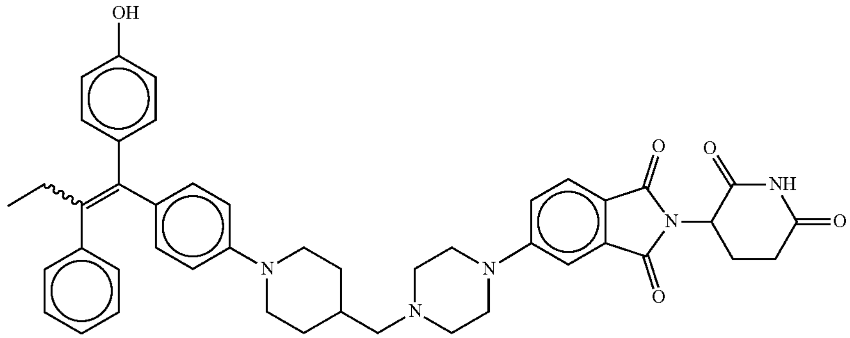 | (E)/(Z)-2-(2,6-dioxopiperidin-3-yl)-5-(4-((1-(4-(4-hydroxyphenyl)-2-phenylbut-1-en-1-yl)phenyl)piperidin-4-yl)methyl)piperazin-1-yl)isoindoline-1,3-dione |
| 184 | 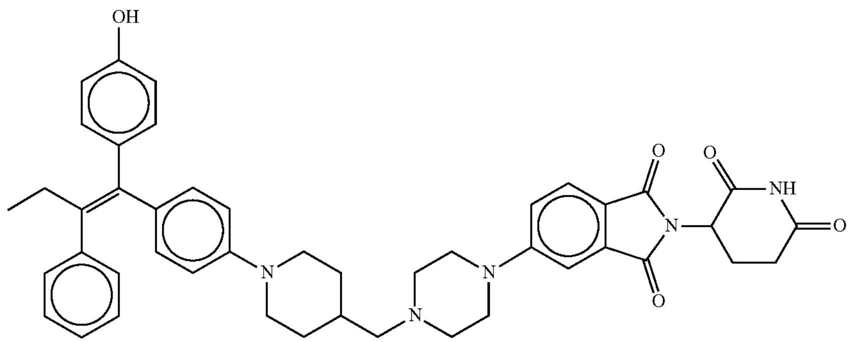 | (E)-2-(2,6-dioxopiperidin-3-yl)-5-(4-((1-(4-(4-hydroxyphenyl)-2-phenylbutyl)piperidin-4-yl)methyl)piperazin-1-yl)isoindoline-1,3-dione |

TABLE 1A-continued

Exemplary Compound of the Present Disclosure

| # | Structure | IUPAC Name |
|---|---|---|
| 185a | 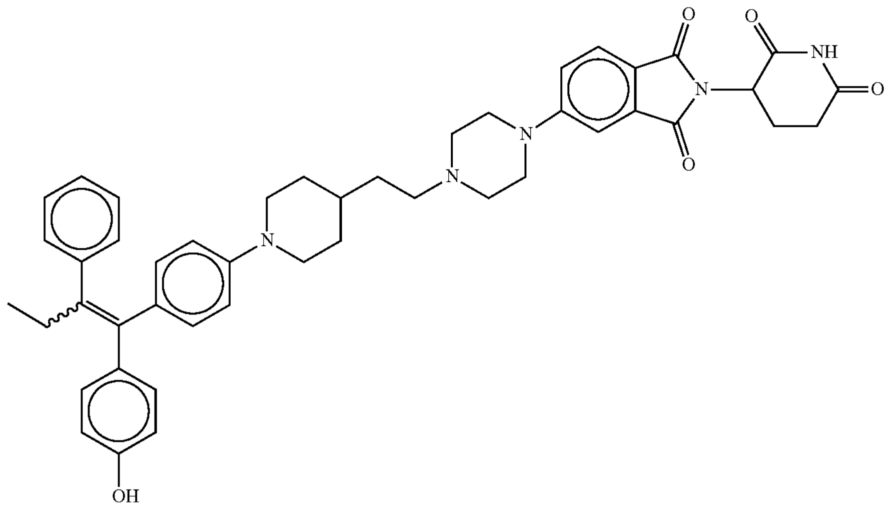 | (E)/(Z)-2-(2,6-dioxopiperidin-3-yl)-5-(4-(2-(1-(4-(1-(4-hydroxyphenyl)-2-phenylbut-1-en-1-yl)phenyl)piperidin-4-yl)ethyl)piperazin-1-yl)isoindoline-1,3-dione |
| 185 | 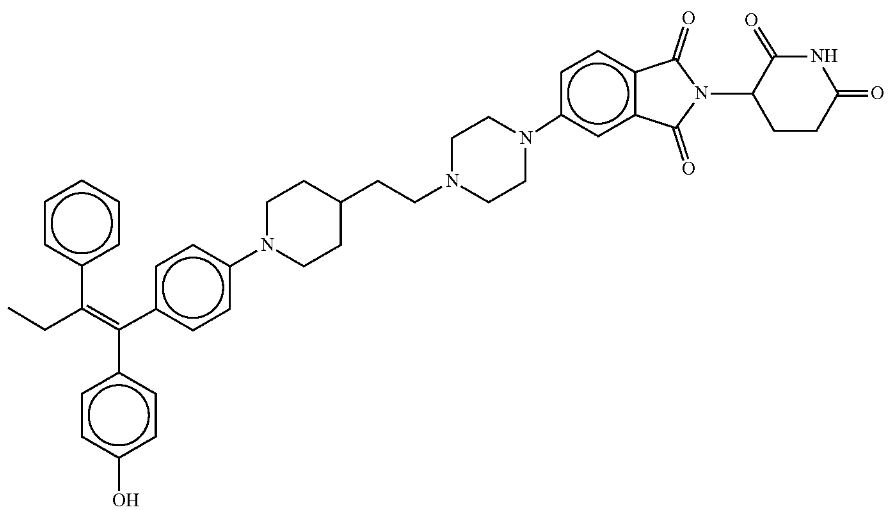 | (E)-2-(2,6-dioxopiperidin-3-yl)-5-(4-(2-(1-(4-(1-(4-hydroxyphenyl)-2-phenylbut-1-en-1-yl)phenyl)piperidin-4-yl)ethyl)piperazin-1-yl)isoindoline-1,3-dione |

TABLE 1A-continued
Exemplary Compound of the Present Disclosure
| # | Structure | IUPAC Name |
|---|---|---|
| 186 | 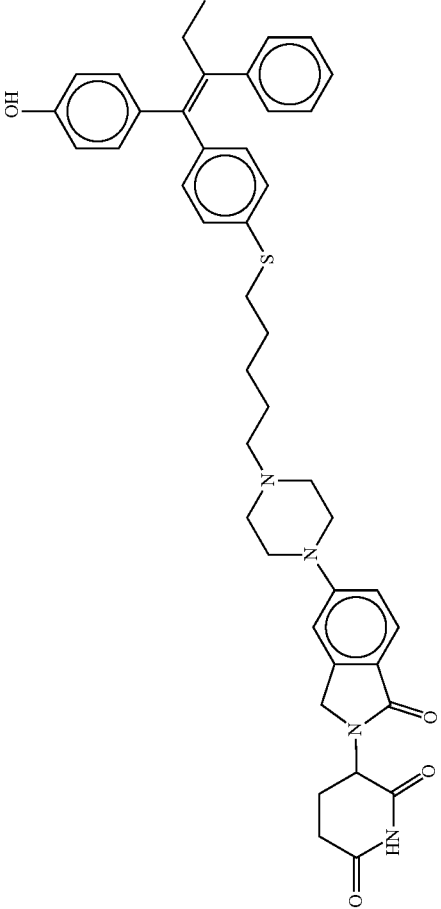 | (Z)-3-(5-(4-(5-((4-(1-(4-hydroxyphenyl)-2-phenylbut-1-en-1-yl)phenyl)thio)pentyl)piperazin-1-yl)-1-oxoisoindolin-2-yl)piperidine-2,6-dione |
| 187 | 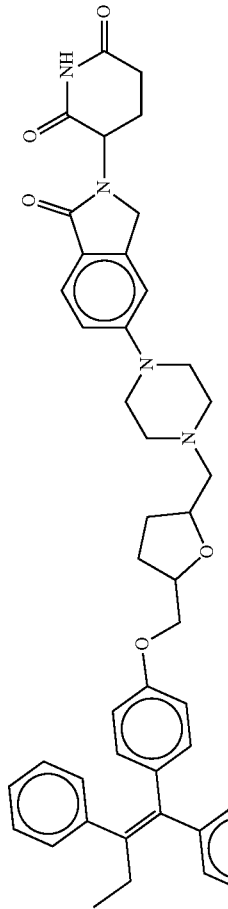 | (Z)-3-(5-(4-((5-((4-(1-(4-hydroxyphenyl)-2-phenylbut-1-en-1-yl)phenoxy)methyl)tetrahydrofuran-2-yl)methyl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 188 | 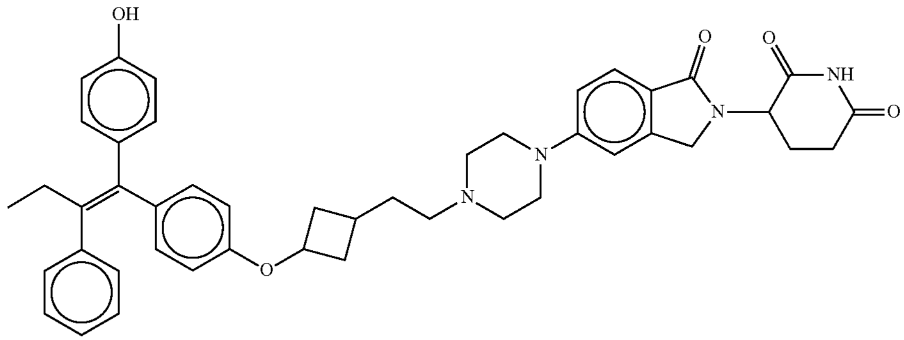 | (Z)-3-(5-(4-(2-(3-(4-(1-(4-hydroxyphenyl)-2-phenylbut-1-en-1-yl)phenoxy)cyclobutyl)ethyl)piperazin-1-yl)-1-oxoisoindolin-2-yl)piperidine-2,6-dione |
| 189 | 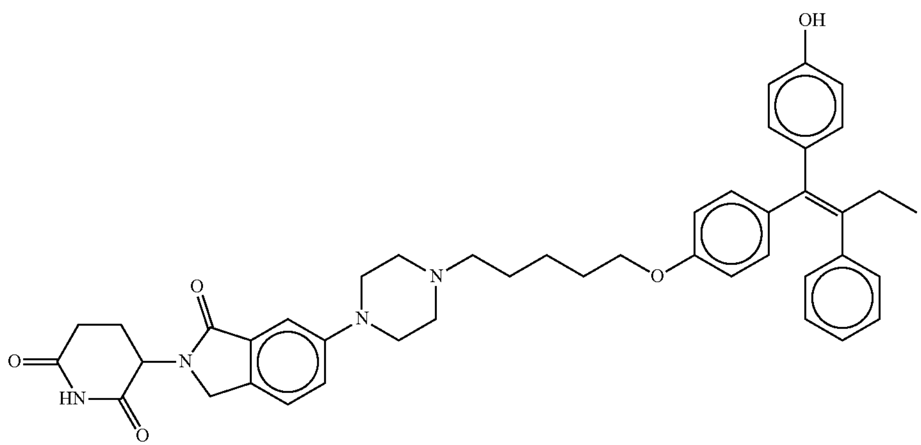 | (Z)-3-(6-(4-(5-(4-(1-(4-hydroxyphenyl)-2-phenylbut-1-en-1-yl)phenoxy)pentyl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 190 | 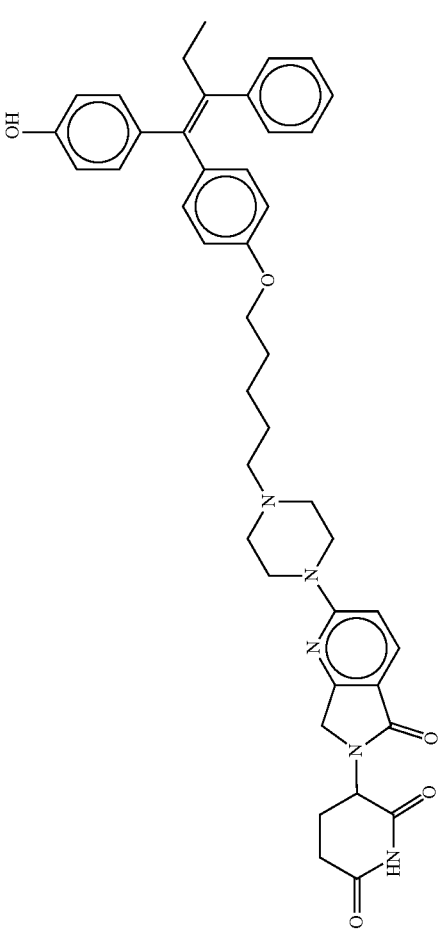 | (Z)-3-(2-(4-(5-(4-(1-(4-hydroxyphenyl)-2-phenylbut-1-en-1-yl)phenoxy)pentyl)piperazin-1-yl)-5-oxo-5,7-dihydro-6H-pyrrolo[3,4-b]pyridin-6-yl)piperidine-2,6-dione |
| 191 | 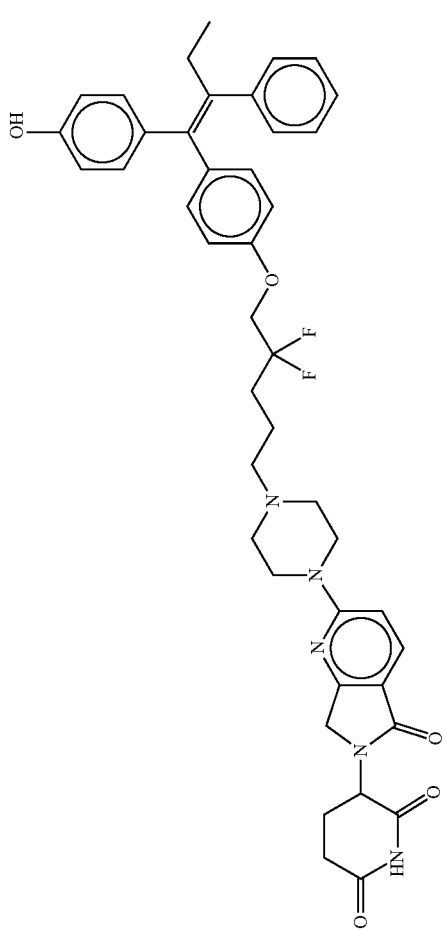 | (Z)-3-(2-(4-(4,4-difluoro-5-(4-(1-(4-hydroxyphenyl)-2-phenylbut-1-en-1-yl)phenoxy)pentyl)piperazin-1-yl)-5-oxo-5,7-dihydro-6H-pyrrolo[3,4-b]pyridin-6-yl)piperidine-2,6-dione |

TABLE 1A-continued

Exemplary Compound of the Present Disclosure

| # | Structure | IUPAC Name |
|---|---|---|
| 192 | 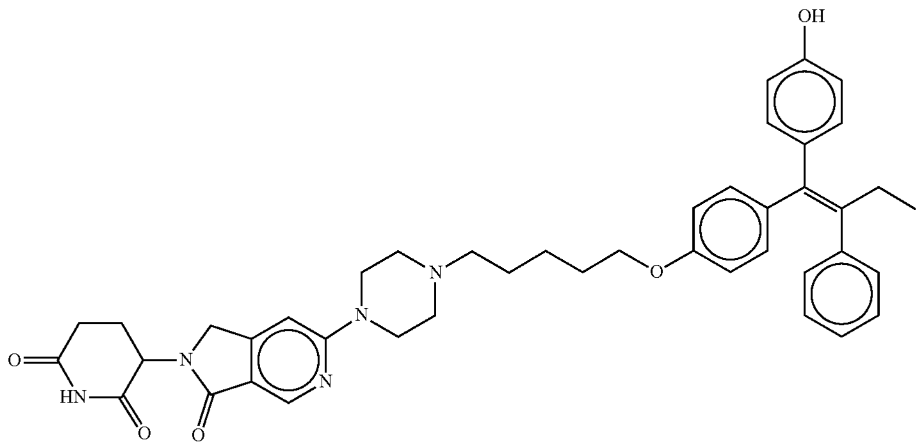 | (Z)-3-(6-(4-(5-(4-(1-(4-hydroxyphenyl)-2-phenylbut-1-en-1-yl)phenoxy)pentyl)piperazin-1-yl)-3-oxo-1,3-dihydro-2H-pyrrolo[3,4-c]pyridin-2-yl)piperidine-2,6-dione |
| 193 | 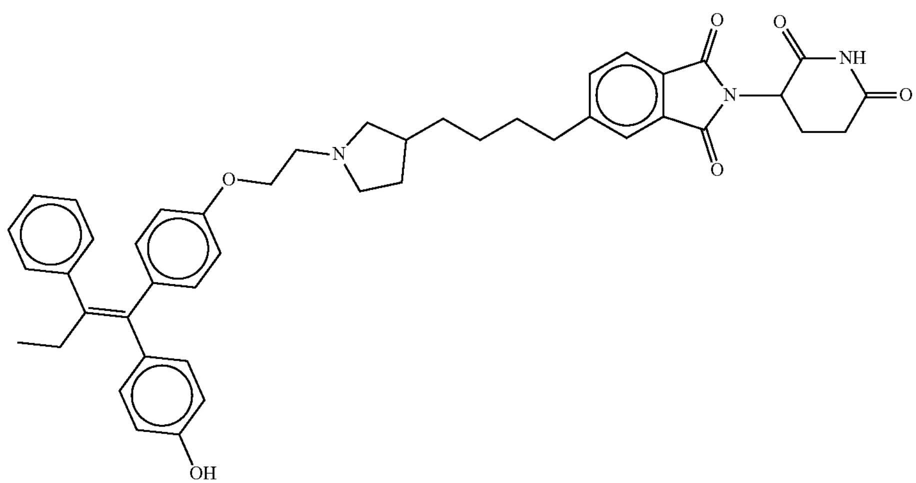 | (Z)-2-(2,6-dioxopiperidin-3-yl)-5-(4-(1-(2-(4-(1-(4-hydroxyphenyl)-2-phenylbut-1-en-1-yl)phenoxy)ethyl)pyrrolidin-3-yl)butyl)isoindoline-1,3-dione |

TABLE 1A-continued

Exemplary Compound of the Present Disclosure

| # | Structure | IUPAC Name |
|---|---|---|
| 194 | 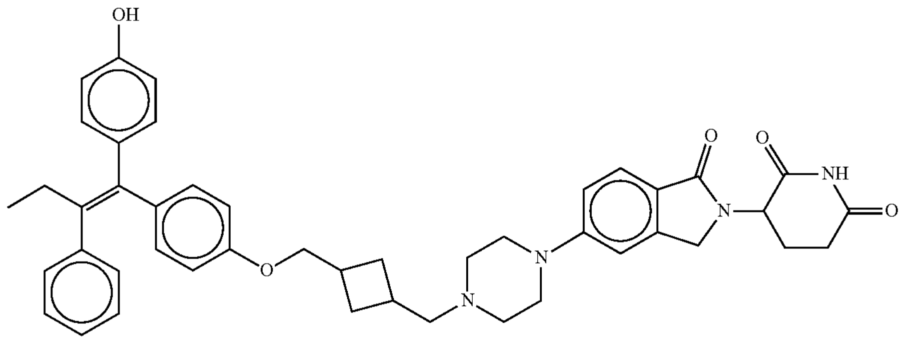 | (Z)-3-(5-(4-((3-((4-(1-(4-hydroxyphenyl)-2-phenylbut-1-en-1-yl)phenoxy)methyl)cyclobutyl)methyl)piperazin-1-yl)-1-oxoisoindolin-2-yl)piperidine-2,6-dione |
| 195 | 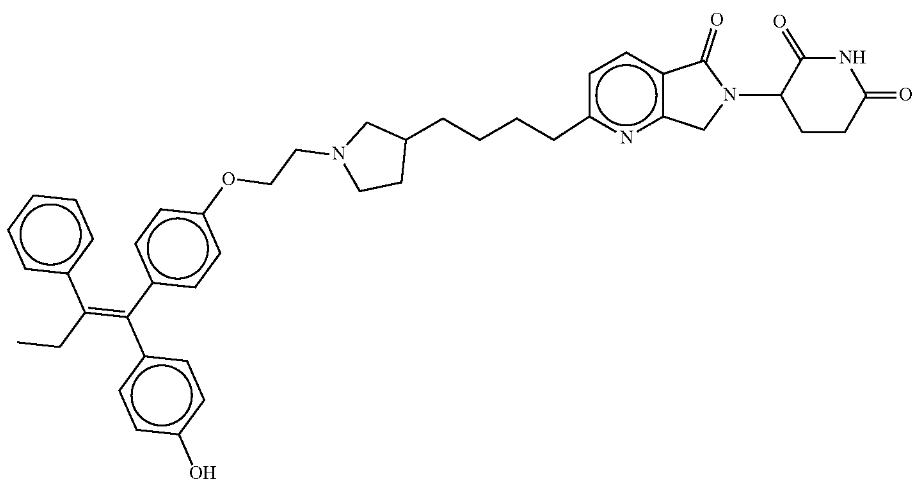 | (Z)-3-(2-(4-(1-(2-(4-(1-(4-hydroxyphenyl)-2-phenylbut-1-en-1-yl)phenoxy)ethyl)pyrrolidin-3-yl)butyl)-5-oxo-5,7-dihydro-6H-pyrrolo[3,4-b]pyridin-6-yl)piperidine-2,6-dione |

TABLE 1A-continued
Exemplary Compound of the Present Disclosure
| # | Structure | IUPAC Name |
|---|---|---|
| 196 | 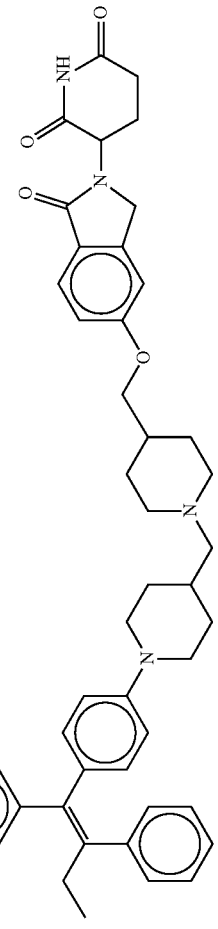 | (E)-3-(5-((1-((1-(4-(4-(1-(4-hydroxyphenyl)-2-phenylbut-1-en-1-yl)phenyl)piperidin-4-yl)methyl)piperidin-4-yl)methoxy)-1-oxoisoindolin-2-yl)piperidine-2,6-dione |
| 197 | 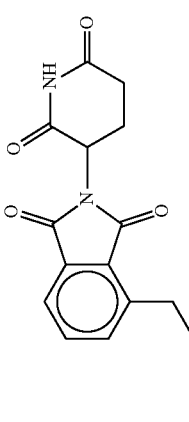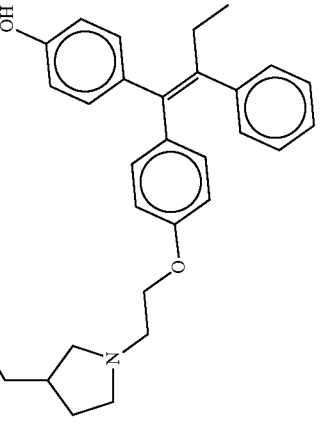 | (Z)-2-(2,6-dioxopiperidin-3-yl)-4-(4-(1-(2-(4-(1-(4-hydroxyphenyl)-2-phenylbut-1-en-1-yl)phenoxy)ethyl)pyrrolidin-3-yl)butyl)isoindoline-1,3-dione |

TABLE 1A-continued

Exemplary Compound of the Present Disclosure

| # | Structure | IUPAC Name |
|---|---|---|
| 198 | 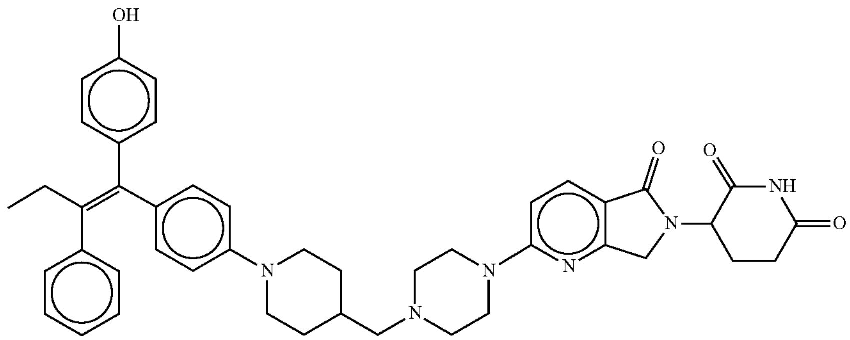 | (E)-3-(2-(4-(1-(4-(1-(4-hydroxyphenyl)-2-phenylbut-1-en-1-yl)phenyl)piperidin-4-yl)methyl)piperazin-1-yl)-5-oxo-5,7-dihydro-6H-pyrrolo[3,4-b]pyridin-6-yl)piperidine-2,6-dione |
| 199 | 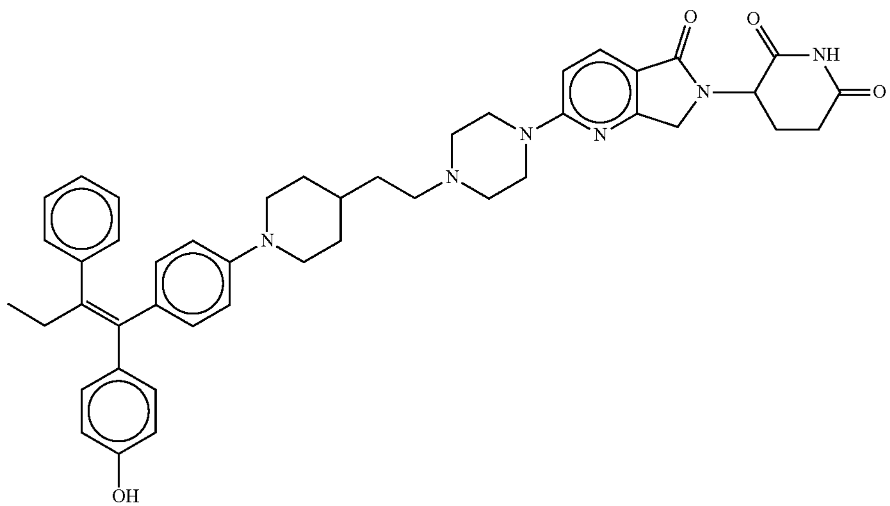 | (E)-3-(2-(4-(2-(1-(4-(1-(4-hydroxyphenyl)-2-phenylbut-1-en-1-yl)phenyl)piperidin-4-yl)ethyl)piperazin-1-yl)-5-oxo-5,7-dihydro-6H-pyrrolo[3,4-b]pyridin-6-yl)piperidine-2,6-dione |

TABLE 1A-continued

Exemplary Compound of the Present Disclosure

| # | Structure | IUPAC Name |
|---|---|---|
| 200 | 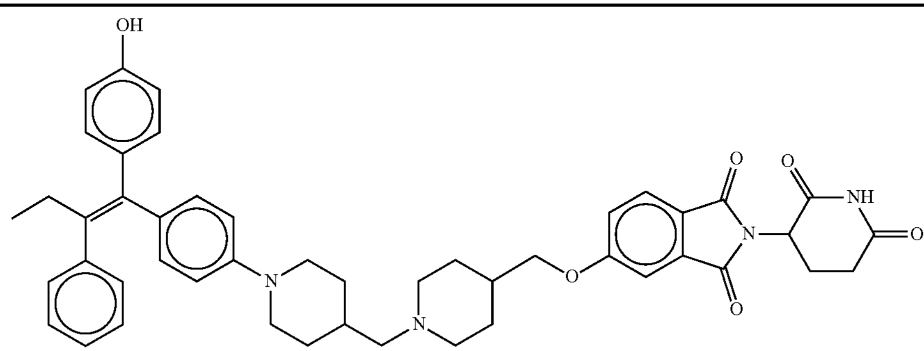 | (E)-2-(2,6-dioxopiperidin-3-yl)-5-((1-(4-(1-(4-hydroxyphenyl)-2-phenylbut-1-en-1-yl)phenyl)piperidin-4-yl)methyl)piperidin-4-yl)methoxy)isoindoline-1,3-dione |
| 201 | 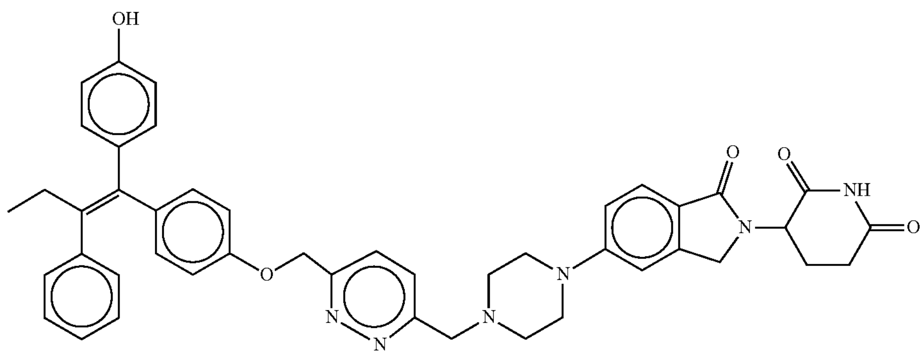 | (Z)-3-(5-(4-((6-((4-(1-(4-hydroxyphenyl)-2-phenylbut-1-en-1-yl)phenoxy)methyl)pyridazin-3-yl)methyl)piperazin-1-yl)-1-oxoisoindolin-2-yl)piperidine-2,6-dione |
| 202 | 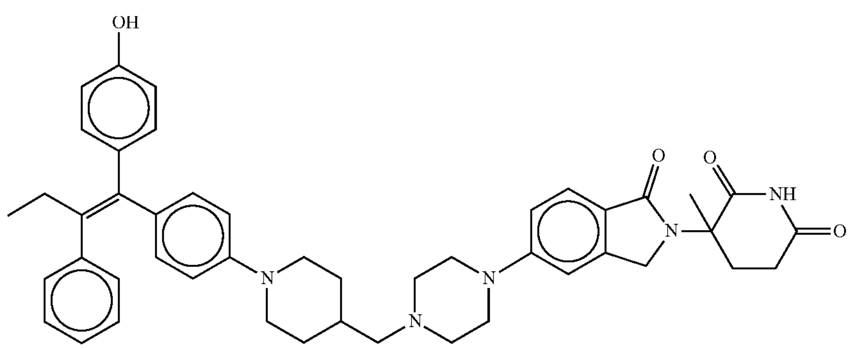 | (E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)-3-methylpiperidine-2,6-dione |

TABLE 1A-continued

Exemplary Compound of the Present Disclosure

| # | Structure | IUPAC Name |
|---|---|---|
| 203 | 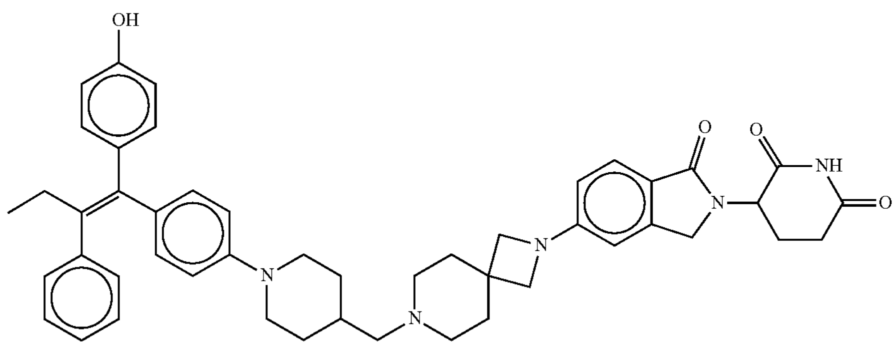 | (E)-3-(5-(7-((1-(4-(1-(4-hydroxyphenyl)-2-phenylbut-1-en-1-yl)phenyl)piperidin-4-yl)methyl)-2,7-diazaspiro[3.5]nonan-2-yl)-1-oxoisoindolin-2-yl)piperidine-2,6-dione |
| 204 | 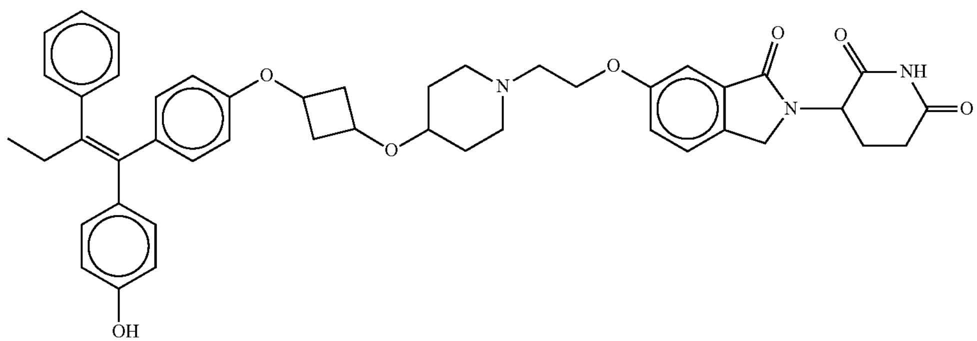 | (Z)-3-(6-(2-(4-(3-(4-(1-(4-hydroxyphenyl)-2-phenylbut-1-en-1-yl)phenoxy)cyclobutoxy)piperidin-1-yl)ethoxy)-1-oxoisoindolin-2-yl)piperidine-2,6-dione |

TABLE 1A-continued
Exemplary Compound of the Present Disclosure
| # | Structure | IUPAC Name |
|---|---|---|
| 205 | 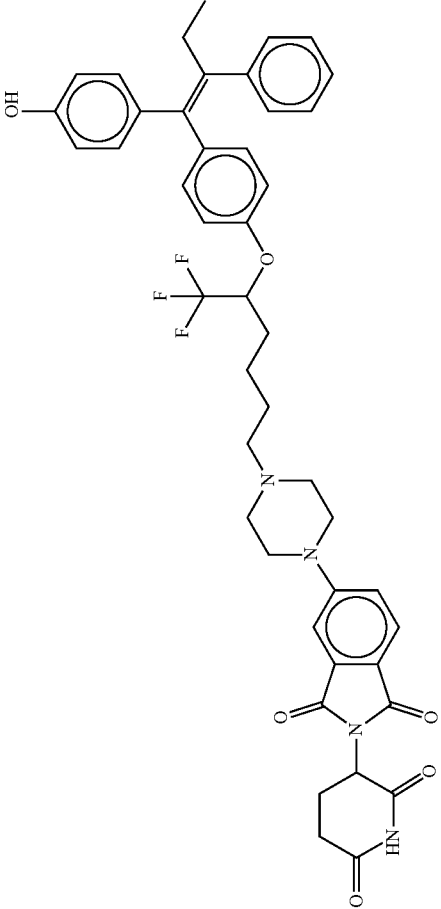 | (Z)-2-(2,6-dioxopiperidin-3-yl)-5-(4-(6,6,6-trifluoro-5-(4-(1-(4-hydroxyphenyl)-2-phenylbut-1-en-1-yl)phenoxy)hexyl)piperazin-1-yl)isoindoline-1,3-dione |
| 206 | 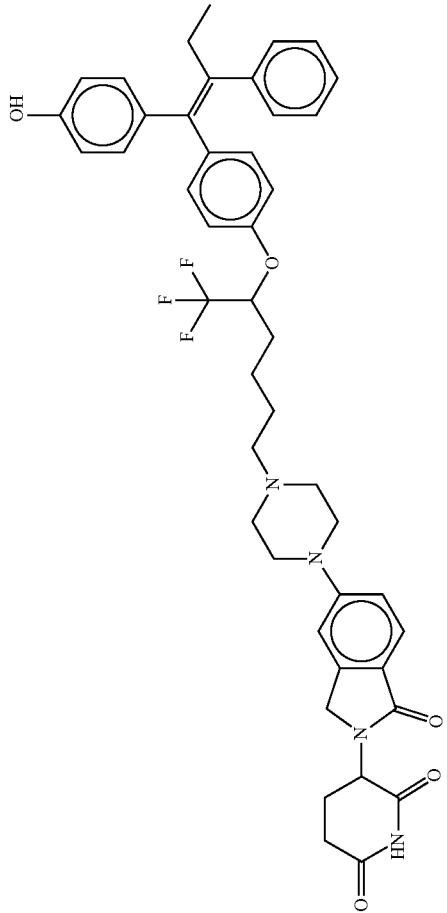 | (Z)-3-(1-oxo-5-(4-(6,6,6-trifluoro-5-(4-(1-(4-hydroxyphenyl)-2-phenylbut-1-en-1-yl)phenoxy)hexyl)piperazin-1-yl)isoindolin-2-yl)piperidine-2,6-dione |

TABLE 1A-continued
Exemplary Compound of the Present Disclosure
| # | Structure | IUPAC Name |
|---|---|---|
| 207 | 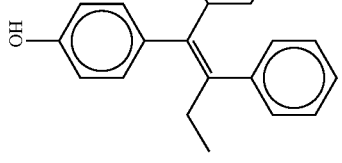 | (Z)-3-(5-(4-((5-((4-(1-(4-hydroxyphenyl)-2-phenylbut-1-en-1-yl)phenoxy)methyl)pyridin-2-yl)methyl)piperazin-1-yl)-1-oxoisoindolin-2-yl)piperidine-2,6-dione |
| 208 | 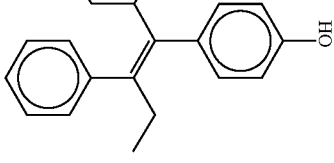 | (E)-3-(6-(4-((1-(4-(1-(4-hydroxyphenyl)-2-phenylbut-1-en-1-yl)phenyl)piperidin-4-yl)methyl)piperazin-1-yl)-3-oxo-1,3-dihydro-2H-pyrrolo[3,4-c]pyridin-2-yl)piperidine-2,6-dione |

TABLE 1A-continued

Exemplary Compound of the Present Disclosure

| # | Structure | IUPAC Name |
|---|---|---|
| 209 | 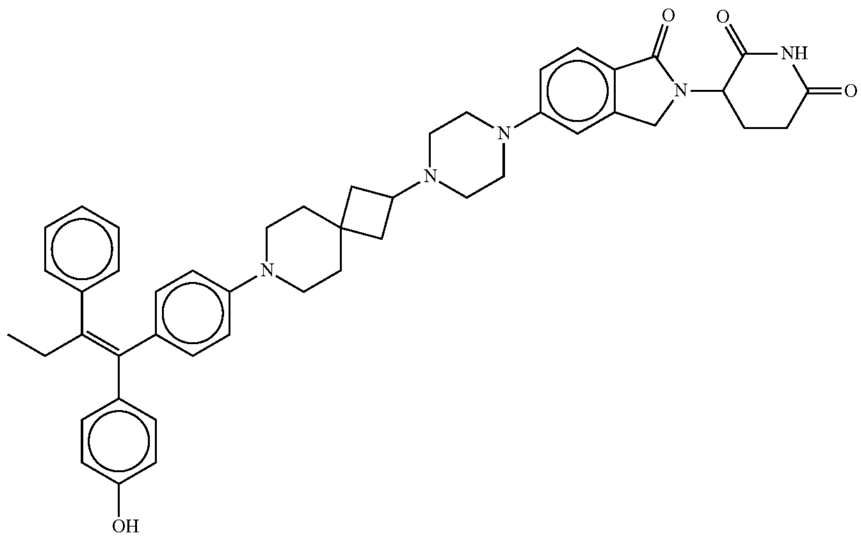 | (E)-3-(5-(4-(7-(4-(1-(4-hydroxyphenyl)-2-phenylbut-1-en-1-yl)phenyl)-7-azaspiro[3.5]nonan-2-yl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 210 | 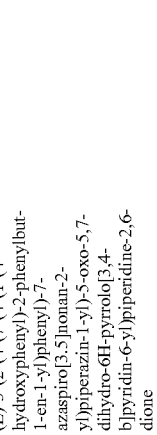 | (E)-3-(2-(4-(7-(4-(1-(4-hydroxyphenyl)-2-phenylbut-1-en-1-yl)phenyl)-7-azaspiro[3.5]nonan-2-yl)piperazin-1-yl)-5-oxo-5,7-dihydro-6H-pyrrolo[3,4-b]pyridin-6-yl)piperidine-2,6-dione |
| 211 | 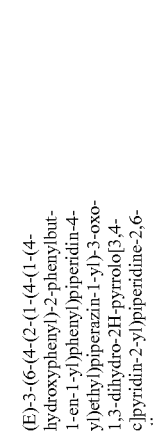 | (E)-3-(6-(4-(2-(1-(4-(1-(4-hydroxyphenyl)-2-phenylbut-1-en-1-yl)phenyl)piperidin-4-yl)ethyl)piperazin-1-yl)-3-oxo-1,3-dihydro-2H-pyrrolo[3,4-c]pyridin-2-yl)piperidine-2,6-dione |

TABLE 1A-continued
Exemplary Compound of the Present Disclosure
| # | Structure | IUPAC Name |
|---|---|---|
| 212 | 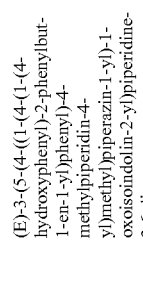 | (E)-3-(5-(4-((1-(4-(1-(4-hydroxyphenyl)-2-phenylbut-1-en-1-yl)phenyl)-4-methylpiperidin-4-yl)methyl)piperazin-1-yl)-1-oxoisoindolin-2-yl)piperidine-2,6-dione |
| 213 | 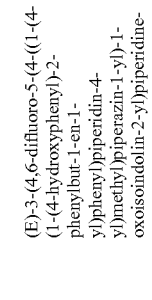 | (E)-3-(4,6-difluoro-5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |

TABLE 1A-continued

Exemplary Compound of the Present Disclosure

| # | Structure | IUPAC Name |
|---|---|---|
| 214 | 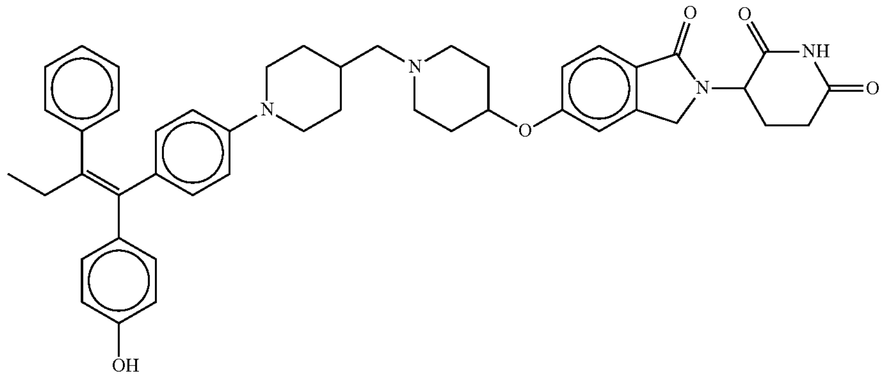 | (E)-3-(5-((1-((1-(4-(1-(4-hydroxyphenyl)-2-phenylbut-1-en-1-yl)phenyl)piperidin-4-yl)methyl)piperidin-4-yl)oxy)-1-oxoisoindolin-2-yl)piperidine-2,6-dione |
| 215 | 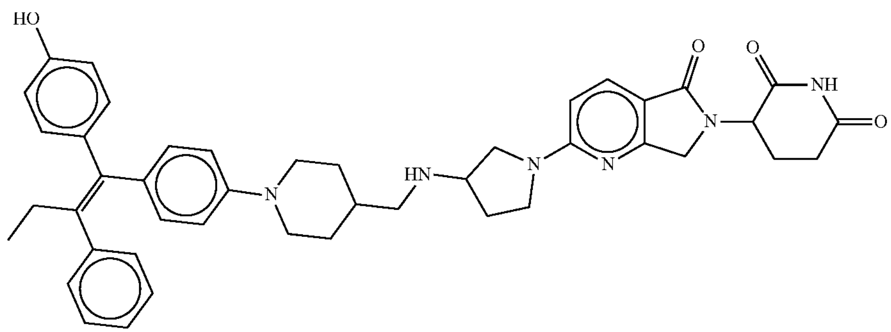 | (E)-3-(2-(3-(((1-(4-(1-(4-hydroxyphenyl)-2-phenylbut-1-en-1-yl)phenyl)piperidin-4-yl)methyl)amino)pyrrolidin-1-yl)-5-oxo-5,7-dihydro-6H-pyrrolo[3,4-b]pyridin-6-yl)piperidine-2,6-dione |

TABLE 1A-continued

Exemplary Compound of the Present Disclosure

| # | Structure | IUPAC Name |
|---|---|---|
| 216 | 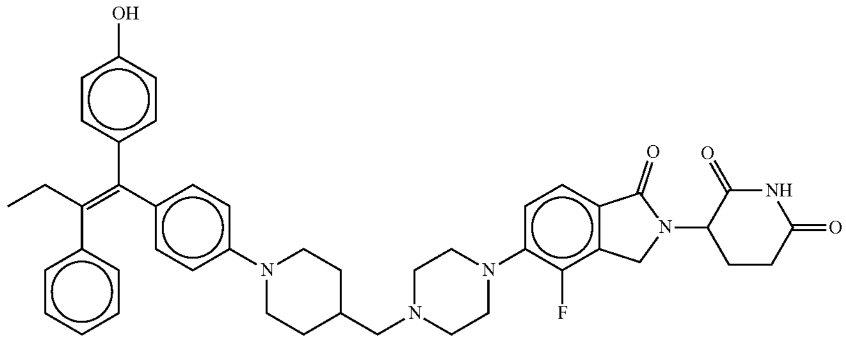 | (E)-3-(4-fluoro-5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |
| 217 | 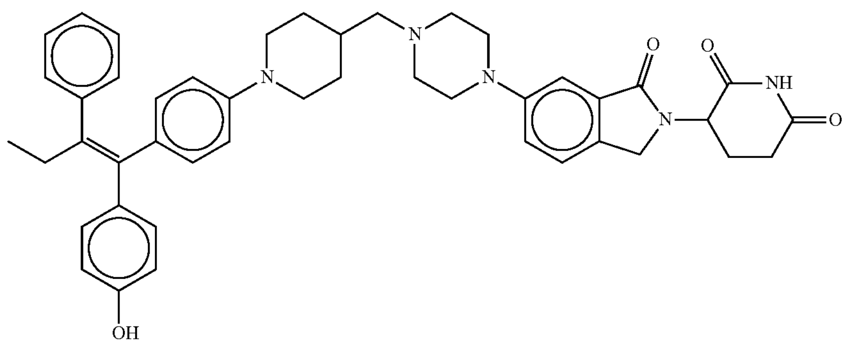 | (E)-3-(6-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |
| 218 | 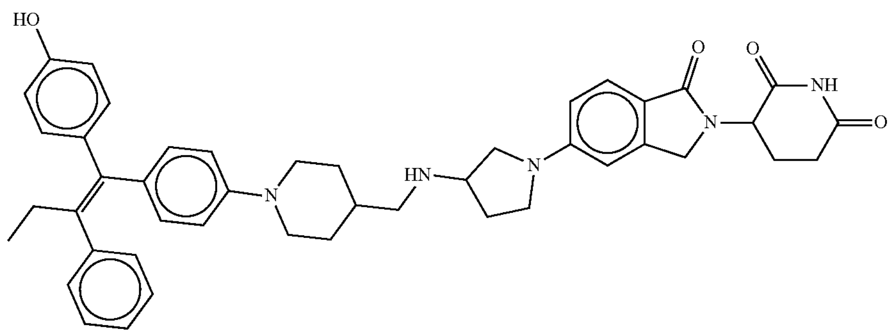 | (E)-3-(5-(3-(((1-(4-(1-(4-hydroxyphenyl)-2-phenylbut-1-en-1-yl)phenyl)piperidin-4-yl)methyl)amino)pyrrolidin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 219 | 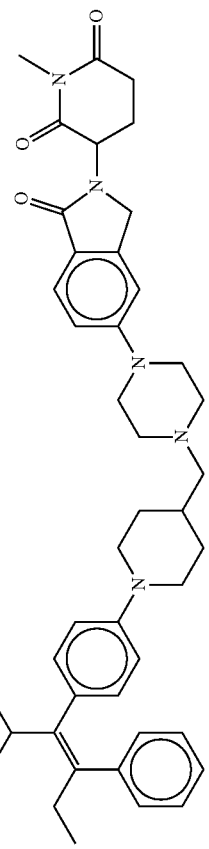 | (E)-3-(5-(4-((1-(4-(1-(4-hydroxyphenyl)-2-phenylbut-1-en-1-yl)phenyl)piperidin-4-yl)methyl)piperazin-1-yl)-1-oxoisoindolin-2-yl)-1-methylpiperidine-2,6-dione |
| 220 | 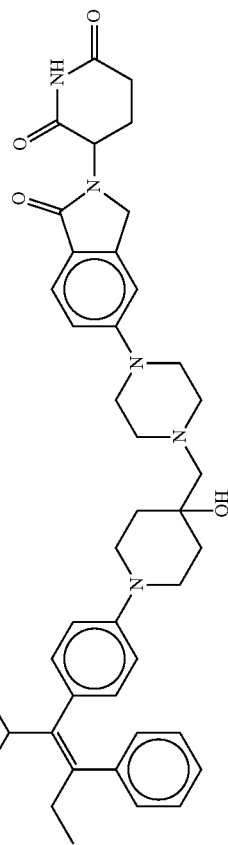 | (E)-3-(5-(4-((4-hydroxy-1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |

TABLE 1A-continued
Exemplary Compound of the Present Disclosure
| # | Structure | IUPAC Name |
|---|-----------|------------|
| 221 | 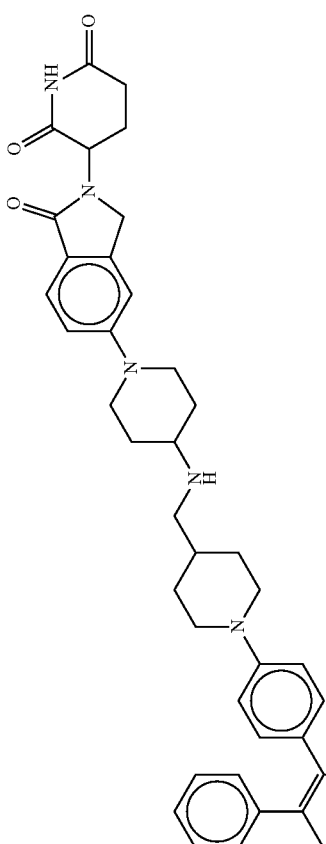 | (E)-3-(5-(4-(((1-(4-(4-hydroxyphenyl)-2-phenylbut-1-en-1-yl)phenyl)piperidin-4-yl)methyl)amino)piperidin-1-yl)-1-oxoisoindolin-2-yl)piperidine-2,6-dione |
| 222 | 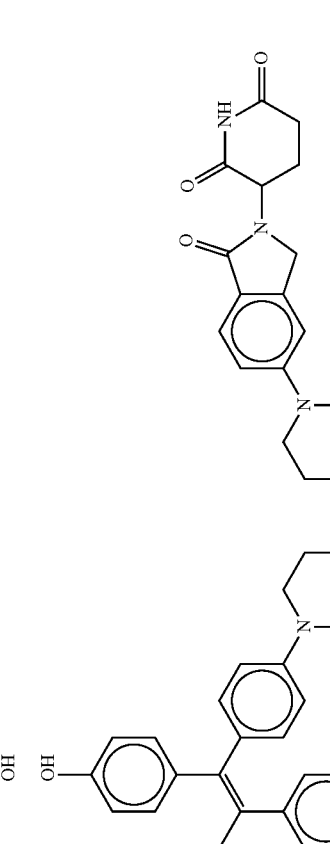 | (E)-3-(5-(4-(1-(4-(4-hydroxyphenyl)-2-phenylbut-1-en-1-yl)phenyl)piperidin-4-yl)amino)piperidin-1-yl)-1-oxoisoindolin-2-yl)piperidine-2,6-dione |

TABLE 1A-continued
Exemplary Compound of the Present Disclosure
| # | Structure | IUPAC Name |
|---|---|---|
| 223 | 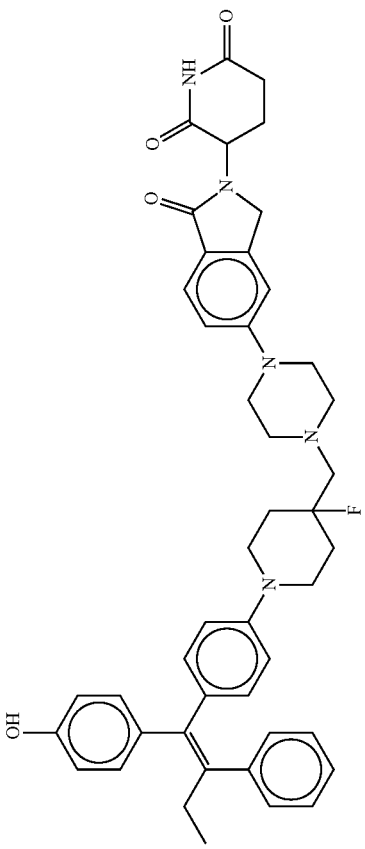 | (E)-3-(5-(4-((4-fluoro-1-(4-(1-(4-hydroxyphenyl)-2-phenylbut-1-en-1-yl)phenyl)piperidin-4-yl)methyl)piperazin-1-yl)-1-oxoisoindolin-2-yl)piperidine-2,6-dione |
| 224 | 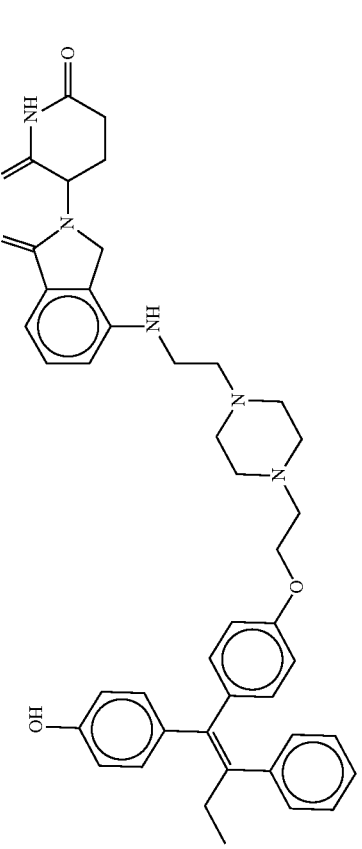 | (Z)-3-(4-((2-(4-(2-(4-(1-(4-hydroxyphenyl)-2-phenylbut-1-en-1-yl)phenoxy)ethyl)piperazin-1-yl)ethyl)amino)-1-oxoisoindolin-2-yl)piperidine-2,6-dione |

TABLE 1A-continued

Exemplary Compound of the Present Disclosure

| # | Structure | IUPAC Name |
|---|---|---|
| 225 | 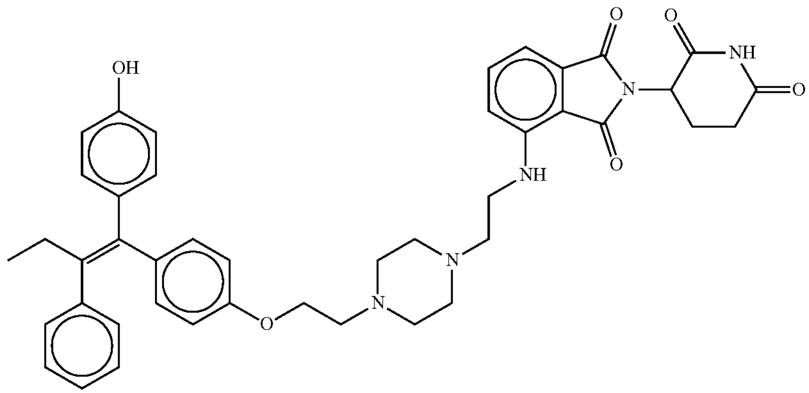 | (Z)-2-(2,6-dioxopiperidin-3-yl)-4-((2-(4-(2-(4-(1-(4-hydroxyphenyl)-2-phenylbut-1-en-1-yl)phenoxy)ethyl)piperazin-1-yl)ethyl)amino)isoindoline-1,3-dione |
| 226 | 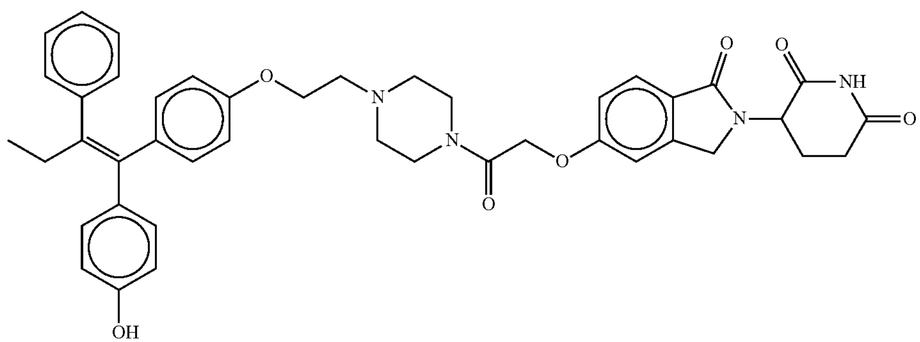 | (Z)-3-(5-(2-(4-(2-(4-(1-(4-hydroxyphenyl)-2-phenylbut-1-en-1-yl)phenoxy)ethyl)piperazin-1-yl)-2-oxoethoxy)-1-oxoisoindolin-2-yl)piperidine-2,6-dione |

TABLE 1A-continued
Exemplary Compound of the Present Disclosure
| # | Structure | IUPAC Name |
|---|---|---|
| 227 | 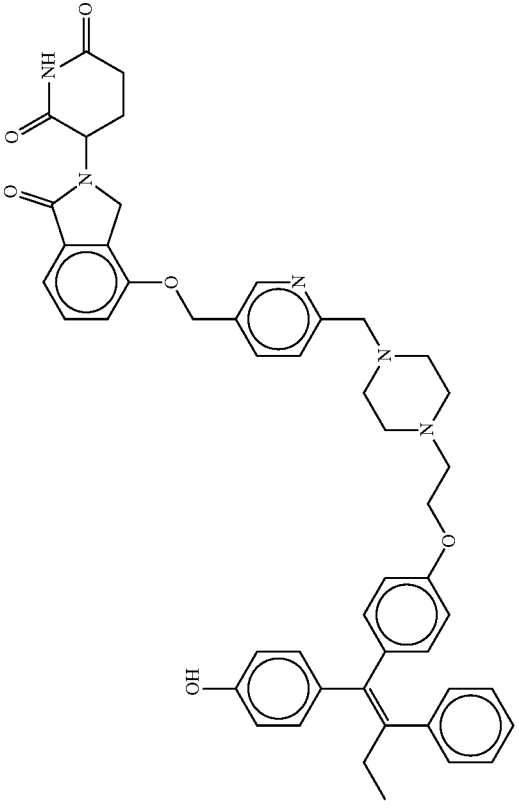 | (Z)-3-(4-((6-((4-(2-(4-(1-(4-hydroxyphenyl)-2-phenylbut-1-en-1-yl)phenoxy)ethyl)piperazin-1-yl)methyl)pyridin-3-yl)methoxy)-1-oxoisoindolin-2-yl)piperidine-2,6-dione |
| 228 | 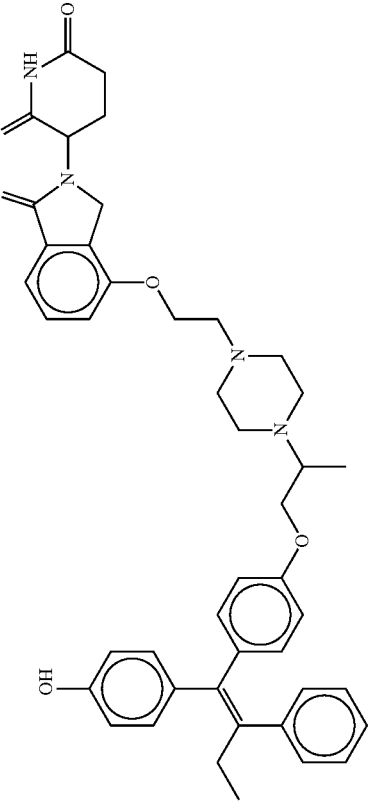 | (Z)-3-(4-(2-(4-(1-(4-(1-(4-hydroxyphenyl)-2-phenylbut-1-en-1-yl)phenoxy)propan-2-yl)piperazin-1-yl)ethoxy)-1-oxoisoindolin-2-yl)piperidine-2,6-dione |

TABLE 1A-continued

Exemplary Compound of the Present Disclosure

| # | Structure | IUPAC Name |
|---|---|---|
| 229 | 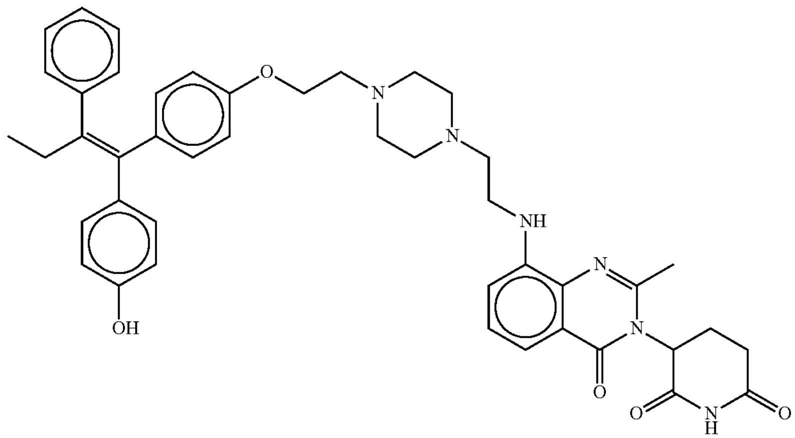 | (Z)-3-(8-((2-(4-(2-(4-(1-(4-hydroxyphenyl)-2-phenylbut-1-en-1-yl)phenoxy)ethyl)piperazin-1-yl)ethyl)amino)-2-methyl-4-oxoquinazolin-3(4H)-yl)piperidine-2,6-dione |
| 230 | 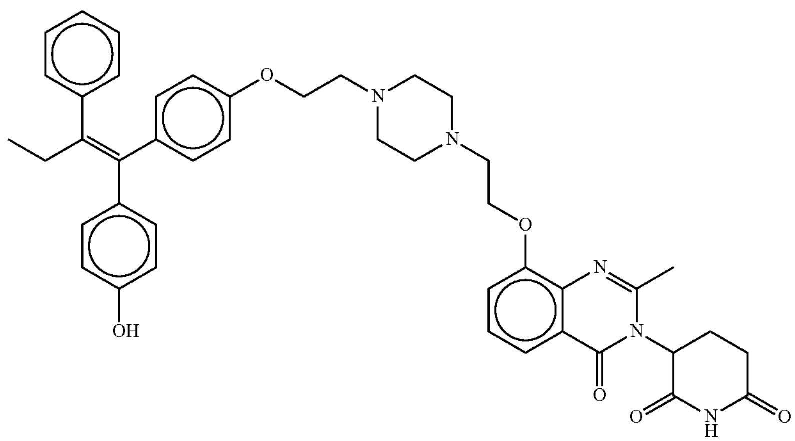 | (Z)-3-(8-(2-(4-(2-(4-(1-(4-hydroxyphenyl)-2-phenylbut-1-en-1-yl)phenoxy)ethyl)piperazin-1-yl)ethoxy)-2-methyl-4-oxoquinazolin-3(4H)-yl)piperidine-2,6-dione |

TABLE 1A-continued
Exemplary Compound of the Present Disclosure
| # | Structure | IUPAC Name |
|---|-----------|------------|
| 231 | 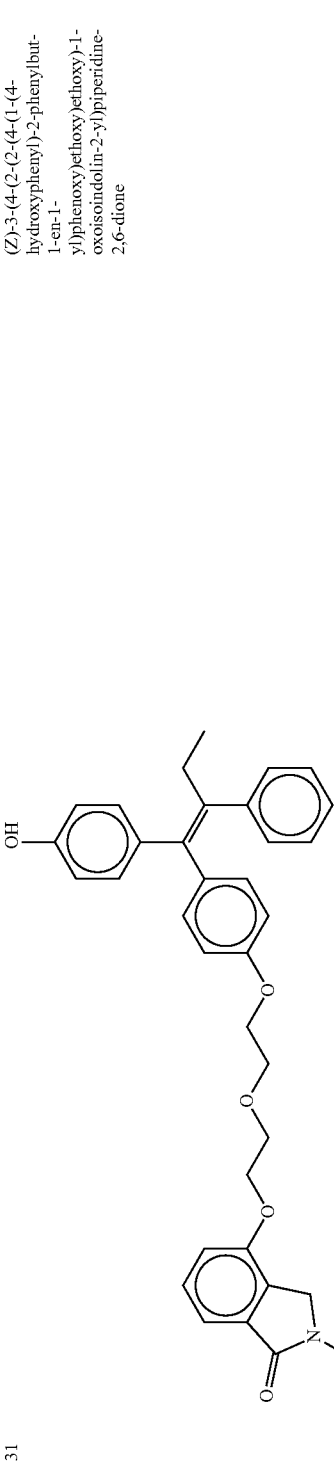 | (Z)-3-(4-(2-(2-(4-(1-(4-hydroxyphenyl)-2-phenylbut-1-en-1-yl)phenoxy)ethoxy)ethoxy)-1-oxoisoindolin-2-yl)piperidine-2,6-dione |
| 232 | 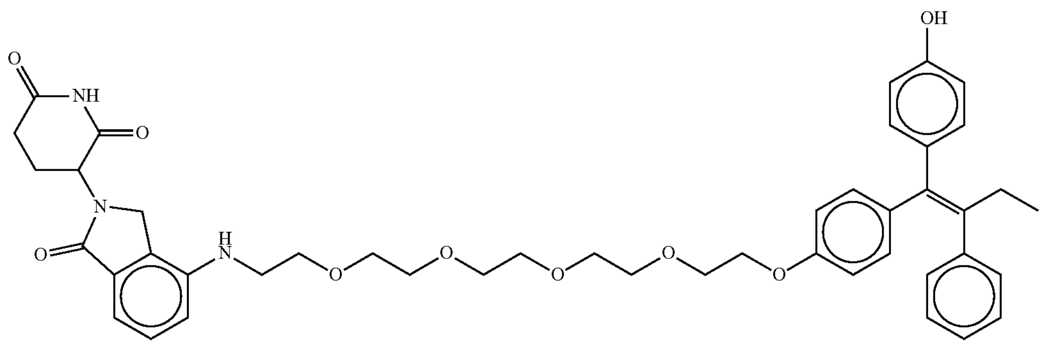 | (Z)-3-(4-((14-(4-(1-(4-hydroxyphenyl)-2-phenylbut-1-en-1-yl)phenoxy)-3,6,9,12-tetraoxatetradecyl)amino)-1-oxoisoindolin-2-yl)piperidine-2,6-dione |

TABLE 1A-continued
Exemplary Compound of the Present Disclosure
| # | Structure | IUPAC Name |
|---|---|---|
| 233 | 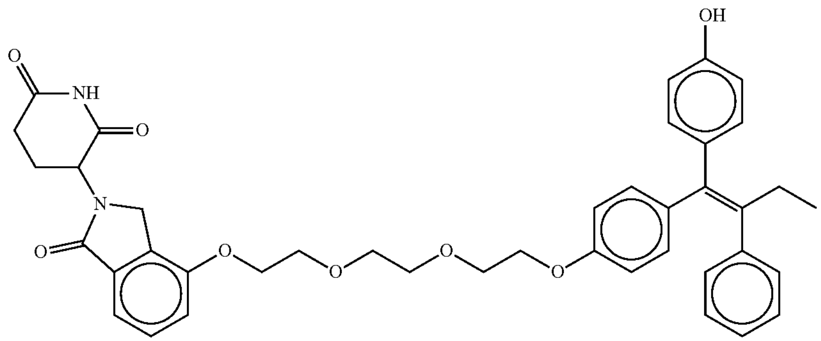 | (Z)-3-(4-(2-(2-(2-(4-(1-(4-hydroxyphenyl)-2-phenylbut-1-en-1-yl)phenoxy)ethoxy)ethoxy)ethoxy)-1-oxoisoindolin-2-yl)piperidine-2,6-dione |
| 234 | 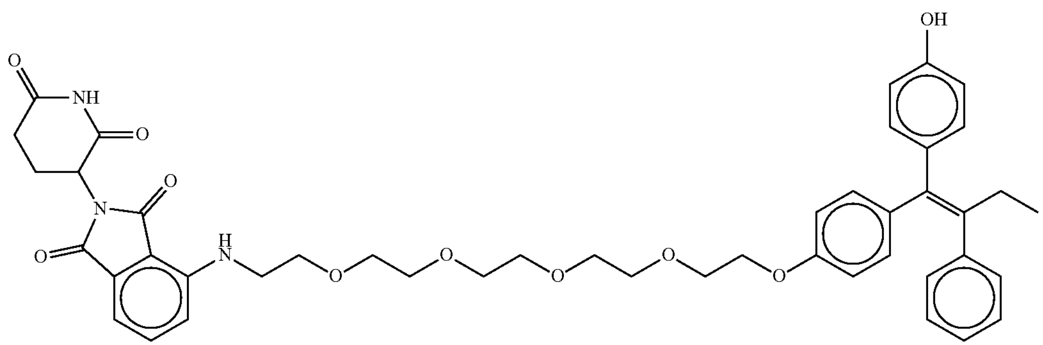 | (Z)-2-(2,6-dioxopiperidin-3-yl)-4-((14-(4-(1-(4-hydroxyphenyl)-2-phenylbut-1-en-1-yl)phenoxy)-3,6,9,12-tetraoxatetradecyl)amino)isoindoline-1,3-dione |

TABLE 1A-continued
Exemplary Compound of the Present Disclosure
| # | Structure | IUPAC Name |
|---|-----------|------------|
| 235 | 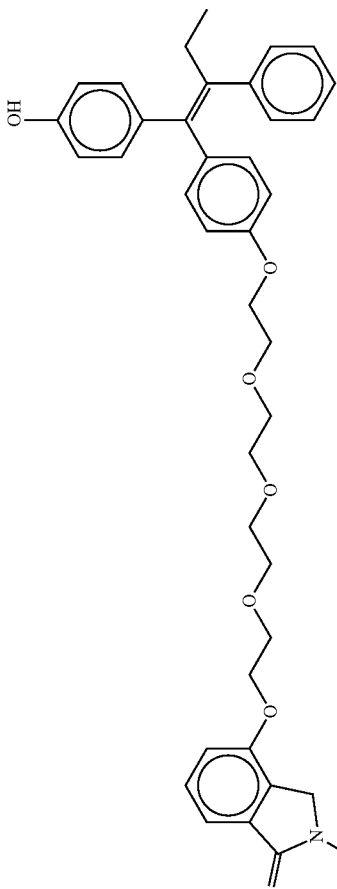 | (Z)-3-(4-(2-(2-(2-(2-(4-(1-(4-hydroxyphenyl)-2-phenylbut-1-en-1-yl)phenoxy)ethoxy)ethoxy)ethoxy)ethoxy)-1-oxoisoindolin-2-yl)piperidine-2,6-dione |
| 236 | 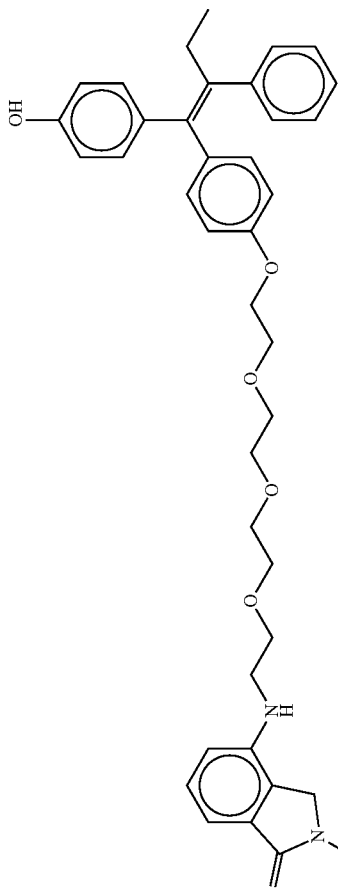 | (Z)-3-(4-((2-(2-(2-(4-(1-(4-hydroxyphenyl)-2-phenylbut-1-en-1-yl)phenoxy)ethoxy)ethoxy)ethyl)amino)-1-oxoisoindolin-2-yl)piperidine-2,6-dione |

TABLE 1A-continued
Exemplary Compound of the Present Disclosure
| # | Structure | IUPAC Name |
|---|---|---|
| 237 | 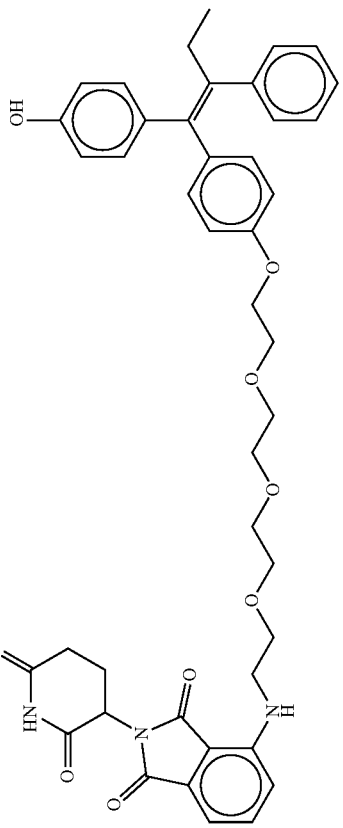 | (Z)-2-(2,6-dioxopiperidin-3-yl)-4-((2-(2-(2-(2-(4-(1-(4-hydroxyphenyl)-2-phenylbut-1-en-1-yl)phenoxy)ethoxy)ethoxy)ethoxy)ethyl)amino)isoindoline-1,3-dione |
| 238 | 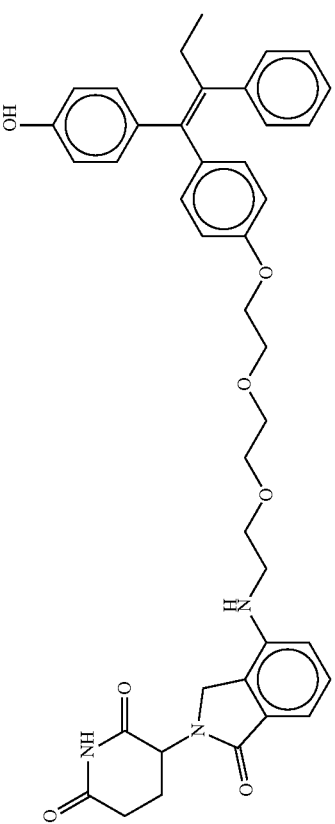 | (Z)-3-(4-((2-(2-(2-(4-(1-(4-hydroxyphenyl)-2-phenylbut-1-en-1-yl)phenoxy)ethoxy)ethoxy)ethyl)amino)-1-oxoisoindolin-2-yl)piperidine-2,6-dione |

TABLE 1A-continued
Exemplary Compound of the Present Disclosure
| # | Structure | IUPAC Name |
|---|---|---|
| 239 | 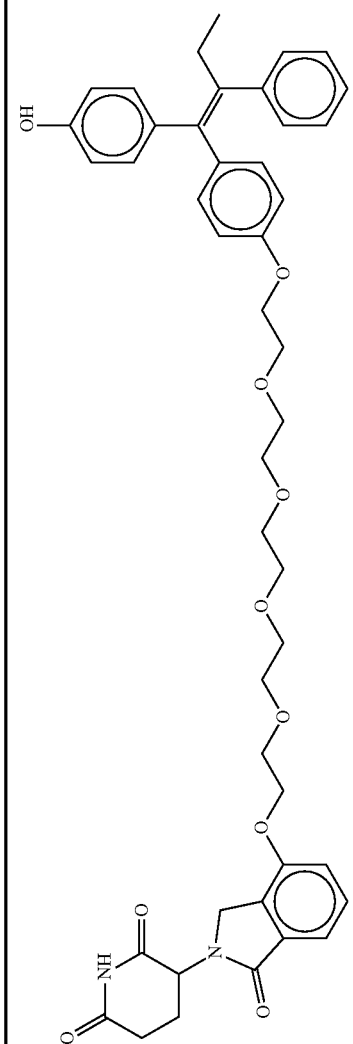 | (Z)-3-(4-((14-(4-(1-(4-hydroxyphenyl)-2-phenylbut-1-en-1-yl)phenoxy)-3,6,9,12-tetraoxatetradecyl)oxy)-1-oxoisoindolin-2-yl)piperidine-2,6-dione |
| 240 | 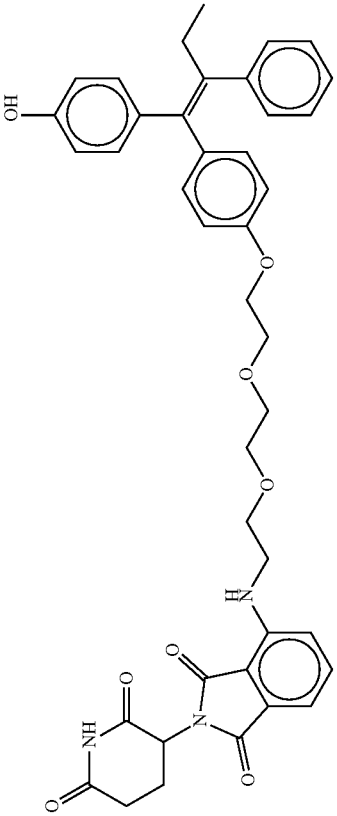 | (Z)-2-(2,6-dioxopiperidin-3-yl)-4-((2-(2-(4-(1-(4-hydroxyphenyl)-2-phenylbut-1-en-1-yl)phenoxy)ethoxy)ethyl)amino)isoindoline-1,3-dione |

TABLE 1A-continued
Exemplary Compound of the Present Disclosure
| # | Structure | IUPAC Name |
|---|---|---|
| 241 | 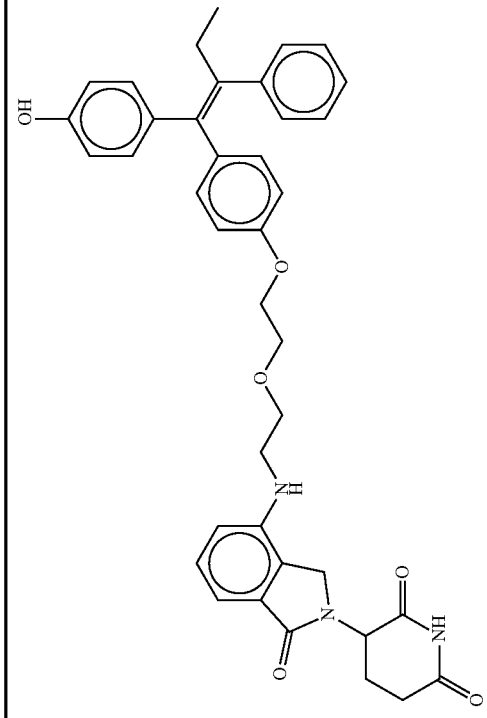 | (Z)-3-(4-((2-(2-(4-(1-(4-hydroxyphenyl)-2-phenylbut-1-en-1-yl)phenoxy)ethoxy)ethyl)amino)-1-oxoisoindolin-2-yl)piperidine-2,6-dione |
| 242 | 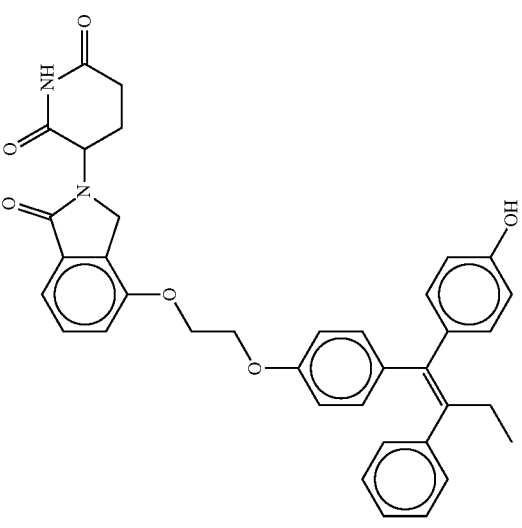 | (Z)-3-(4-(2-(4-(1-(4-hydroxyphenyl)-2-phenylbut-1-en-1-yl)phenoxy)ethoxy)-1-oxoisoindolin-2-yl)piperidine-2,6-dione |

TABLE 1A-continued
Exemplary Compound of the Present Disclosure
| # | Structure | IUPAC Name |
|---|---|---|
| 243 | 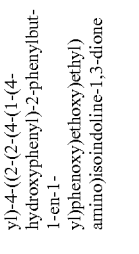 | (Z)-2-(2,6-dioxopiperidin-3-yl)-4-((2-(2-(4-(1-(4-hydroxyphenyl)-2-phenylbut-1-en-1-yl)phenoxy)ethoxy)ethyl)amino)isoindoline-1,3-dione |
| 244 | 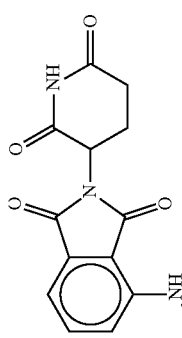 | (Z)-2-(2,6-dioxopiperidin-3-yl)-4-((2-(4-(1-(4-hydroxyphenyl)-2-phenylbut-1-en-1-yl)phenoxy)ethyl)amino)isoindoline-1,3-dione |

TABLE 1A-continued
Exemplary Compound of the Present Disclosure
| # | Structure | IUPAC Name |
|---|---|---|
| 245 | 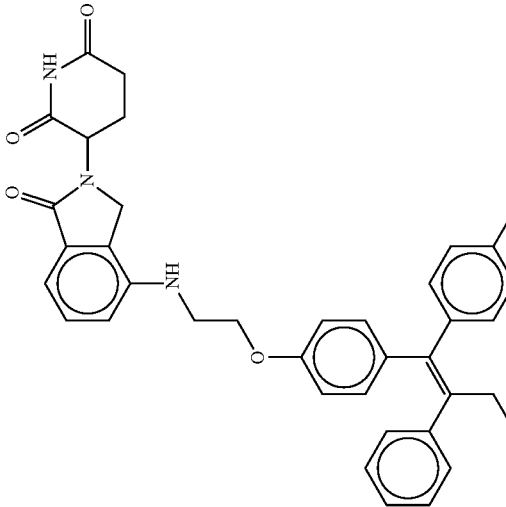 | (Z)-3-(4-((2-(4-(1-(4-hydroxyphenyl)-2-phenylbut-1-en-1-yl)phenoxy)ethyl)amino)-1-oxoisoindolin-2-yl)piperidine-2,6-dione |
| 246 | 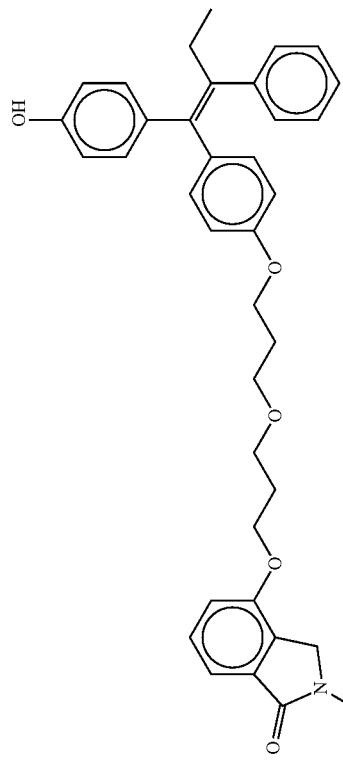 | (Z)-3-(4-(3-(4-(1-(4-hydroxyphenyl)-2-phenylbut-1-en-1-yl)phenoxy)propoxy)-1-oxoisoindolin-2-yl)piperidine-2,6-dione |

TABLE 1A-continued
Exemplary Compound of the Present Disclosure
| # | Structure | IUPAC Name |
|---|---|---|
| 247 | 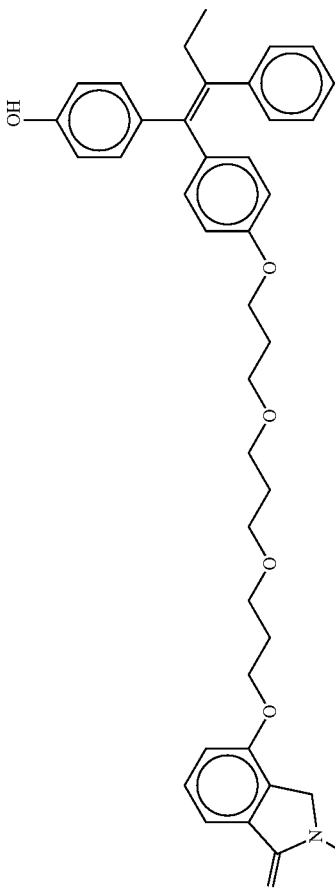 | (Z)-3-(4-(3-(3-(3-(4-(1-(4-hydroxyphenyl)-2-phenylbut-1-en-1-yl)phenoxy)propoxy)propoxy)propoxy)-1-oxoisoindolin-2-yl)piperidine-2,6-dione |
| 248 | 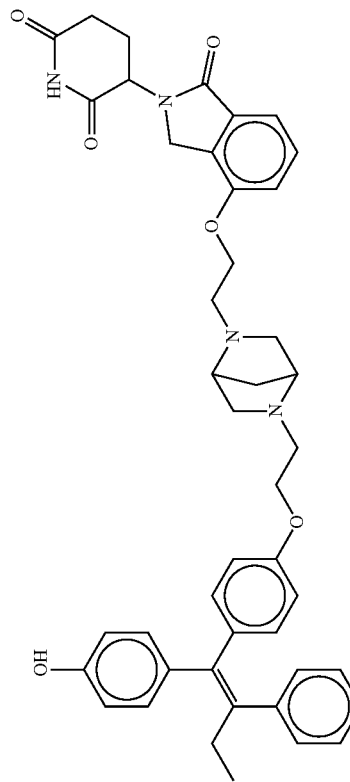 | (Z)-3-(4-(2-(5-(2-(4-(1-(4-hydroxyphenyl)-2-phenylbut-1-en-1-yl)phenoxy)ethyl)-2,5-diazabicyclo[2.2.1]heptan-2-yl)ethoxy)-1-oxoisoindolin-2-yl)piperidine-2,6-dione |

TABLE 1A-continued

Exemplary Compound of the Present Disclosure

| # | Structure | IUPAC Name |
|---|---|---|
| 249 | 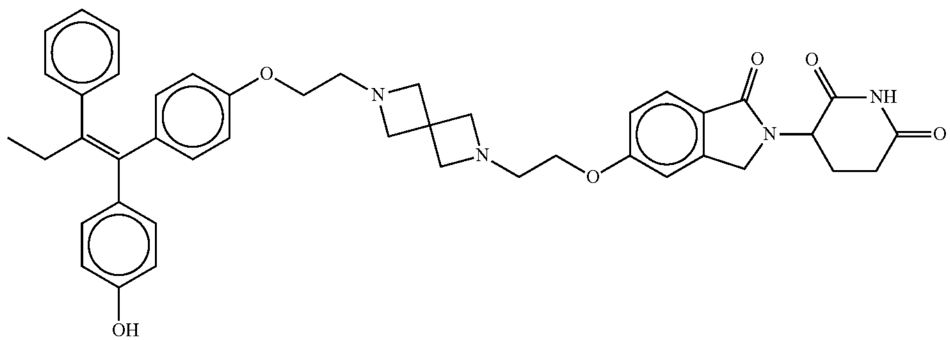 | (Z)-3-(5-(2-(6-(2-(4-(1-(4-hydroxyphenyl)-2-phenylbut-1-en-1-yl)phenoxy)ethyl)-2,6-diazaspiro[3.3]heptan-2-yl)ethoxy)-1-oxoisoindolin-2-yl)piperidine-2,6-dione |
| 250 | 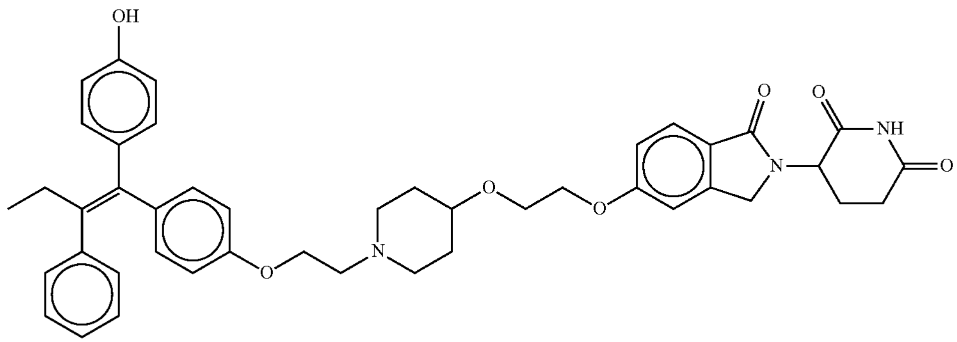 | (Z)-3-(5-(2-((1-(2-(4-(1-(4-hydroxyphenyl)-2-phenylbut-1-en-1-yl)phenoxy)ethyl)piperidin-4-yl)oxy)ethoxy)-1-oxoisoindolin-2-yl)piperidine-2,6-dione |
| 251 | 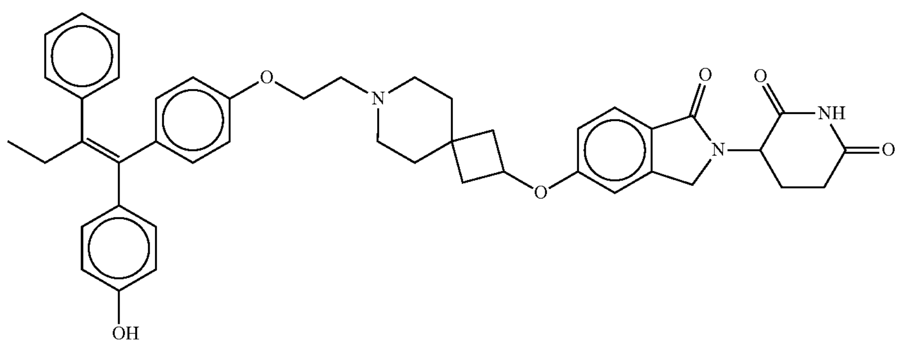 | (Z)-3-(5-((7-(2-(4-(1-(4-hydroxyphenyl)-2-phenylbut-1-en-1-yl)phenoxy)ethyl)-7-azaspiro[3.5]nonan-2-yl)oxy)-1-oxoisoindolin-2-yl)piperidine-2,6-dione |

TABLE 1A-continued

Exemplary Compound of the Present Disclosure

| # | Structure | IUPAC Name |
|---|---|---|
| 252 | 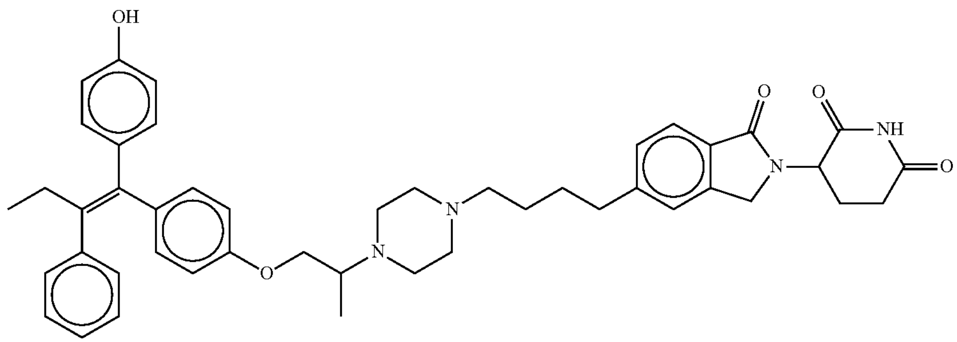 | (Z)-3-(5-(4-(4-(1-(4-(1-(4-hydroxyphenyl)-2-phenylbut-1-en-1-yl)phenoxy)propan-2-yl)piperazin-1-yl)butyl)-1-oxoisoindolin-2-yl)piperidine-2,6-dione |
| 253 | 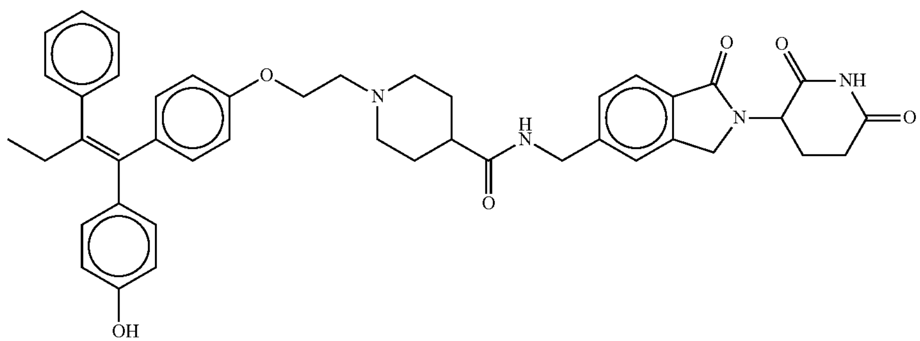 | (Z)-N-((2-(2,6-dioxopiperidin-3-yl)-1-oxoisoindolin-5-yl)methyl)-1-(2-(4-(1-(4-hydroxyphenyl)-2-phenylbut-1-en-1-yl)phenoxy)ethyl)piperidine-4-carboxamide |

TABLE 1A-continued
Exemplary Compound of the Present Disclosure
| # | Structure | IUPAC Name |
|---|---|---|
| 254 | 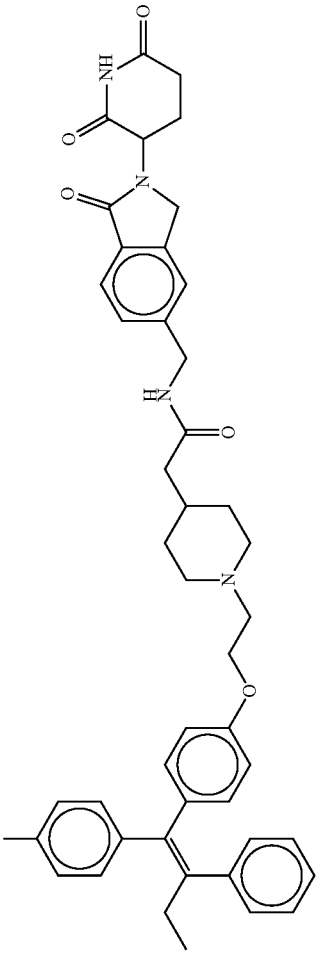 | (Z)-N-((2-(2,6-dioxopiperidin-3-yl)-1-oxoisoindolin-5-yl)methyl)-2-(1-(2-(4-(1-(4-hydroxyphenyl)-2-phenylbut-1-en-1-yl)phenoxy)ethyl)piperidin-4-yl)acetamide |
| 255 | 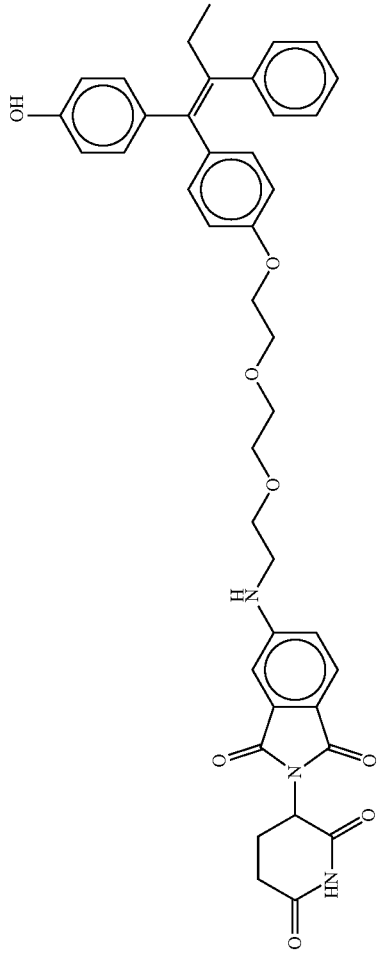 | (Z)-2-(2,6-dioxopiperidin-3-yl)-5-((2-(2-(4-(1-(4-hydroxyphenyl)-2-phenylbut-1-en-1-yl)phenoxy)ethoxy)ethyl)amino)isoindoline-1,3-dione |

TABLE 1A-continued
Exemplary Compound of the Present Disclosure
| # | Structure | IUPAC Name |
|---|---|---|
| 256 | 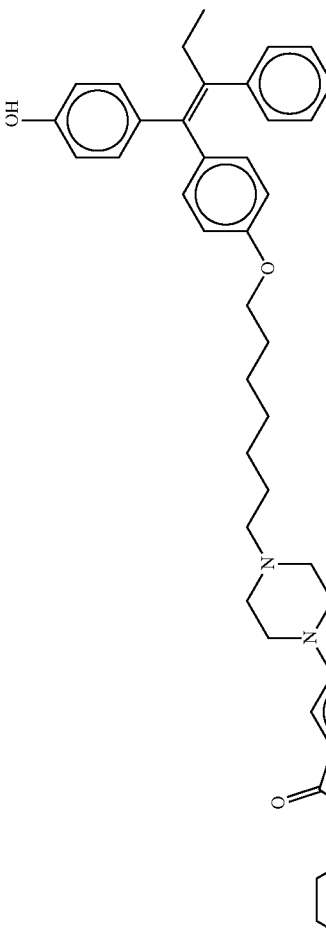 | (Z)-2-(2,6-dioxopiperidin-3-yl)-5-(4-(7-(4-(1-(4-hydroxyphenyl)-2-phenylbut-1-en-1-yl)phenoxy)heptyl)piperazin-1-yl)isoindoline-1,3-dione |
| 257 | 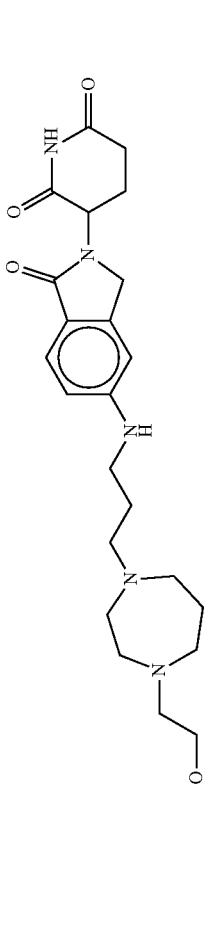 | (Z)-3-(5-((3-(4-(2-(4-(1-(4-hydroxyphenyl)-2-phenylbut-1-en-1-yl)phenoxy)ethyl)-1,4-diazepan-1-yl)propyl)amino)-1-oxoisoindolin-2-yl)piperidine-2,6-dione |

TABLE 1A-continued
Exemplary Compound of the Present Disclosure
| # | Structure | IUPAC Name |
|---|---|---|
| 258 | 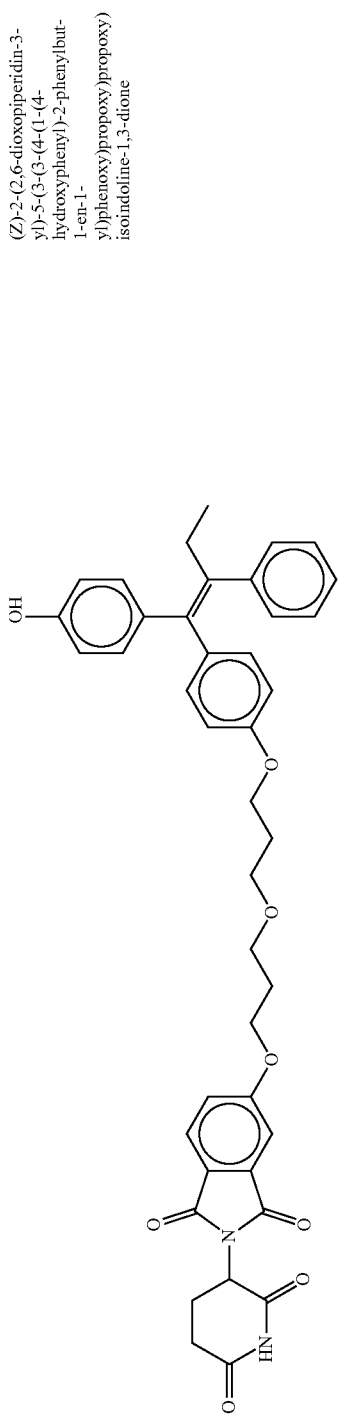 | (Z)-2-(2,6-dioxopiperidin-3-yl)-5-(3-(3-(4-(1-(4-hydroxyphenyl)-2-phenylbut-1-en-1-yl)phenoxy)propoxy)propoxy)isoindoline-1,3-dione |
| 259 | 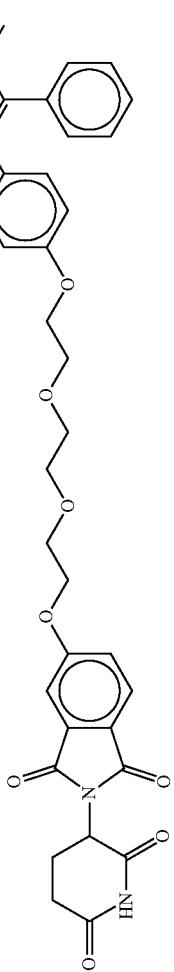 | (Z)-2-(2,6-dioxopiperidin-3-yl)-5-(2-(2-(4-(1-(4-hydroxyphenyl)-2-phenylbut-1-en-1-yl)phenoxy)ethoxy)ethoxy)isoindoline-1,3-dione |

TABLE 1A-continued

Exemplary Compound of the Present Disclosure

| # | Structure | IUPAC Name |
|---|-----------|------------|
| 260 | 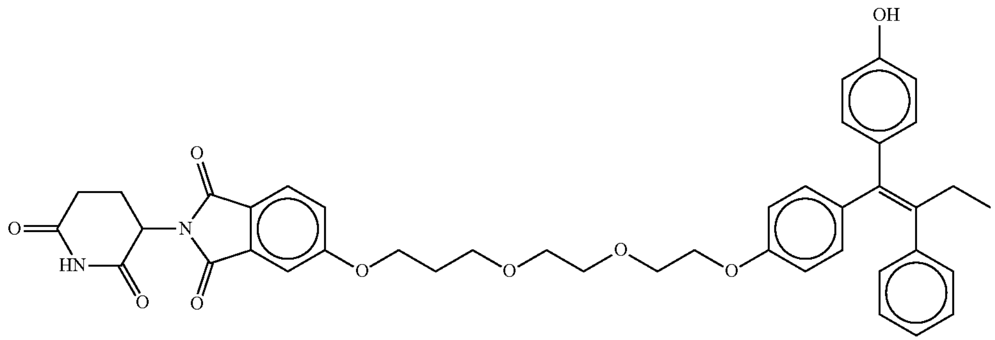 | (Z)-2-(2,6-dioxopiperidin-3-yl)-5-(3-(2-(2-(4-(1-(4-hydroxyphenyl)-2-phenylbut-1-en-1-yl)phenoxy)ethoxy)ethoxy)propoxy)isoindoline-1,3-dione |
| 261 | 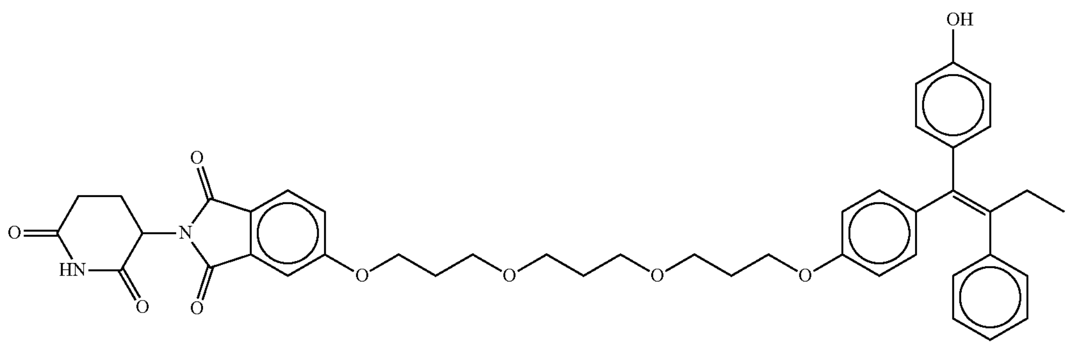 | (Z)-2-(2,6-dioxopiperidin-3-yl)-5-(3-(3-(4-(1-(4-hydroxyphenyl)-2-phenylbut-1-en-1-yl)phenoxy)propoxy)propoxy)isoindoline-1,3-dione |
| 262 | 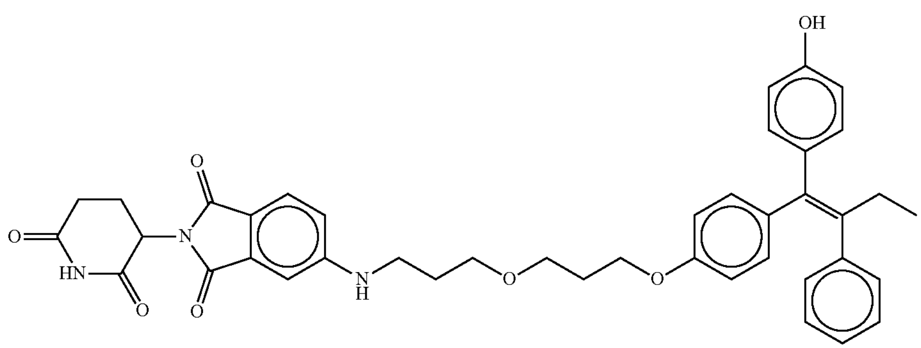 | (Z)-2-(2,6-dioxopiperidin-3-yl)-5-((3-(4-(1-(4-hydroxyphenyl)-2-phenylbut-1-en-1-yl)phenoxy)propoxy)propyl)amino)isoindoline-1,3 dione |

TABLE 1A-continued

Exemplary Compound of the Present Disclosure

| # | Structure | IUPAC Name |
|---|---|---|
| 263 | 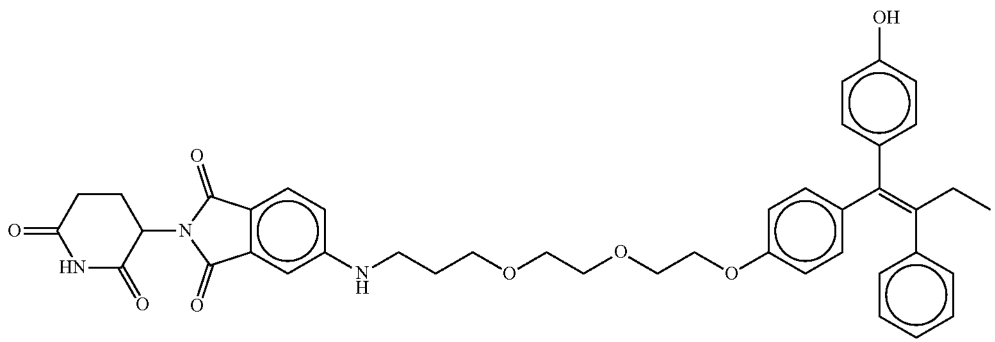 | (Z)-2-(2,6-dioxopiperidin-3-yl)-5-((3-(2-(2-(4-(1-(4-hydroxyphenyl)-2-phenylbut-1-en-1-yl)phenoxy)ethoxy)ethoxy)propyl)amino)isoindoline-1,3-dione |
| 264 | 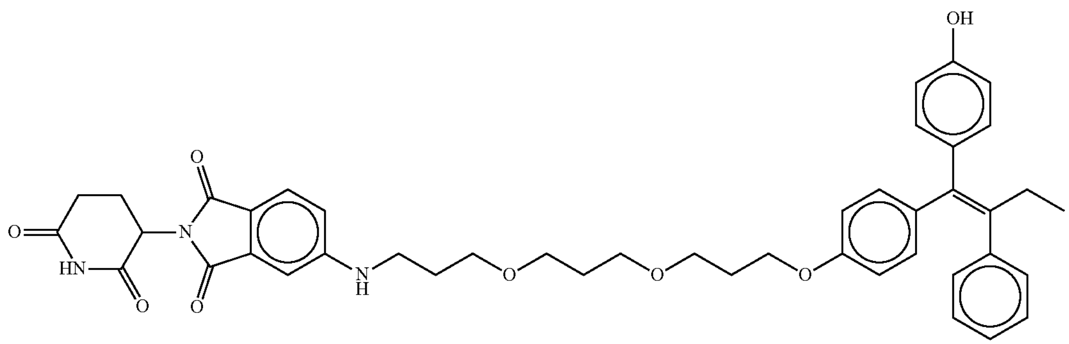 | (Z)-2-(2,6-dioxopiperidin-3-yl)-5-(3-(3-(4-(1-(4-hydroxyphenyl)-2-phenylbut-1-en-1-yl)phenoxy)propoxy)propyl)amino)isoindoline-1,3-dione |

TABLE 1A-continued
Exemplary Compound of the Present Disclosure
| # | Structure | IUPAC Name |
|---|---|---|
| 265 | 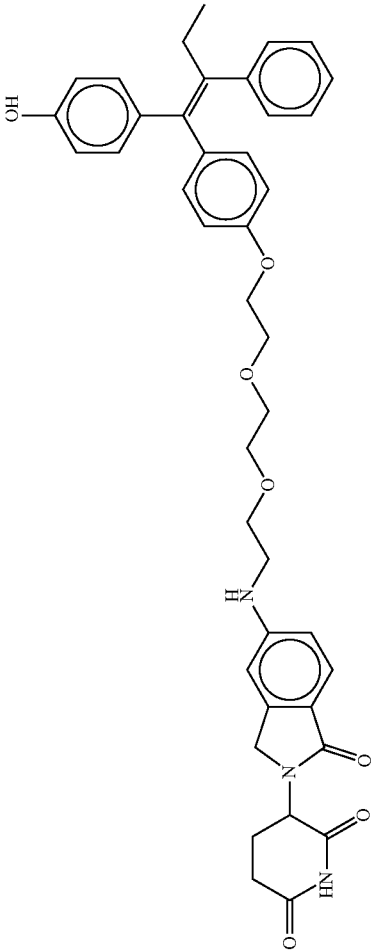 | (Z)-3-(5-((2-(2-(2-(4-(1-(4-hydroxyphenyl)-2-phenylbut-1-en-1-yl)phenoxy)ethoxy)ethoxy)ethyl)amino)-1-oxoisoindolin-2-yl)piperidine-2,6-dione |
| 266 | 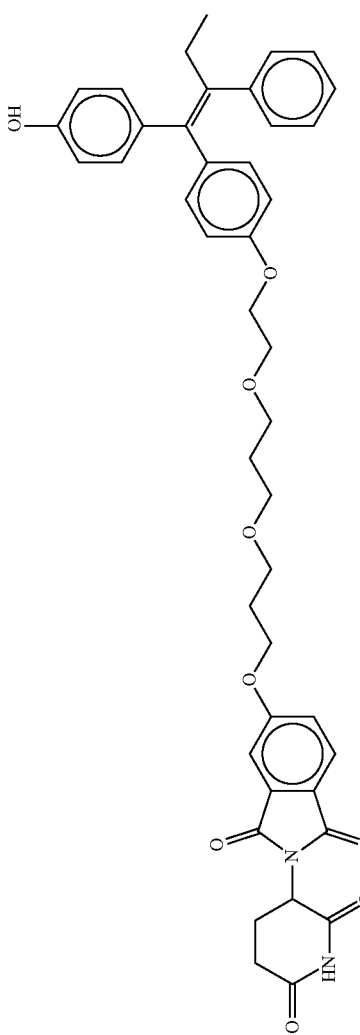 | (Z)-2-(2,6-dioxopiperidin-3-yl)-5-(3-(2-(4-(1-(4-hydroxyphenyl)-2-phenylbut-1-en-1-yl)phenoxy)ethoxy)propoxy)isoindoline-1,3-dione |

TABLE 1A-continued
Exemplary Compound of the Present Disclosure
| # | Structure | IUPAC Name |
|---|---|---|
| 267 | 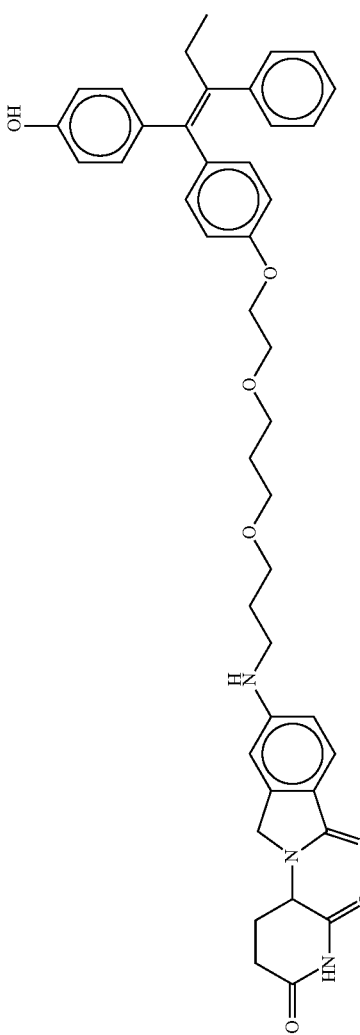 | (Z)-3-(5-((3-(2-(4-(1-(4-hydroxyphenyl)-2-phenylbut-1-en-1-yl)phenoxy)ethoxy)propoxy)propyl)amino)-1-oxoisoindolin-2-yl)piperidine-2,6-dione |
| 268 | 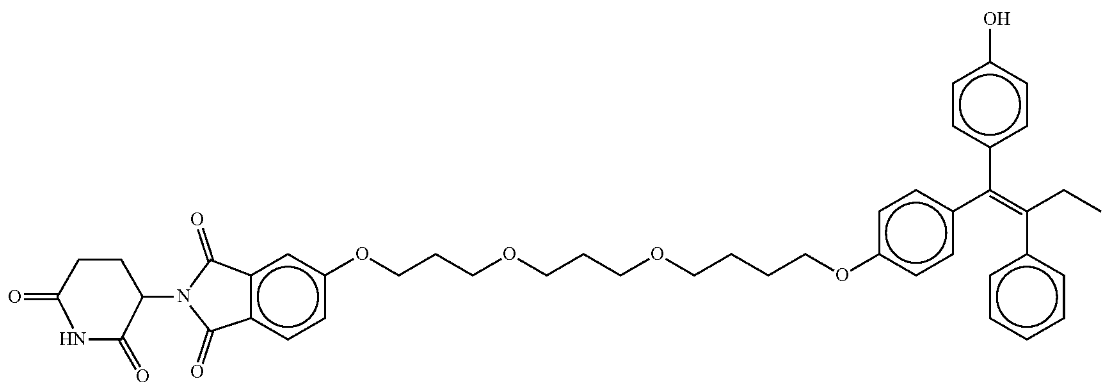 | (Z)-2-(2,6-dioxopiperidin-3-yl)-5-(3-(4-(4-(1-(4-hydroxyphenyl)-2-phenylbut-1-en-1-yl)phenoxy)butoxy)propoxy)propoxy)isoindoline-1,3-dione |

TABLE 1A-continued
Exemplary Compound of the Present Disclosure
| # | Structure | IUPAC Name |
|---|---|---|
| 269 | 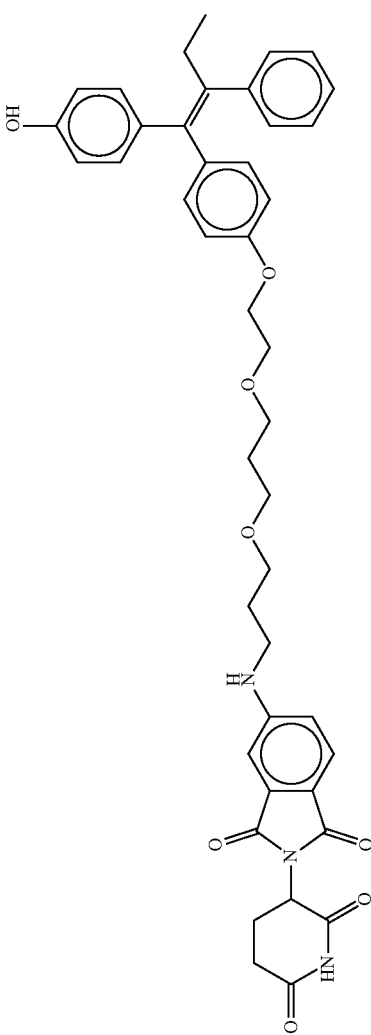 | (Z)-2-(2,6-dioxopiperidin-3-yl)-5-((3-(2-(4-(1-(4-hydroxyphenyl)-2-phenylbut-1-en-1-yl)phenoxy)ethoxy)propoxy)propyl)amino)isoindoline-1,3-dione |
| 270 | 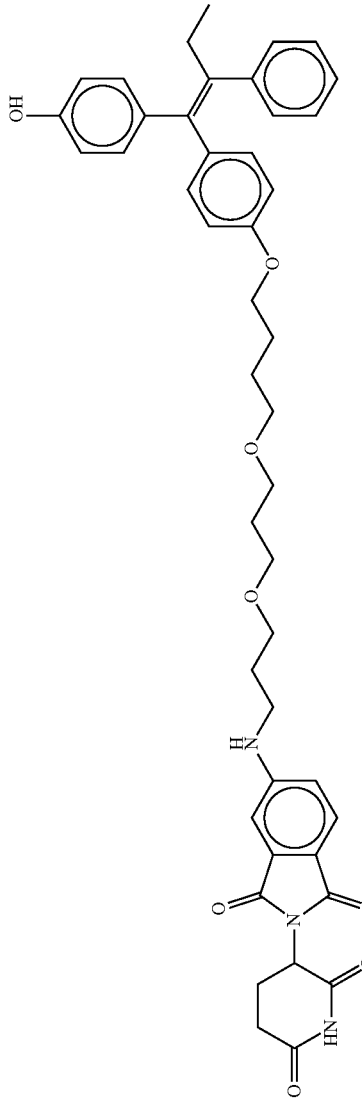 | (Z)-2-(2,6-dioxopiperidin-3-yl)-5-((3-(4-(4-(1-(4-hydroxyphenyl)-2-phenylbut-1-en-1-yl)phenoxy)butoxy)propoxy)propyl)amino)isoindoline-1,3-dione |

TABLE 1A-continued
Exemplary Compound of the Present Disclosure
| # | Structure | IUPAC Name |
|---|---|---|
| 271 | 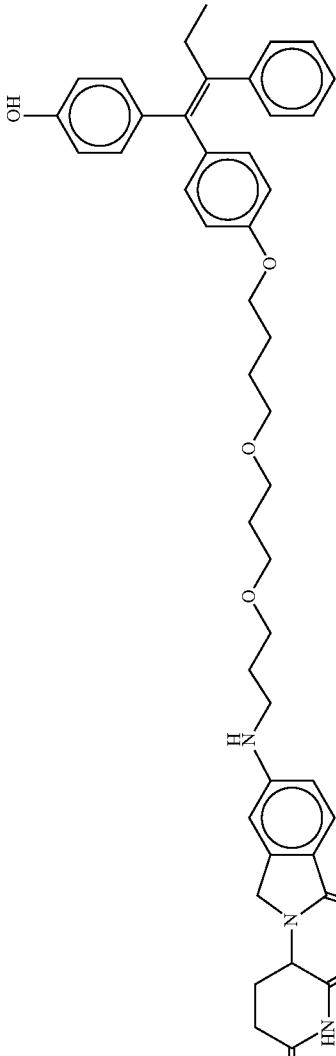 | (Z)-3-(5-((3-(4-(4-(1-(4-hydroxyphenyl)-2-phenylbut-1-en-1-yl)phenoxy)butoxy)propoxy)propyl)amino)-1-oxoisoindolin-2-yl)piperidine-2,6-dione |
| 272 | 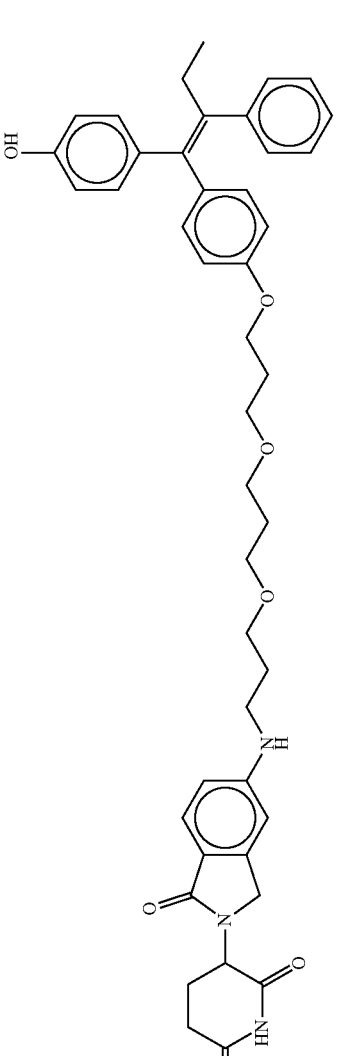 | (Z)-3-(5-((3-(3-(4-(1-(4-hydroxyphenyl)-2-phenylbut-1-en-1-yl)phenoxy)propoxy)propyl)amino)-1-oxoisoindolin-2-yl)piperidine-2,6-dione |

TABLE 1A-continued

Exemplary Compound of the Present Disclosure

| # | Structure | IUPAC Name |
|---|---|---|
| 273 | 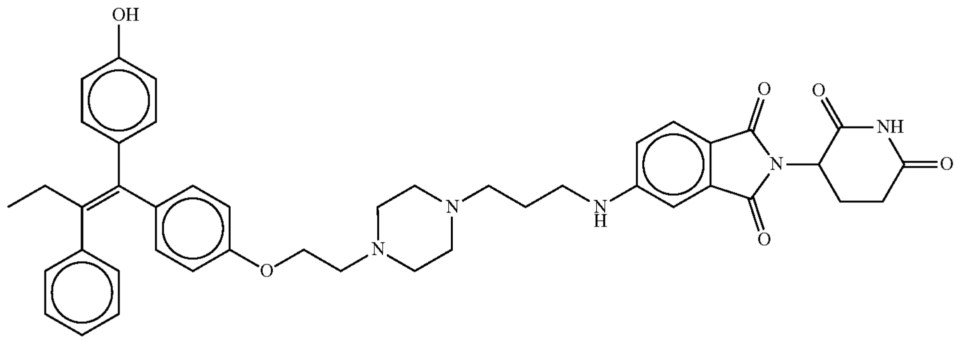 | (Z)-2-(2,6-dioxopiperidin-3-yl)-5-((3-(4-(2-(4-(1-(4-hydroxyphenyl)-2-phenylbut-1-en-1-yl)phenoxy)ethyl)piperazin-1-yl)propyl)amino)isoindoline-1,3-dione |
| 274 | 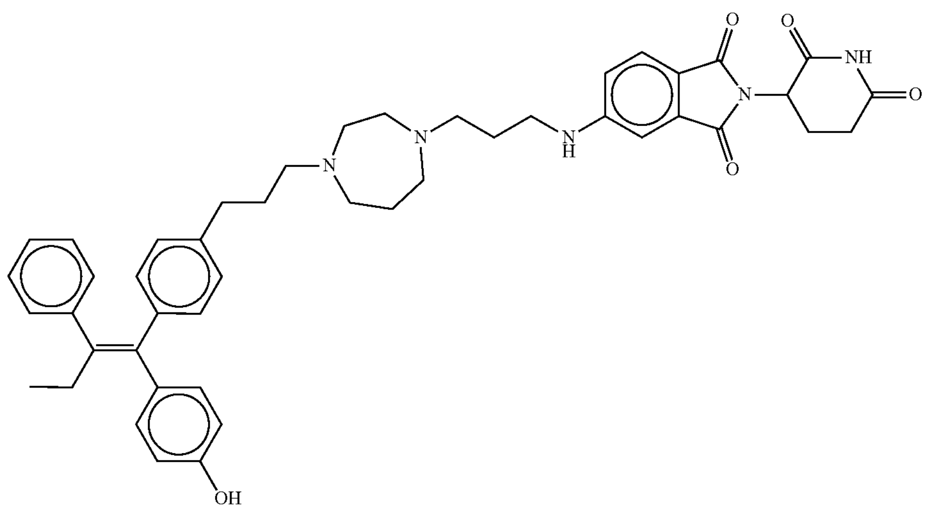 | (Z)-2-(2,6-dioxopiperidin-3-yl)-5-((3-(4-(2-(4-(1-(4-hydroxyphenyl)-2-phenylbut-1-en-1-yl)phenoxy)ethyl)-1,4-diazepan-1-yl)propyl)amino)isoindoline-1,3-dione |

TABLE 1A-continued
Exemplary Compound of the Present Disclosure
| # | Structure | IUPAC Name |
|---|---|---|
| 275 | 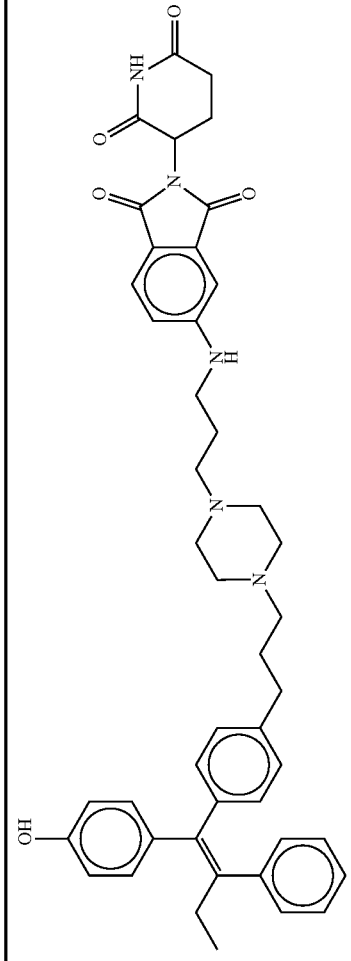 | (E)-2-(2,6-dioxopiperidin-3-yl)-5-((3-(4-(3-(4-(1-(4-hydroxyphenyl)-2-phenylbut-1-en-1-yl)phenyl)propyl)piperazin-1-yl)propyl)amino)isoindoline-1,3-dione |
| 276 | 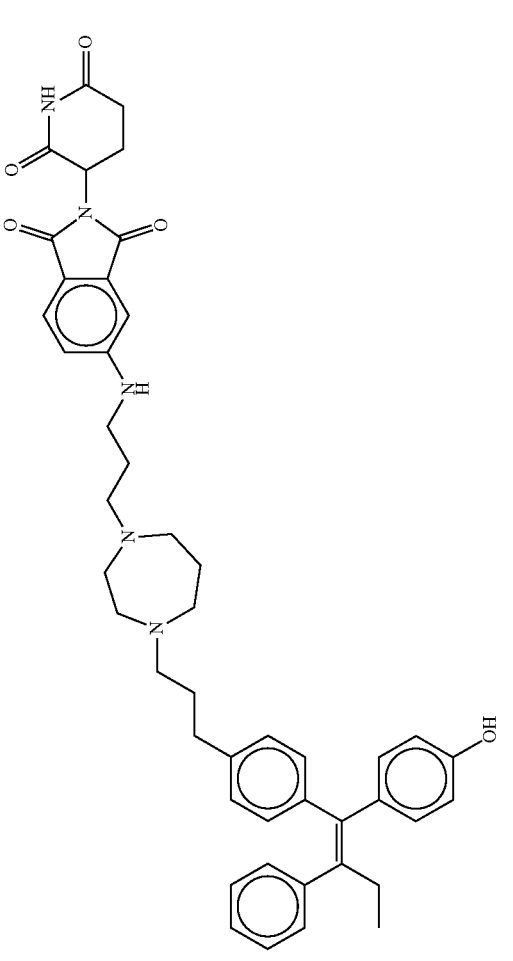 | (E)-2-(2,6-dioxopiperidin-3-yl)-5-((3-(4-(3-(4-(1-(4-hydroxyphenyl)-2-phenylbut-1-en-1-yl)phenyl)propyl)-1,4-diazepan-1-yl)propyl)amino)isoindoline-1,3-dione |

TABLE 1A-continued
Exemplary Compound of the Present Disclosure
| # | Structure | IUPAC Name |
|---|---|---|
| 277 | 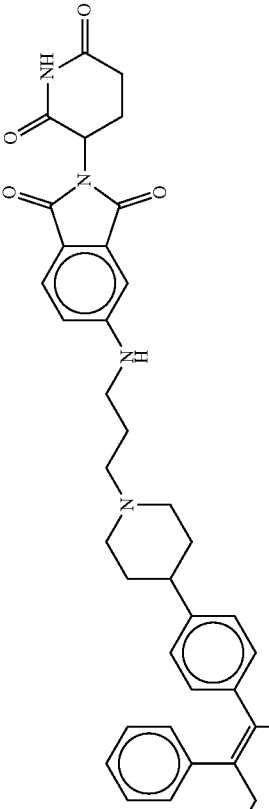 | (E)-2-(2,6-dioxopiperidin-3-yl)-5-((3-(4-(4-(1-(4-hydroxyphenyl)-2-phenylbut-1-en-1-yl)phenyl)piperidin-1-yl)propyl)amino)isoindoline-1,3-dione |
| 278 | 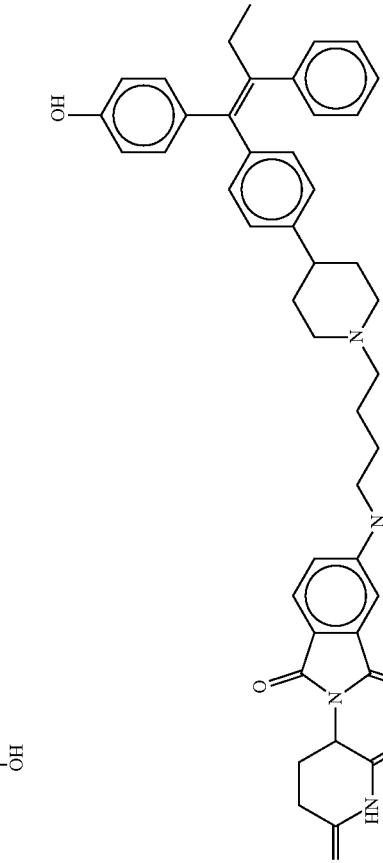 | (E)-2-(2,6-dioxopiperidin-3-yl)-5-((4-(4-(1-(4-hydroxyphenyl)-2-phenylbut-1-en-1-yl)phenyl)piperidin-1-yl)butyl)amino)isoindoline-1,3-dione |

TABLE 1A-continued
Exemplary Compound of the Present Disclosure
| # | Structure | IUPAC Name |
|---|---|---|
| 279 | 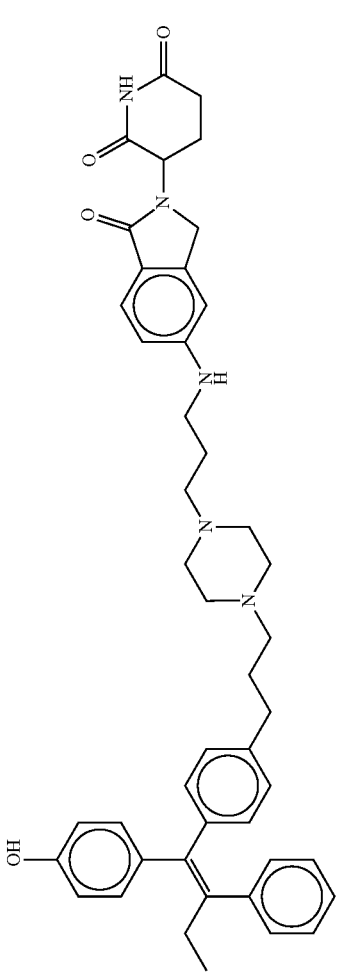 | (E)-3-(5-((3-(4-(3-(4-(1-(4-hydroxyphenyl)-2-phenylbut-1-en-1-yl)phenyl)propyl)piperazin-1-yl)propyl)amino)-1-oxoisoindolin-2-yl)piperidine-2,6-dione |
| 280 | 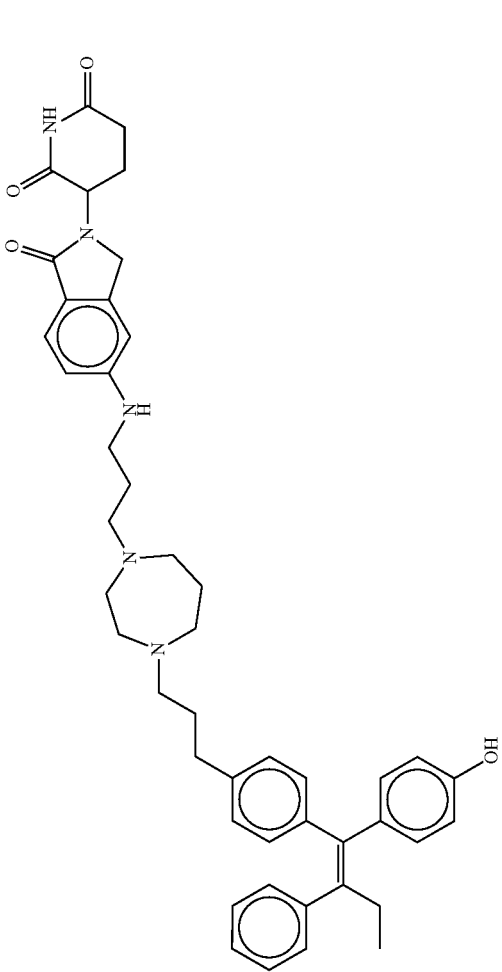 | (E)-3-(5-((3-(4-(3-(4-(1-(4-hydroxyphenyl)-2-phenylbut-1-en-1-yl)phenyl)propyl)-1,4-diazepan-1-yl)propyl)amino)-1-oxoisoindolin-2-yl)piperidine-2,6-dione |

TABLE 1A-continued
Exemplary Compound of the Present Disclosure
| # | Structure | IUPAC Name |
|---|---|---|
| 281 | 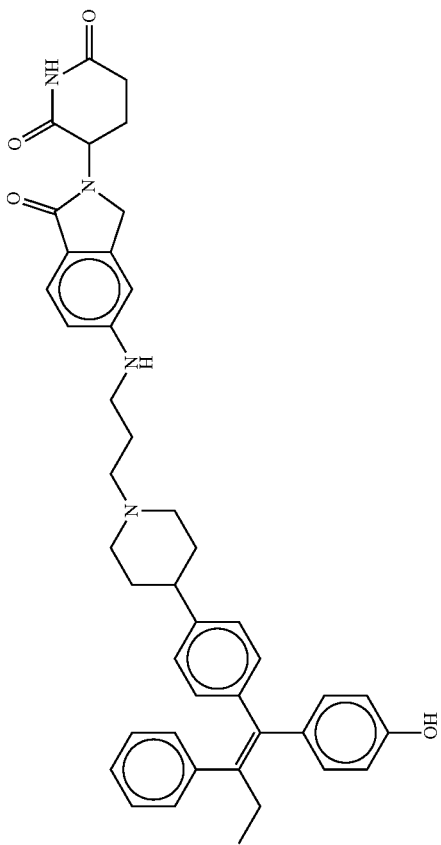 | (E)-3-(4-(4-(1-(4-hydroxyphenyl)-2-phenylbut-1-en-1-yl)phenyl)piperidin-1-yl)propyl)amino)-1-oxoisoindolin-2-yl)piperidine-2,6-dione |
| 282 | 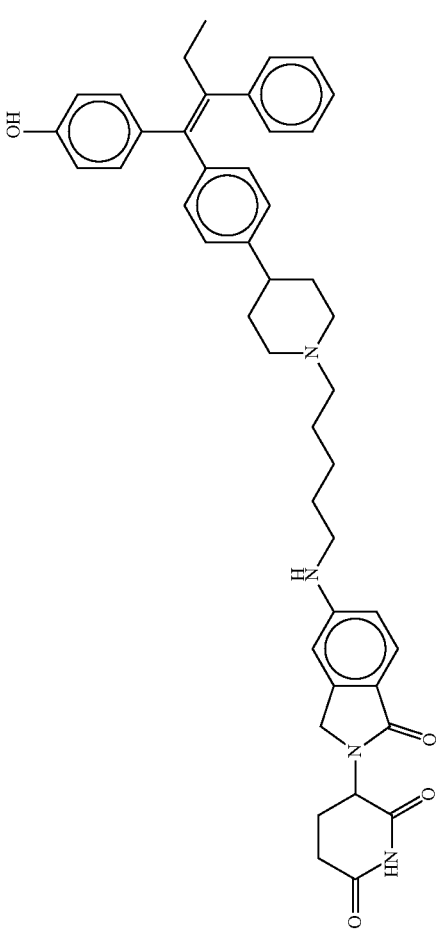 | (E)-3-(5-((4-(1-(4-hydroxyphenyl)-2-phenylbut-1-en-1-yl)phenyl)piperidin-1-yl)pentyl)amino)-1-oxoisoindolin-2-yl)piperidine-2,6-dione |

TABLE 1A-continued
Exemplary Compound of the Present Disclosure
| # | Structure | IUPAC Name |
|---|---|---|
| 283 | 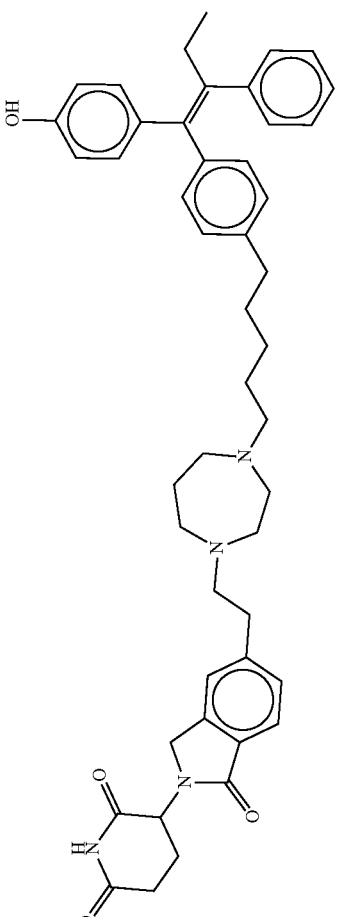 | (E)-3-(5-(2-(4-(5-(4-(1-(4-hydroxyphenyl)-2-phenylbut-1-en-1-yl)phenyl)pentyl)-1,4-diazepan-1-yl)ethyl)-1-oxoisoindolin-2-yl)piperidine-2,6-dione |

In some embodiments, the compound with ER degradation activity (aka an ER degrader) has a structure according to Formula (I-C).

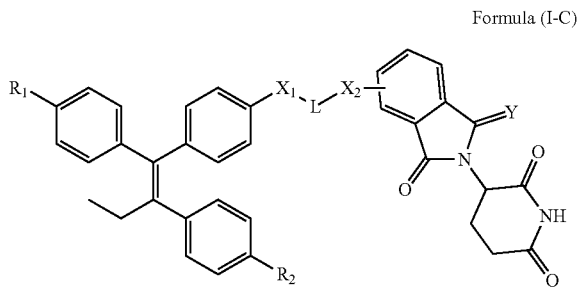

Formula (I-C)

or a tautomer, stereoisomer or a mixture of stereoisomers, or a pharmaceutically acceptable salt, solvate, ester, or hydrate thereof wherein:

$X^1$ and $X^2$ are each independently selected from $C(R^3)_2$, $NR^4$, O, S, cycloalkyl, aryl, heterocycle, and heteroaryl, each of which is independently substituted with 0, 1, 2, or 3 $R^5$;

L is a linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$;

$R^1$ and $R^2$ are each independently selected from H, $C_1$-$C_6$ alkyl, halo, alkoxy, acyl, hydroxy, and sulfhydryl, each of which is substituted with 0, 1, 2, or 3 $R^5$;

$R^3$ is independently selected from H, $C_1$-$C_6$ alkyl, halo, and hydroxy;

$R^4$ is independently selected from H, $C_1$-$C_6$ alkyl, and acyl, each of which is substituted with 0, 1, 2, or 3 $R^5$;

$R^5$ is independently selected from $C_1$-$C_6$ alkyl, halo, cyano, and hydroxy;

Y is (H, H) or O;

In some embodiments of the compound of Formula (I-C), the compound is a -trans or -cis olefin, or a mixture thereof.

In some embodiments, the estrogen receptor (ER) degraders provided herein are compounds of Formula (I-B), or a tautomer, stereoisomer or a mixture of stereoisomers, pharmaceutically acceptable salt, or hydrate thereof:

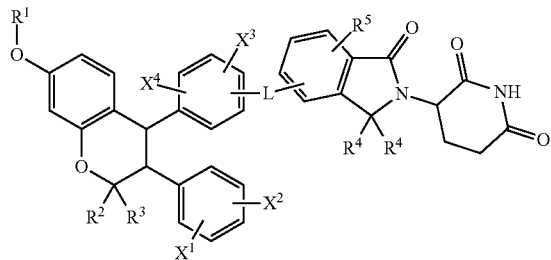

(I-B)

wherein:

$R^1$ is selected from H, $C_1$-$C_6$ acyl, or $C_1$-$C_6$ alkyl, each of which is substituted with 0, 1, 2, or 3 $R^6$ $R^2$ and $R^3$ are each independently selected from H, $C_1$-$C_3$ alkyl, or $C_1$-$C_3$ haloalkyl, each of which is substituted with 0, 1, 2, or 3 $R^6$;

each $R^4$ is independently selected from H, hydroxyl, $C_1$-$C_3$ alkyl, $C_1$-$C_3$ alkoxyl, or $C_1$-$C_3$ haloalkyl, each of which is substituted with 0, 1, 2, or 3 $R^6$, or two $R^4$ groups are taken together to form an oxo;

$R^5$ is selected from hydrogen, halogen, hydroxy, $C_1$-$C_3$ alkyl, $C_1$-$C_3$ alkoxy, $C_1$-$C_3$ haloalkyl, $-N(R^7)_2$, and $-CN$, each of which is substituted with 0, 1, 2, or 3 $R^6$;

$X^1$ and $X^2$ are each independently selected from H, halogen, cyano, $C_1$-$C_6$ alkyl, $C_1$-$C_6$ alkoxyl, or $C_1$-$C_6$ haloalkyl each of which is substituted with 0, 1, 2, or 3 $R^6$;

$X^3$ and $X^4$ are each independently selected from H or halo;

L is a linker of 1 to 22 carbon atoms in length, wherein one or more carbon atoms are each optionally and independently replaced by a group selected from C(O), O, $NR^7$, S, $C_2$-alkenyl, $C_2$-alkynyl, cycloalkyl, aryl, heterocycle, and heteroaryl, each of which is substituted with 0, 1, 2, or 3 $R^6$;

each $R^6$ is independently selected from $C_1$-$C_6$ alkyl, halo, cyano, and hydroxy, each $R^7$ is independently selected from hydrogen, $C_1$-$C_6$ alkyl, and acyl, each of which is substituted with 0, 1, 2, or 3 $R^6$, or two $R^7$ groups are taken together to form a 3- to 6-membered heterocycle or heteroaryl.

In some embodiments of the compound of Formula (I) or Formula (I-B), $R^1$ is selected from H, or $C_1$-$C_6$ alkyl, each of which is substituted with 0, 1, 2, or 3 $R^6$. In some embodiments, $R^1$ may be selected from H or methyl, each of which is substituted with 0, 1, 2, or 3 $R^6$. In some embodiments, $R^1$ may each be independently H or methyl. In some embodiments, $R^1$ is H. In some embodiments, $R^1$ is methyl.

In some embodiments of the compound of Formula (I) or Formula (I-B), $R^2$ and $R^3$ are each independently selected from H, $C_1$-$C_3$ alkyl, or $C_1$-$C_3$ haloalkyl, each of which is substituted with 0, 1, 2, or 3 $R^6$. In some embodiments, $R^2$ and $R^3$ are each independently selected from H and methyl, each of which is substituted with 0, 1, 2, or 3 $R^6$. In some embodiments, $R^2$ and $R^3$ are each independently selected from H and methyl. In some embodiments, $R^2$ may be H and $R^3$ may be H. In some embodiments, $R^2$ may be H and $R^3$ may be methyl. In some embodiments, $R^2$ may be methyl and $R^3$ may be H. In some embodiments, $R^2$ may be methyl and $R^3$ may be methyl.

In some embodiments of the compound of Formula (I) or Formula (I-B), each $R^4$ is independently selected from H, hydroxyl, $C_1$-$C_3$ alkyl, $C_1$-$C_3$ alkoxyl, or $C_1$-$C_3$ haloalkyl, each of which is substituted with 0, 1, 2, or 3 $R^6$, or two $R^4$ groups are taken together to form an oxo. In some embodiments, each $R^4$ is independently selected from H, hydroxyl, $C_1$-$C_3$ alkyl, $C_1$-$C_3$ alkoxyl, or $C_1$-$C_3$ haloalkyl, or two $R^4$ groups are taken together to form an oxo. In some embodiments, $R^4$ is H. In some embodiments, two $R^4$ groups are taken together to form an oxo.

In some embodiments of the compound of Formula (I) or Formula (I-B), $R^5$ is selected from hydrogen, halogen, hydroxy, $C_1$-$C_3$ alkyl, $C_1$-$C_3$ alkoxy, $C_1$-$C_3$ haloalkyl, $-N(R^7)_2$, and $-CN$, each of which is substituted with 0, 1, 2, or 3 $R^6$. In some embodiments, $R^5$ is selected from hydrogen, halogen, hydroxy, $C_1$-$C_3$ alkyl, $C_1$-$C_3$ alkoxy, $C_1$-$C_3$ haloalkyl, $-N(R^7)_2$, and $-CN$. In some embodiments, $R^5$ is selected from hydrogen. In some embodiments, $R^5$ is selected from halogen. In some embodiments, $R^5$ may be F.

In some embodiments of the compound of Formula (I) or Formula (I-B), $X^1$ and $X^2$ are each independently selected from H, halogen, cyano, $C_1$-$C_6$ alkyl, $C_1$-$C_6$ alkoxyl, or $C_1$-$C_6$ haloalkyl, each of which is substituted with 0, 1, 2, or 3 $R^6$. In some embodiments, $X^1$ and $X^2$ are each independently selected from H, halogen, cyano, $C_1$-$C_6$ alkyl, $C_1$-$C_6$ alkoxyl, or $C_1$-$C_6$ haloalkyl. In some embodiments, $X^1$ and $X^2$ are each independently selected from H, F, CN, methyl, methoxy, trifluoromethyl. In some embodiments, $X^1$ is H and $X^2$ is H. In some embodiments, $X^1$ is F and $X^2$ is F. In some embodiments, $X^1$ is H and $X^2$ is methyl. In some embodiments, $X^1$ is methyl and $X^2$ is H. In some embodiments, $X^1$ is H and $X^2$ is F. In some embodiments, $X^1$ is F and $X^2$ is H. In some embodiments, $X^1$ is H and $X^2$ is methoxy. In some embodiments, $X^1$ is methoxy and $X^2$ is H. In some embodiments, $X^1$ is F and $X^2$ is methyl. In some embodiments, $X^1$ is methyl and $X^2$ is F. In some embodiments, $X^1$ is F and $X^2$ is methoxy. In some embodiments, $X^1$ is methoxy and $X^2$ is F. In some embodiments, $X^1$ is F and $X^2$ is trifluoromethyl. In some embodiments, $X^1$ is trifluoromethyl and $X^2$ is F.

In some embodiments of the compound of Formula (I) or Formula (I-B), $X^3$ and $X^4$ are each independently selected from H or halo. In some embodiments, $X^3$ and $X^4$ are each independently selected from H or F. In some embodiments, $X^3$ is H and $X^4$ is H. In some embodiments, $X^3$ is F and $X^4$ is F. In some embodiments, $X^3$ is H and $X^4$ is F. In some embodiments, $X^3$ is F and $X^4$ is H.

In some embodiments of the compound of Formula (I) or Formula (I-B), L is linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L is linker of 1 to 20 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L is linker of 1 to 18 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L is linker of 1 to 16 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L is a linker of 1 to 14 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L is a linker of 1 to 12 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L is a linker of 1 to 10 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$.

In some embodiments of the compound of Formula (I) or Formula (I-B), L is a linker of 1 to 8 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L is a linker of 1 to 6 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$. In some embodiments, L is linker of 1 to 4 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is independently substituted with 0, 1, 2, or 3 $R^5$.

In some embodiments of the compound of Formula (I) or Formula (I-B), L is a linker wherein two carbon atoms are each independently replaced by a heterocycle, each of which is independently substituted with 0, 1, 2, or 3 $R^5$. In some embodiments, L is a linker wherein one carbon atom is replaced by a heterocycle and one carbon atom is replaced by a cycloalkyl, each of which is independently substituted with 0, 1, 2, or 3 $R^5$. In some embodiments, L is a linker wherein more than one carbon atoms are each independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$. In some embodiments, L is a linker wherein more than one carbon atoms are each independently replaced by a group selected from C(O), O, and $NR^4$, each of which is substituted with 0, 1, 2, or 3 $R^5$.

In some embodiments of the compound of Formula (I) or Formula (I-B), L is

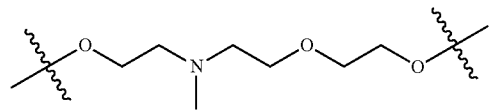

In some embodiments, L is

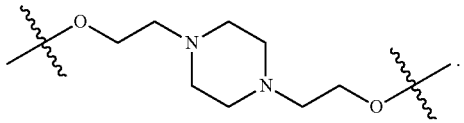 [SMILES: *OCCN1CCN(CCO*)CC1]

In some embodiments, L is

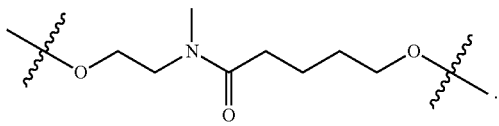 [SMILES: *OCCCCC(=O)N(C)CCO*]

In some embodiments, L is

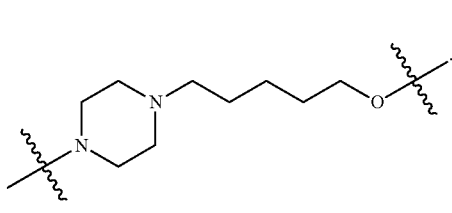

In some embodiments, L is

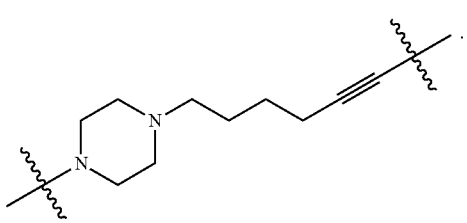 [SMILES: *C#CCCCCN1CCN(*)CC1]

In some embodiments, L is

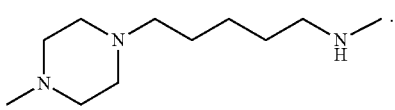

In some embodiments, L is

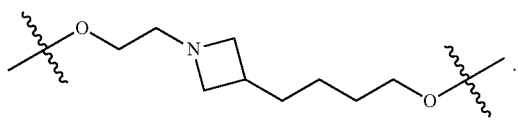 [SMILES: *OCCCCC1CN(CCO*)C1]

In some embodiments, L is

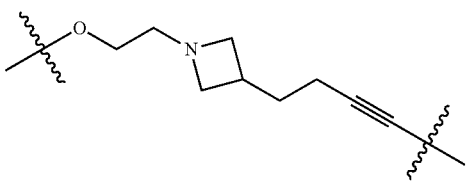

In some embodiments, L is

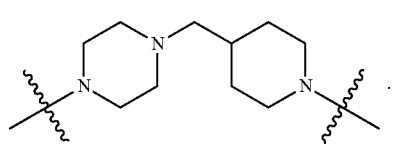 [SMILES: *N1CCC(CN2CCN(*)CC2)CC1]

In some embodiments, L is

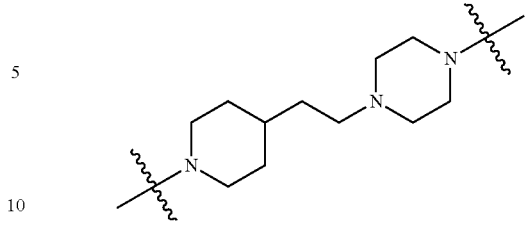

In some embodiments, L is

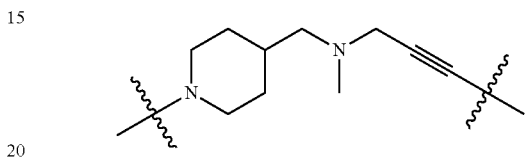

In some embodiments of the compound of Formula (I) or Formula (I-B), the compound of formula (I) is a stereoisomer. In some embodiments, the compound of Formula (I) or Formula (I-B), is a cis-isomer.

In some embodiments, the compound with ER degradation activity or tautomer, stereoisomer, pharmaceutically acceptable salt, or hydrate thereof provided herein, is a compound of Formula Formula (I-B)*:

(I-B)*

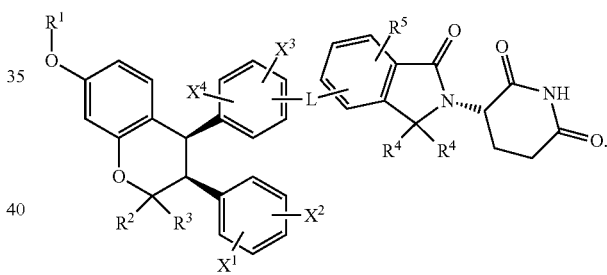

In some embodiments, the ER degrader is has a structure according to Formula III-C:

Formula (III-C)

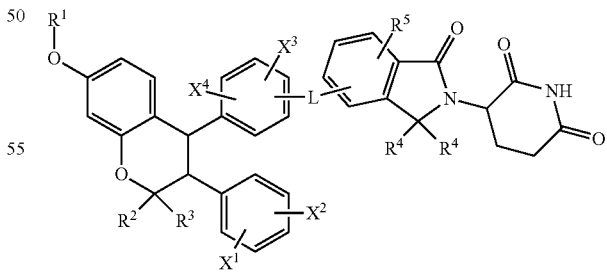

wherein:

$R^1$ is selected from H, $C_1$-$C_6$ acyl, or $C_1$-$C_6$ alkyl, each of which is substituted with 0, 1, 2, or 3 $R^6$;

$R^2$ and $R^3$ are each independently selected from H, $C_1$-$C_3$ alkyl, or $C_1$-$C_3$ haloalkyl, each of which is substituted with 0, 1, 2, or 3 $R^6$;

each $R^4$ is independently selected from H, hydroxyl, $C_1$-$C_3$ alkyl, $C_1$-$C_3$ alkoxy, or $C_1$-$C_3$ haloalkyl, each of which is substituted with 0, 1, 2, or 3 $R^6$, or two $R^4$ groups are taken together to form an oxo;

$R^5$ is selected from hydrogen, halogen, hydroxy, $C_1$-$C_3$ alkyl, $C_1$-$C_3$ alkoxy, $C_1$-$C_3$ haloalkyl, —N($R^7$)$_2$, and —CN, each of which is substituted with 0, 1, 2, or 3 $R^6$;

$X^1$ and $X^2$ are each independently selected from H, halogen, cyano, $C_1$-$C_6$ alkyl, $C_1$-$C_6$ alkoxy, or $C_1$-$C_6$ haloalkyl each of which is substituted with 0, 1, 2, or 3 $R^6$;

$X^3$ and $X^4$ are each independently selected from H or halo;

L is a linker of 1 to 22 carbon atoms in length, wherein one or more carbon atoms are each optionally and independently replaced by a group selected from C(O), O, $NR^7$, S, $C_2$-alkenyl, $C_2$-alkynyl, cycloalkyl, aryl, heterocycle, and heteroaryl, each of which is substituted with 0, 1, 2, or 3 $R^6$;

each $R^6$ is independently selected from $C_1$-$C_6$ alkyl, haloII, cyano, and hydroxy, each $R^7$ is independently selected from hydrogen, $C_1$-$C_6$ alkyl, and acyl, each of which is substituted with 0, 1, 2, or 3 $R^6$, or two $R^7$ groups are taken together to form a 3- to 6-membered heterocycle or heteroaryl.

In some embodiments the compound with ER degradation activity or tautomer, stereoisomer, pharmaceutically acceptable salt, or hydrate thereof provided herein, is a pharmaceutically acceptable salt of a compound of Formula (I-B) or Formula (I-B)*.

In some embodiments, the compound with ER degradation activity or tautomer, stereoisomer, pharmaceutically acceptable salt, or hydrate thereof provided herein, is one or more compounds selected from Table 1B.

TABLE 1B

Exemplary Compound of the Present Disclosure

| Cpd # | Chemical Structure | IUPAC Name |
|---|---|---|
| 1 | 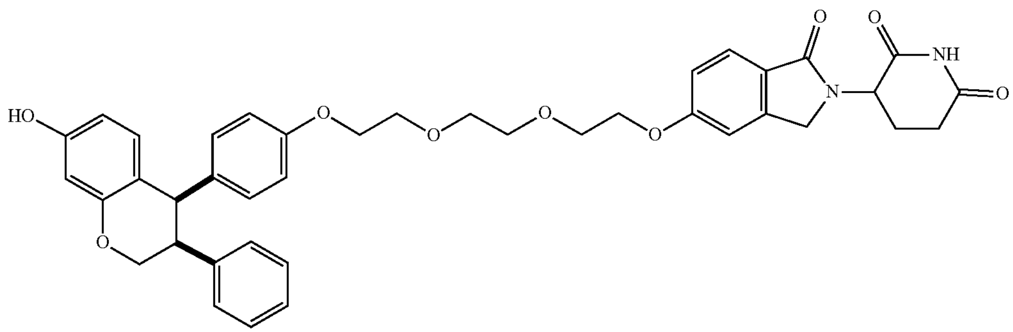 [SMILES: O=C1CCC(N2Cc3cc(OCCOCCOCCOc4ccc([C@@H]5c6ccc(O)cc6OC[C@@H]5c5ccccc5)cc4)ccc3C2=O)C(=O)N1] | cis-3-(5-(2-(2-(2-(4-(7-hydroxy-3-phenyl)chroman-4-yl)phenoxy)ethoxy)ethoxy)ethoxy)-1-oxoisoindolin-2-yl)piperidine-2,6-dione |
| 2 | 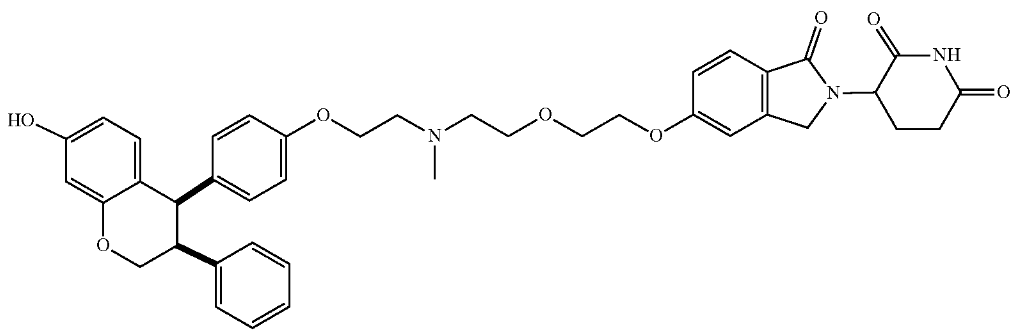 | cis-3-(5-(2-(2-(2-(4-(7-hydroxy-3-phenylchroman-4-yl)phenoxy)ethyl)(methyl)amino)ethoxy)ethoxy)-1-oxoisoindolin-2-yl)piperidine-2,6-dione |
| 3 | 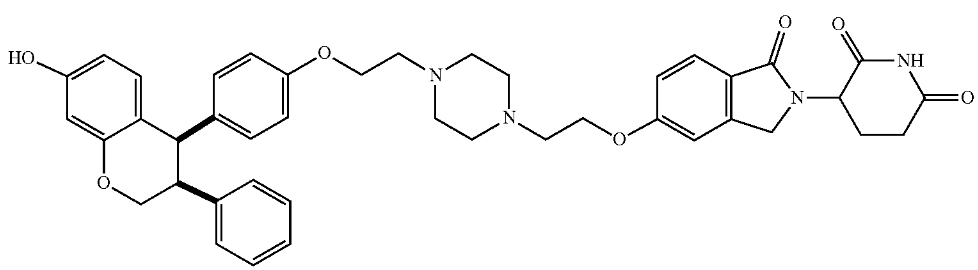 [SMILES: O=C1CCC(N2Cc3cc(OCCN4CCN(CCOc5ccc([C@@H]6c7ccc(O)cc7OC[C@@H]6c6ccccc6)cc5)CC4)ccc3C2=O)C(=O)N1] | cis-3-(5-(2-(4-(2-(4-(7-hydroxy-3-phenylchroman-4-yl)phenoxy)ethyl)piperazin-1-yl)ethoxy)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 4 | 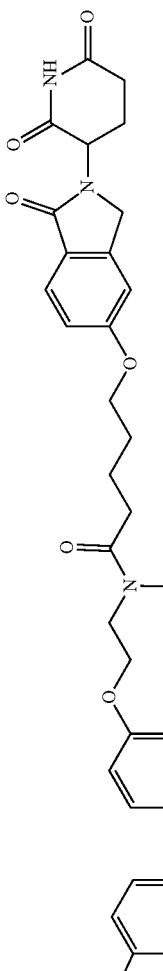 | cis-5-((2-(2,6-dioxopiperidin-3-yl)-1-oxoisoindolin-5-yl)oxy)-N-(2-(4-(7-hydroxy-3-phenylchroman-4-yl)phenoxy)ethyl)-N-methylpentanamide |
| 5 | 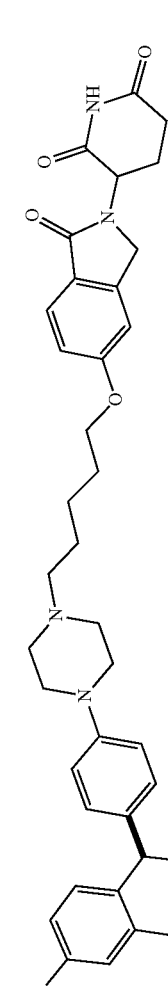 | cis-3-(5-(5-(4-(4-(7-hydroxy-3-phenylchroman-4-yl)phenyl)piperazin-1-yl)pentyl)oxy)-1-oxoisoindolin-2-yl)piperidine-2,6-dione |
| 6 | 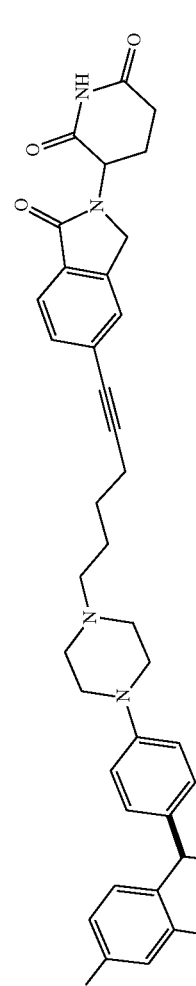 | cis-3-(5-(6-(4-(4-(7-hydroxy-3-phenylchroman-4-yl)phenyl)piperazin-1-yl)hex-1-yn-1-yl)-1-oxoisoindolin-2-yl)piperidine-2,6-dione |

TABLE1B-continued

Exemplary Compound of the Present Disclosure

| Cpd # | Chemical Structure | IUPACName |
|---|---|---|
| 7 | 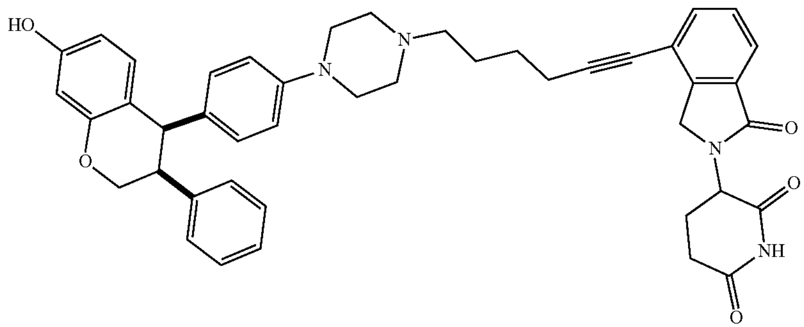 [SMILES: O=C1CCC(N2Cc3c(C#CCCCCN4CCN(c5ccc([C@@H]6c7ccc(O)cc7OC[C@@H]6c6ccccc6)cc5)CC4)cccc3C2=O)C(=O)N1] | cis-3-(4-(6-(4-(4-(7-hydroxy-3-phenylchroman-4-yl)phenyl)piperazin-1-yl)hex-1-yn-1-yl)-1-oxoisoindolin-2-yl)piperidine-2,6-dione |
| 8 | 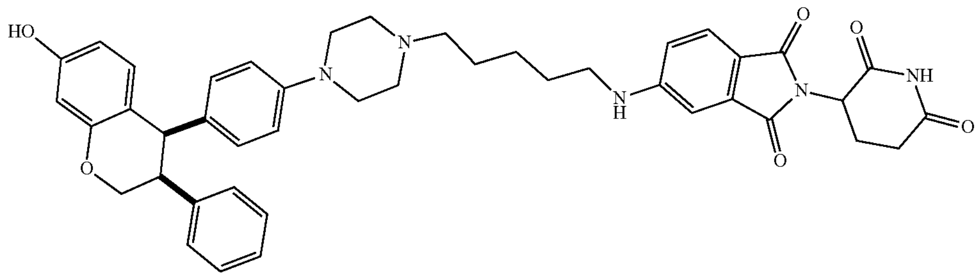 [SMILES: O=C1CCC(N2C(=O)c3ccc(NCCCCCN4CCN(c5ccc([C@@H]6c7ccc(O)cc7OC[C@@H]6c6ccccc6)cc5)CC4)cc3C2=O)C(=O)N1] | cis-2-(2,6-dioxopiperidin-3-yl)-5-((5-(4-(4-(7-hydroxy-3-phenylchroman-4-yl)phenyl)piperazin-1-yl)pentyl)amino)isoindoline-1,3-dione |
| 9 | 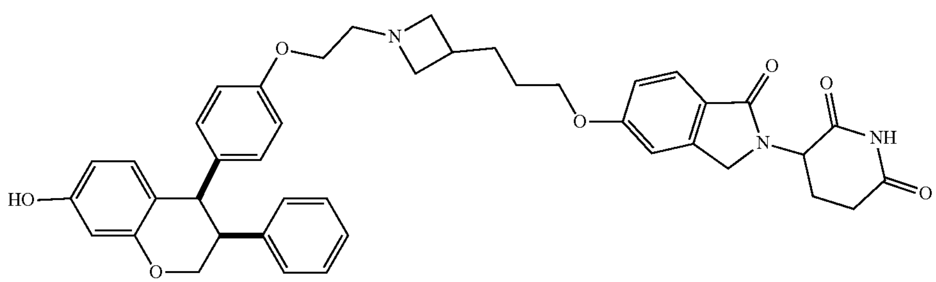 [SMILES: O=C1CCC(N2Cc3cc(OCCCC4CN(CCOc5ccc([C@@H]6c7ccc(O)cc7OC[C@@H]6c6ccccc6)cc5)C4)ccc3C2=O)C(=O)N1] | cis-3-(5-(3-(1-(2-(4-(7-hydroxy-3-phenylchroman-4-yl)phenoxy)ethyl)azetidin-3-yl)propoxy)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 10 | | cis-3-(5-(4-(1-(2-(4-(7-hydroxy-3-phenylchroman-4-yl)phenoxy)ethyl)azetidin-3-yl)but-1-yn-1-yl)-1-oxoisoindolin-2-yl)piperidine-2,6-dione |
| 11 | | cis-3-(4-(4-(1-(2-(4-(7-hydroxy-3-phenylchroman-4-yl)phenoxy)ethyl)azetidin-3-yl)but-1-yn-1-yl)-1-oxoisoindolin-2-yl)piperidine-2,6-dione |
| 12 | | cis-2-(2,6-dioxopiperidin-3-yl)-5-(4-(5-(4-(7-hydroxy-3-phenylchroman-4-yl)phenoxy)pentyl)piperazin-1-yl)isoindoline-1,3-dione |

TABLE 1B-continued

Exemplary Compound of the Present Disclosure

| Cpd # | Chemical Structure | IUPAC Name |
|---|---|---|
| 13 | 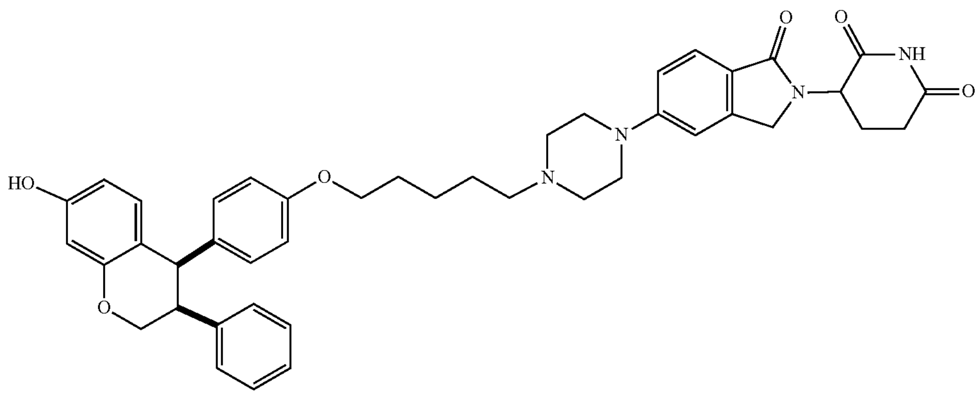 [SMILES: O=C1CCC(N2Cc3cc(N4CCN(CCCCCOc5ccc([C@@H]6c7ccc(O)cc7OC[C@@H]6c6ccccc6)cc5)CC4)ccc3C2=O)C(=O)N1] | cis-3-(5-(4-(5-(4-(7-hydroxy-3-phenylchroman-4-yl)phenoxy)pentyl)piperazin-1-yl)-1-oxoisoindolin-2-yl)piperidine-2,6-dione |
| 14 | 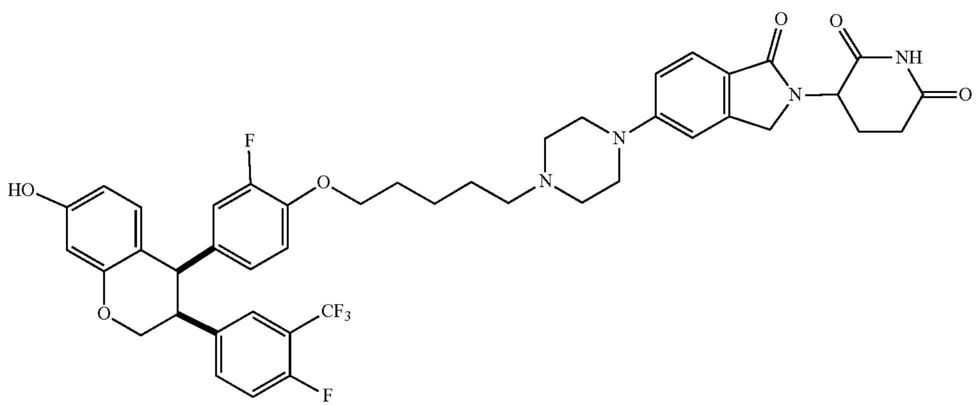 [SMILES: O=C1CCC(N2Cc3cc(N4CCN(CCCCCOc5ccc([C@@H]6c7ccc(O)cc7OC[C@@H]6c6ccc(F)c(C(F)(F)F)c6)cc5F)CC4)ccc3C2=O)C(=O)N1] | cis-3-(5-(4-(5-(2-fluro-4-(3-(4-fluoro-3-(trifluoromethyl)phenyl)-7-hydroxychroman-4-yl)phenoxy)pentyl)piperazin-1-yl)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 15 | 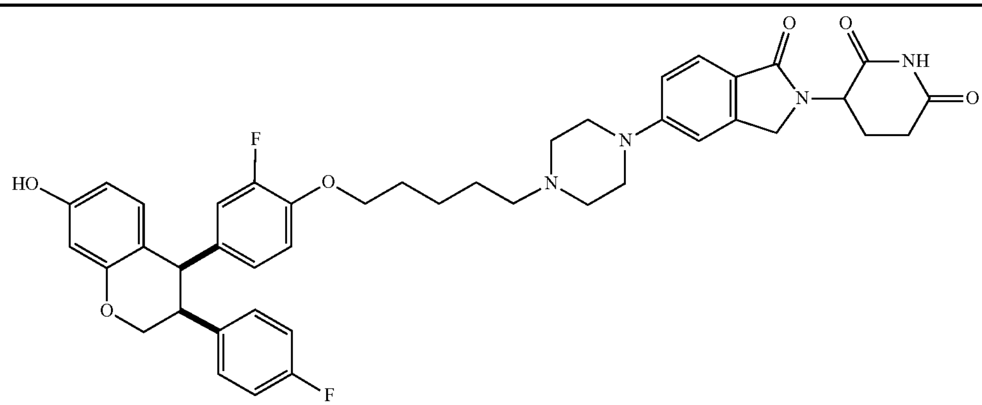 | cis-3-(5-(4-(5-(2-fluoro-4-(3-(4-fluorophenyl)-7-hydroxychroman-4-yl)phenoxy)pentyl)piperazin-1-yl)-1-oxoisoindolin-2-yl)piperidine-2,6-dione |
| 16 | 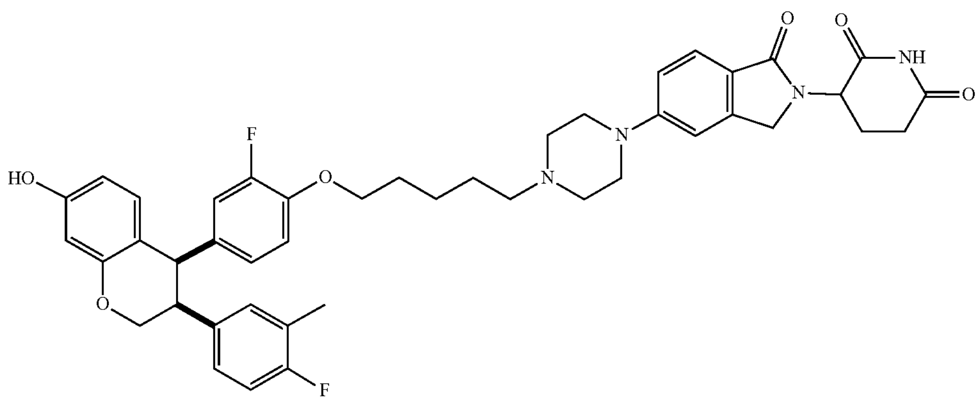 [SMILES: Cc1cc([C@H]2COc3cc(O)ccc3[C@H]2c2ccc(OCCCCCN3CCN(c4ccc5c(c4)CN(C4CCC(=O)NC4=O)C5=O)CC3)c(F)c2)ccc1F] | cis-3-(5-(4-(5-(2-fluoro-4-(3-(4-fluoro-3-methylphenyl)-7-hydroxychroman-4-yl)phenoxy)pentyl)piperazin-1-yl)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 17 | 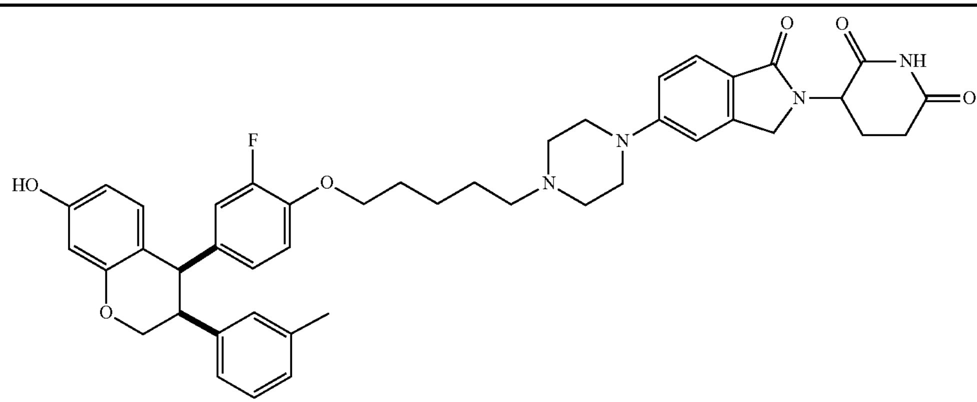 | cis-3-(5-(4-(5-(2-fluoro-4-(7-hydroxy-3-(m-tolyl)chroman-4-yl)phenoxy)pentyl)piperazin-1-yl)-1-oxoisoindolin-2-yl)piperidine-2,6-dione |
| 18 | 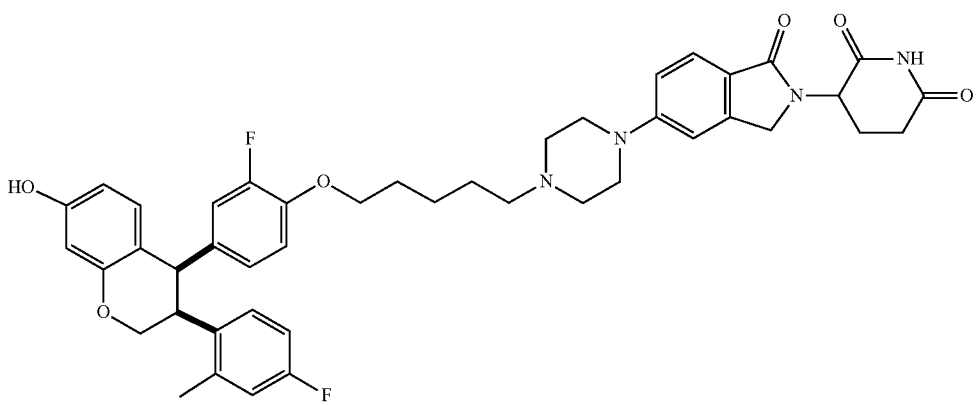 [SMILES: Cc1cc(F)ccc1[C@H]1COc2cc(O)ccc2[C@H]1c1ccc(OCCCCCN2CCN(c3ccc4c(c3)CN(C3CCC(=O)NC3=O)C4=O)CC2)c(F)c1] | cis-3-(5-(4-(5-(2-fluoro-4-(3-(4-fluoro-2-methylphenyl)-7-hydroxychroman-4-yl)phenoxy)pentyl)piperazin-1-yl)-1-oxoisoindolin-2-yl)piperidine-2,6-dione |

TABLE 1B-continued
Exemplary Compound of the Present Disclosure
| Cpd # | Chemical Structure | IUPAC Name |
|---|---|---|
| 19 | 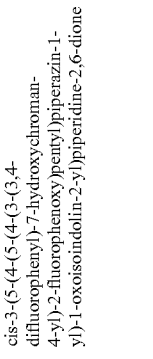 | cis-3-(5-(4-(5-(4-(3-(3,4-difluorophenyl)-7-hydroxychroman-4-yl)-2-fluorophenoxy)pentyl)piperazin-1-yl)-1-oxoisoindolin-2-yl)piperidine-2,6-dione |
| 20 | 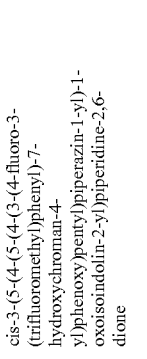 | cis-3-(5-(4-(5-(4-(3-(4-fluoro-3-(trifluoromethyl)phenyl)-7-hydroxychroman-4-yl)phenoxy)pentyl)piperazin-1-yl)-1-oxoisoindolin-2-yl)piperidine-2,6-dione |

TABLE1B-continued
Exemplary Compound of the Present Disclosure
| Cpd # | Chemical Structure | IUPAC Name |
|---|---|---|
| 21 | 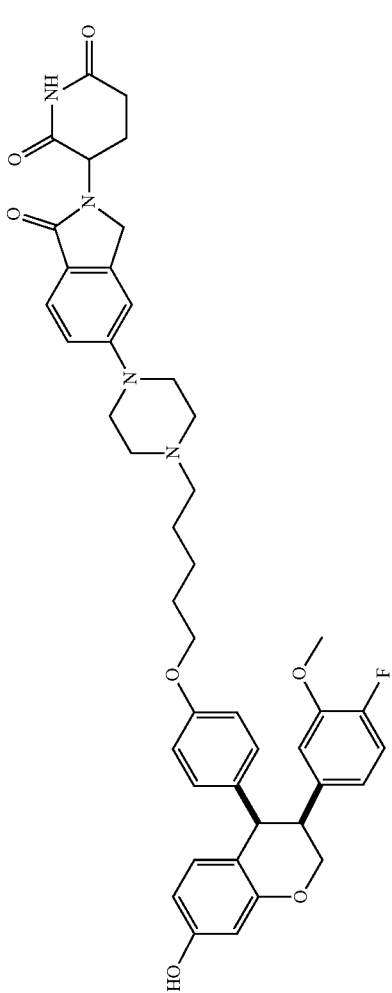 | cis-3-(5-(4-(5-(4-(3-(4-fluoro-3-methoxyphenyl)-7-hydroxychroman-4-yl)phenoxy)pentyl)piperazin-1-yl)-1-oxoisoindolin-2-yl)piperidine-2,6-dione |
| 22 | 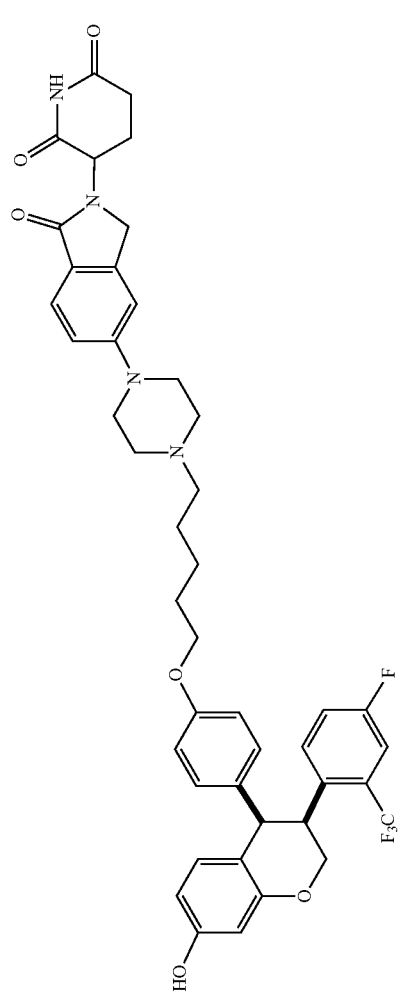 | cis-3-(5-(4-(5-(4-(3-(4-fluoro-2-(trifluoromethyl)phenyl)-7-hydroxychroman-4-yl)phenoxy)pentyl)piperazin-1-yl)-1-oxoisoindolin-2-yl)piperidine-2,6-dione |

TABLE 1B-continued
Exemplary Compound of the Present Disclosure
| Cpd # | Chemical Structure | IUPAC Name |
|---|---|---|
| 23 | 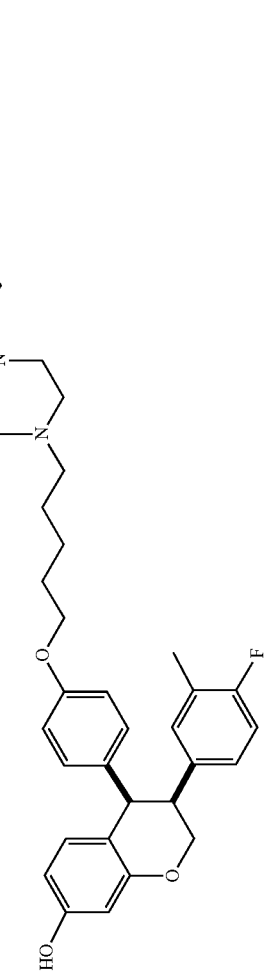 | cis-3-(5-(4-(5-(4-(3-(4-fluoro-3-methylphenyl)-7-hydroxychroman-4-yl)phenoxy)pentyl)piperazin-1-yl)-1-oxoisoindolin-2-yl)piperidine-2,6-dione |
| 24 | 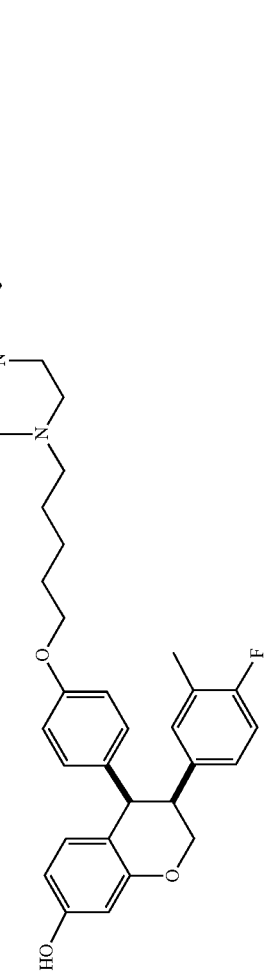 | cis-3-(5-(4-(5-(4-(7-hydroxy-3-(o-tolyl)chroman-4-yl)phenoxy)pentyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 25 | 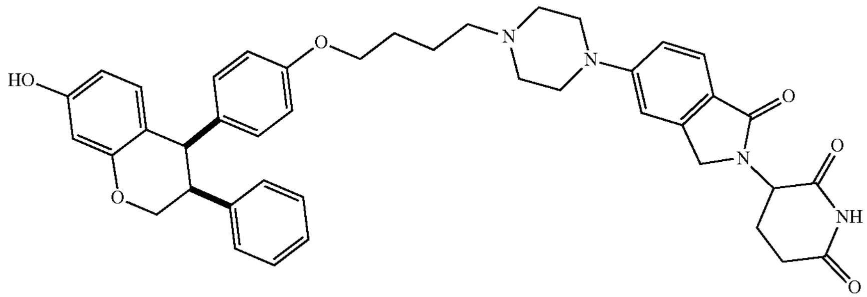 [SMILES: O=C1CCC(N2Cc3cc(N4CCN(CCCCOc5ccc([C@@H]6c7ccc(O)cc7OC[C@@H]6c6ccccc6)cc5)CC4)ccc3C2=O)C(=O)N1] | cis-3-(5-(4-(4-(4-(7-hydroxy-3-phenylchroman-4-yl)phenoxy)butyl)piperazin-1-yl)-1-oxoisoindolin-2-yl)piperidine-2,6-dione |
| 26 | 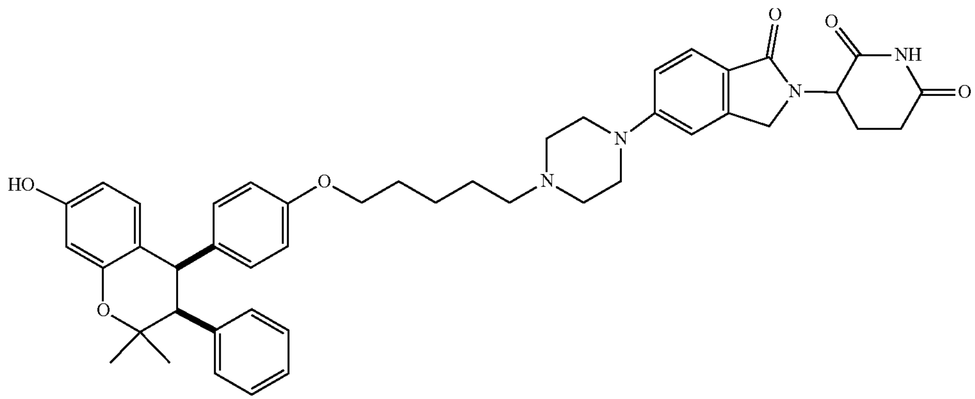 [SMILES: CC1(C)Oc2cc(O)ccc2[C@@H](c2ccc(OCCCCCN3CCN(c4ccc5c(c4)CN(C4CCC(=O)NC4=O)C5=O)CC3)cc2)[C@H]1c1ccccc1] | cis-3-(5-(4-(5-(4-(7-hydroxy-2,2-dimethyl-3-phenylchroman-4-yl)phenoxy)pentyl)piperazin-1-yl)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 27 | 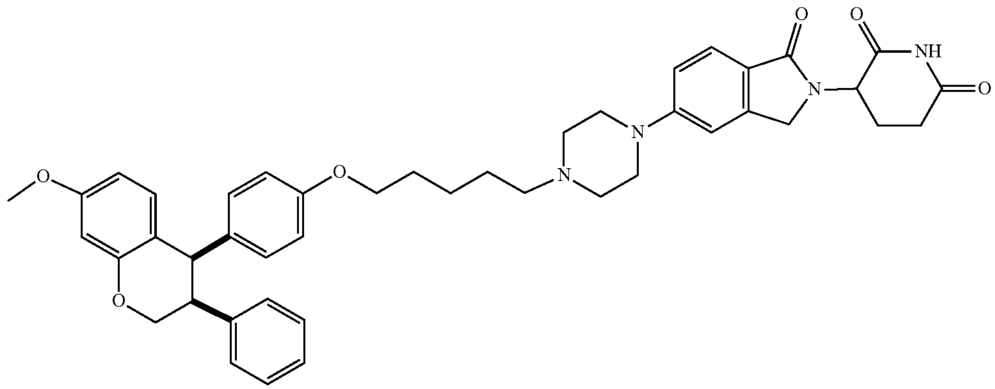 [SMILES: COc1ccc2c(c1)OC[C@H](c1ccccc1)[C@@H]2c1ccc(OCCCCCN2CCN(c3ccc4c(c3)CN(C3CCC(=O)NC3=O)C4=O)CC2)cc1] | cis-3-(5-(4-(5-(4-(7-methoxy-3-phenylchroman-4-yl)phenoxy)pentyl)piperazin-1-yl)-1-oxoisoindolin-2-yl)piperidine-2,6-dione |
| 28 | 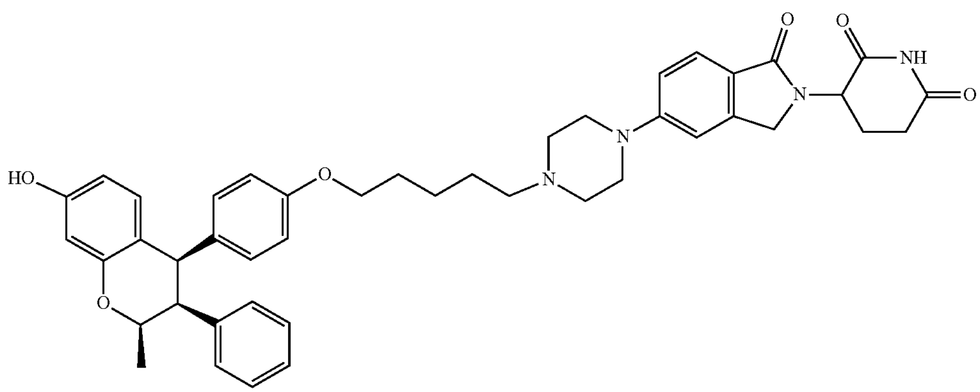 [SMILES: C[C@H]1Oc2cc(O)ccc2[C@@H](c2ccc(OCCCCCN3CCN(c4ccc5c(c4)CN(C4CCC(=O)NC4=O)C5=O)CC3)cc2)[C@H]1c1ccccc1] | 3-(5-(4-(5-(4-((2R,3S,4R)-7-hydroxy-2-methyl-3-phenylchroman-4-yl)phenoxy)pentyl)piperazin-1-yl)-1-oxoisoindolin-2-yl)piperidine-2,6-dione |

TABLE1B-continued

Exemplary Compound of the Present Disclosure

| Cpd # | Chemical Structure | IUPACName |
|---|---|---|
| 29 | 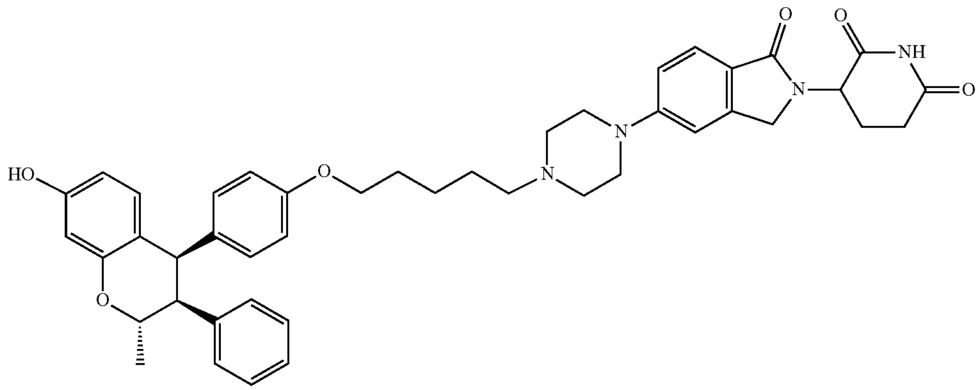 [SMILES: C[C@@H]1Oc2cc(O)ccc2[C@@H](c2ccc(OCCCCCN3CCN(c4ccc5c(c4)CN(C4CCC(=O)NC4=O)C5=O)CC3)cc2)[C@H]1c1ccccc1] | 3-(5-(4-(5-(4-((2S,3S,4R)-7-hydroxy-2-methyl-3-phenylchroman-4-yl)phenoxy)pentyl)piperazin-1-yl)-1-oxoisoindolin-2-yl)piperidine-2,6-dione |
| 30 | 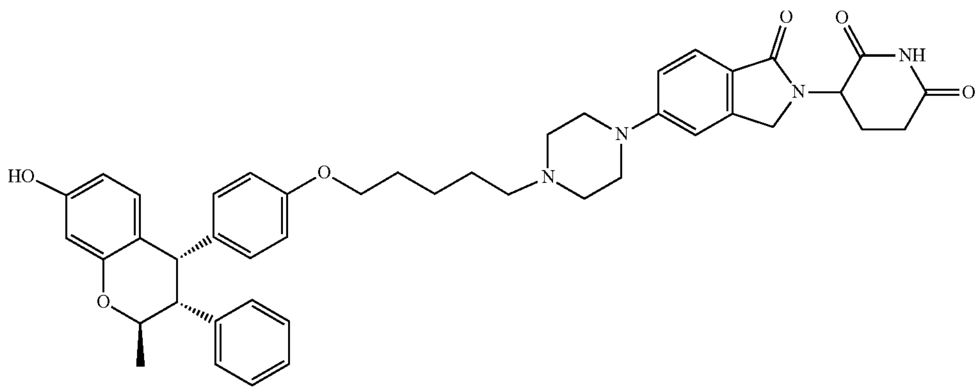 [SMILES: C[C@H]1Oc2cc(O)ccc2[C@H](c2ccc(OCCCCCN3CCN(c4ccc5c(c4)CN(C4CCC(=O)NC4=O)C5=O)CC3)cc2)[C@@H]1c1ccccc1] | 3-(5-(4-(5-(4-((2R,3R,4S)-7-hydroxy-2-methyl-3-phenylchroman-4-yl)phenoxy)pentyl)piperazin-1-yl)-1-oxoisoindolin-2-yl)piperidine-2,6-dione |

TABLE 1B-continued
Exemplary Compound of the Present Disclosure
| Cpd # | Chemical Structure | IUPAC Name |
|---|---|---|
| 31 | 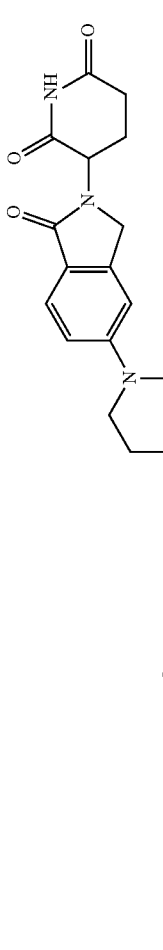 | 3-(5-(4-(5-(4-((2S,3R,4S)-7-hydroxy-2-methyl-3-phenylchroman-4-yl)phenoxy)pentyl)piperazin-1-yl)-1-oxoisoindolin-2-yl)piperidine-2,6-dione |
| 32 | 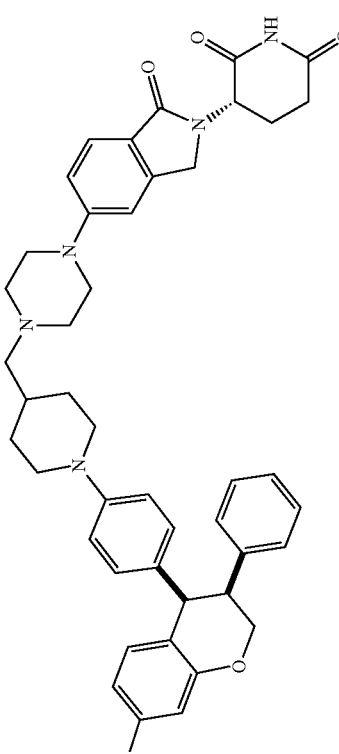 | cis-(S)-3-(5-(4-((1-(4-(7-hydroxy-3-phenylchroman-4-yl)phenyl)piperidin-4-yl)methyl)piperazin-1-yl)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 33 | 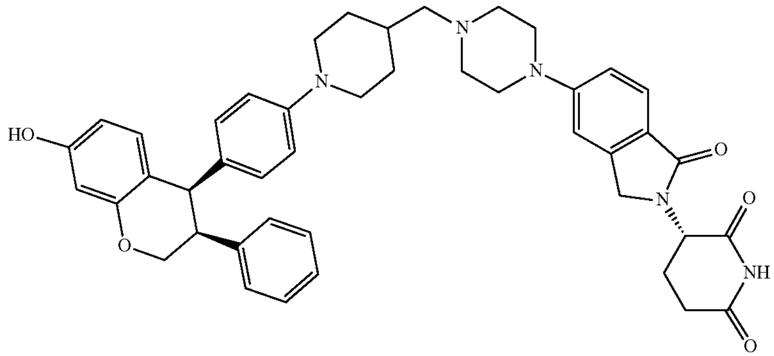 [SMILES: O=C1CC[C@H](N2Cc3cc(N4CCN(CC5CCN(c6ccc([C@@H]7c8ccc(O)cc8OC[C@@H]7c7ccccc7)cc6)CC5)CC4)ccc3C2=O)C(=O)N1] | (S)-3-(5-(4-((1-(4-((3S,4R)-7-hydroxy-3-phenylchroman-4-yl)phenyl)piperidin-4-yl)methyl)piperazin-1-yl)-1-oxoisoindolin-2-yl)piperidine-2,6-dione |
| 34 | 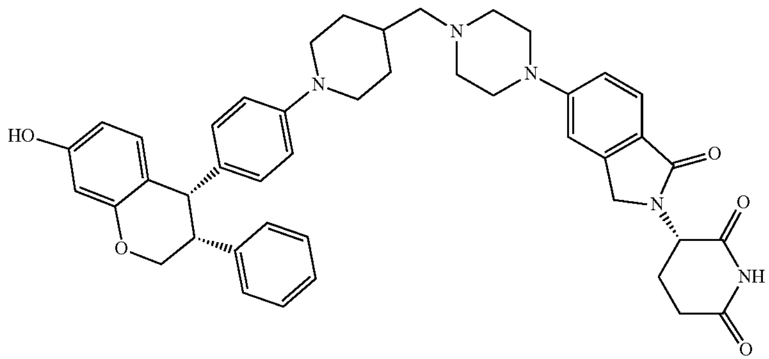 [SMILES: O=C1CC[C@H](N2Cc3cc(N4CCN(CC5CCN(c6ccc([C@H]7c8ccc(O)cc8OC[C@H]7c7ccccc7)cc6)CC5)CC4)ccc3C2=O)C(=O)N1] | (S)-3-(5-(4-((1-(4-((3R,4S)-7-hydroxy-3-phenylchroman-4-yl)phenyl)piperidin-4-yl)methyl)piperazin-1-yl)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 35 | 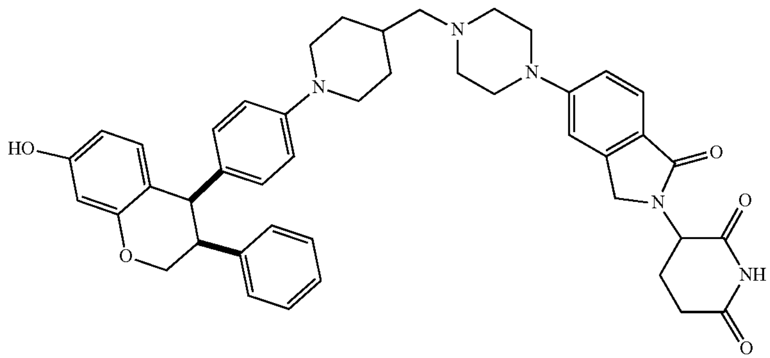 [SMILES: O=C1CCC(N2Cc3cc(N4CCN(CC5CCN(c6ccc([C@@H]7c8ccc(O)cc8OC[C@@H]7c7ccccc7)cc6)CC5)CC4)ccc3C2=O)C(=O)N1] | cis-3-(5-(4-((1-(4-(7-hydroxy-3-phenylchroman-4-yl)phenyl)piperidin-4-yl)methyl)piperazin-1-yl)-1-oxoisoindolin-2-yl)piperidine-2,6-dione |
| 36 | 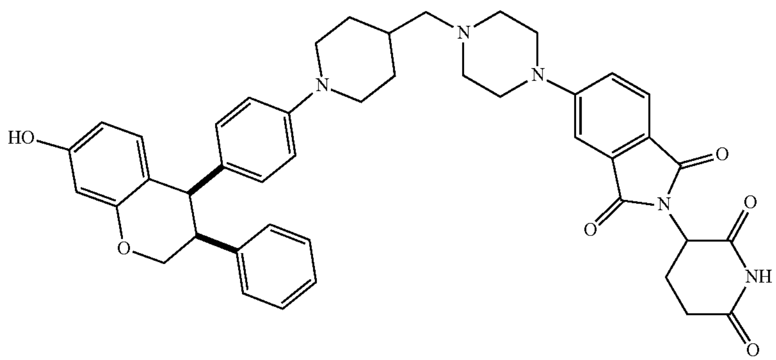 [SMILES: O=C1CCC(N2C(=O)c3ccc(N4CCN(CC5CCN(c6ccc([C@@H]7c8ccc(O)cc8OC[C@@H]7c7ccccc7)cc6)CC5)CC4)cc3C2=O)C(=O)N1] | cis-2-(2,6-dioxopiperidin-3-yl)-5-(4-((1-(4-(7-hydroxy-3-phenylchroman-4-yl)phenyl)piperidin-4-yl)methyl)piperazin-1-yl)isoindoline-1,3-dione |
| 37 | 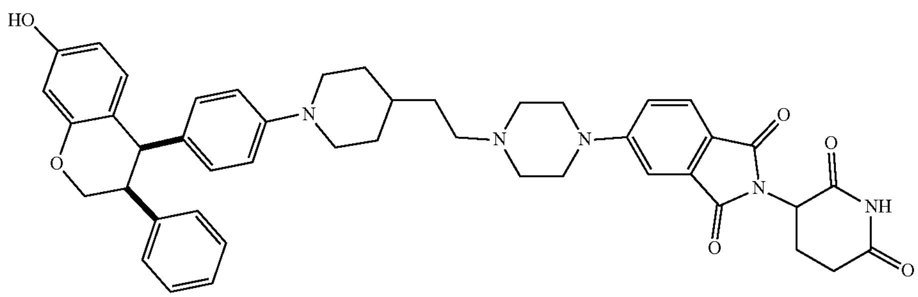 [SMILES: O=C1CCC(N2C(=O)c3ccc(N4CCN(CCC5CCN(c6ccc([C@@H]7c8ccc(O)cc8OC[C@@H]7c7ccccc7)cc6)CC5)CC4)cc3C2=O)C(=O)N1] | cis-2-(2,6-dioxopiperidin-3-yl)-5-(4-(2-(1-(4-(7-hydroxy-3-phenylchroman-4-yl)phenyl)piperidin-4-yl)ethyl)piperazin-1-yl)isoindoline-1,3-dione |

TABLE1B-continued

Exemplary Compound of the Present Disclosure

| Cpd # | Chemical Structure | IUPACName |
|---|---|---|
| 38 | 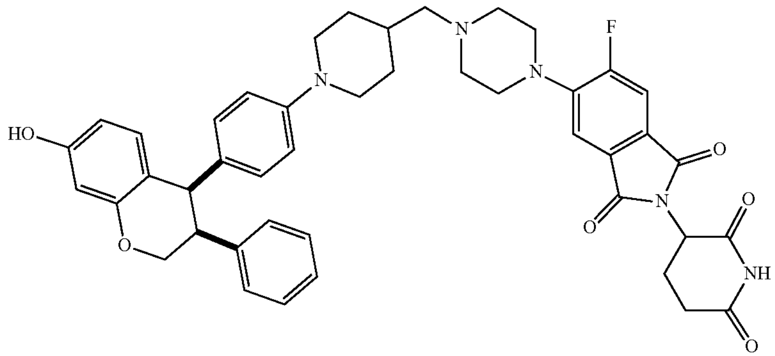 [SMILES: O=C1CCC(N2C(=O)c3cc(F)c(N4CCN(CC5CCN(c6ccc([C@@H]7c8ccc(O)cc8OC[C@@H]7c7ccccc7)cc6)CC5)CC4)cc3C2=O)C(=O)N1] | cis-2-(2,6-dioxopiperidin-3-yl)-5-fluoro-6-(4-((1-(4-(7-hydroxy-3-phenylchroman-4-yl)phenyl)piperidin-4-yl)methyl)piperazin-1-yl)isoindoline-1,3-dione |
| 39 | 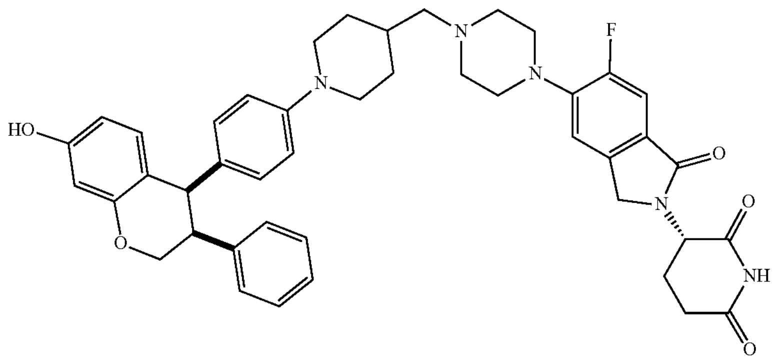 [SMILES: O=C1CC[C@H](N2Cc3cc(N4CCN(CC5CCN(c6ccc([C@@H]7c8ccc(O)cc8OC[C@@H]7c7ccccc7)cc6)CC5)CC4)c(F)cc3C2=O)C(=O)N1] | cis-(S)-3-(6-fluoro-5-(4-((1-(4-(7-hydroxy-3-phenylchroman-4-yl)phenyl)piperidin-4-yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 40 | 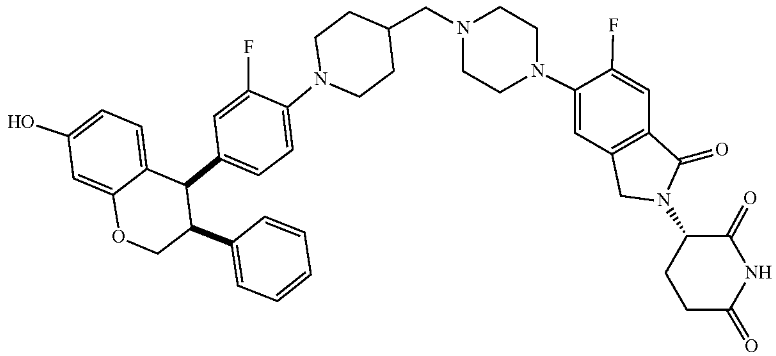 [SMILES: O=C1CC[C@H](N2Cc3cc(N4CCN(CC5CCN(c6ccc([C@@H]7c8ccc(O)cc8OC[C@@H]7c7ccccc7)cc6F)CC5)CC4)c(F)cc3C2=O)C(=O)N1] | cis-(S)-3-(6-fluoro-5-(4-((1-(2-fluoro-4-(7-hydroxy-3-phenylchroman-4-yl)phenyl)piperidin-4-yl)methyl)piperazin-1-yl)-1-oxoisoindolin-2-yl)piperidine-2,6-dione |
| 41 | 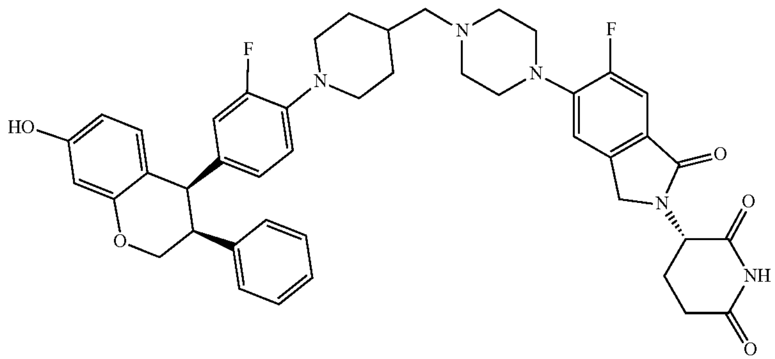 [SMILES: O=C1CC[C@H](N2Cc3cc(N4CCN(CC5CCN(c6ccc([C@@H]7c8ccc(O)cc8OC[C@@H]7c7ccccc7)cc6F)CC5)CC4)c(F)cc3C2=O)C(=O)N1] | (S)-3-(6-fluoro-5-(4-((1-(2-fluoro-4-((3S,4R)-7-hydroxy-3-phenylchroman-4-yl)phenyl)piperidin-4-yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 42 | 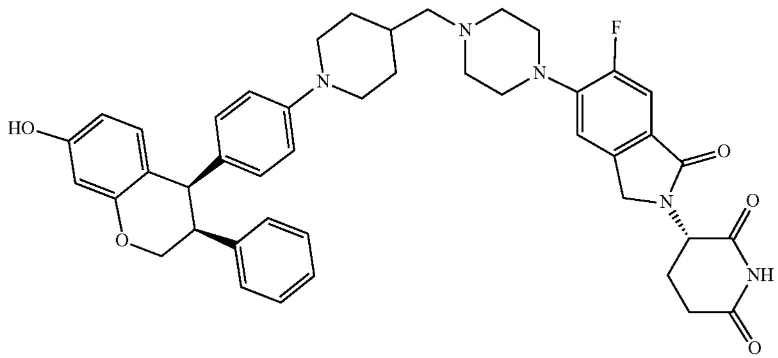 [SMILES: O=C1CC[C@H](N2Cc3cc(N4CCN(CC5CCN(c6ccc([C@@H]7c8ccc(O)cc8OC[C@@H]7c7ccccc7)cc6)CC5)CC4)c(F)cc3C2=O)C(=O)N1] | (S)-3-(6-fluoro-5-(4-((1-(4-((3S,4R)-7-hydroxy-3-phenylchroman-4-yl)phenyl)piperidin-4-yl)methyl)piperazin-1-yl)-1-oxoisoindolin-2-yl)piperidine-2,6-dione |
| 43 | 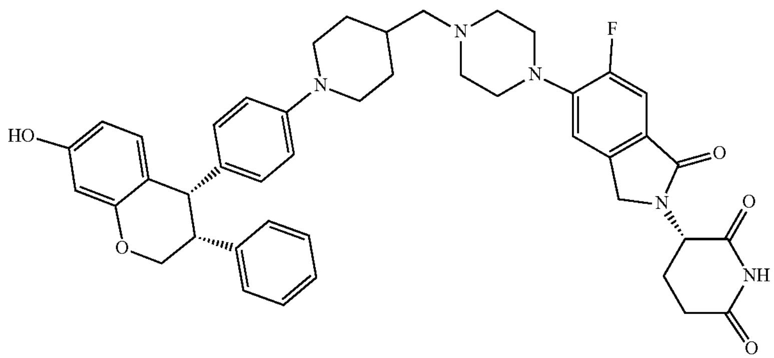 [SMILES: O=C1CC[C@H](N2Cc3cc(N4CCN(CC5CCN(c6ccc([C@H]7c8ccc(O)cc8OC[C@H]7c7ccccc7)cc6)CC5)CC4)c(F)cc3C2=O)C(=O)N1] | (S)-3-(6-fluoro-5-(4-((1-(4-((3R,4S)-7-hydroxy-3-phenylchroman-4-yl)phenyl)piperidin-4-yl)methyl)piperazin-1-yl)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 44 | 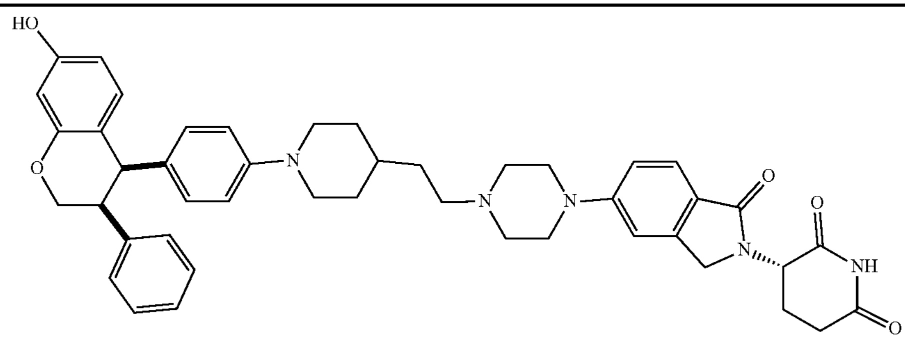 | cis-(S)-3-(5-(4-(2-(1-(4-(7-hydroxy-3-phenylchroman-4-yl)phenyl)piperidin-4-yl)ethyl)piperazin-1-yl)-1-oxoisoindolin-2-yl)piperidine-2,6-dione |
| 45 | 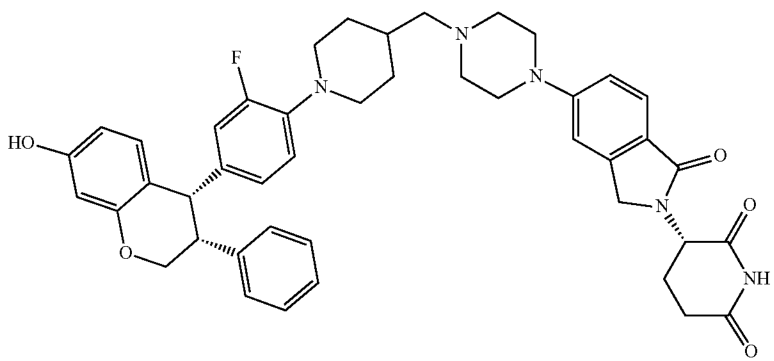 [SMILES: O=C1CC[C@H](N2Cc3cc(N4CCN(CC5CCN(c6ccc([C@H]7c8ccc(O)cc8OC[C@H]7c7ccccc7)cc6F)CC5)CC4)ccc3C2=O)C(=O)N1] | (S)-3-(5-(4-((1-(2-fluoro-4-((3R,4S)-7-hydroxy-3-phenylchroman-4-yl)phenyl)piperidin-4-yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 46 | 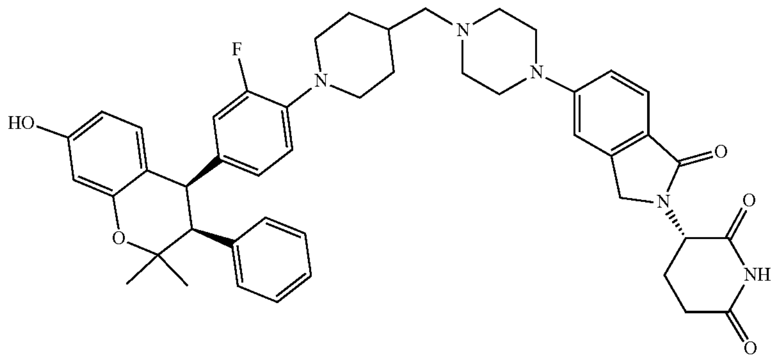 [SMILES: CC1(C)Oc2cc(O)ccc2[C@@H](c2ccc(N3CCC(CN4CCN(c5ccc6c(c5)CN([C@H]5CCC(=O)NC5=O)C6=O)CC4)CC3)c(F)c2)[C@H]1c1ccccc1] | (S)-3-(5-(4-((1-(2-fluoro-4-((3S,4R)-7-hydroxy-2,2-dimethyl-3-phenylchroman-4-yl)phenyl)piperidin-4-yl)methyl)piperazin-1-yl)-1-oxoisoindolin-2-yl)piperidine-2,6-dione |
| 47 | 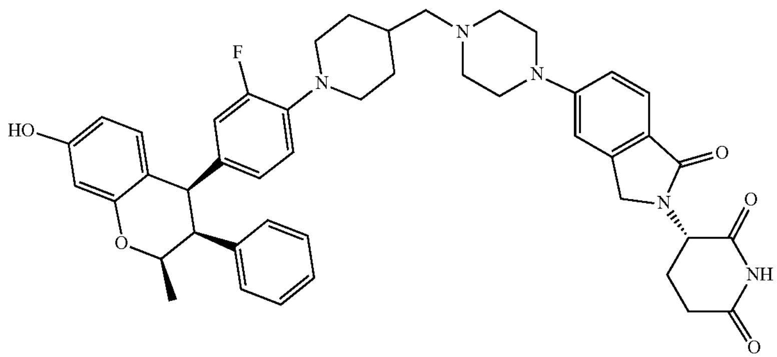 [SMILES: C[C@H]1Oc2cc(O)ccc2[C@@H](c2ccc(N3CCC(CN4CCN(c5ccc6c(c5)CN([C@H]5CCC(=O)NC5=O)C6=O)CC4)CC3)c(F)c2)[C@H]1c1ccccc1] | (S)-3-(5-(4-((1-(2-fluoro-4-((2R,3S,4R)-7-hydroxy-2-methyl-3-phenylchroman-4-yl)phenyl)piperidin-4-yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 48 | 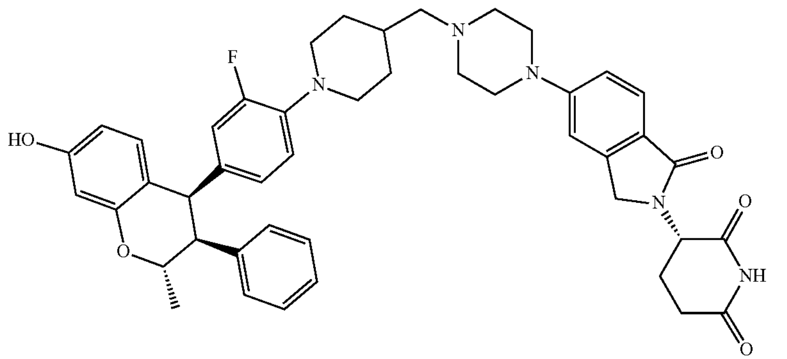 [SMILES: C[C@@H]1Oc2cc(O)ccc2[C@@H](c2ccc(N3CCC(CN4CCN(c5ccc6c(c5)CN([C@H]5CCC(=O)NC5=O)C6=O)CC4)CC3)c(F)c2)[C@H]1c1ccccc1] | (S)-3-(5-(4-((1-(2-fluoro-4-((2S,3S,4R)-7-hydroxy-2-methyl-3-phenylchroman-4-yl)phenyl)piperidin-4-yl)methyl)piperazin-1-yl)-1-oxoisoindolin-2-yl)piperidine-2,6-dione |
| 49 | 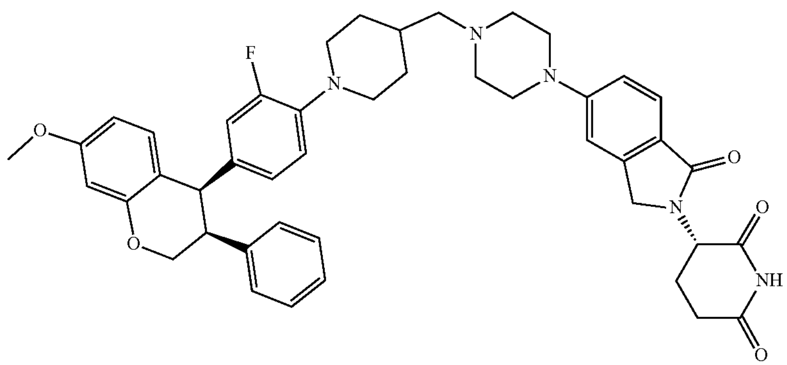 [SMILES: COc1ccc2c(c1)OC[C@H](c1ccccc1)[C@@H]2c1ccc(N2CCC(CN3CCN(c4ccc5c(c4)CN([C@H]4CCC(=O)NC4=O)C5=O)CC3)CC2)c(F)c1] | (S)-3-(5-(4-((1-(2-fluoro-4-((3S,4R)-7-methoxy-3-phenylchroman-4-yl)phenyl)piperidin-4-yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 50 | 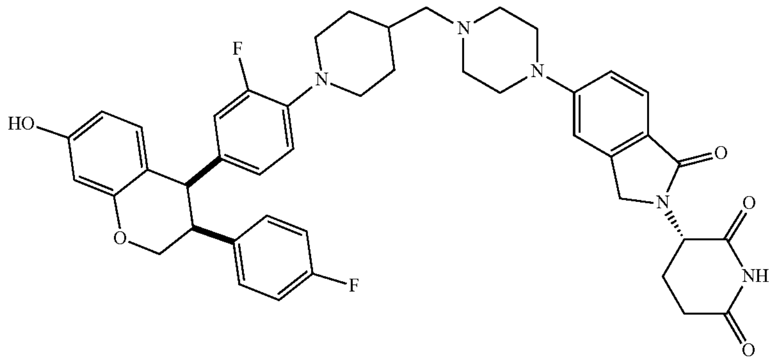 [SMILES: O=C1CC[C@H](N2Cc3cc(N4CCN(CC5CCN(c6ccc([C@@H]7c8ccc(O)cc8OC[C@@H]7c7ccc(F)cc7)cc6F)CC5)CC4)ccc3C2=O)C(=O)N1] | cis-(S)-3-(5-(4-((1-(2-fluoro-4-(3-(4-fluorophenyl)-7-hydroxychroman-4-yl)phenyl)piperidin-4-yl)methyl)piperazin-1-yl)-1-oxoisoindolin-2-yl)piperidine-2,6-dione |
| 51 | 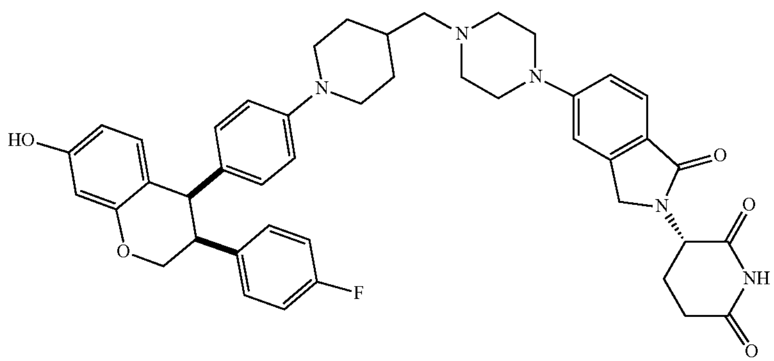 [SMILES: O=C1CC[C@H](N2Cc3cc(N4CCN(CC5CCN(c6ccc([C@@H]7c8ccc(O)cc8OC[C@@H]7c7ccc(F)cc7)cc6)CC5)CC4)ccc3C2=O)C(=O)N1] | cis-(S)-3-(5-(4-((1-(4-(3-(4-fluorophenyl)-7-hydroxychroman-4-yl)phenyl)piperidin-4-yl)methyl)piperazin-1-yl)-1-oxoisoindolin-2-yl)piperidine-2,6-dione |

TABLE1B-continued
Exemplary Compound of the Present Disclosure
| Cpd # | Chemical Structure | IUPAC Name |
|---|---|---|
| 52 | 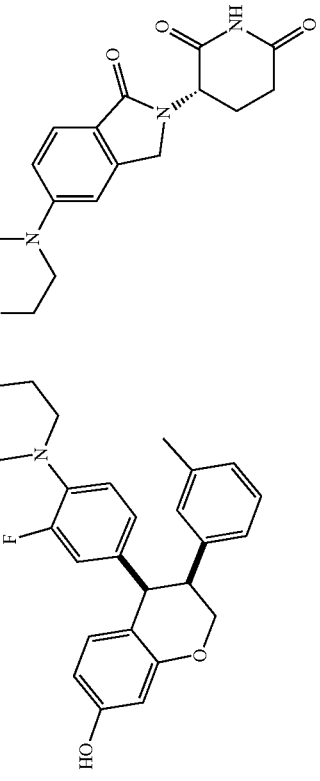 | cis-(S)-3-(5-(4-((1-(2-fluoro-4-(7-hydroxy-3-(m-tolyl)chroman-4-yl)phenyl)piperidin-4-yl)methyl)piperazin-1-yl)-1-oxoisoindolin-2-yl)piperidine-2,6-dione |
| 53 | 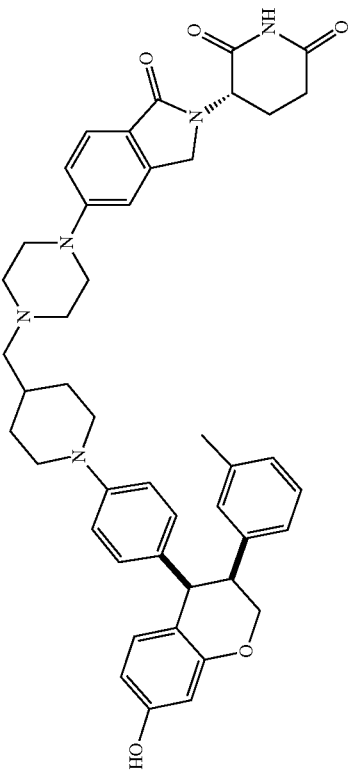 | cis-(S)-3-(5-(4-((1-(4-(7-hydroxy-3-(m-tolyl)chroman-4-yl)phenyl)piperidin-4-yl)methyl)piperazin-1-yl)-1-oxoisoindolin-2-yl)piperidine-2,6-dione |

TABLE1B-continued

Exemplary Compound of the Present Disclosure

| Cpd # Chemical Structure | IUPACName |
|---|---|
| 54 | cis-(S)-3-(5-(4-((1-(2-fluoro-4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione |
| 55 | (S)-3-(5-(4-((1-(2-fluoro-4-((3S,4R)-7-hydroxy-3-(3-methoxyphenyl)chroman-4-yl)phenyl)piperidin-4-yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 56 | 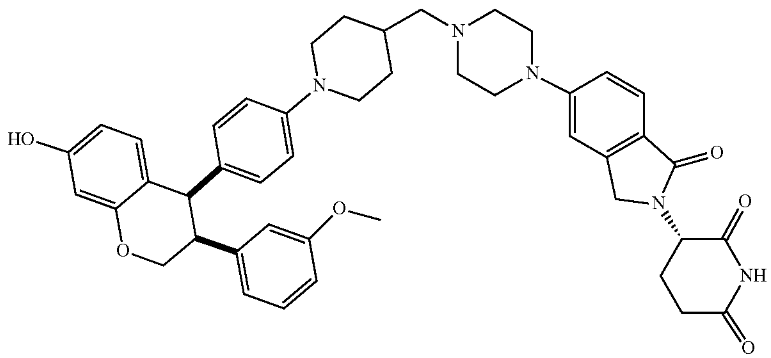 [SMILES: COc1cccc([C@H]2COc3cc(O)ccc3[C@H]2c2ccc(N3CCC(CN4CCN(c5ccc6c(c5)CN([C@H]5CCC(=O)NC5=O)C6=O)CC4)CC3)cc2)c1] | cis-(S)-3-(5-(4-((1-(4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione |
| 57 | 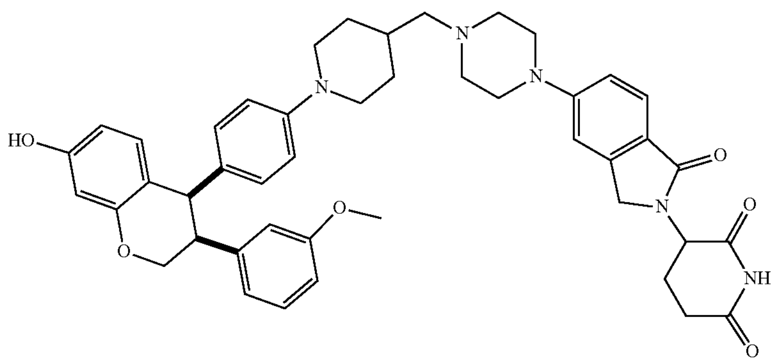 [SMILES: COc1cccc([C@H]2COc3cc(O)ccc3[C@H]2c2ccc(N3CCC(CN4CCN(c5ccc6c(c5)CN(C5CCC(=O)NC5=O)C6=O)CC4)CC3)cc2)c1] | cis-3-(5-(4-((1-(4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione |

TABLE 1B-continued
Exemplary Compound of the Present Disclosure
| Cpd # | Chemical Structure | IUPAC Name |
|---|---|---|
| 58 | 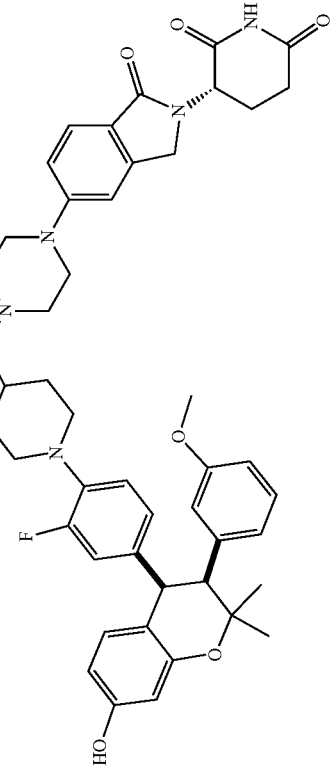 | cis-(S)-3-(5-(4-((1-(2-fluoro-4-(7-hydroxy-3-(3-methoxyphenyl)-2,2-dimethylchroman-4-yl)phenyl)piperidin-4-yl)methyl)piperazin-1-yl)-1-oxoisoindolin-2-yl)piperidine-2,6-dione |
| 59 | 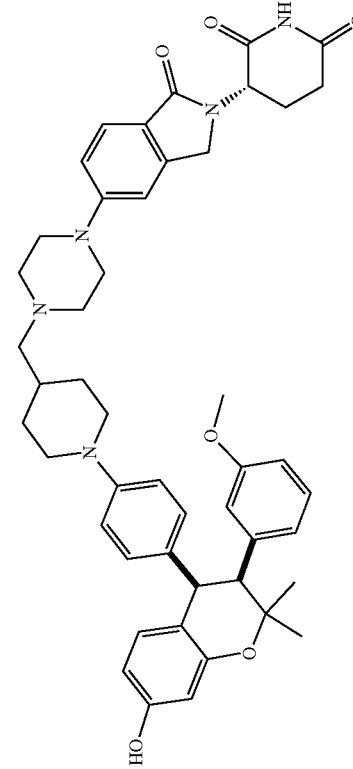 | cis-(S)-3-(5-(4-((1-(4-(7-hydroxy-3-(3-methoxyphenyl)-2,2-dimethylchroman-4-yl)phenyl)piperidin-4-yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 60 | 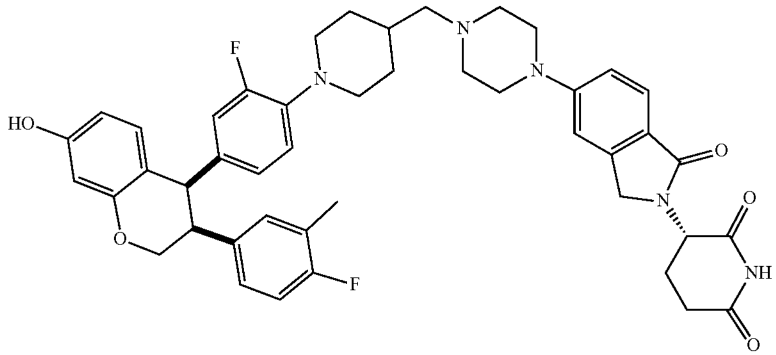 [SMILES: Cc1cc([C@H]2COc3cc(O)ccc3[C@H]2c2ccc(N3CCC(CN4CCN(c5ccc6c(c5)CN([C@H]5CCC(=O)NC5=O)C6=O)CC4)CC3)c(F)c2)ccc1F] | cis-(S)-3-(5-(4-((1-(2-fluoro-4-(3-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione |
| 61 | 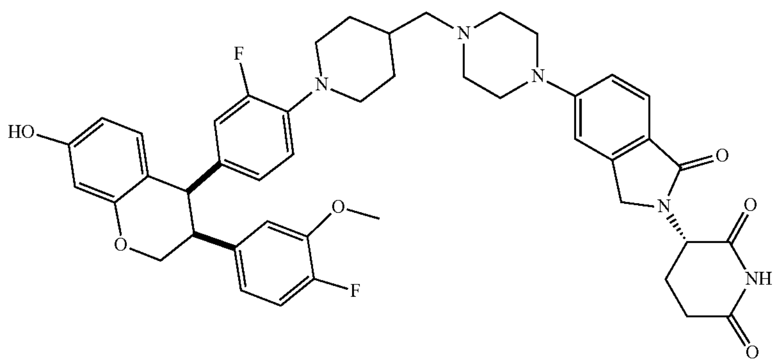 [SMILES: COc1cc([C@H]2COc3cc(O)ccc3[C@H]2c2ccc(N3CCC(CN4CCN(c5ccc6c(c5)CN([C@H]5CCC(=O)NC5=O)C6=O)CC4)CC3)c(F)c2)ccc1F] | cis-(S)-3-(5-(4-((1-(2-fluoro-4-(3-(4-fluoro-3-methoxyphenyl)-7-hydroxychroman-4-yl)phenyl)piperidin-4-yl)methyl)piperazin-1-yl)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 62 | 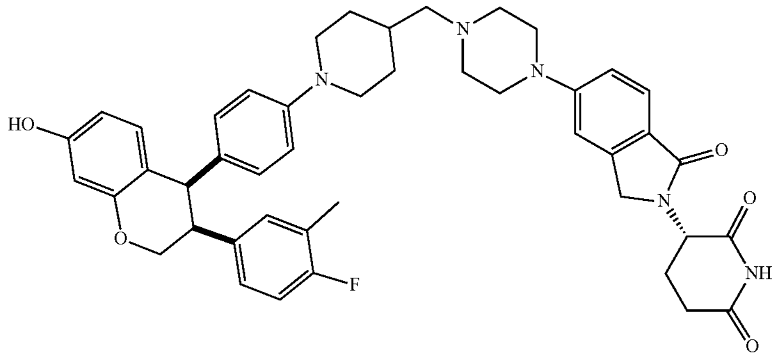 [SMILES: Cc1cc([C@H]2COc3cc(O)ccc3[C@H]2c2ccc(N3CCC(CN4CCN(c5ccc6c(c5)CN([C@H]5CCC(=O)NC5=O)C6=O)CC4)CC3)cc2)ccc1F] | cis-(S)-3-(5-(4-((1-(4-(3-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione |
| 63 | 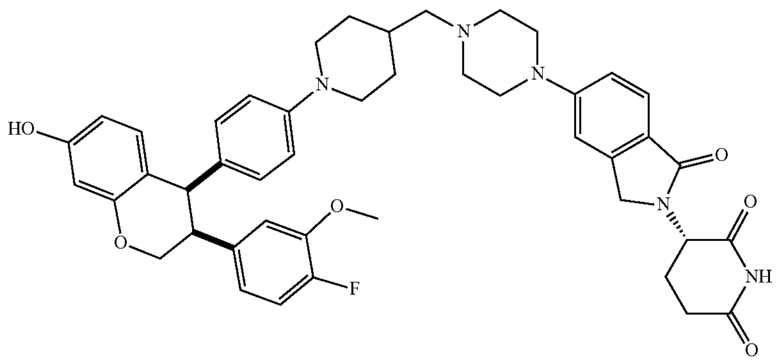 [SMILES: COc1cc([C@H]2COc3cc(O)ccc3[C@H]2c2ccc(N3CCC(CN4CCN(c5ccc6c(c5)CN([C@H]5CCC(=O)NC5=O)C6=O)CC4)CC3)cc2)ccc1F] | cis-(S)-3-(5-(4-((1-(4-(3-(4-fluoro-3-methoxyphenyl)-7-hydroxychroman-4-yl)phenyl)piperidin-4-yl)methyl)piperazin-1-yl)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 64 | 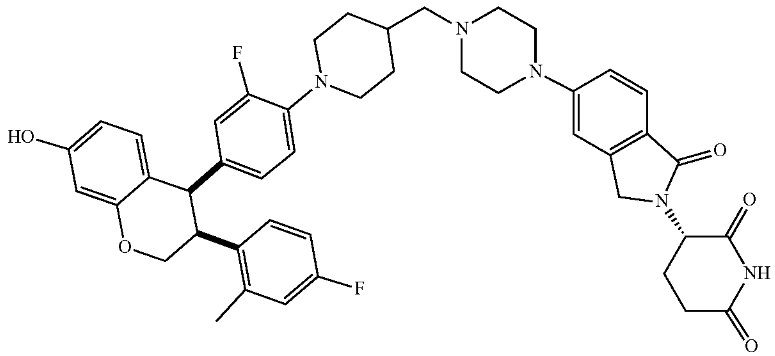 [SMILES: Cc1cc(F)ccc1[C@H]1COc2cc(O)ccc2[C@H]1c1ccc(N2CCC(CN3CCN(c4ccc5c(c4)CN([C@H]4CCC(=O)NC4=O)C5=O)CC3)CC2)c(F)c1] | cis-(S)-3-(5-(4-((1-(2-fluoro-4-(3-(4-fluoro-2-methylphenyl)-7-hydroxychroman-4-yl)phenyl)piperidin-4-yl)methyl)piperazin-1-yl)-1-oxoisoindolin-2-yl)piperidine-2,6-dione |
| 65 | 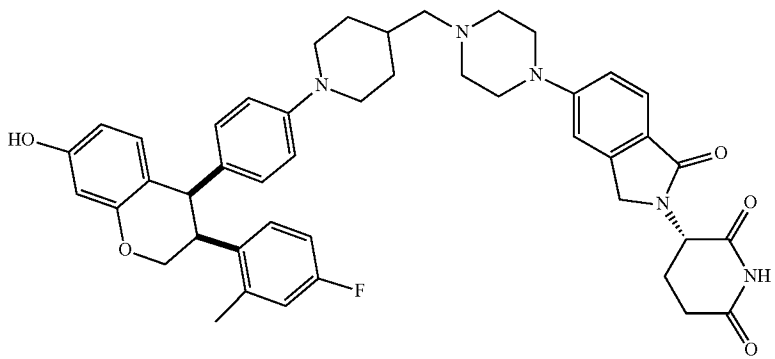 | cis-(S)-3-(5-(4-((1-(4-(3-(4-fluoro-2-methylphenyl)-7-hydroxychroman-4-yl)phenyl)piperidin-4-yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 66 | 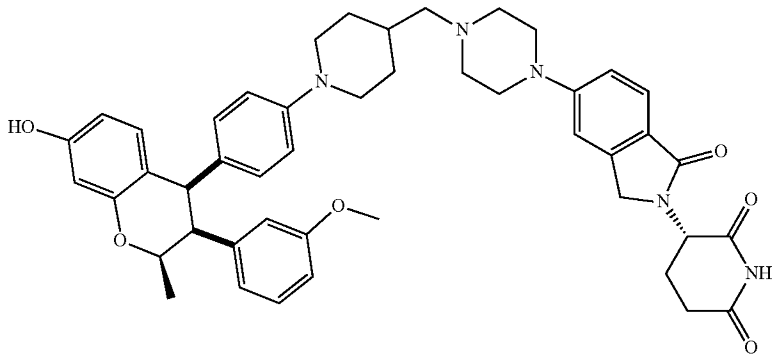 [SMILES: COc1cccc([C@@H]2[C@H](c3ccc(N4CCC(CN5CCN(c6ccc7c(c6)CN([C@H]6CCC(=O)NC6=O)C7=O)CC5)CC4)cc3)c3ccc(O)cc3O[C@@H]2C)c1] | cis-(S)-3-(5-(4-((1-(4-((2R)-7-hydroxy-3-(3-methoxyphenyl)-2-methylchroman-4-yl)phenyl)piperidin-4-yl)methyl)piperazin-1-yl)-1-oxoisoindolin-2-yl)piperidine-2,6-dione |
| 67 | 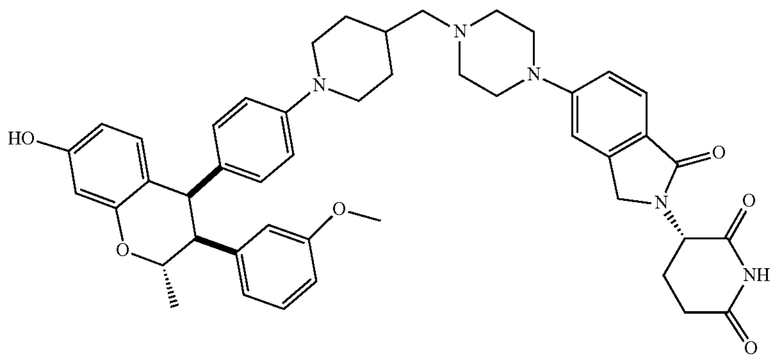 [SMILES: COc1cccc([C@@H]2[C@H](c3ccc(N4CCC(CN5CCN(c6ccc7c(c6)CN([C@H]6CCC(=O)NC6=O)C7=O)CC5)CC4)cc3)c3ccc(O)cc3O[C@H]2C)c1] | cis-(S)-3-(5-(4-((1-(4-((2S)-7-hydroxy-3-(3-methoxyphenyl)-2-methylchroman-4-yl)phenyl)piperidin-4-yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 68 | 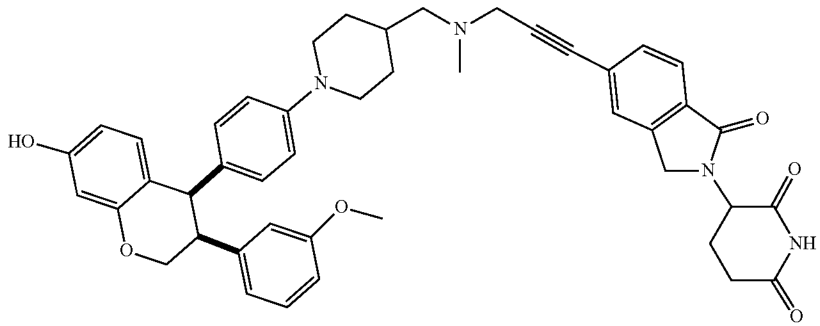 [SMILES: COc1cccc([C@H]2COc3cc(O)ccc3[C@H]2c2ccc(N3CCC(CN(C)CC#Cc4ccc5c(c4)CN(C4CCC(=O)NC4=O)C5=O)CC3)cc2)c1] | cis-3-(5-(3-((1-(4-(7-hydroxy-3-(3-methoxyphenyl)chroman-4-yl)phenyl)piperidin-4-yl)methyl)(methyl)amino)prop-1-yn-1-yl)-1-oxoisoindolin-2-yl)piperidine-2,6-dione |
| 69 | 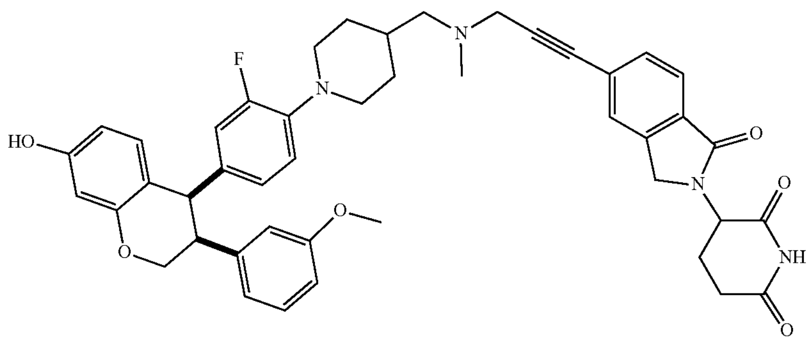 [SMILES: COc1cccc([C@H]2COc3cc(O)ccc3[C@H]2c2ccc(N3CCC(CN(C)CC#Cc4ccc5c(c4)CN(C4CCC(=O)NC4=O)C5=O)CC3)c(F)c2)c1] | cis-3-(5-(3-(((1-(2-fluoro-4-(7-hydroxy-3-(3-methoxyphenyl)chroman-4-yl)phenyl)piperidin-4-yl)methyl)(methyl)amino)prop-1-yn-1-yl)-1-oxoisoindolin-2-yl)piperidine-2,6-dione |
| 70 | 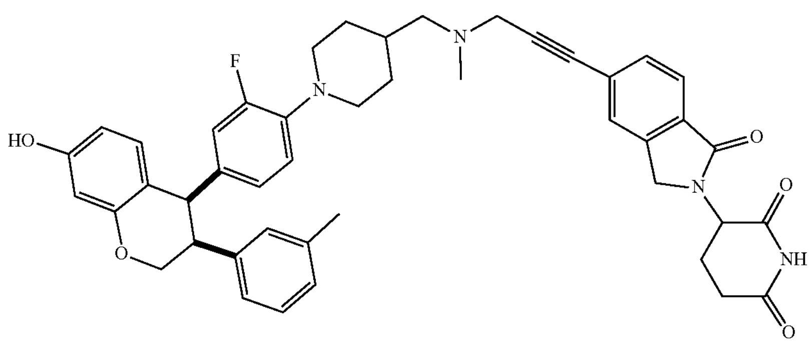 [SMILES: Cc1cccc([C@H]2COc3cc(O)ccc3[C@H]2c2ccc(N3CCC(CN(C)CC#Cc4ccc5c(c4)CN(C4CCC(=O)NC4=O)C5=O)CC3)c(F)c2)c1] | cis-3-(5-(3-(((1-(2-fluoro-4-(7-hydroxy-3-(m-tolyl)chroman-4-yl)phenyl)piperidin-4-yl)methyl)(methyl)amino)prop-1-yn-1-yl)-1-oxoisoindolin-2-yl)piperidine-2,6-dione |

TABLE1B-continued

Exemplary Compound of the Present Disclosure

| Cpd # Chemical Structure | IUPACName |
|---|---|
| 71 | cis-3-(5-(3-(((1-(4-(7-hydroxy-3-(m-tolyl)chroman-4-yl)phenyl)piperidin-4-yl)methyl)(methyl)amino)prop-1-yn-1-yl)-1-oxoisoindolin-2-yl)piperidine-2,6-dione |
| 72 | cis-(S)-3-(6-fluoro-5-(4-((1-(2-fluoro-4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 73 | 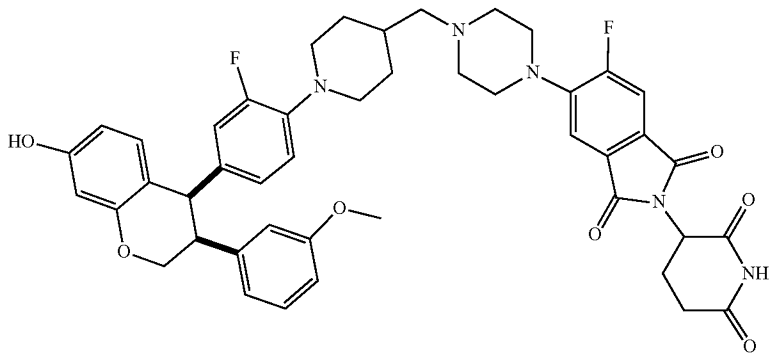 [SMILES: COc1cccc([C@H]2COc3cc(O)ccc3[C@H]2c2ccc(N3CCC(CN4CCN(c5cc6c(cc5F)C(=O)N(C5CCC(=O)NC5=O)C6=O)CC4)CC3)c(F)c2)c1] | cis-2-(2,6-dioxopiperidin-3-yl)-5-fluoro-6-(4-((1-(2-fluoro-4-(7-hydroxy-3-(3-methoxyphenyl)chroman-4-yl)phenyl)piperidin-4-yl)methyl)piperazin-1-yl)isoindoline-1,3-dione |
| 74 | 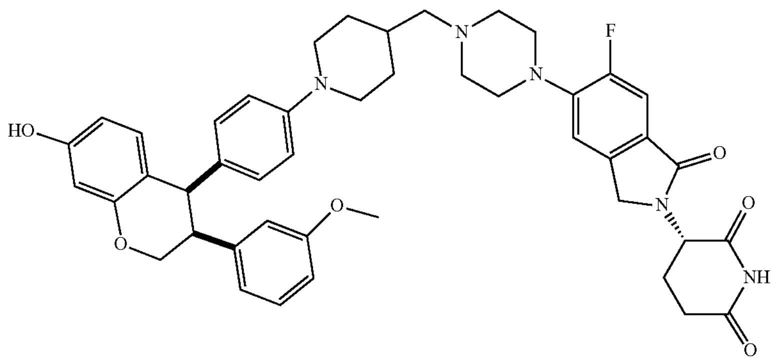 [SMILES: COc1cccc([C@H]2COc3cc(O)ccc3[C@H]2c2ccc(N3CCC(CN4CCN(c5cc6c(cc5F)C(=O)N([C@H]5CCC(=O)NC5=O)C6)CC4)CC3)cc2)c1] | cis-(S)-3-(6-fluoro-5-(4-((1-(4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 75 | 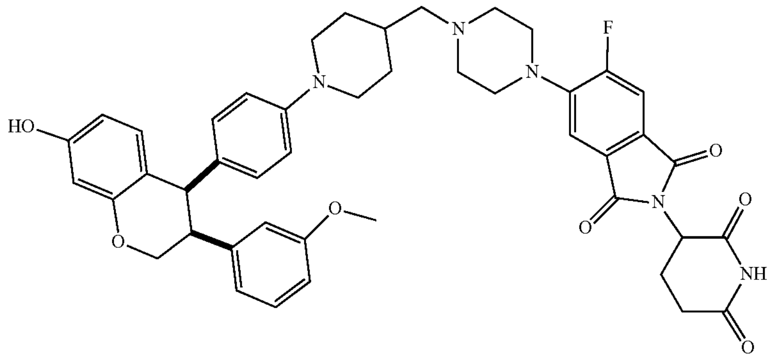 [SMILES: COc1cccc([C@H]2COc3cc(O)ccc3[C@H]2c2ccc(N3CCC(CN4CCN(c5cc6c(cc5F)C(=O)N(C5CCC(=O)NC5=O)C6=O)CC4)CC3)cc2)c1] | cis-2-(2,6-dioxopiperidin-3-yl)-5-fluoro-6-(4-((1-(4-(7-hydroxy-3-(3-methoxyphenyl)chroman-4-yl)phenyl)piperidin-4-yl)methyl)piperazin-1-yl)isoindoline-1,3-dione |
| 76 | 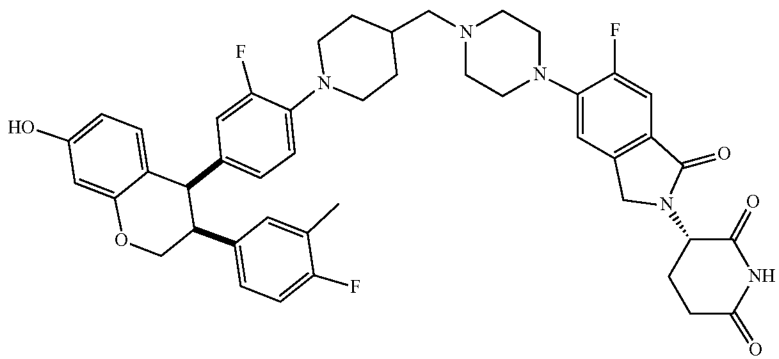 [SMILES: Cc1cc([C@H]2COc3cc(O)ccc3[C@H]2c2ccc(N3CCC(CN4CCN(c5cc6c(cc5F)C(=O)N([C@H]5CCC(=O)NC5=O)C6)CC4)CC3)c(F)c2)ccc1F] | cis-(S)-3-(6-fluoro-5-(4-((1-(2-fluoro-4-(3-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 77 | 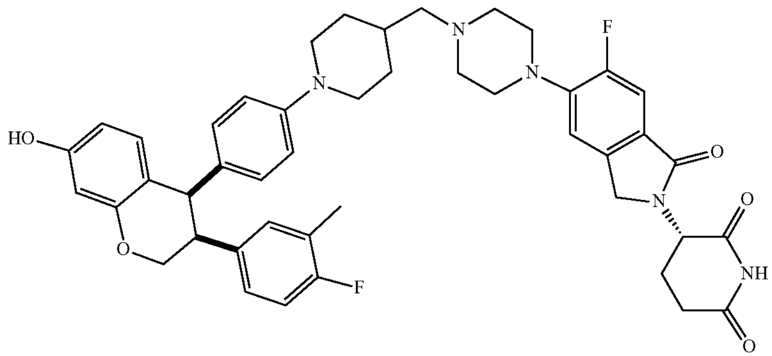 [SMILES: Cc1cc([C@H]2COc3cc(O)ccc3[C@H]2c2ccc(N3CCC(CN4CCN(c5cc6c(cc5F)C(=O)N([C@H]5CCC(=O)NC5=O)C6)CC4)CC3)cc2)ccc1F] | cis-(S)-3-(6-fluoro-5-(4-((1-(4-(3-(4-fluoro-3-methylphenyl)-7-hydroxychroman-4-yl)phenyl)piperidin-4-yl)methyl)piperazin-1-yl)-1-oxoisoindolin-2-yl)piperidine-2,6-dione |
| 78 | 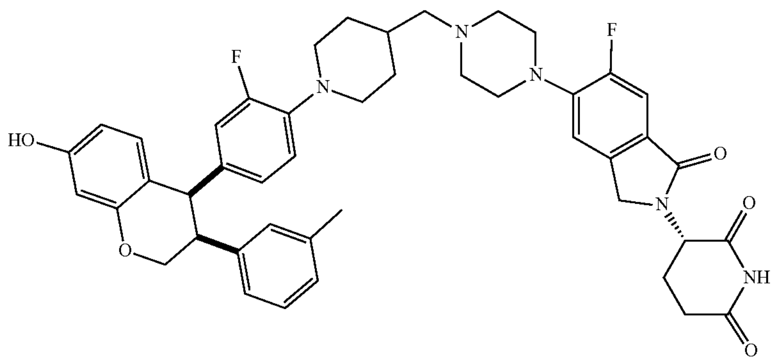 [SMILES: Cc1cccc([C@H]2COc3cc(O)ccc3[C@H]2c2ccc(N3CCC(CN4CCN(c5cc6c(cc5F)C(=O)N([C@H]5CCC(=O)NC5=O)C6)CC4)CC3)c(F)c2)c1] | cis-(S)-3-(6-fluoro-5-(4-((1-(2-fluoro-4-(7-hydroxy-3-(m-tolyl)chroman-4-yl)phenyl)piperidin-4-yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 79 | 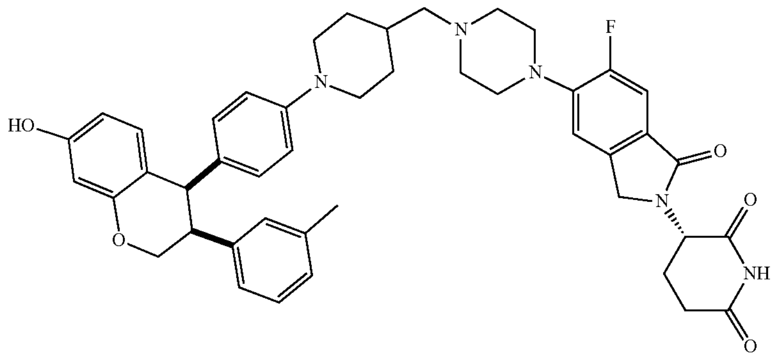 [SMILES: Cc1cccc([C@H]2COc3cc(O)ccc3[C@H]2c2ccc(N3CCC(CN4CCN(c5cc6c(cc5F)C(=O)N([C@H]5CCC(=O)NC5=O)C6)CC4)CC3)cc2)c1] | cis-(S)-3-(6-fluoro-5-(4-((1-(4-(7-hydroxy-3-(m-tolyl)chroman-4-yl)phenyl)piperidin-4-yl)methyl)piperazin-1-yl)-1-oxoisoindolin-2-yl)piperidine-2,6-dione |
| 80 | 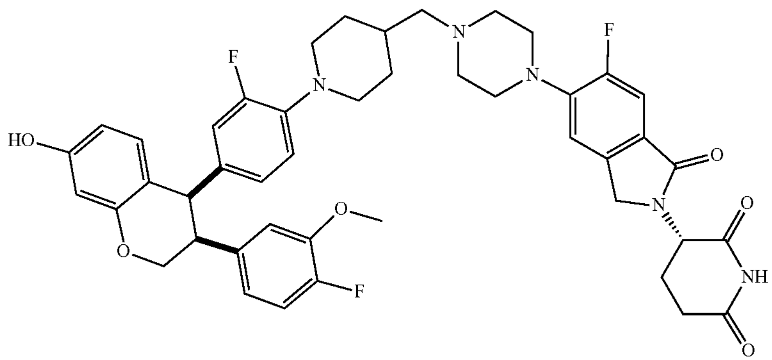 [SMILES: COc1cc([C@H]2COc3cc(O)ccc3[C@H]2c2ccc(N3CCC(CN4CCN(c5cc6c(cc5F)C(=O)N([C@H]5CCC(=O)NC5=O)C6)CC4)CC3)c(F)c2)ccc1F] | cis-(S)-3-(6-fluoro-5-(4-((1-(2-fluoro-4-(3-(4-fluoro-3-methoxyphenyl)-7-hydroxychroman-4-yl)phenyl)piperidin-4-yl)methyl)piperazin-1-yl)-1-oxoisoindolin-2-yl)piperidine-2,6-dione |

TABLE1B-continued

Exemplary Compound of the Present Disclosure

| Cpd # | Chemical Structure | IUPAC Name |
|---|---|---|
| 81 | 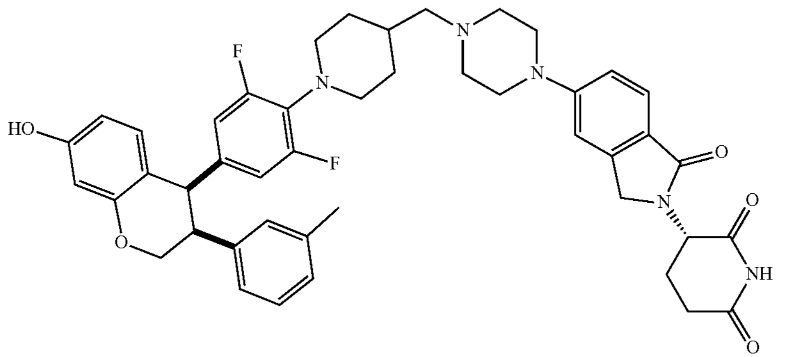 [SMILES: Cc1cccc([C@H]2COc3cc(O)ccc3[C@H]2c2cc(F)c(N3CCC(CN4CCN(c5ccc6c(c5)CN([C@H]5CCC(=O)NC5=O)C6=O)CC4)CC3)c(F)c2)c1] | cis-(S)-3-(5-(4-((1-(2,6-difluoro-4-(7-hydroxy-3-(m-tolyl)chroman-4-yl)phenyl)piperidin-4-yl)methyl)piperazin-1-yl)-1-oxoisoindolin-2-yl)piperidine-2,6-dione |
| 82 | 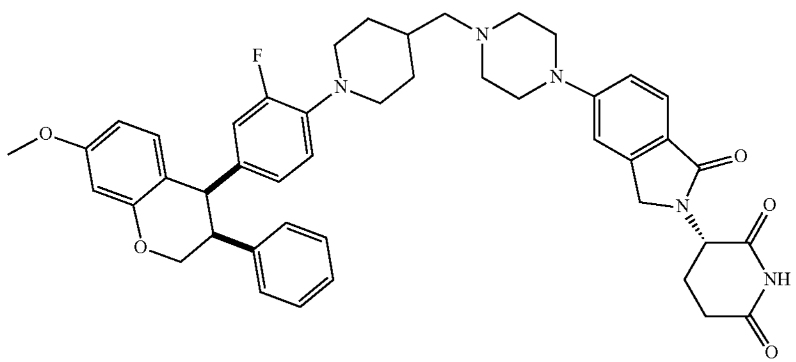 [SMILES: COc1ccc2c(c1)OC[C@H](c1ccccc1)[C@@H]2c1ccc(N2CCC(CN3CCN(c4ccc5c(c4)CN([C@H]4CCC(=O)NC4=O)C5=O)CC3)CC2)c(F)c1] | cis-(S)-3-(5-(4-((1-(2-fluoro-4-(7-methoxy-3-phenylchroman-4-yl)phenyl)piperidin-4-yl)methyl)piperazin-1-yl)-1-oxoisoindolin-2-yl)piperidine-2,6-dione |

TABLE1B-continued

Exemplary Compound of the Present Disclosure

| Cpd # | Chemical Structure | IUPACName |
|---|---|---|
| 83 | 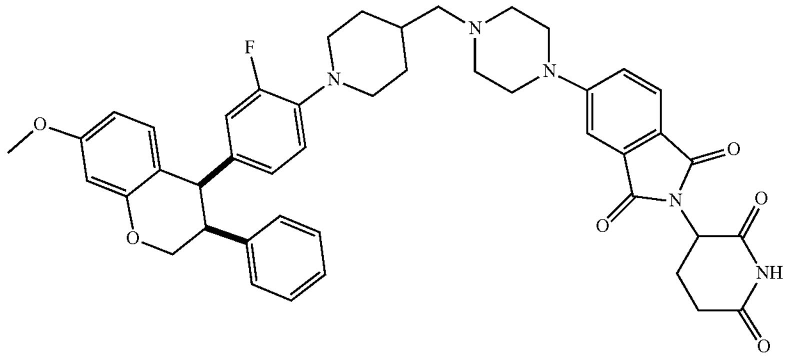 [SMILES: COc1ccc2c(c1)OC[C@H](c1ccccc1)[C@@H]2c1ccc(N2CCC(CN3CCN(c4ccc5c(c4)C(=O)N(C4CCC(=O)NC4=O)C5=O)CC3)CC2)c(F)c1] | cis-2-(2,6-dioxopiperidin-3-yl)-5-(4-((1-(2-fluoro-4-(7-methoxy-3-phenylchroman-4-yl)phenyl)piperidin-4-yl)methyl)piperazin-1-yl)isoindoline-1,3-dione |
| 84 | 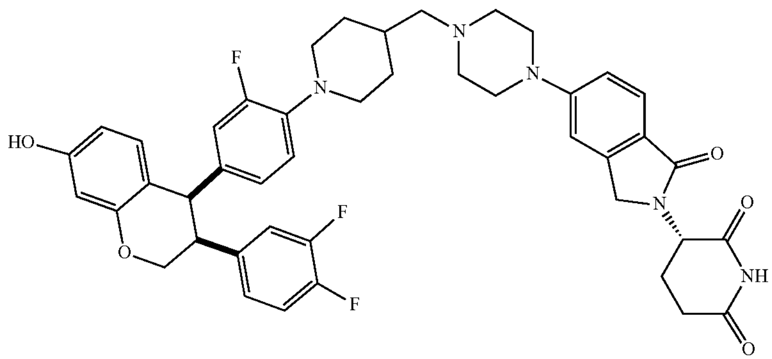 [SMILES: O=C1CC[C@H](N2Cc3cc(N4CCN(CC5CCN(c6ccc([C@@H]7c8ccc(O)cc8OC[C@@H]7c7ccc(F)c(F)c7)cc6F)CC5)CC4)ccc3C2=O)C(=O)N1] | cis-(S)-3-(5-(4-((1-(4-(3-(3,4-difluorophenyl)-7-hydroxychroman-4-yl)-2-fluorophenyl)piperidin-4-yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 85 | 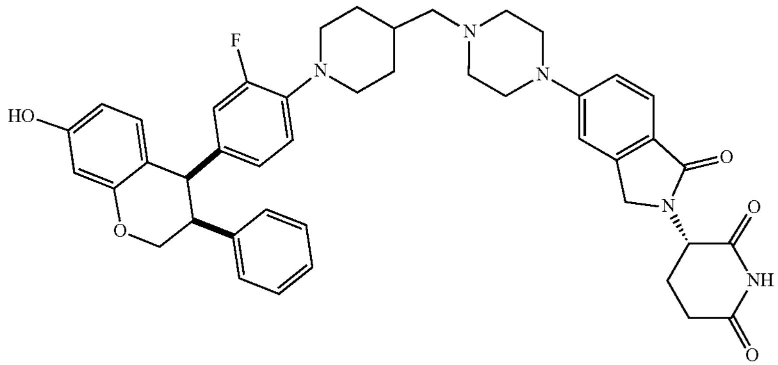 [SMILES: O=C1CC[C@H](N2Cc3cc(N4CCN(CC5CCN(c6ccc([C@@H]7c8ccc(O)cc8OC[C@@H]7c7ccccc7)cc6F)CC5)CC4)ccc3C2=O)C(=O)N1] | cis-(S)-3-(5-(4-((1-(2-fluoro-4-(7-hydroxy-3-phenylchroman-4-yl)phenyl)piperidin-4-yl)methyl)piperazin-1-yl)-1-oxoisoindolin-2-yl)piperidine-2,6-dione |
| 86 | 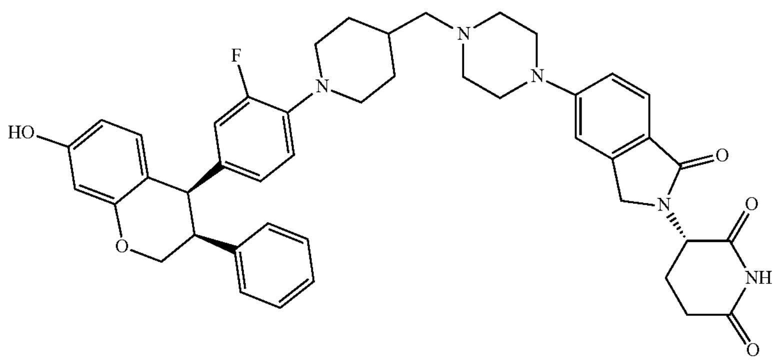 [SMILES: O=C1CC[C@H](N2Cc3cc(N4CCN(CC5CCN(c6ccc([C@@H]7c8ccc(O)cc8OC[C@@H]7c7ccccc7)cc6F)CC5)CC4)ccc3C2=O)C(=O)N1] | (S)-3-(5-(4-((1-(2-fluoro-4-((3S,4R)-7-hydroxy-3-phenylchroman-4-yl)phenyl)piperidin-4yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 87 | 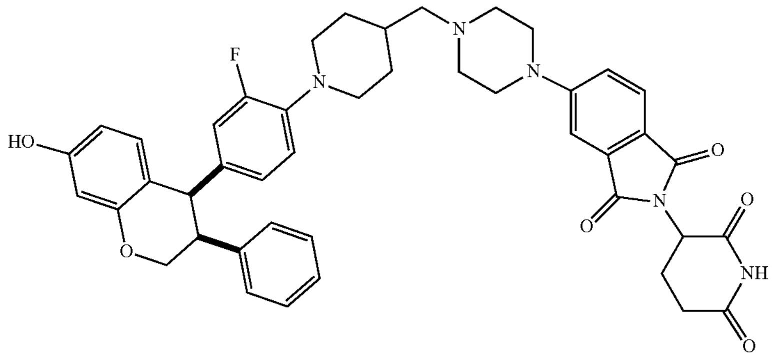 [SMILES: O=C1CCC(N2C(=O)c3ccc(N4CCN(CC5CCN(c6ccc([C@@H]7c8ccc(O)cc8OC[C@@H]7c7ccccc7)cc6F)CC5)CC4)cc3C2=O)C(=O)N1] | cis-2-(2,6-dioxopiperidin-3-yl)-5-(4-((1-(2-fluoro-4-(7-hydroxy-3-phenylchroman-4-yl)phenyl)piperidin-4-yl)methyl)piperazin-1-yl)isoindoline-1,3-dione |
| 88 | 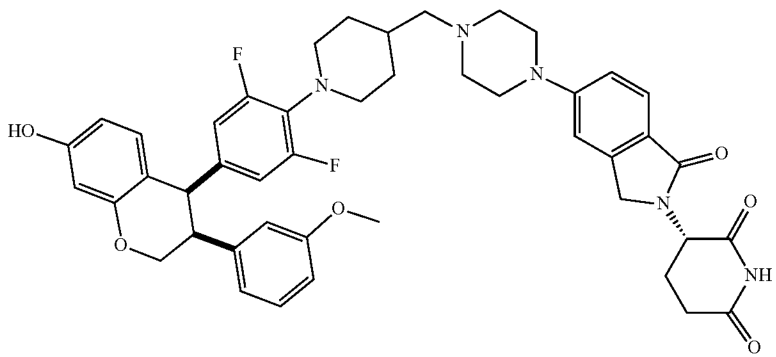 [SMILES: COc1cccc([C@H]2COc3cc(O)ccc3[C@H]2c2cc(F)c(N3CCC(CN4CCN(c5ccc6c(c5)CN([C@H]5CCC(=O)NC5=O)C6=O)CC4)CC3)c(F)c2)c1] | cis-(S)-3-(5-(4-((1-(2,6-difluoro-4-(7-hydroxy-3-(3-methoxyphenyl)chroman-4-yl)phenyl)piperidin-4-yl)methyl)piperazin-1-yl)-1-oxoisoindolin-2-yl)piperidine-2,6-dione |

TABLE 1B-continued

Exemplary Compound of the Present Disclosure

| Cpd # | Chemical Structure | IUPAC Name |
|---|---|---|
| 89 | 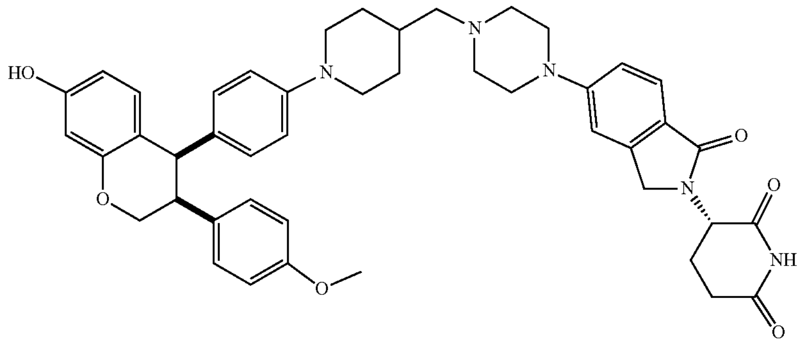 [SMILES: COc1ccc([C@H]2COc3cc(O)ccc3[C@H]2c2ccc(N3CCC(CN4CCN(c5ccc6c(c5)CN([C@H]5CCC(=O)NC5=O)C6=O)CC4)CC3)cc2)cc1] | cis-(S)-3-(5-(4-((1-(4-(7-hydroxy-3-(4-methoxyphenyl)chroman-4-yl)phenyl)piperidin-4-yl)methyl)piperazin-1-yl)-1-oxoisoindolin-2-yl)piperidine-2,6-dione |
| 90 | 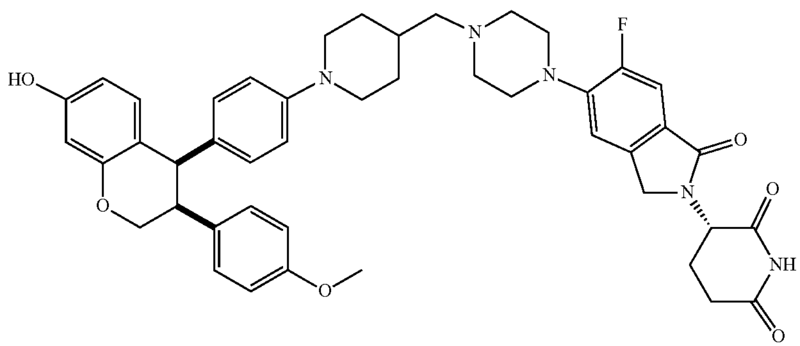 [SMILES: COc1ccc([C@H]2COc3cc(O)ccc3[C@H]2c2ccc(N3CCC(CN4CCN(c5cc6c(cc5F)C(=O)N([C@H]5CCC(=O)NC5=O)C6)CC4)CC3)cc2)cc1] | cis-(S)-3-(6-fluoro-5-(4-((1-(4-(7-hydroxy-3-(4-methoxyphenyl)chroman-4-yl)phenyl)piperidin-4-yl)methyl)piperazin-1-yl)-1-oxoisoindolin-2-yl)piperidine-2,6-dione |

In some embodiments, the compound of Formula (I-C) and/or (III-C) may encompass both the cis- and trans-isomers. In some embodiments, the compound of Formula (I-C) and/or (III-C) may be a mixture of cis- and trans-isomers. In some embodiments, the compound of Formula (I-C) and/or (III-C) may be cis-isomer.

In some embodiments, the compound of Formula (I-C) and/or (III-C) may encompass both stereoisomers and a mixture of stereoisomers. In some embodiments, the compound of Formula (I-C) and/or (III-C) is stereoisomer. In some embodiments, the compound of Formula (I-C) and/or (III-C) may encompass both racemic isomers and enantiomeric isomers.

In some embodiments, the ER degrader is Fulvestrant or Tamoxifen. Fluvestrant has the following structure:

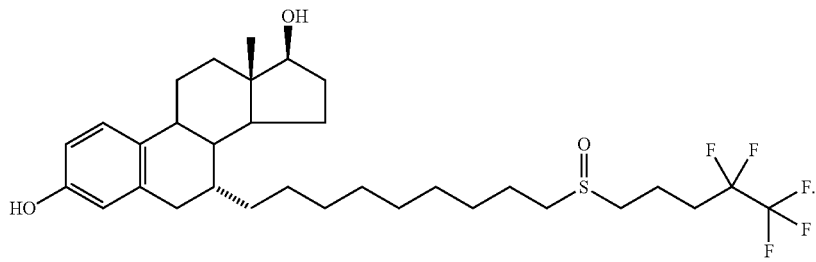 [SMILES: C[C@]12CCC3c4ccc(O)cc4C[C@@H](CCCCCCCCCS(=O)CCCC(F)(F)C(F)(F)F)C3C1CC[C@@H]2O]

Tamoxifen has the following structure:

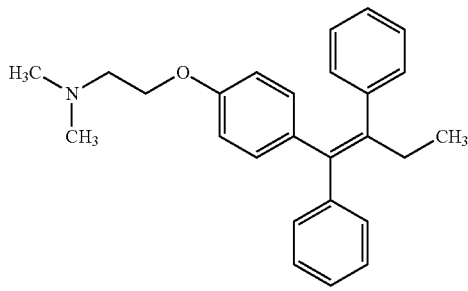 [SMILES: CC/C(=C(\c1ccccc1)c1ccc(OCCN(C)C)cc1)c1ccccc1]

CDK Inhibitor

The function of CDKs is to phosphorylate and thus activate or deactivate certain proteins, including, e.g., retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in, e.g., Fischer, P. M. Curr. Opin. Drug Discovery Dev. 2001, 4, 623-634) have been found to possess anti-proliferative properties by virtue of CDK-specific ATP antagonism.

In some embodiments, the CDK inhibitor may inhibit any CDK, for example CDK1, CDK2, CDK3, CDK4, CDK5, CDK6, CDK7, CDK8, CDK9, CDK10, CDK11, CDK12, and CDK13. In some embodiments, the CDK inhibitor is a CDK6 and/or 6 inhibitor.

In some embodiments, the CDK1 inhibitor has a structure according to Formula (II):

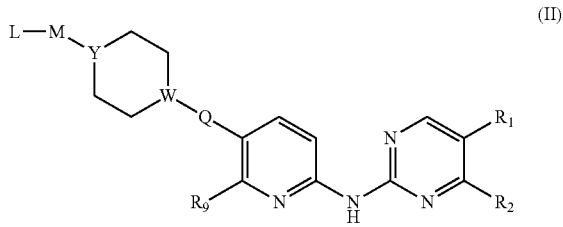

or a tautomer, stereoisomer or a mixture of stereoisomers, or a pharmaceutically acceptable salt, or hydrate thereof, wherein:
M is a bond, —NH—, or —C(O)—;
L is a H, alkyl, carbocyclyl, arylalkyl, heteroarylalkyl, or heterocycle, each of which is optionally substituted with one or more substituents;
Q is $CH_2$, O, S or a bond;
W and Y are independently CH or N, provided that at least one of W or Y is N, and when W is CH, Q is O or S; and
$R_1$ and $R_2$ are independently selected from hydrogen, halogen, alkyl, and heterocycle, wherein each of alkyl and heterocyclyl are optionally substituted with one or more substituents; or
$R_1$ and $R_2$ together with the atoms are to which they are attached form a carbocyclyl or heterocycle, each of which is optionally substituted with one or more substituents; and
$R_9$ is hydrogen, halogen, or alkyl, wherein alkyl is optionally substituted.

In some embodiments, L is $C_{1-3}$ alkyl. In some embodiments, L is ethyl. In some embodiments, L is H.

L is carbocyclyl, arylalkyl, heteroarylalkyl, or heterocycle, each of which is optionally substituted with one or more substituents.

In some embodiments of the CDK1 inhibitor of Formula (II), W is N. In some embodiments, wherein Y is N. In some embodiments, each of W and Y are N. In some embodiments, $R_9$ is hydrogen.

In some embodiments, the CDK1 inhibitor of Formula (II), has a structure according to Formula (III):

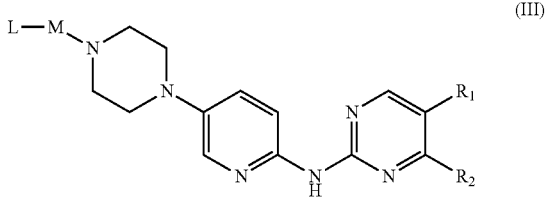

or a tautomer, stereoisomer or a mixture of stereoisomers, or a pharmaceutically acceptable salt, or hydrate thereof, wherein:

M is a bond, —NH—, or —C(O)—;

L is a H, alkyl, carbocyclyl, arylalkyl, heteroarylalkyl, or heterocycle, each of which is optionally substituted with one or more substituents;

$R_1$ and $R_2$ are independently selected from hydrogen, halogen, alkyl, and heterocycle, wherein alkyl and heterocyclyl are optionally substituted with one or more substituents; and or $R_1$ and $R_2$ together with the atoms are to which they are attached form a carbocyclyl or heterocycle, each of which is optionally substituted with one or more substituents.

In some embodiments, L is $C_{1-3}$ alkyl. In some embodiments, L is ethyl. In some embodiments, L is H.

In some embodiments of the CDK1 inhibitor of Formula (II), L is substituted with one or more halogen, aryl, heteroaryl, arylalkyl, heteroarylalkyl, wherein aryl, heteroaryl, arylalkyl, and heteroarylalkyl are each optionally substituted with one or more substituents. In some embodiments, each of the aryl, heteroaryl, arylalkyl, heteroarylalkyl are optionally substituted with one or more substituents selected from the group consisting of halogen, nitro, hydroxyl, alkyl, aryl, heterocycle, —C(O), —C(O)$NR_gR_h$, wherein each of $R_g$ and $R_h$ are independently hydrogen or alkyl. In some embodiments, L is (i) aryl which is optionally substituted with a halogen and a heteroarylalkyl which is optionally substituted with —C(O), (ii) arylalkyl which is optionally substituted with a heteroaryl which is optionally substituted with one or more halogen, —C(O), or combinations thereof, or (iii) aryl which is optionally substituted with a heteroaryl which is optionally substituted with —C(O)$NR_gR_h$, wherein each of $R_g$ and $R_h$ are independently hydrogen or alkyl. In some embodiments, L is a $C_{5-8}$ aryl which is optionally substituted with a halogen and a heteroarylalkyl comprising an 8-12-membered heteroaryl ring having from 1 to 4 atoms independently selected from nitrogen, oxygen and sulfur and which is optionally substituted with one or more substituents. In some embodiments, L is a $C_6$ aryl which is substituted with a halogen and a heteroarylalkyl comprising a 10-membered heteroaryl ring having 2 nitrogen atom and which is substituted with —C(O). In some embodiments, L is a $C_{5-8}$ aryl-$C_{1-3}$ alkyl which is optionally substituted with a 10-15-membered heteroaryl having from 1 to 4 atoms independently selected from nitrogen, oxygen and sulfur and which is optionally substituted with one or more halogen, —C(O), or combinations thereof. In some embodiments, L is $C_6$ aryl-$C_1$ alkyl which is substituted with 13-membered heteroaryl which having 2 nitrogen atoms and which is substituted with a halogen and —C(O). In some embodiments, L is a $C_{5-8}$ aryl which is optionally substituted a 6-12-membered heteroaryl having from 1 to 4 atoms independently selected from nitrogen, oxygen and sulfur and which is optionally substituted with —C(O)$NR_gR_h$, wherein each of $R_g$ and $R_h$ are independently hydrogen or alkyl. In some embodiments, L is a $C_6$ aryl which is substituted with a 9-membered heteroaryl having from 2 nitrogen atoms and is substituted with —C(O)$NH_2$.

In some embodiments of the CDK1 inhibitor of Formula (II) or Formula (III), L is selected from the group consisting of:

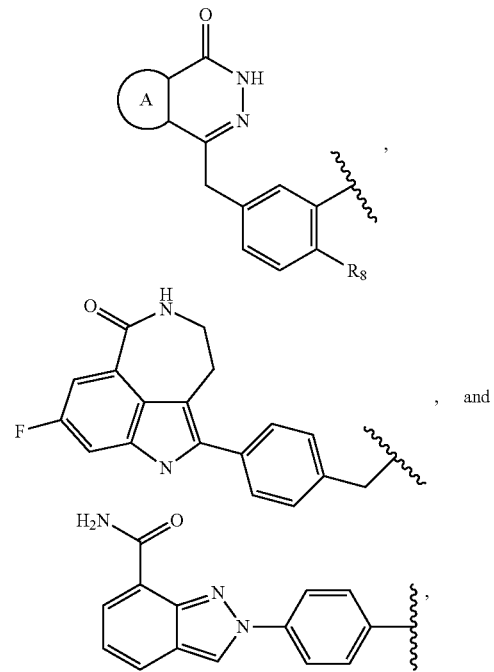

wherein:

the A ring represents a fused aryl or heteroaryl group, which is optionally substituted with one or more substituent groups selected from halogen, nitro, hydroxyl, ether, thiol, thioether, amino, alkyl, aryl and a heterocycle; and $R_8$ is hydrogen or halogen.

In some embodiments of the CDK1 inhibitor of Formula (II) or Formula (III), L is

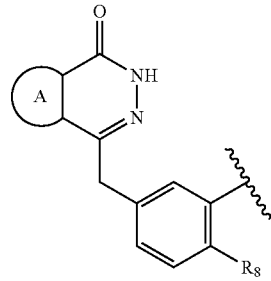

wherein:

the A ring represents a fused aryl or heteroaryl group, which is optionally substituted with one or more substituent groups selected from halogen, nitro, hydroxyl, amino, alkyl, aryl and a heterocycle; and $R_8$ is hydrogen or halogen.

In some embodiments of the CDK1 inhibitor of Formula (II) or Formula (III), the A ring is a $C_{5-8}$ aryl. In some embodiments, the A ring is benzene. In some embodiments, R8 is selected from H, $C_1$, and F.

In some embodiments of the CDK1 inhibitor of Formula (II) or Formula (III), $R_1$ is a halogen. In some embodiments, $R_2$ is a 6-12 membered heteroaryl which is optionally substituted with one or more substituents. In some embodiments, $R_2$ is 9-membered heteroaryl substituted with one or more substituents selected from halogen, alkyl, and combinations thereof.

In some embodiments of the CDK1 inhibitor of Formula (II) or Formula (III), $R_2$ is

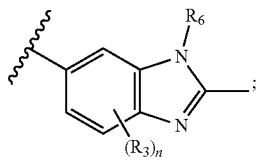

wherein
n is 0, 1, 2, or 3;
each $R_3$ is independently halogen or alkyl; and
$R_6$ is alkyl or cycloalkyl, each of which is optionally substituted with one or more substituents.

In some embodiments of the CDK1 inhibitor of Formula (II) or Formula (III), n is 1. In some embodiments, $R_3$ is a $C_{1-3}$ alkyl. In some embodiments, $R_6$ is a $C_{1-3}$ alkyl. In still other embodiments, $R_2$ is selected from the group consisting of:

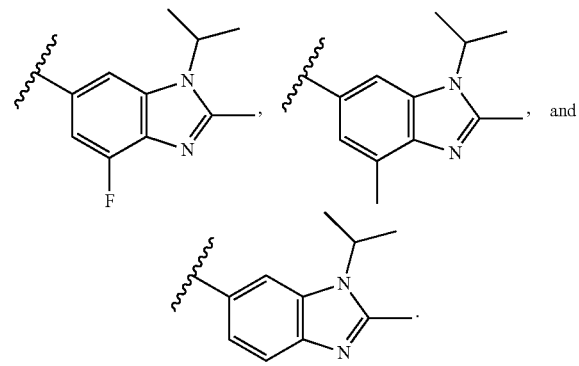

In some embodiments of the CDK1 inhibitor of Formula (II) or Formula (III), $R_2$ is:

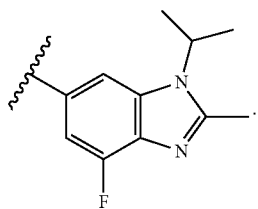 [SMILES: *c1cc(F)c2nc(C)n(C(C)C)c2c1]

In some embodiments of the CDK1 inhibitor of Formula (II) or Formula (III), $R_1$ and $R^2$ together with the atoms to which they are attached form a heteroaryl which is optionally substituted with one or more substituents. In some embodiments, $R^1$ and $R^2$ together with the atoms are to which they are attached form a 5 to 6-membered heteroaryl which is substituted with one or more substituents selected from the group consisting of halogen, alkyl, cycloalkyl, and combinations thereof.

In some embodiments of the CDK1 inhibitor of Formula (II) or Formula (III), $R_1$ and $R_2$ together with the atoms to which they are attached form a ring selected from the group consisting of:

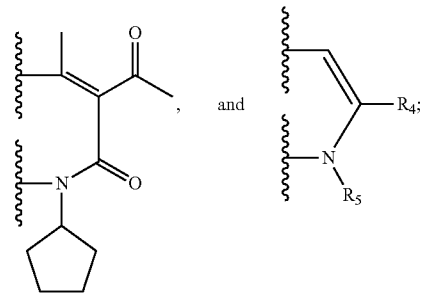

wherein:
$R_4$ is hydrogen or —C(O)$NR_aR_b$, wherein each of $R_a$ and $R_b$ are independently selected from hydrogen and alkyl; and
$R_5$ is cycloalkyl.

In some embodiments of the CDK1 inhibitor of Formula (II) or Formula (III), $R_1$ and $R_2$ together with the atoms to which they are attached form

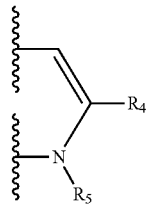

wherein $R_5$ is cyclopentyl, and $R_4$ is —C(O)N(CH_3)_2.

In some embodiments of the CDK1 inhibitor of Formula (II) or Formula (III), $R_5$ is cyclopentyl, and each of $R_a$ and $R_b$ are both methyl.

In some embodiments of the CDK1 inhibitor of Formula (II) or Formula (III), the compound is selected from the group consisting of:

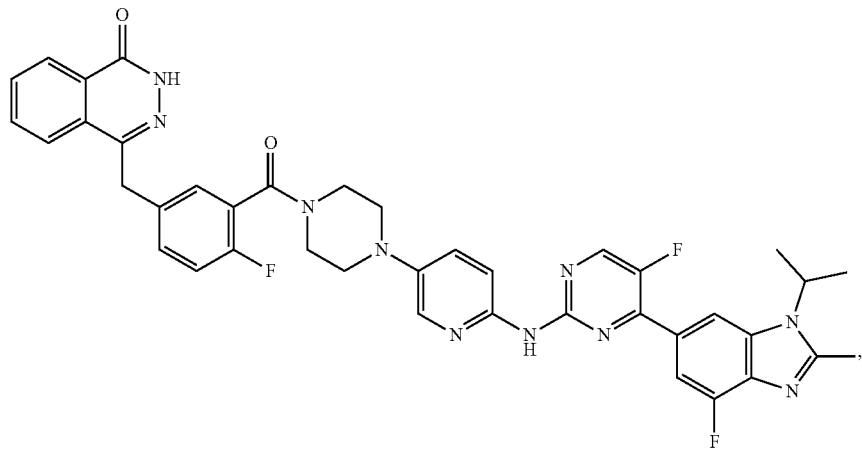

-continued
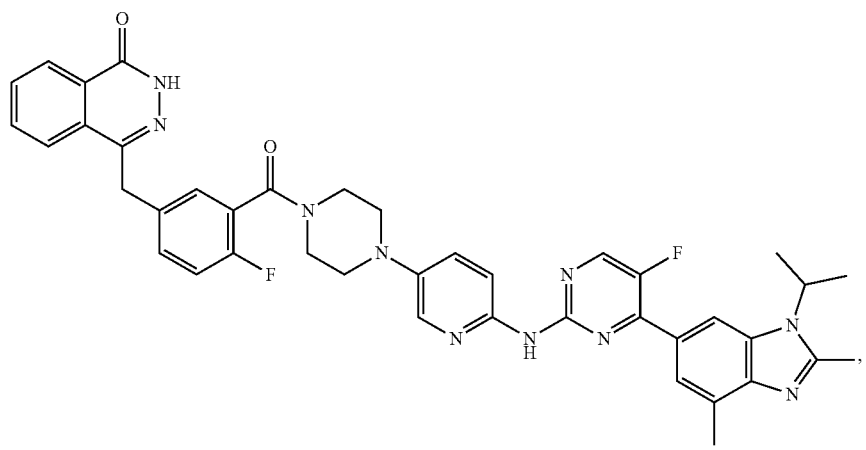
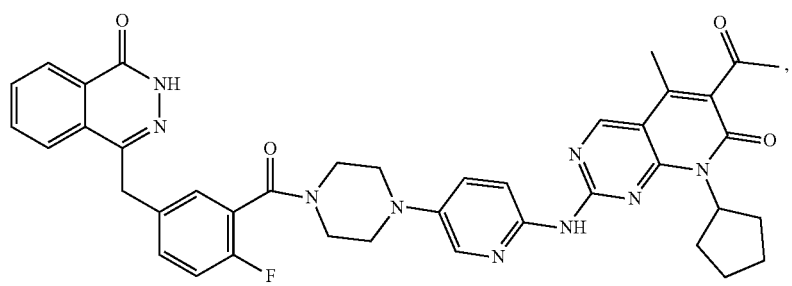
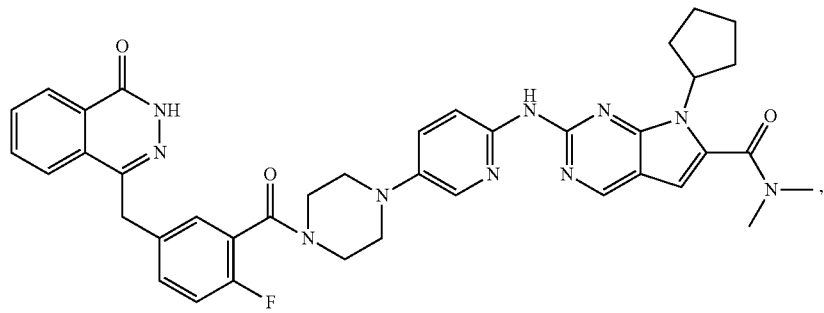
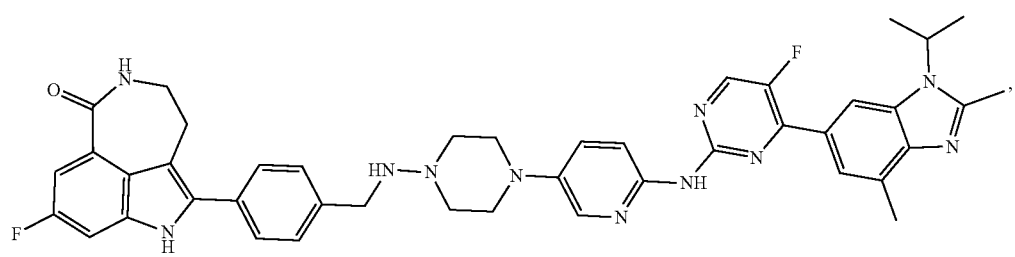
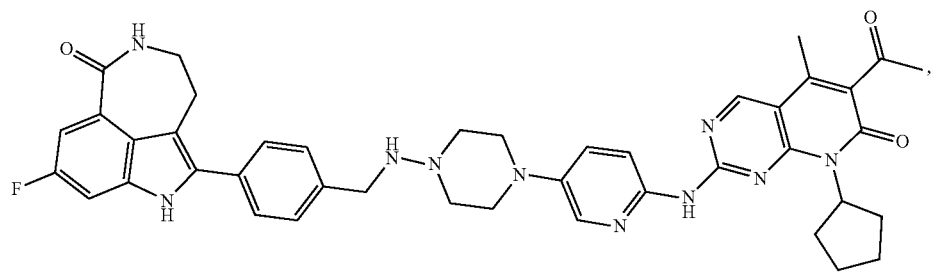

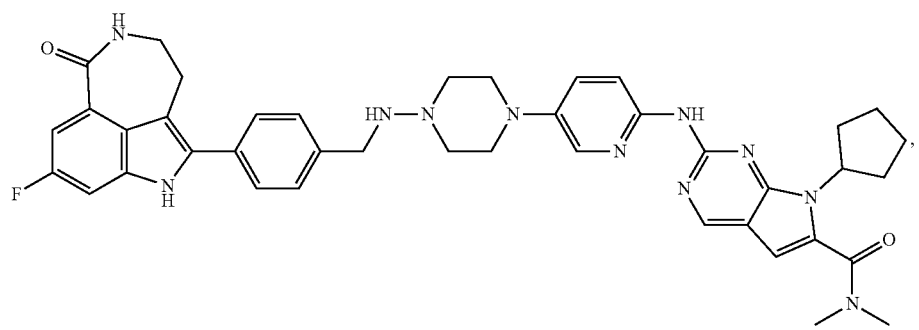
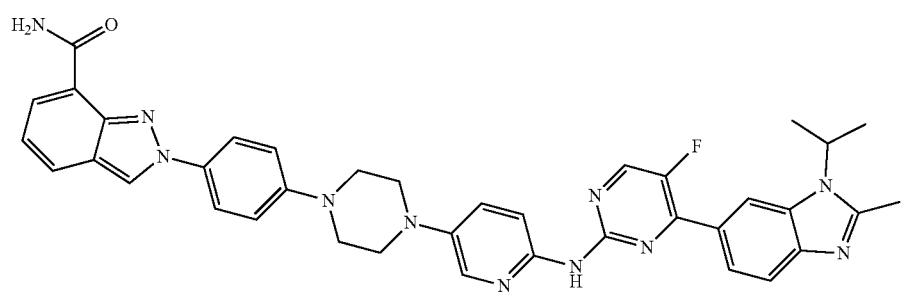
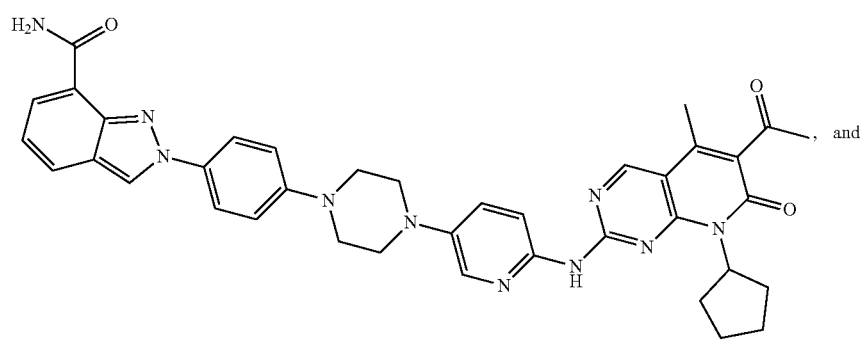
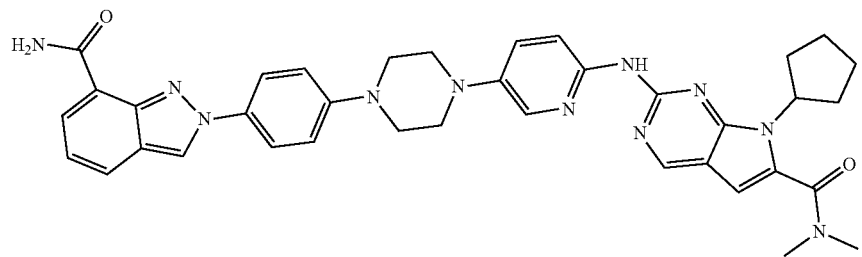

or a tautomer, stereoisomer or a mixture of stereoisomers, or a pharmaceutically acceptable salt, or hydrate thereof.

In some embodiments, the CDK inhibitors of Formula (II) and (III) are described in U.S. Pub. No. 2019/0202806, which is herein incorporated by reference in its entirety for all purposes.

In some embodiments, the CDK4/6 inhibitor is selected from the group consisting of palbociclib, ribociclib, and abemaciclib or a pharmaceutically acceptable salt, polymorph, or solvate thereof. In some embodiments, the CDK4/6 inhibitor is selected from the group consisting of palbociclib, ribociclib, and abemaciclib or a pharmaceutically acceptable salt thereof. In some embodiments, the CDK4/6 inhibitor is a pharmaceutically acceptable salt of palbociclib, ribociclib, or abemaciclib. In some embodiments, the CDK4/6 inhibitor is polymorph of palbociclib, ribociclib, or abemaciclib. In some embodiments, the CDK4/6 inhibitor is or solvate of palbociclib, ribociclib, or abemaciclib.

In some embodiments, CDK4/6 inhibitors are administered. In some embodiments, an FDA approved CDK4/6 inhibitor is administered. In some embodiments, the FDA approved CDK4/6 inhibitor is selected from the group consisting of palbociclib, ribociclib, and abemaciclib. The structures of palbociclib, ribociclib, and abemaciclib are below.

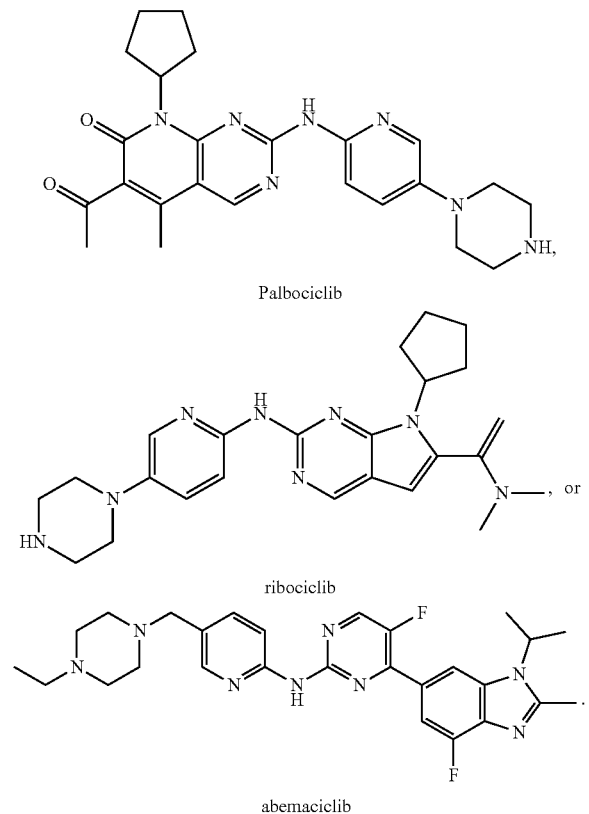

Palbociclib ribociclib abemaciclib

The FDA approved indications and dosage for palbociclib, ribociclib, and abemaciclib are described in Table 2.

TABLE 2

| \| | FDA Approved CDK4/6 Inhibitors | |
|---|---|---|
| Drug | Indication | Dose |
| palbociclib | Palbociclib is indicated for the treatment of HR-positive, HER2-negative advanced or metastatic breast cancer in combination with: an aromatase inhibitor as initial endocrine based therapy in postmenopausal women; or fulvestrant in women with disease progression following endocrine therapy. | The recommended dose of palbociclib is a 125 mg capsule taken orally once daily for 21 consecutive days followed by 7 days off treatment to comprise a complete cycle of 28 days. |
| ribociclib | Ribociclib is indicated in combination with: an aromatase inhibitor for the treatment of pre/perimenopausal or postmenopausal women, with hormone receptor (HR)-positive, human epidermal growth factor receptor 2 (HER2)-negative advanced or metastatic breast cancer, as initial endocrine-based therapy; or fulvestrant for the treatment of postmenopausal women with HR-positive, HER2-negative advanced or metastatic breast cancer, as initial endocrine based therapy or following disease progression on endocrine therapy. | The recommended dose of ribociclib is 600 mg (three 200 mg film-coated tablets) taken orally, once daily for 21 consecutive days followed by 7 days off treatment resulting in a complete cycle of 28 days. |

TABLE 2-continued

FDA Approved CDK4/6 Inhibitors

| Drug | Indication | Dose |
|---|---|---|
| abemaciclib | In combination with fulvestrant for the treatment of women with hormone receptor (HR)-positive, human epidermal growth factor receptor 2 (HER2)-negative advanced or metastatic breast cancer with disease progression following endocrine therapy. As monotherapy for the treatment of adult patients with HR-positive, HER2-negative advanced or metastatic breast cancer with disease progression following endocrine therapy and prior chemotherapy in the metastatic setting. | When used in combination with fulvestrant, the recommended dose of abemaciclib is 150 mg taken orally twice daily. When given with abemaciclib, the recommended dose of fulvestrant is 500 mg administered on Days 1, 15, and 29; and once monthly thereafter. When used as monotherapy, the recommended dose of abemaciclib is 200 mg taken orally twice daily. |

Formulations

The present disclosure also provides pharmaceutical compositions comprising one or more ER degraders disclosed herein and one or more CDK inhibitors disclosed herein.

In some embodiments, pharmaceutical compositions described herein can be combined with one or more therapeutically active agents used in the treatment of cancer. The additional therapeutic agent can be administering subsequently, simultaneously, or sequentially (e.g., before or after) with respect to the ER degrader.

In some embodiments of the present disclosure, pharmaceutical compositions comprising one or more compounds described herein, and a pharmaceutically acceptable excipient or adjuvant is provided. The pharmaceutically acceptable excipients and adjuvants are added to the composition or formulation for a variety of purposes. In other embodiments, pharmaceutical compositions further comprise a pharmaceutically acceptable carrier. In some embodiments, a pharmaceutically acceptable carrier includes a pharmaceutically acceptable excipient, binder, and/or diluent. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles.

The term parenteral as used here includes subcutaneous, intravenous, intramuscular, and intraarterial injections with a variety of infusion techniques. Intraarterial and intravenous injection as used herein includes administration through catheters.

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In certain embodiments, a pharmaceutical composition of the present disclosure is prepared using known techniques, including, but not limited to mixing, dissolving, granulating, dragee-making, levigating, emulsifying, encapsulating, entrapping or tableting processes.

In some embodiments, the present disclosure provides pharmaceutical compositions comprising one or more compounds disclosed herein combined with a pharmaceutically acceptable carrier. In some embodiments, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 M phosphate buffer or saline (e.g., about 0.8%). Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellent.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

In various embodiments, the pharmaceutical composition may be selected from the group consisting of a solid, powder, liquid and a gel. In certain embodiments, the pharmaceutical compositions of the present disclosure is a solid (e.g., a powder, tablet, a capsule, granulates, and/or aggregates). In certain of such embodiments, the solid pharmaceutical composition comprises one or more excipients known in the art, including, but not limited to, starches, sugars, diluents, granulating agents, lubricants, binders, and disintegrating agents.

Solid pharmaceutical compositions that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

Liquid pharmaceutical compositions can be prepared using compounds of the disclosure, and any other solid excipients where the components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions can contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition can also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

In some embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In certain embodiments, a pharmaceutical compositions of the present invention are formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

Appropriate pharmaceutical compositions of the present disclosure can be determined according to any clinically-acceptable route of administration of the composition to the subject. The manner in which the composition is administered is dependent, in part, upon the cause and/or location. One skilled in the art will recognize the advantages of certain routes of administration. The method includes administering an effective amount of one or more of Formula I (including compounds in Table 1A or Table 1), or a pharmaceutically acceptable salt, solvate, ester, or tautomer thereof, (or composition comprising such) to achieve a desired biological response, e.g., an amount effective to alleviate, ameliorate, or prevent, in whole or in part, a symptom of a condition to be treated. In various embodiments, the route of administration is systemic, e.g., oral or by injection.

In certain embodiments, the pharmaceutical compositions of the present disclosure are prepared for oral administration. In certain of such embodiments, the pharmaceutical compositions are formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, the pharmaceutical compositions for oral administration are soft, sealed capsules made of gelatin and a plasticizer, such as glycerol or sorbitol. In certain soft capsules, one or more compounds disclosed herein, are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In other embodiments the compound of the present disclosure are administered by the intravenous route. In further embodiments, the parenteral administration may be provided in a bolus or by infusion.

In certain embodiments, a pharmaceutical composition is prepared for rectal administration, such as a suppository or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, one or more compounds disclosed herein are formulated as a prodrug. In certain embodiments, upon in vivo administration, a prodrug is chemically converted to the biologically, pharmaceutically or therapeutically more active form. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In various aspects, the amount of compounds disclosed herein can be administered at about 0.001 mg/kg to about 100 mg/kg body weight including all values therebetween (e.g., about 0.01 mg/kg to about 10 mg/kg or about 0.1 mg/kg to about 5 mg/kg, including all ranges and values there between).

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. Treatments may be once administered daily or more frequently depending upon a number of factors, including the overall health of a patient, and the formulation and route of administration of the selected compound(s).

The compounds or pharmaceutical compositions of the present disclosure may be manufactured and/or administered in single or multiple unit dose forms.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., Cancer Chemother. Reports 50(4):219-244 (1966) and the following Table for Equivalent Surface Area Dosage Factors).

TABLE 2

Equivalent Surface Area Dosage Factors.

| From: | Mouse (20 g) | Rat (150 g) | To: Monkey (3.5 kg) | Dog (8 kg) | Human (60 kg) |
|---|---|---|---|---|---|
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

Methods of Treatment

In some embodiments, provided herein is a use of a pharmaceutical combination comprising an estrogen receptor (ER) degrader and a cyclin-dependent kinase (CDK) inhibitor in a therapeutic treatment. In some embodiments, the ER degrader and CDK inhibitor are administered in amounts which are synergistically effective for the treatment of a disease or disorder disclosed herein (e.g., cancer). In some embodiments, the estrogen receptor (ER) degrader and the cyclin-dependent kinase (CDK) inhibitor are administered as a pharmaceutical formulation further comprising a pharmaceutically acceptable excipient or a pharmaceutically acceptable carrier. In some embodiments, the therapeutic treatment is for the treatment of breast cancer, lung cancer, ovarian cancer, endometrial cancer, prostate cancer, and esophageal cancer. In some embodiments, the therapeutic treatment is for the treatment of breast cancer. In some embodiments, the therapeutic treatment is for lung cancer. In some embodiments, the therapeutic treatment is for the treatment of ovarian cancer. In some embodiments, the therapeutic treatment is for the treatment of endometrial cancer. In some embodiments, the therapeutic treatment is for the treatment of prostate cancer. In some embodiments, the therapeutic treatment is for the treatment of esophageal cancer. In some embodiments, the therapeutic treatment is for the treatment of estrogen-related diseases and conditions. In some embodiments, the therapeutic treatment is for the treatment of infertility. In some embodiments, the therapeutic treatment is for the treatment of ovulatory dysfunction. In some embodiments, the therapeutic treatment is for the treatment of postmenopausal osteoporosis. In some embodiments, the therapeutic treatment is for the treatment of estrogen-related gynecomastia. In some embodiments, the therapeutic treatment is for the treatment of dyspareunia due to menopause. In some embodiments, the therapeutic treatment is for the treatment of retroperitoneal fibrosis. In some embodiments, the therapeutic treatment is for the treatment of idiopathic sclerosing mesenteritis.

In some embodiments, provided herein a use of a pharmaceutical combination disclosed herein in the preparation of a medicament. In some embodiments, provided herein is a method of inhibiting cell growth comprising contacting a cell with a pharmaceutical combination comprising a compound of Formula (I), Formula (I-A), Formula (II-A), Formula (I-B), Formula (I-B)*, Formula (I-C), Formula (III-C) or a tautomer, stereoisomer, pharmaceutically acceptable salt or hydrate thereof and a cyclin-dependent kinase (CDK) inhibitor. In some embodiments, the cell may express ERα. In some embodiments, the estrogen receptor (ER) degrader and the cyclin-dependent kinase (CDK) inhibitor are administered as a pharmaceutical formulation further comprising a pharmaceutically acceptable excipient or a pharmaceutically acceptable carrier.

In some embodiments, the pharmaceutical combinations disclosed herein are administered to treat cancer. In some embodiments, the compounds disclosed herein are administered to treat cancer.

In one embodiment, the cancer is a solid tumor. The term "solid tumor" especially means melanoma, breast cancer, ovarian cancer, colorectal cancer, and generally gastrointestinal tract, cervix cancer, lung cancer (including small-cell lung cancer and non-small cell lung cancer), head and neck cancer, bladder cancer, or prostate cancer. The present combination inhibits the growth of solid tumors and also liquid tumors. Further, depending on the tumor type and particular combination used, a decrease of the tumor volume can be obtained. The combination of the invention disclosed herein is also suited to prevent the metastatic spread of tumors and the growth or development of micrometastases. The combination of the invention disclosed herein is suitable for the treatment of poor prognosis patients, especially such poor prognosis patients having colon cancer, rectal cancer, colorectal cancer, breast cancer, stomach cancer or pancreatic cancer.

In some embodiments, the cancer is chosen from breast cancer, lung cancer, ovarian cancer, endometrial cancer, prostate cancer, and esophageal cancer. In some embodiments, the cancer is breast cancer. In some embodiments, the cancer is lung cancer. In some embodiments, the cancer is ovarian cancer. In some embodiments, the cancer is endometrial cancer. In some embodiments, the cancer is prostate cancer. In some embodiments, the cancer is esophageal cancer.

In some embodiments, the cancer is positive for Estrogen Receptor alpha.

In some embodiments, the method is for treating estrogen-related disease and condition. In some embodiments, the estrogen-related disease and condition is infertility. In some embodiments, the estrogen-related disease and condition is ovulatory dysfunction. In some embodiments, estrogen-related disease and condition is postmenopausal osteoporosis. In some embodiments, estrogen-related disease and condition is estrogen-related gynecomastia. In some embodiments, the estrogen-related disease and condition is dyspareunia due to menopause. In some embodiments, the estrogen-related disease and condition is retroperitoneal fibrosis. In some embodiments, estrogen-related disease and condition is idiopathic sclerosing mesenteritis.

In some embodiments, the cancer is colorectal cancer, breast cancer, lung cancer, especially non-small cell lung cancer (NSCLC), prostate cancer, glioblastoma, mantel cell lymphoma (MCL), chronic myeloid leukemia (CML) and acute myeloid leukemia (AML), tyrosine kinase-activated leukemia, endometrial cancer, neuroblastoma, testicular cancer, germ cell tumors, Ewing's sarcoma, malignant lymphoma, ovarian cancer, fallopian tube cancer, or primary peritoneal cancer.

In other embodiments, the breast cancer is hormone receptor (HR)-positive breast cancer, and/or human epidermal growth factor receptor 2 (HER2)-negative advanced or metastatic breast cancer. In some embodiments, the breast cancer is hormone receptor (HR)-positive breast cancer, and the patient has disease progression following endocrine therapy and/or prior chemotherapy in metastatic setting.

In some embodiments, the breast cancer is human epidermal growth factor receptor 2 (HER2)-negative advanced or metastatic breast cancer, and the patient has disease progression following endocrine therapy and/or prior chemotherapy in the metastatic setting. In other embodiments, the ovarian cancer is recurrent epithelial ovarian cancer. In some embodiments, the ovarian cancer is BRCA-mutated ovarian cancer. In some embodiments, the BRCA-mutated ovarian cancer is BRCA-mutated serous ovarian cancer. In some embodiments, the patient has suspected deleterious germline BRCA-mutated advanced ovarian cancer. In some embodiments, the patient has been treated with three or more prior lines of chemotherapy.

In some embodiments, the cancer is triple negative breast cancers (TNBC), which are characterized by breast cancer cells that test negative for estrogen receptors (ER−), progesterone receptors (PR−), and HER2 (HER2−). Testing negative for all three of these means the cancer is triple-negative. In some embodiments, the cancer is estrogen-receptor positive breast cancer.

In another embodiment the cancer may be selected from one or more of the group consisting of Acute Lymphoblastic Leukemia, Acute Myeloid Leukemia, Adrenocortical Carcinoma, AIDS-Related Cancers, Kaposi Sarcoma, Lymphoma, Anal Cancer, Appendix Cancer, Astrocytomas, Childhood Atypical Teratoid/Rhabdoid Tumor, Basal Cell Carcinoma, Skin Cancer (Nonmelanoma), Childhood Bile Duct Cancer, Extrahepatic Bladder Cancer, Bone Cancer, Ewing Sarcoma Family of Tumors, Osteosarcoma and Malignant Fibrous Histiocytoma, Brain Stem Glioma, Brain Tumors, Embryonal Tumors, Germ Cell Tumors, Craniopharyngioma, Ependymoma, Bronchial Tumors, Burkitt Lymphoma (Non-Hodgkin Lymphoma), Carcinoid Tumor, Gastrointestinal Carcinoma of Unknown Primary, Cardiac (Heart) Tumors, Lymphoma, Primary, Cervical Cancer, Childhood Cancers, Chordoma, Chronic Lymphocytic Leukemia, Chronic Myelogenous Leukemia, Chronic Myeloproliferative Neoplasms Colon Cancer, Colorectal Cancer, Cutaneous T-Cell Lymphoma, Ductal Carcinoma In Situ, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Intraocular Melanoma, Retinoblastoma, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors, Extragonadal Cancer, Ovarian Cancer, Testicular Cancer, Gestational Trophoblastic Disease, Glioma, Brain Stem Cancer, Hairy Cell Leukemia, Head and Neck Cancer, Heart Cancer, Hepatocellular (Liver) Cancer, Histiocytosis, Langerhans Cell Cancer, Hodgkin Lymphoma, Hypopharyngeal Cancer, Intraocular Melanoma, Islet Cell Tumors, Pancreatic Neuroendocrine Tumors, Kaposi Sarcoma, Kidney Cancer, Renal Cell Cancer, Wilms Tumor and Other Childhood Kidney Tumors, Langerhans Cell Histiocytosis, Laryngeal Cancer, Leukemia, Chronic Lymphocytic Cancer, Chronic Myelogenous Cancer, Hairy Cell Cancer, Lip and Oral Cavity Cancer, Liver Cancer (Primary), Lobular Carcinoma In Situ (LCIS), Lung Cancer, Non-Small Cell Cancer, Small Cell Cancer, Lymphoma, Cutaneous T-Cell (Mycosis Fungoides and Sézary Syndrome), Hodgkin Cancer, Non-Hodgkin Cancer, Macroglobulinemia, Waldenström, Male Breast Cancer, Malignant Fibrous Histiocytoma of Bone and Osteosarcoma, Melanoma, Intraocular (Eye) Cancer, Merkel Cell Carcinoma, Mesothelioma, Malignant, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic, Myeloid Leukemia, Acute, Myeloma Multiple, Chronic Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Epithelial Cancer, Low Malignant Potential Tumor, Pancreatic Cancer, Pancreatic Neuroendocrine Tumors (Islet Cell Tumors), Papillomatosis, Paraganglioma, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System Lymphoma, Rectal Cancer, Renal Cell (Kidney) Cancer, Retinoblastoma, Rhabdomyosarcoma, Salivary Gland Cancer, Sarcoma, Ewing Cancer, Kaposi Cancer, Osteosarcoma (Bone Cancer), Soft Tissue Cancer, Uterine Cancer, Sézary Syndrome, Skin Cancer, Childhood Melanoma, Merkel Cell Carcinoma, Nonmelanoma, Small Cell Lung Cancer, Small Intestine Cancer, Soft Tissue Sarcoma, Squamous Cell Carcinoma, Skin Cancer (Nonmelanoma), Childhood Squamous Neck Cancer with Occult Primary, Metastatic Cancer, Stomach (Gastric) Cancer, T-Cell Lymphoma, Cutaneous Cancer, Testicular Cancer, Throat Cancer, Thymoma and Thymic Carcinoma, Thyroid Cancer, Transitional Cell Cancer of the Renal Pelvis and Ureter, Unknown Primary, Carcinoma of Childhood, Unusual Cancers of Childhood, Urethral Cancer, Uterine Cancer, Endometrial Cancer, Uterine Sarcoma, Vaginal Cancer, Vulvar Cancer, Waldenström Macroglobulinemia, Wilms Tumor, and Women's Cancers.

The ER degrader is administered at any suitable dose, e.g., about 0.01 mg, about 0.05 mg, about 0.1 mg, about 0.2 mg, about 0.3 mg, about 0.4 mg about 0.5 mg, about 1 mg, about 5 mg, about 10 mg, about 20 mg, about 30 mg, about 35 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, or about 1 g, including all values therebetween. The ER degrader is administered in a dose of from about 0.01 mg to about 1 g, including from about 0.01 mg, about 0.05 mg, about 0.1 mg about 0.5 mg, about 1 mg, about 5 mg, about 10 mg, about 20 mg, about 30 mg, about 35 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, to about 1 g, including all all ranges therebetween. In some embodiments, the ER degrader is administered in a dose of from about 30 mg to about 600 mg.

The CDK inhibitor may be administered at any suitable dose, e.g., about 0.5 mg, about 1 mg, about 5 mg, about 10 mg, about 20 mg, about 35 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, or about 1 g, including all values therebetween. In some embodiments, the CDK inhibitor may be administered in a dose of from about 0.5 mg to about 1 g, including from about 0.5 mg, about 1 mg, about 5 mg, about 10 mg, about 20 mg, about 35 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, to about 1 g, including all all ranges therebetween.

In some embodiments, the CDK inhibitor is palbociclib, ribociclib, or abemaciclib. The CDK inhibitor may be administered at the FDA approved dose or doses (i.e., as provided on the label approved by the FDA as of the filing date of this application), or at a reduced dose. As used herein, a "reduced dose" refers to a dose that is less than the approved dose as provided on the FDA approved label. In some embodiments, the reduced dose may be 10%, 15%, 20%, 25%, 30%, 35%, 40%, 45%, 50%, 55%, 60%, 65%, 70%, 75%, 80%, 85%, 90%, or 95% less than the approved dose.

In some embodiments, the method comprises administering from about 25 mg to about 200 mg palbociclib, from about 50 mg to about 150 mg palbociclib, or from about 75 mg to about 125 mg palbociclib, including all ranges and values therebetween. In some embodiments, the oral dosage form comprises about 125 mg, about 100 mg, about 75, about 50, or about 25 mg of palbociclib, including all values and ranges between these values.

In some embodiments, the method comprises administering ribociclib succinate in amount ranging from about 50 mg to about 600 mg (e.g., 50, 100, 150, 200, 250, 300, 350, 400, 450, 500, 550, or 600 mg, including all values and ranges between these values. In some embodiments, the oral dosage form comprises ribociclib succinate in about 150 mg to about 600 mg of the Equivalent Amount of ribociclib free base, including all ranges and values therebetween. In some embodiments, the oral dosage form comprises about 200 mg of the Equivalent Amount of ribociclib free base.

In some embodiments, the methods disclosed herein comprises administering about 25 mg to about 500 mg of abemaciclib (e.g., 25, 50, 75, 100, 125, 150, 175, 200, 225, 250, 275, 300, 325, 350, 375, 400, 425, 450, 475, 500, 525, 550, 575, or 600 mg, including all values and ranges between these values), about 50 mg, to about 200 mg, or about 50 mg to about 300 mg, including all ranges and values therebetween. In some embodiments, the oral dosage form comprises about 50 mg, about 100 mg, about 150 mg, or about 200 mg of abemaciclib.

In some embodiments, a pharmaceutical combination is provided comprising an estrogen receptor (ER) degrader and a cyclin-dependent kinase (CDK) inhibitor in a single dosage form or in separate dosage forms. In some embodiments, the pharmaceutical combination is provided comprising an estrogen receptor (ER) degrader and a cyclin-dependent kinase (CDK) inhibitor are in separate dosage forms are administered by the same mode of administration or a different mode of administration. In some embodiment, the separate dosage forms of a pharmaceutical combination provided herein, are co-administered by simultaneous administration, sequential administration, overlapping administration, interval administration, continuous administration, or a combination thereof. In some embodiments, the dosage form is an oral dosage form. In some embodiments, the oral dosage for is a tablet or a capsule.

A dosage form of the present invention may be administered, hourly, daily, weekly, or monthly. The dosage form of the present invention may be administered once a day, twice a day, three times a day, four times a day etc. The dosage form of the present invention may be administered with food or without food.

In some embodiments, palbociclib is administered to the subject at an initial dose of about 125 mg/day of palbociclib in combination with the estrogen receptor (ER) degrader.

In some embodiments, ribociclib succinate is administered to the subject at an initial dose of about 600 mg/day of the Equivalent Amount of ribociclib free base in combination with the estrogen receptor (ER) degrader.

In some embodiments, abemaciclib is administered to the subject at an initial dose of about 150 mg twice daily to about 200 mg twice daily in combination with the estrogen receptor (ER) degrader. In some embodiments, abemaciclib is administered to the subject at an initial dose of about 150 mg twice daily. In some embodiments, abemaciclib is administered to the subject at an initial dose of about 200 mg twice daily.

In some embodiments, a pharmaceutical combination comprising an ER degrader and CDK inhibitor, is administered with an additional therapeutic agent. The additional therapeutic agent can provide additive or synergistic value relative to the administration of one or more compounds in the combinations of the present disclosure alone. The additional therapeutic agent can be selected from, for example, hormones and hormonal analogues; signal transduction pathway inhibitors; topoisomerase I inhibitors; topoisomerase II inhibitors; antimetabolite neoplastic agents; antibiotic neoplastic agents; alkylating agents; anti-microtubule agents; platinum coordination complexes; aromatase inhibitors; and anti-mitotic agents.

In some embodiments, the additional therapeutic agent may be a hormone or hormonal analogue. In some embodiments, the additional therapeutic agent may be a signal transduction pathway inhibitor. In some embodiments, the additional therapeutic agent may be a topoisomerase I inhibitor. In some embodiments, the additional therapeutic agent may be a topoisomerase II inhibitor. In some embodiments, the additional therapeutic agent may be an antimetabolite neoplastic agent. In some embodiments, the additional therapeutic agent may be an antibiotic neoplastic agent. In some embodiments, the additional therapeutic agent may be an alkylating agent. In some embodiments, the additional therapeutic agent may be an anti-microtubule agent. In some embodiments, the additional therapeutic agent may be a platinum coordination complex. In some embodiments, the additional therapeutic agent may be an aromatase inhibitor. In some embodiments, the additional therapeutic agent may be an anti-mitotic agent.

In some embodiments, the aromatase inhibitor may be selected from anastrazole, letrozole, vorozole, fadrozole, exemestane, and formestane. In some embodiments, the aromatase inhibitor is anastrazole. In some embodiments, the aromatase inhibitor may be letrozole. In some embodiments, the aromatase inhibitor may be vorozole. In some embodiments, the aromatase inhibitor may be fadrozole. In some embodiments, the aromatase inhibitor may be exemestane. In some embodiments, the aromatase inhibitor may be formestane.

In some embodiments, the anti-mitotic agent may be selected from paclitaxel, docetaxel, and Abraxane. In some embodiments, the anti-mitotic agent may be paclitaxel. In some embodiments, the anti-mitotic agent may be docetaxel. In some embodiments, the anti-mitotic agent may be Abraxane.

In some embodiments, the additional therapeutic agent is tamoxifen. In some embodiments, the additional therapeutic agent is fulvestrant.

EMBODIMENTS

1. A method of treating cancer in a patient in need thereof, comprising administering an estrogen receptor (ER) degrader and a cyclin-dependent kinase (CDK) inhibitor.
2. The method of embodiment 1, wherein the estrogen receptor (ER) degrader is a compound of formula (I):

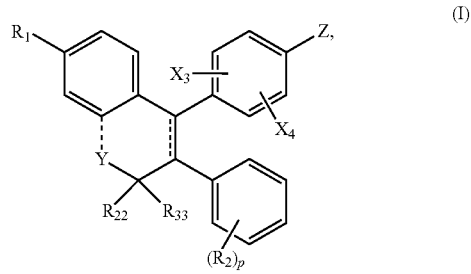

or a tautomer, stereoisomer or a mixture of stereoisomers, or a pharmaceutically acceptable salt, or hydrate thereof;
wherein:
=== is a single or double bond;
--- is a single bond or absent;
Y is —CH$_3$, or —O—;
wherein, when Y is —CH$_3$, --- is absent, and === is a double bond; and when Y is —O—, --- and === are both single bonds;

Z is

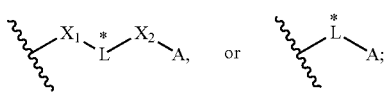

$X^3$ and $X^4$ are each independently selected from H or halo;

$X^1$ and $X^2$ are each independently selected from the group consisting of $C(R^3)_2$, $NR^4$, O, S, cycloalkyl, aryl, heterocycle, and heteroaryl, each of which is independently substituted with 0, 1, 2, or 3 $R^5$;

A is selected from:

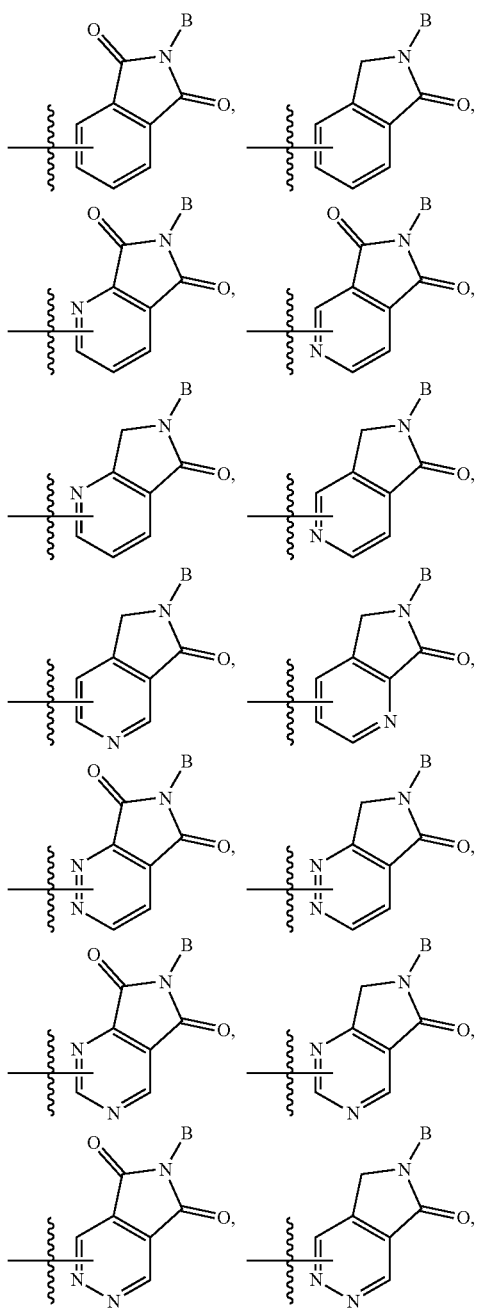

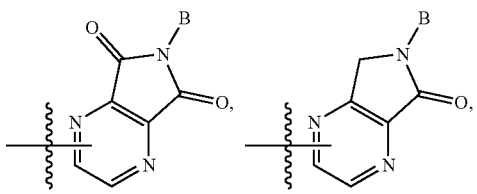

each of which is substituted with $R^{55}$ or 0, 1, 2, or 3 $R^5$;

B is selected from 5- to 6-membered cycloalkyl, 5- to 6-membered aryl, 5- to 6-membered heterocycle, and 5- to 6-membered heteroaryl, each of which is substituted with 0, 1, 2, or 3 $R^5$;

L* is a linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$;

$R^1$ and $R^2$ are each independently selected from the group consisting of H, $C_1$-$C_6$ acyl, cyano, $C_1$-$C_6$ alkyl, $C_1$-$C_6$ haloalkyl, halo, alkoxy, acyloxy, hydroxy, and sulfhydryl, each of which is substituted with 0, 1, 2, or 3 $R^5$;

each $R^3$ is independently selected from H, $C_1$-$C_6$ alkyl, halo, and hydroxy;

each $R^4$ is independently selected from H, $C_1$-$C_6$ alkyl, and acyl, each of which is substituted with 0, 1, 2, or 3 $R^5$;

each $R^{55}$ is independently selected from halogen, hydroxy, $C_1$-$C_3$ alkyl, $C_1$-$C_3$ alkoxy, $C_1$-$C_3$ haloalkyl, —$N(R^7)_2$, and —CN, each of which is substituted with 0, 1, 2, or 3 $R^5$;

each $R^7$ is independently selected from hydrogen, $C_1$-$C_6$ alkyl, and acyl, each of which is substituted with 0, 1, 2, or 3 $R^6$, or two $R^7$ groups are taken together to form a 3- to 6-membered heterocycle or heteroaryl.

each $R^5$ is independently selected from $C_1$-$C_6$ alkyl, $C_1$-$C_6$ alkoxy, $C_1$-$C_6$ haloalkyl, oxo, halo, cyano, and hydroxy;

$R^{22}$ and $R^{33}$ are each independently selected from H, $C_1$-$C_3$ alkyl, or $C_1$-$C_3$ haloalkyl, each of which is substituted with 0, 1, 2, or 3 $R^5$;

wherein

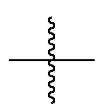

represents the point of attachment of A to $X^2$; and p is 1, or 2.

3. The method of embodiment 1 or 2, wherein the estrogen receptor (ER) degrader is a compound of formula (I-A):

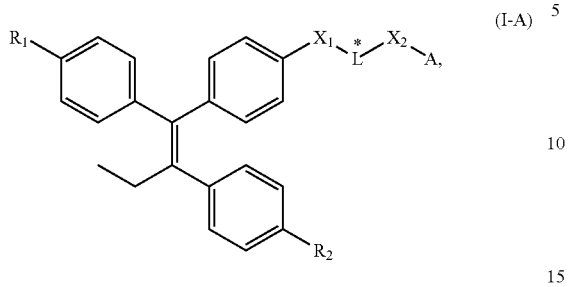

(I-A)

or a tautomer, stereoisomer or a mixture of stereoisomers, or a pharmaceutically acceptable salt, or hydrate thereof;

wherein:

$X^1$ and $X^2$ are each independently selected from the group consisting of $C(R^3)_2$, $NR^4$, O, S, cycloalkyl, aryl, heterocycle, and heteroaryl, each of which is independently substituted with 0, 1, 2, or 3 $R^5$;

A is selected from:

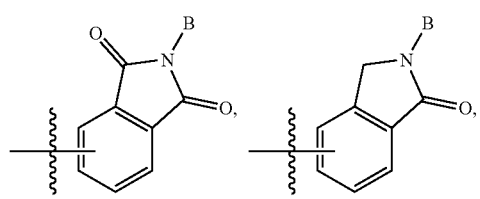

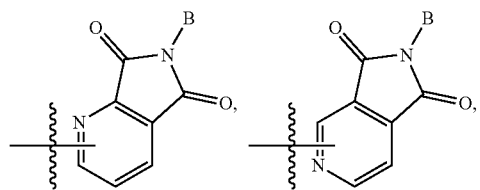

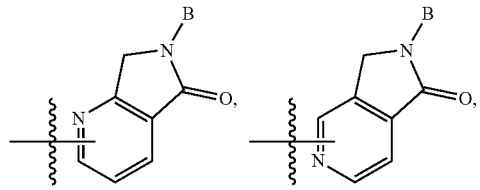

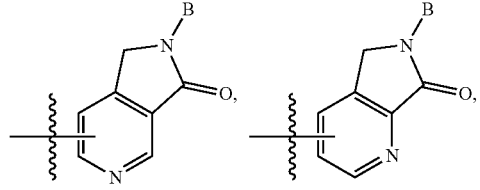

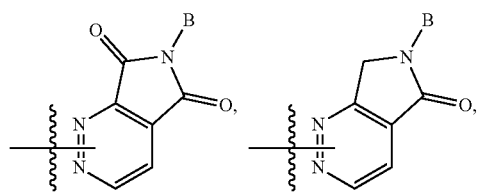

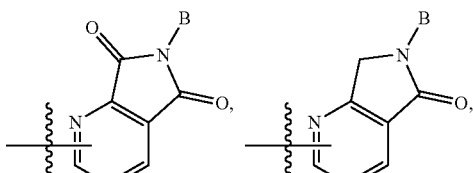

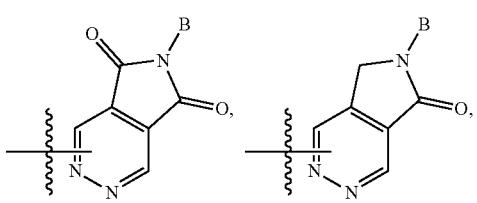

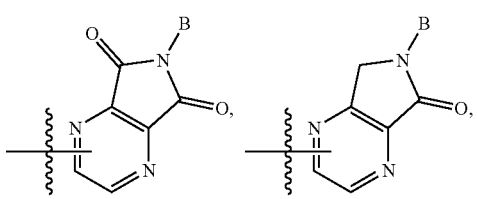

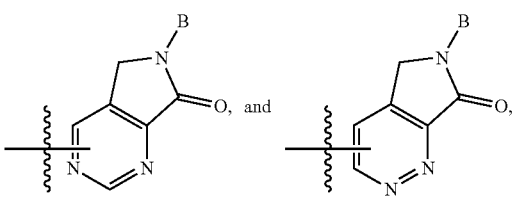

each of which is substituted with 0, 1, 2, or 3 $R^5$;

B is selected from 5- to 6-membered cycloalkyl, 5- to 6-membered aryl, 5- to 6-membered heterocycle, and 5- to 6-membered heteroaryl, each of which is substituted with 0, 1, 2, or 3 $R^5$;

L* is a linker of 1 to 22 carbon atoms in length, wherein one or more carbon atoms are each optionally and independently replaced by a group selected from C(O), O, $NR^4$, S, $C_2$-alkenyl, $C_2$-alkynyl, cycloalkyl, aryl, heterocycle, and heteroaryl, each of which is substituted with 0, 1, 2, or 3 $R^5$;

$R^1$ and $R^2$ are each independently selected from H, $C_1$-$C_6$ alkyl, halo, alkoxy, acyloxy, hydroxy, and sulfhydryl, each of which is substituted with 0, 1, 2, or 3 $R^5$;

each $R^3$ is independently selected from H, $C_1$-$C_6$ alkyl, halo, and hydroxy;

each $R^4$ is independently selected from H, $C_1$-$C_6$ alkyl, and acyl, each of which is substituted with 0, 1, 2, or 3 $R^5$; and each $R^5$ is independently selected from $C_1$-$C_6$ alkyl, halo, cyano, oxo, and hydroxy;

wherein

represents the point of attachment of A to $X^2$

4. The method of embodiment 3, wherein A is:

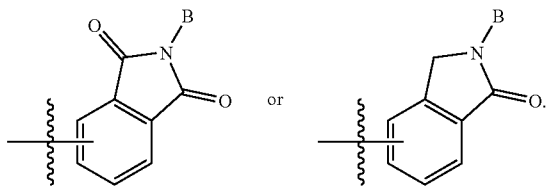

5. The method of to embodiment 3 or 4, wherein B is a 5-membered heterocycle substituted with 0, 1, 2, or 3 $R^5$.
6. The method of embodiment 3 or 4, wherein B is selected from the group consisting of:

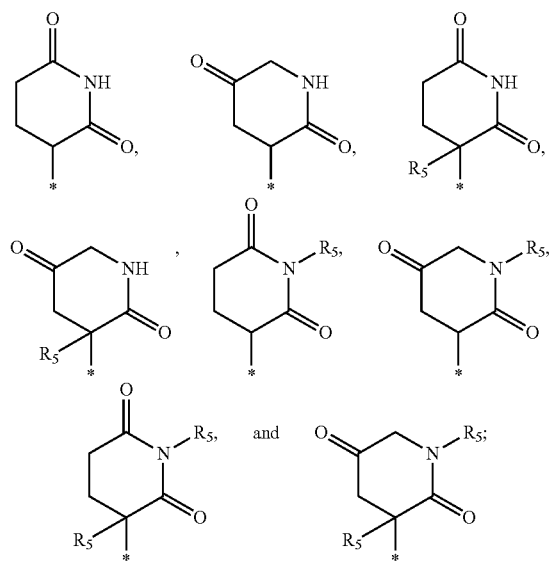

wherein *⌒ represents the point of attachment of B to A.

7. The method of embodiment 3 or 4, wherein B is a 6-membered heterocycle substituted with 0, 1, 2, or 3 $R^5$.
8. The method of any one of embodiments 3-7, wherein $R^1$ and $R^2$ are each independently selected from the group consisting of H, $C_1$-$C_3$ alkyl, halo, alkoxy, acyloxy, hydroxy, and sulfhydryl, each of which may be substituted with 0, 1, 2, or 3 $R^5$.
9. The method of embodiment 8, wherein $R^1$ and $R^2$ are each independently H or OH.
10. The method of any one of embodiments 3-9, wherein $X^1$ and $X^2$ are each independently selected from $C(R^3)_2$, $NR^4$, O, S, 5 or 6-membered cycloalkyl, 5- or 6-membered aryl, 5- or 6-membered heterocycle, and 5- or 6-membered heteroaryl, each of which is independently substituted with 0, 1, 2, or 3 $R^5$.
11. The method of embodiment 10, wherein $R^4$ is selected from H, $C_1$-$C_3$ alkyl, and acyl, each of which is substituted with 0, 1, 2, or 3 $R^5$.
12. The method of embodiment 10, wherein $X^1$ is selected from 5 or 6-membered cycloalkyl, 5- or 6-membered aryl, 5- or 6-membered heterocycle, and 5- or 6-membered heteroaryl.
13. The method of any one of embodiments 3-9, wherein $X^1$ is selected from the group consisting of aziridinyl, azetidinyl, pyrrolidinyl, piperidinyl, piperazinyl, pyrrolyl, pyridinyl, pyrimidinyl, oxiranyl, oxetanyl, tetrahydrofuranyl, furanyl, pyranyl, tetrahydropyranyl, dioxanyl, imidazolyl, pyrazolyl, oxazole, isoxazole, thiazole, isothiazole, triazole, tetrazole, indole, benzimidazole, benzofuran, benzoxazole, benzothiazole, quinoline, isoquinoline, and quinazoline, each of which is independently substituted with 0, 1, 2, or 3 $R^5$.
14. The method of any one of embodiments 3-9, wherein $X^1$ is selected from the group consisting of:

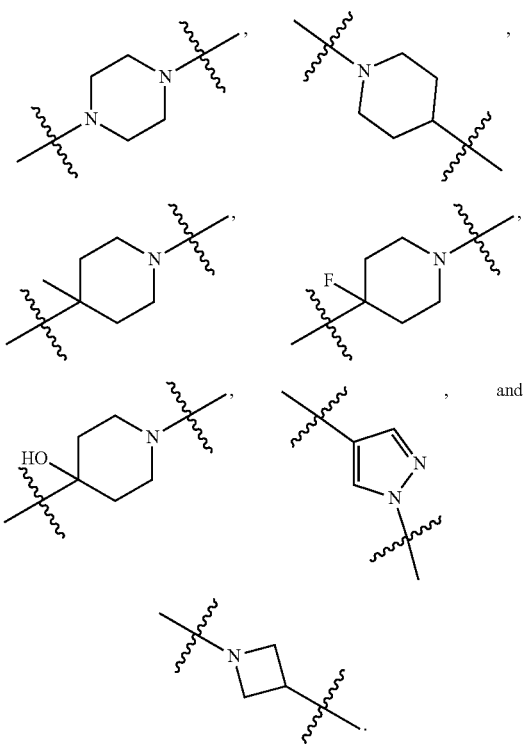

15. The method of any one of embodiments 3-9, wherein $X^2$ is selected from the group consisting of:

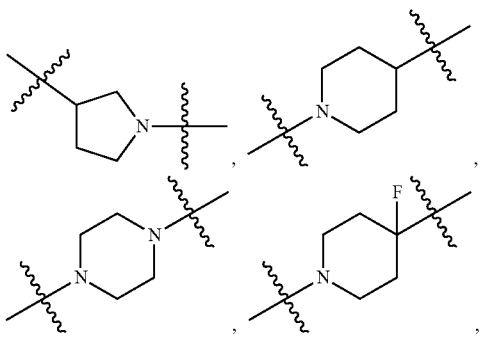

-continued

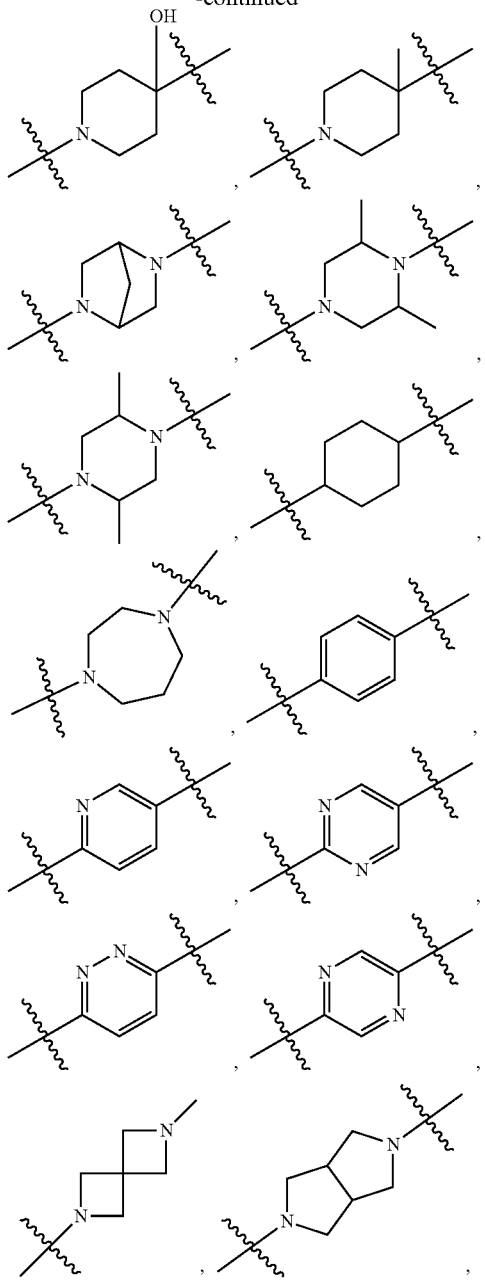

-continued

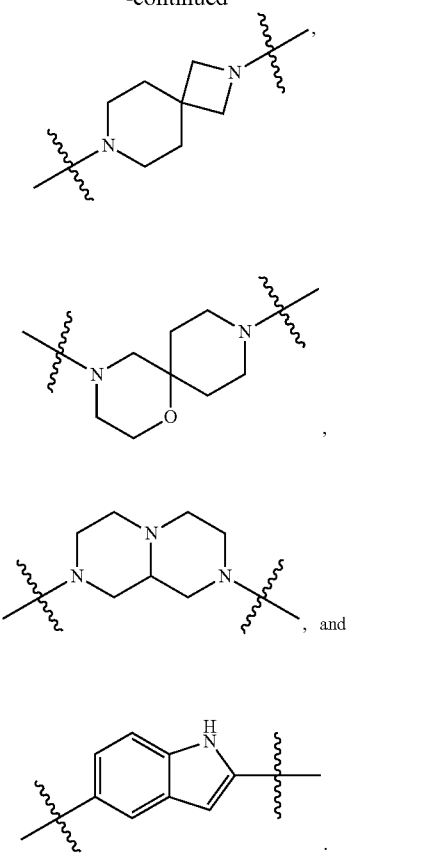

, and

16. The method of any one of embodiments 3-15, wherein L* is a linker of 1 to 16 carbon atoms in length, wherein one or more carbon atoms are each optionally and independently replaced by a group selected from C(O), O, NR⁴, S, C₂-alkenyl, C₂-alkynyl, cycloalkyl, aryl, heterocycle, and heteroaryl, each of which is independently substituted with 0, 1, 2, or 3 R⁵.

17. The method of any one of embodiments 3-15, wherein L* is a linker wherein one carbon atom is replaced by a heterocycle and one carbon atom is replaced by a cycloalkyl, each of which is independently substituted with 0, 1, 2, or 3 R⁵.

18. The method of any one of embodiments 3-15, wherein L* is selected from the group consisting of:

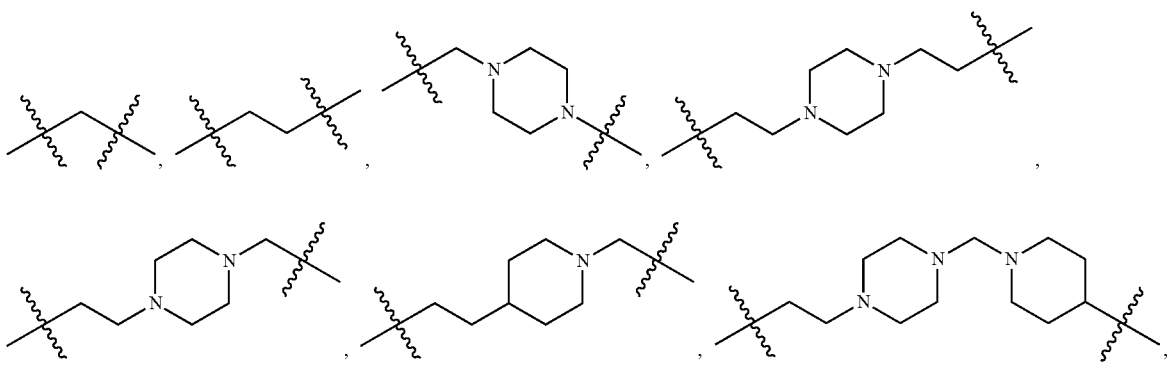

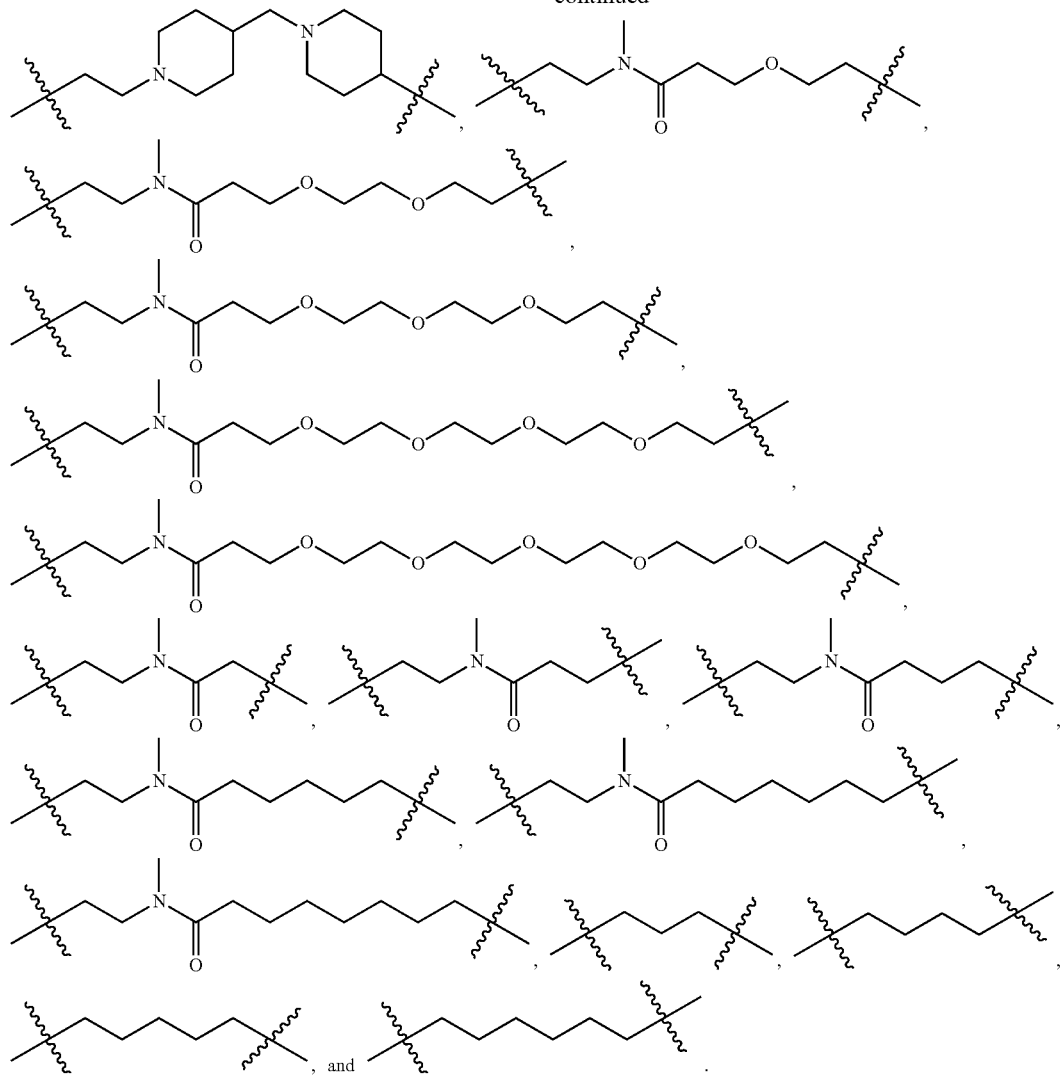

19. The method of any one of embodiments 1-18, wherein the estrogen receptor (ER) degrader is a compound from Table 1A.

20. The method of embodiment 1 or 2, wherein the estrogen receptor (ER) degrader is a compound of Formula (I-B):

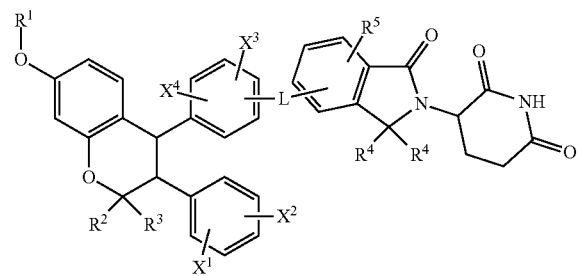

(I-B)

or a stereoisomer or a mixture of stereoisomers, a pharmaceutically acceptable salt, or hydrate thereof, wherein:

$R^1$ is selected from H, $C_1$-$C_6$ acyl or $C_1$-$C_6$ alkyl, each of which is substituted with 0, 1, 2, or 3 $R^6$;

$R^2$ and $R^3$ are each independently selected from H, $C_1$-$C_3$ alkyl, or $C_1$-$C_3$ haloalkyl, each of which is substituted with 0, 1, 2, or 3 $R^6$;

each $R^4$ is independently selected from H, hydroxyl, $C_1$-$C_3$ alkyl, $C_1$-$C_3$ alkoxyl, or $C_1$-$C_3$ haloalkyl, each of which is substituted with 0, 1, 2, or 3 $R^6$, or two $R^4$ groups are taken together to form an oxo;

$R^5$ is selected from hydrogen, halogen, hydroxy, $C_1$-$C_3$ alkyl, $C_1$-$C_3$ alkoxy, $C_1$-$C_3$ haloalkyl, —N(R)$_2$, and —CN, each of which is substituted with 0, 1, 2, or 3 $R^6$;

$X^1$ and $X^2$ are each independently selected from H, halogen, cyano, $C_1$-$C_6$ alkyl, $C_1$-$C_6$ alkoxyl, or $C_1$-$C_6$ haloalkyl each of which is substituted with 0, 1, 2, or 3 $R^6$;

$X^3$ and $X^4$ are each independently selected from H or halo;

L is a linker of 1 to 22 carbon atoms in length, wherein one or more carbon atoms are each optionally and independently replaced by a group selected from C(O), O, $NR^7$, S, $C_2$-alkenyl, $C_2$-alkynyl, cycloalkyl, aryl, heterocycle, and heteroaryl, each of which is substituted with 0, 1, 2, or 3 $R^6$;

each $R^6$ is independently selected from $C_1$-$C_6$ alkyl, halo, cyano, and hydroxy, each R⁷ is independently selected from hydrogen, $C_1$-$C_6$ alkyl, and acyl, each of which is substituted with 0, 1, 2, or 3 $R^6$, or two $R^7$ groups are taken together to form a 3- to 6-membered heterocycle or heteroaryl.

21. The method of embodiment 20, wherein $R^1$ is H or methyl.
22. The method of embodiment 20 or 21, wherein $R^2$ and $R^3$ are each independently selected from H and methyl.
23. The method of any one of embodiments 20-22, wherein $R^4$ is H.
24. The method of any one of embodiments 20-22, wherein two $R^4$ groups are taken together to form an oxo.
25. The method of any one of embodiments 20-24, wherein $R^5$ is hydrogen or halogen.
26. The method of any one of embodiments 20-25, wherein $X^1$ and $X^2$ are each independently selected from the group consisting of H, F, CN, methyl, methoxy, and trifluoromethyl.
27. The method of any one of embodiments 20-26, wherein $X^3$ and $X^4$ are each independently selected from H or halo.
28. The method of any one of embodiments 20-27, wherein $X^3$ and $X^4$ are each independently selected from H or F.
29. The method of any one of embodiments 20-28, wherein L is a linker of 1 to 22 carbon atoms in length, wherein one or more carbon atoms are each optionally and independently replaced by a group selected from C(O), O, $NR^7$, S, $C_2$-alkenyl, $C_2$-alkynyl, cycloalkyl, aryl, heterocycle, and heteroaryl, each of which is independently substituted with 0, 1, 2, or 3 $R^6$.
30. The method of any one of embodiments 20-29, wherein L is a linker wherein one carbon atom is replaced by a heterocycle and one carbon atom is replaced by a cycloalkyl, each of which is independently substituted with 0, 1, 2, or 3 $R^6$.
31. The method of any one of embodiments 20-28, wherein L is selected from the group consisting of:

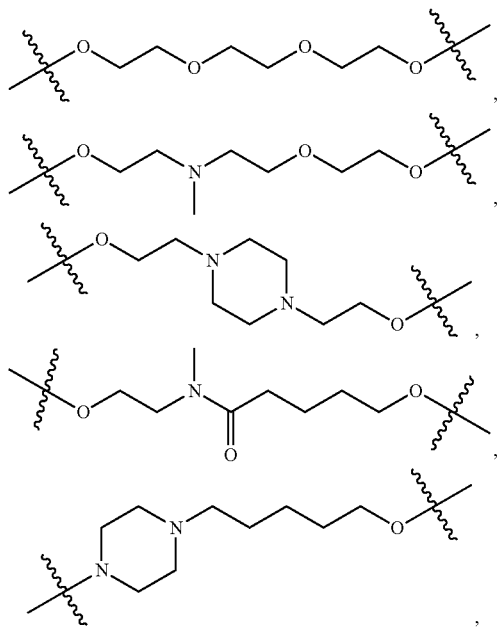

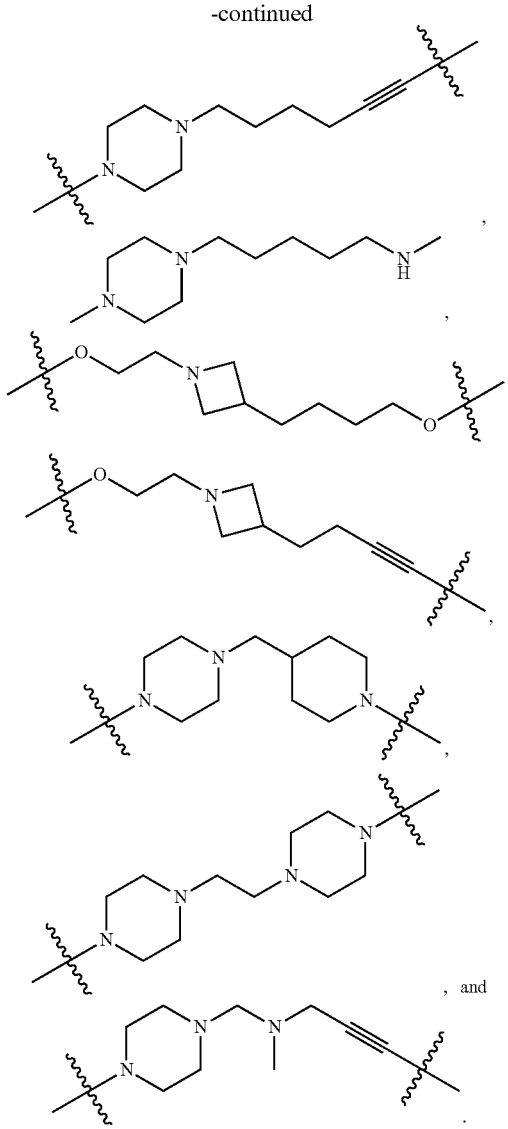

32. The method of any one of embodiments 20-31, wherein the compound is stereoisomer.
33. The method of embodiment 32, wherein the compound is cis-isomer.
34. The method of embodiment 32, wherein the compound is of Formula (I-B)*:

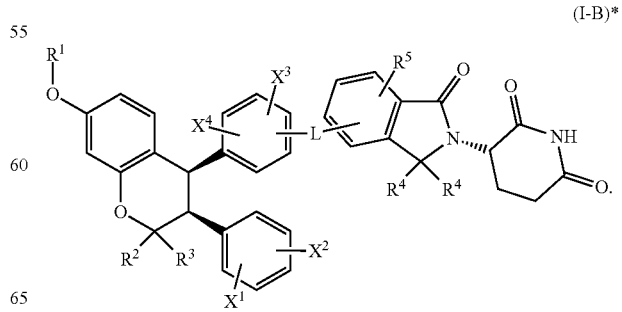

35. The method of any one of embodiments 20-34, wherein the estrogen receptor (ER) degrader is a compound from Table 1B.
36. The method of any one of the preceding embodiments, wherein the CDK inhibitor is a CDK1 inhibitor.
37. The method of any one of the preceding embodiments, wherein the CDK inhibitor has a structure according to Formula (II):

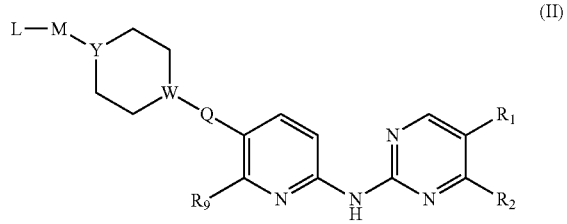

or a tautomer, or stereoisomer or mixture of stereoisomers, or a pharmaceutically acceptable salt, or hydrate thereof, wherein:
M is a bond, —NH—, or —C(O)—;
L is a H, alkyl, carbocyclyl, arylalkyl, heteroarylalkyl, or heterocycle, each of which is optionally substituted with one or more substituents;
Q is $CH_2$, O, S or a bond;
W and Y are independently CH or N, provided that at least one of W or Y is N, and when W is CH, Q is O or S; and
$R_1$ and $R_2$ are independently selected from hydrogen, halogen, alkyl, and heterocycle, wherein each of alkyl and heterocycle are optionally substituted with one or more substituents; or
$R_1$ and $R_2$ together with the atoms are to which they are attached form a carbocyclyl or heterocycle, each of which is optionally substituted with one or more substituents; and
$R_9$ is hydrogen, halogen, or alkyl, wherein alkyl is optionally substituted.
38. The method of any one of the preceding embodiments, wherein the CDK inhibitor has a structure according to Formula (III):

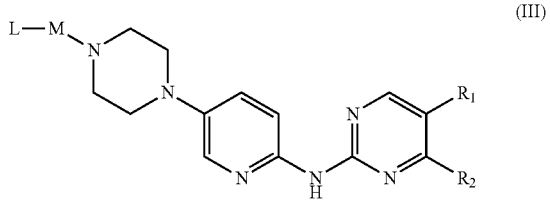

or a tautomer, stereoisomer or a mixture of stereoisomers, or a pharmaceutically acceptable salt, or hydrate thereof, wherein:
M is a bond, —NH—, or —C(O)—;
L is a H, carbocyclyl, arylalkyl, heteroarylalkyl, or heterocycle, each of which is optionally substituted with one or more substituents; and
$R_1$ and $R_2$ are independently selected from hydrogen, halogen, alkyl, and heterocycle, wherein alkyl and heterocycle are optionally substituted with one or more substituents;
or $R_1$ and $R_2$ together with the atoms are to which they are attached form a carbocyclyl or heterocycle, each of which is optionally substituted with one or more substituents.

39. The method of embodiment 37 or 38, wherein L is substituted with one or more halogen, aryl, heteroaryl, arylalkyl, heteroarylalkyl, wherein aryl, heteroaryl, arylalkyl, heteroarylalkyl is optionally substituted with one or more substituents.
40. The method of embodiment 39, wherein each of the aryl, heteroaryl, arylalkyl, heteroarylalkyl are optionally substituted with one or more substituents selected from the group consisting of halogen, nitro, hydroxyl, alkyl, aryl, heterocycle, —C(O), —C(O)$NR_gR_h$, wherein each of $R_g$ and $R_h$ are independently hydrogen or alkyl.
41. The method of embodiment 39 or 40, wherein L is: (i) aryl which is optionally substituted with a halogen and a heteroarylalkyl which is optionally substituted with —C(O); (ii) arylalkyl which is optionally substituted with a heteroaryl which is optionally substituted with one or more halogen, —C(O), or combinations thereof; or (iii) aryl which is optionally substituted with a heteroaryl which is optionally substituted with —C(O)$NR_gR_h$, wherein each of $R_g$ and $R_h$ are independently hydrogen or alkyl.
42. The method of embodiment 41, wherein L is a $C_{5-8}$ aryl which is optionally substituted with a halogen and a heteroarylalkyl comprising an 8-12-membered heteroaryl ring having from 1 to 4 atoms independently selected from nitrogen, oxygen and sulfur and which is optionally substituted with one or more substituents.
43. The method of embodiment 42, L is a $C_6$ aryl which is substituted with a halogen and a heteroarylalkyl comprising a 10-membered heteroaryl ring having 2 nitrogen atom and which is substituted with —C(O).
44. The method of embodiment 39 or 40, wherein L is a $C_{5-8}$ aryl-$C_{1-3}$ alkyl which is optionally substituted with a 10-15-membered heteroaryl having from 1 to 4 atoms independently selected from nitrogen, oxygen and sulfur and which is optionally substituted with one or more halogen, —C(O), or combinations thereof.
45. The method of embodiment 44, wherein, L is $C_6$ aryl-$C_1$ alkyl which is substituted with 13-membered heteroaryl which having 2 nitrogen atoms and which is substituted with a halogen and —C(O).
46. The method of embodiment 39 or 40, wherein L is a $C_{5-8}$ aryl which is optionally substituted a 6-12-membered heteroaryl having from 1 to 4 atoms independently selected from nitrogen, oxygen and sulfur and which is optionally substituted with —C(O)$NR_gR_h$, wherein each of $R_g$ and $R_h$ are independently hydrogen or alkyl.
47. The method of embodiment 46, wherein L is a $C_6$ aryl which is substituted with a 9-membered heteroaryl having from 2 nitrogen atoms and is substituted with —C(O)$NH_2$.
48. The method of embodiment 37, wherein L is selected from the group consisting of:

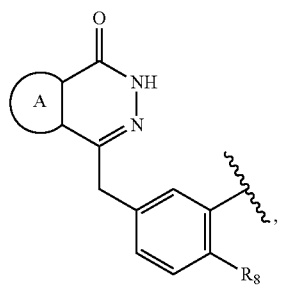

-continued

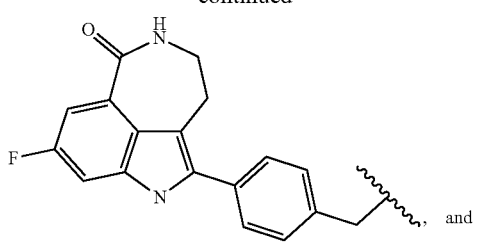, and

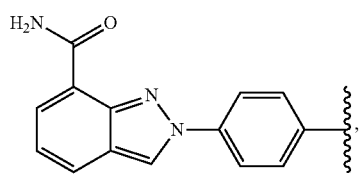

wherein:

the A ring represents a fused aryl or heteroaryl group, which is optionally substituted with one or more substituent groups selected from halogen, nitro, hydroxyl, ether, thiol, thioether, amino, alkyl, aryl and a heterocycle; and $R_8$ is hydrogen or halogen.

49. The method of embodiment 48, wherein L is:

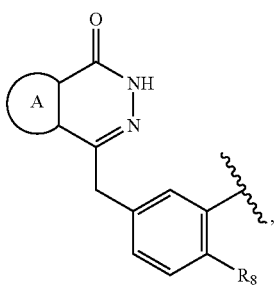

wherein:

the A ring represents a fused aryl or heteroaryl group, which is optionally substituted with one or more substituent groups selected from halogen, nitro, hydroxyl, amino, alkyl, aryl and a heterocycle; and $R_8$ is hydrogen or halogen.

50. The method of embodiment 49, wherein the A ring is a $C_{5-8}$ aryl.
51. The method of embodiment 49, wherein the A ring is benzene.
52. The method of any one of embodiments 49-51, wherein $R_8$ is selected from H, $C_1$, and F.
53. The method of any one of embodiments 37-52, wherein $R_1$ is a halogen.
54. The method of any one of embodiments 37-53, wherein $R_2$ is a 6-12 membered heteroaryl which is optionally substituted with one or more substituents.
55. The method of any one of embodiments 37-53, wherein $R_2$ is 9-membered heteroaryl substituted with one or more substituents selected from halogen, alkyl, and combinations thereof.
56. The method of any one of embodiments 37-53, wherein $R_2$ is:

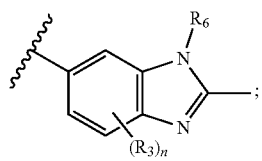

wherein
n is 0, 1, 2, or 3;
each $R_3$ is independently halogen or alkyl; and
$R_6$ is alkyl or cycloalkyl, each of which is optionally substituted with one or more substituents.

57. The method of any one of embodiments 54-56, wherein $R_2$ is selected from the group consisting of:

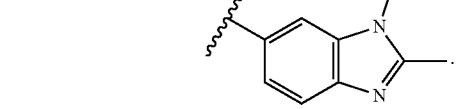

58. The method of any one of embodiments 37-52, wherein $R^1$ and $R^2$ together with the atoms to which they are attached form a heteroaryl which is optionally substituted with one or more substituents.
59. The method of embodiment 58, wherein $R^1$ and $R^2$ together with the atoms are to which they are attached form a 5 to 6-membered heteroaryl which is substituted with one or more substituents selected from the group consisting of halogen, alkyl, cycloalkyl, and combinations thereof.
60. The method of embodiment 59, wherein $R^1$ and $R^2$ together with the atoms to which they are attached form a ring selected from the group consisting of:

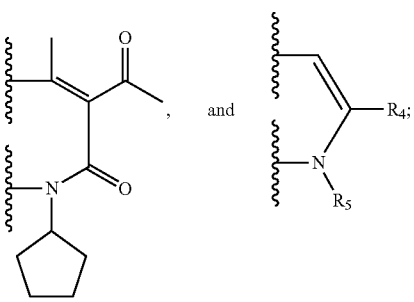

wherein:
$R^4$ is hydrogen or —C(O)NR$_a$R$_b$, wherein each of R$_a$ and R$_b$ are independently selected from hydrogen and alkyl; and
$R^5$ is cycloalkyl.

61. The method of any one of the preceding embodiments, wherein the CDK inhibitor is selected from the group consisting of:
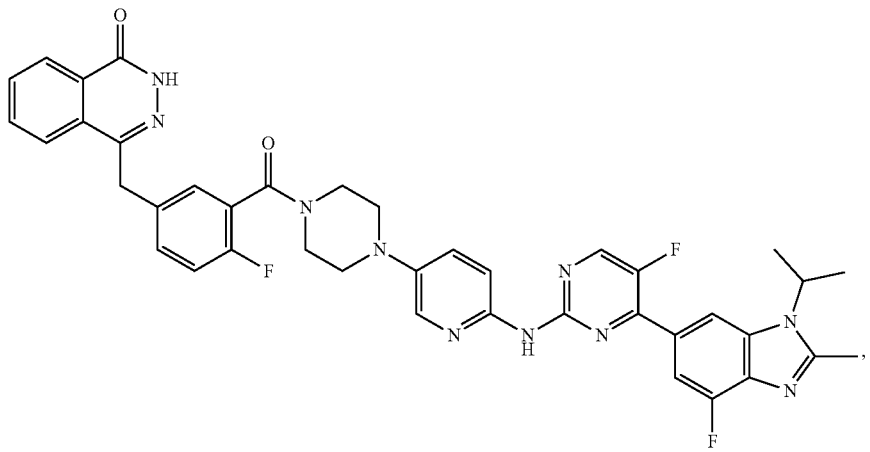
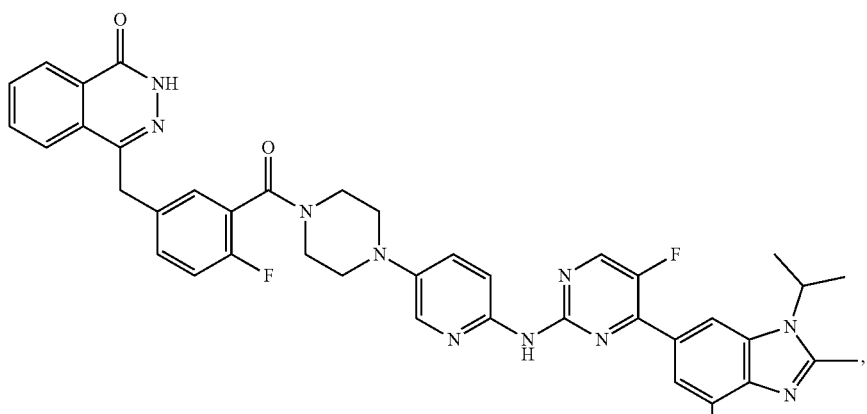
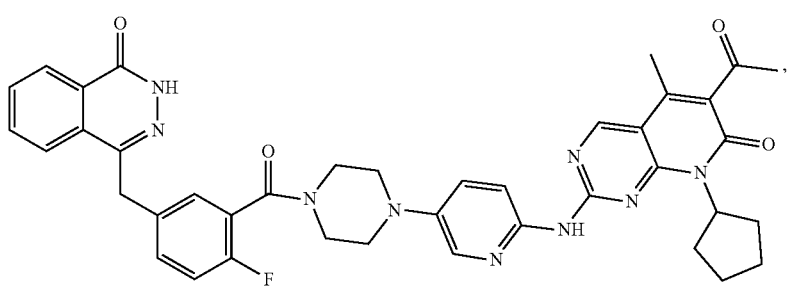
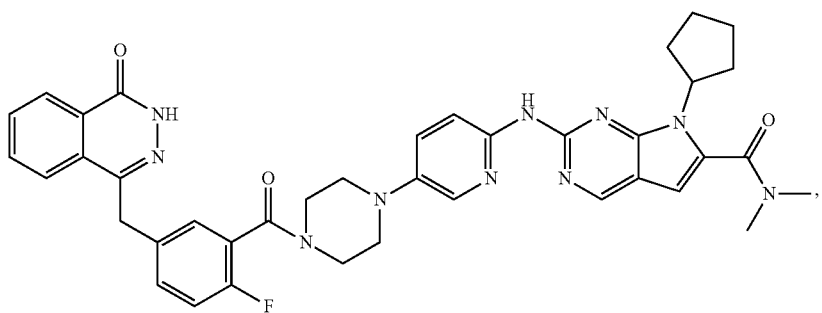

-continued
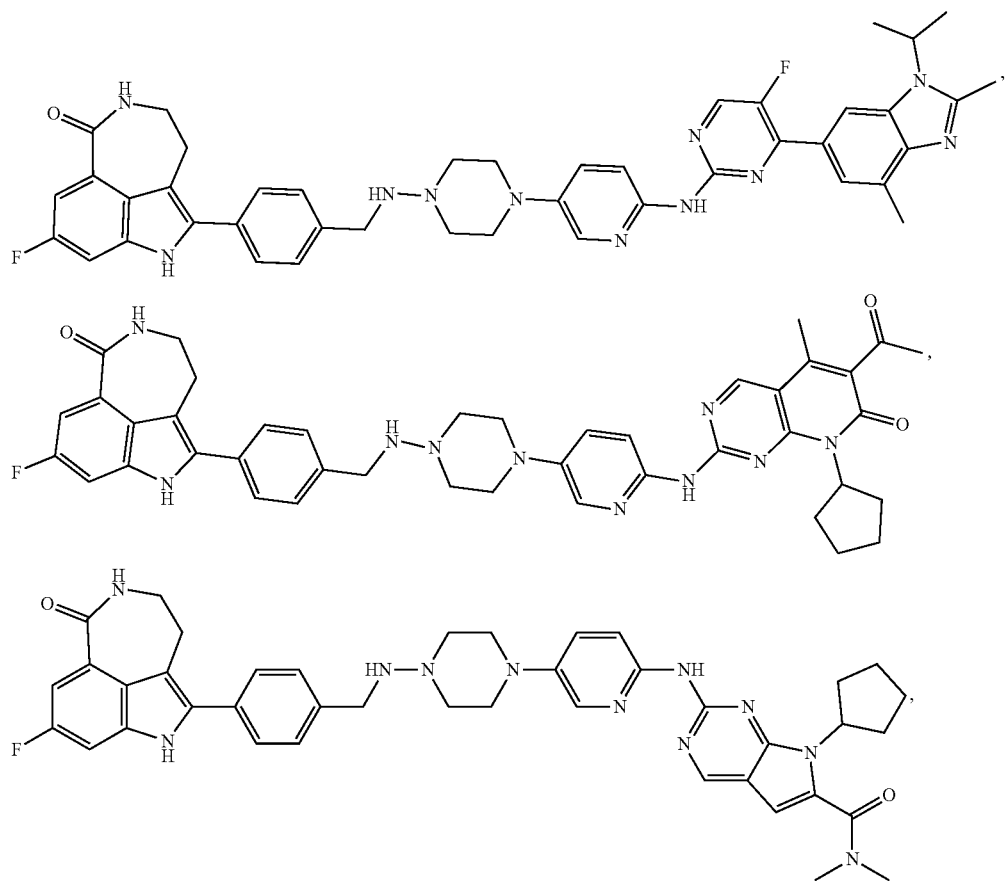
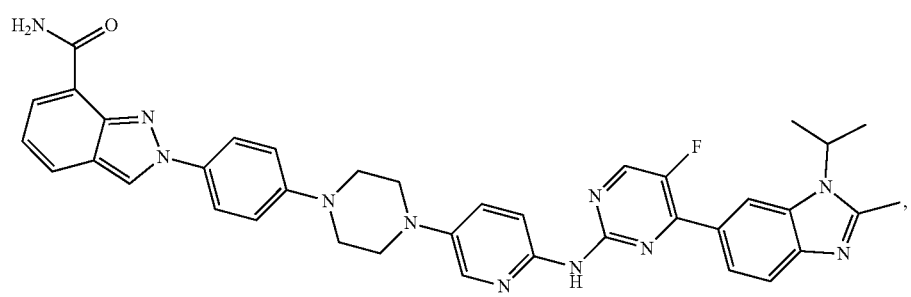
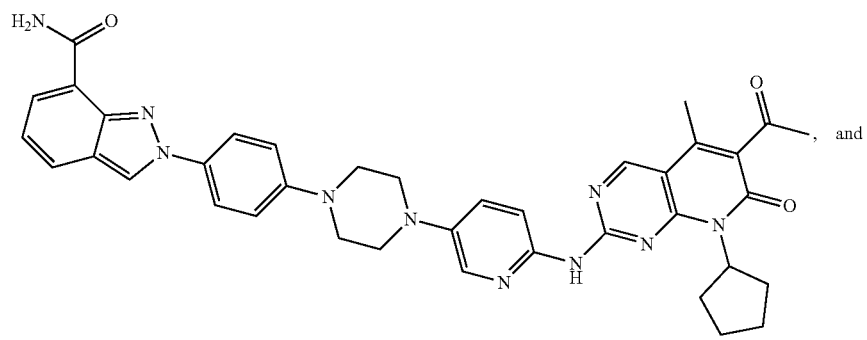

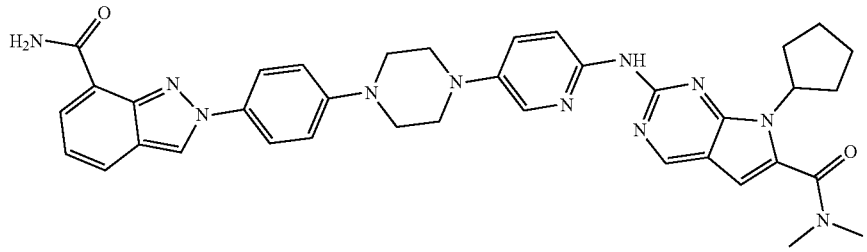

or a tautomer, stereoisomer or a mixture of stereoisomers, or a pharmaceutically acceptable salt, or hydrate thereof.

62. The method of any one of embodiments 1-63, wherein the estrogen receptor (ER) degrader and the cyclin-dependent kinase (CDK) inhibitor are in single dosage form or in separate dosage forms.
63. The method of embodiment 62, wherein the separate dosage forms are administered via same mode of administration or different modes of administration.
64. The method of embodiment 63, wherein the separate dosage forms are co-administered via simultaneous administration, sequential administration, overlapping administration, interval administration, continuous administration, or a combination thereof.
65. The method of any one of embodiments 1-64, wherein the dosage form is an oral dosage form.
66. The method of any one of embodiments 1-65, wherein the CDK inhibitor is a CDK4/6 inhibitor.
67. The method of embodiment 66, wherein the CDK4/6 inhibitor is selected from the group consisting of palbociclib, ribociclib, and abemaciclib or a pharmaceutically acceptable salt, polymorph, or solvate thereof.
68. The method of any one of embodiments 65-67, wherein the oral dosage form comprises about 125 mg, about 100 mg, or about 75 mg of palbociclib.
69. The method of any one of embodiments 65-67, wherein the oral dosage form comprises ribociclib succinate in about 200 mg of the Equivalent Amount of ribociclib free base.
70. The method of any one of any one of embodiments 65-67, wherein the oral dosage form abemaciclib in about 50 mg, about 100 mg, about 150 mg, or about 200 mg of abemaciclib.
71. The method of any one of embodiments 65-70, wherein the oral dosage form is a tablet or a capsule.
72. The method of any one of embodiments 1-71, wherein the estrogen receptor (ER) degrader and the cyclin-dependent kinase (CDK) inhibitor are administered as a pharmaceutical formulation further comprising a pharmaceutically acceptable excipient or a pharmaceutically acceptable carrier.
73. The method of any one of embodiments 1-72, wherein the cancer is selected from breast cancer, lung cancer, ovarian cancer, endometrial cancer, prostate cancer, and esophageal cancer.
74. The method of any one of embodiments 1-73, wherein the cancer is positive for ERα.
75. The method of embodiment 67 comprising administering to the subject an initial dose of about 125 mg/day of palbociclib in combination with the estrogen receptor (ER) degrader.
76. The method of embodiment 67, comprising administering to the subject ribociclib succinate in an initial dose of about 600 mg/day of the Equivalent Amount of ribociclib free base in combination with the estrogen receptor (ER) degrader.
77. The method of embodiment 67, comprising administering to the subject an initial dose of abemaciclib from about 150 mg twice daily to about 200 mg twice daily in combination with the estrogen receptor (ER) degrader.
78. The method of any one of embodiments 1-77, wherein the estrogen receptor (ER) degrader is administered in a dose of from 30 mg to 600 mg once or twice daily.
79. The method of embodiments 1-19, wherein the ER degrader is selected from the group consisting of:

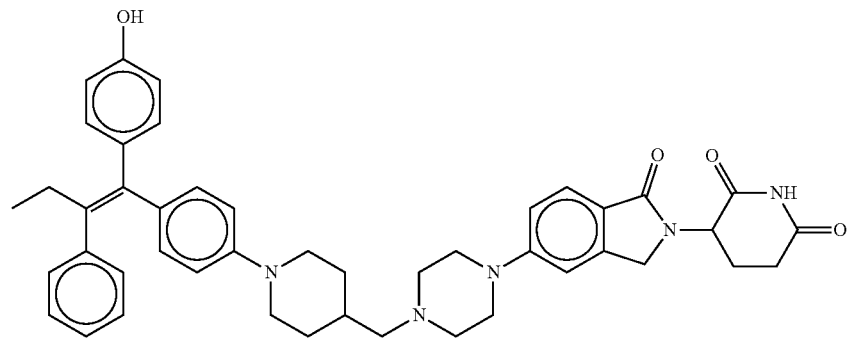

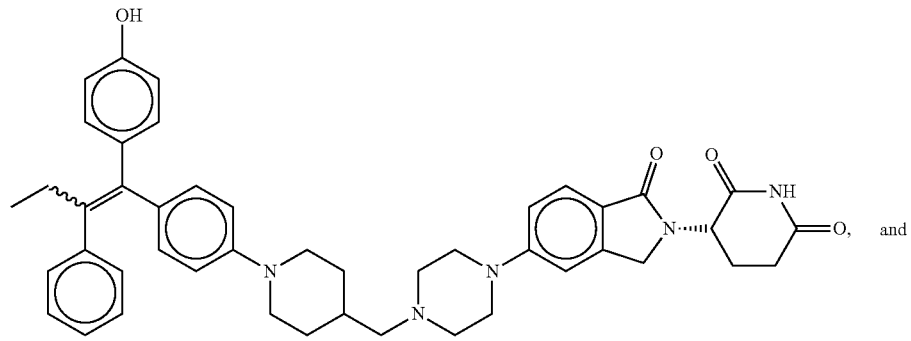
, and
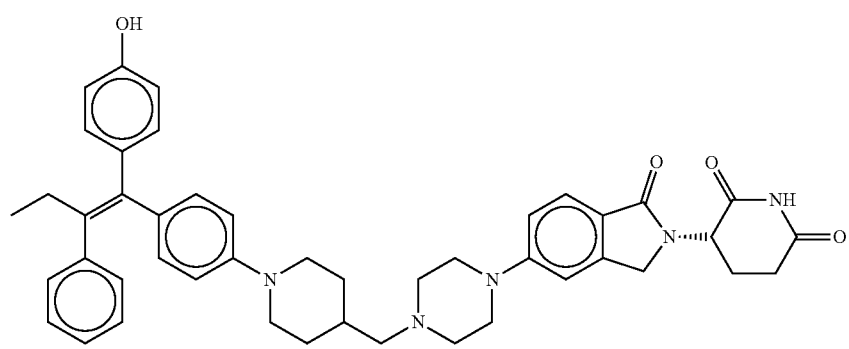
or a pharmaceutically acceptable salt thereof.
80. The method of embodiment 79, wherein the ER degrader is:
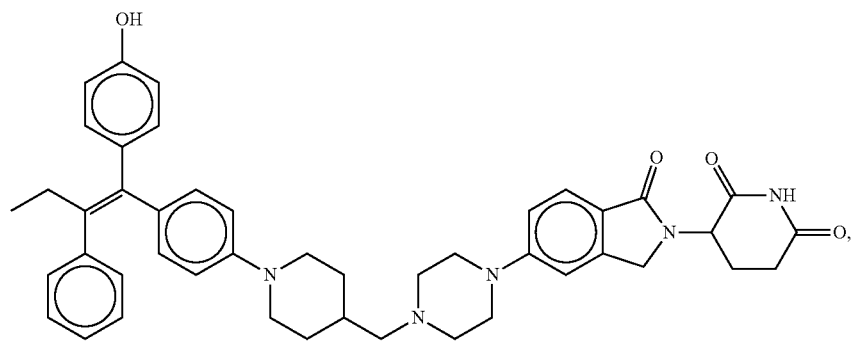
or a pharmaceutically acceptable salt thereof.

81. The method of embodiment 79, wherein the ER degrader is:
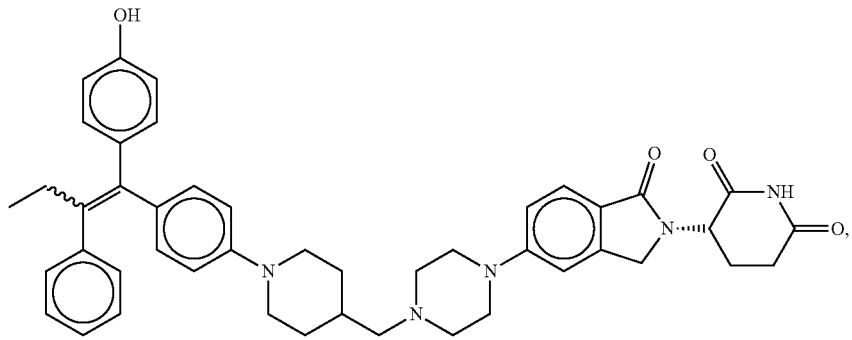
or a pharmaceutically acceptable salt thereof.
82. The method of embodiment 79, wherein the ER degrader is:
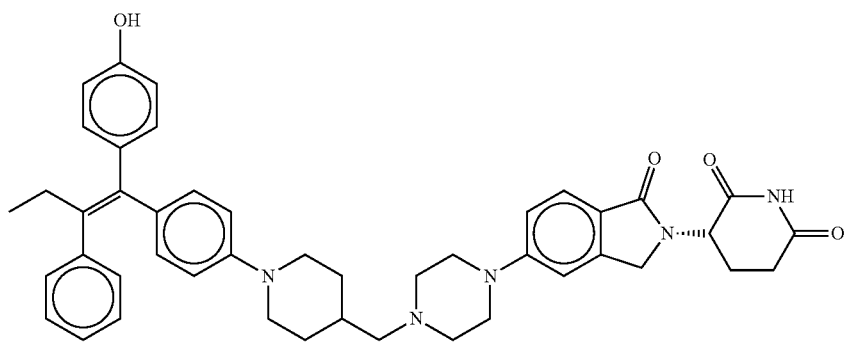
or a pharmaceutically acceptable salt thereof.
83. The method of any one of embodiments 20-35, wherein the ER degrader is selected from the group consisting of:
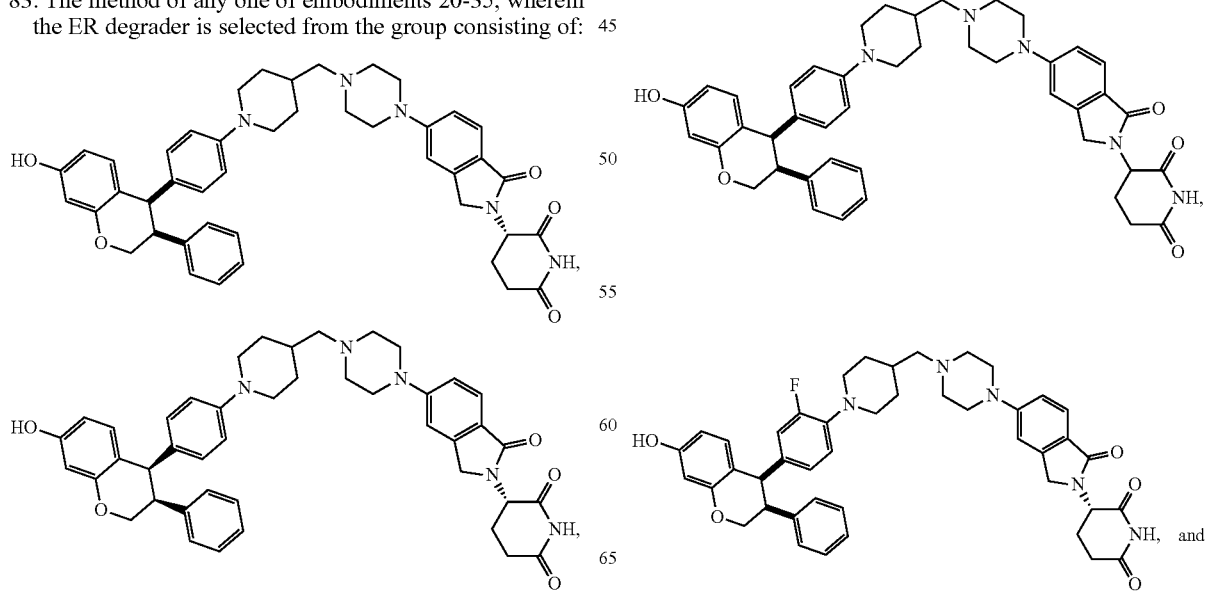

-continued

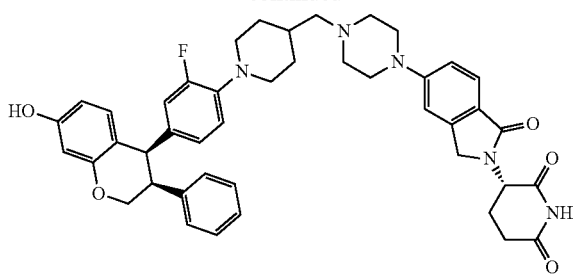

or a pharmaceutically acceptable salt thereof.

84. The method of embodiment 83, wherein the ER degrader is:

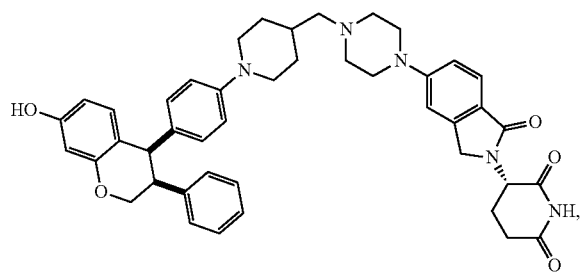

or a pharmaceutically acceptable salt thereof.

85. The method of embodiment 83, wherein the ER degrader is:

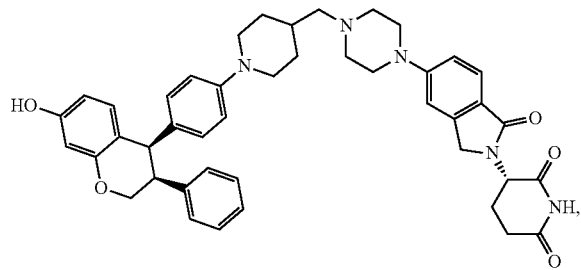 [SMILES: O=C1CC[C@H](N2Cc3cc(N4CCN(CC5CCN(c6ccc([C@@H]7c8ccc(O)cc8OC[C@@H]7c7ccccc7)cc6)CC5)CC4)ccc3C2=O)C(=O)N1]

or a pharmaceutically acceptable salt thereof.

86. The method of embodiment 83, wherein the ER degrader is:

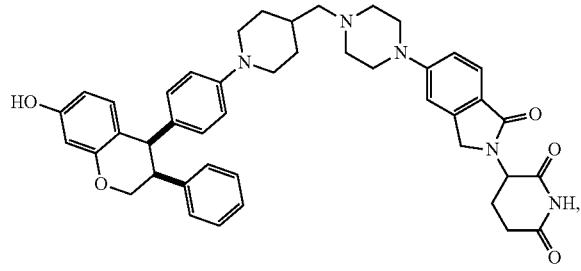

or a pharmaceutically acceptable salt thereof.

87. The method of embodiment 83, wherein the ER degrader is:

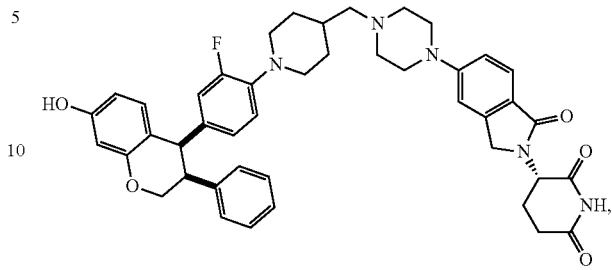

or a pharmaceutically acceptable salt thereof.

88. The method of embodiment 83, wherein the ER degrader is:

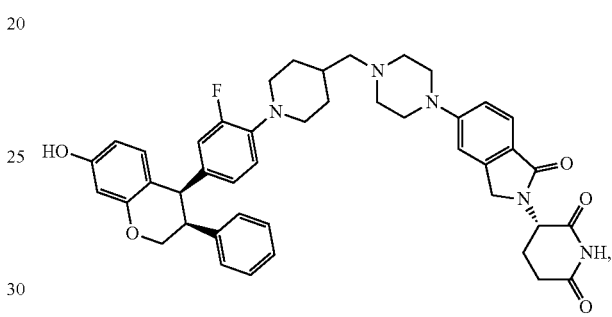

or a pharmaceutically acceptable salt thereof.

Having now generally described the invention, the same will be more readily understood through reference to the following examples, which are provided by way of illustration and are not intended to be limiting of the present invention.

EXAMPLES

The examples and preparations provided below further illustrate and exemplify the compounds as disclosed herein and methods of preparing such compounds. It is to be understood that the scope of the present disclosure is not limited in any way by the scope of the following examples and preparations.

Synthetic Methods

Compounds of the invention and intermediates thereof can be prepared in a number of ways known to one of ordinary skill in the art of organic synthesis. Some of the ER degraders described herein can be synthesized by methods described in U.S. Pat. Nos. 10,696,659 10,800,770 the contents of each of which are hereby incorporated by reference in their entirety. Starting materials and intermediates can be purchased from commercial sources or can be made from known procedures. The skilled artisan will also recognize that conditions and reagents described herein can be interchanged with alternative art-recognized equivalents.

General Methods

T47D cells, an ER-positive human breast cancer cell line, were plated in 96-well tissue culture microplates at 3000 cells/well in 80 ul of RPMI growth medium containing 10% FBS and 1% Penicillin Streptomycin. Cells were incubated at 37° C. overnight. The following day, the two test compounds was administered to the cells by using 10× compound stock solution prepared in growth medium at various concentrations. After administration of the compound, cells were then incubated at 37° C. for 6 days. Before CellTiter-Glo assay, the plates were equilibrated at room temperature for approximately 10 minutes. 100 ul of CellTiter-Glo® Reagent (Promega, G7573) was added to each well. The plates were then incubated at room temperature for 10 minutes and luminescence was recorded by EnSpire plate reader (PerkinElmer).

MCF-7 cells, a breast cancer cell cline, (10×10$^6$) in 0.1 mL of PBS mixed with 0.1 mL matrigel (total 0.2 mL) were inoculated subcutaneously at the right flank of each mouse, which has been implanted with 17β-estradiol (0.18 mg) tablet subcutaneously in the left flank three days before. When the average tumor volume reaches approximately 175 mm$^3$, the animals were randomized and treatment was started.

Example 1. ER Degrader+Palbociclib

ER-positive T47D cells were treated with increasing concentrations of ER degrader 160a disclosed herein, alone (FIG. 1, 0 nM Palbociclib), with a CDK4/6 inhibitor, increasing concentrations of Palbociclib, alone (as shown on Y axis of FIG. 1 when conc. of ER degrader 160a is 0 nM, and conc. of Palbociclib is 10 nM, 30, nM and 100 nM), or the combination of 160a and increasing concentrations of Palbociclib. The cell growth inhibition curve is shown in FIG. 1.

These results indicate that the ER degrader 160a synergizes with CDK4/6 inhibitor Palbociclib in vitro to inhibit cell growth with greater efficacy than the ER degrader or CDK4/6 inhibitor alone.

Example 2. ER Degrader+Abemaciclib

Figure 2:
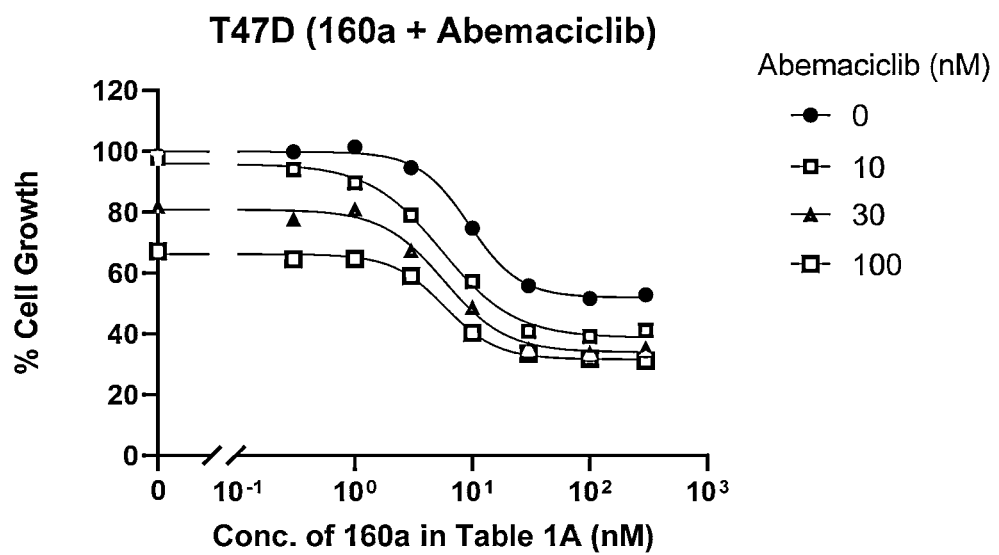
FIG. 2 is a cell growth inhibition curve depicting cell growth (%) in ER-positive T47D cells treated with abemaciclib alone at 10, 30, and 100 nM, and ER degrader 160a in Table 1A alone or in combination with abemaciclib at 10, 30, and 100 nM.

ER-positive T47D cells were treated with increasing concentrations of ER degrader 160a disclosed herein, alone (FIG. 2, 0 nM Abemaciclib), or with CDK4/6 inhibitor, with increasing concentrations of Abemaciclib, alone (as shown on Y axis of FIG. 2 when conc. of ER degrader 160a is 0 nM, and conc. of Abemaciclib is 10 nM, 30 nM, and 100 nM), or with the combination of 160a and increasing concentrations of Abemaciclib. The cell growth inhibition curve is shown in FIG. 2.

These results indicate that the ER degrader 160a synergizes with CDK4/6 inhibitor Abemaciclib in vitro to inhibit cell growth with greater efficacy than the ER degrader alone.

Example 3. ER Degrader+Palbociclib

Figure 3:
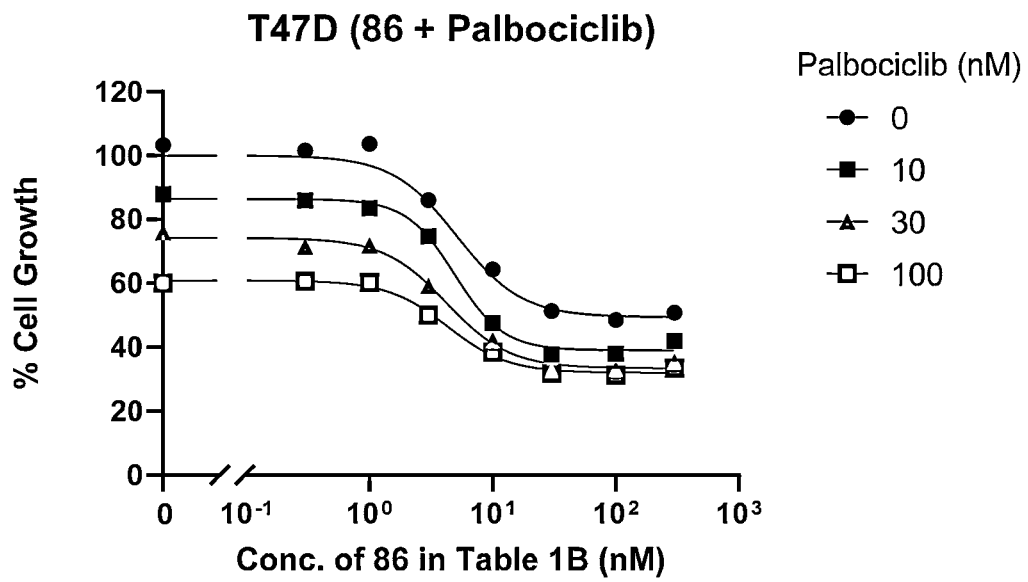
FIG. 3 is a cell growth inhibition curve depicting cell growth (%) in ER-positive T47D cells treated with palbociclib alone at 10, 30, and 100 nM, and with ER degrader 86 in Table 1B alone or in combination with palbociclib at 10, 30, and 100 nM.

ER-positive T47D cells were treated with increasing concentrations of ER degrader 86 disclosed herein, alone (FIG. 3, 0 nM Palbociclib), with CDK4/6 inhibitor, with increasing concentrations of Palbociclib, alone (as shown on Y axis of FIG. 3, when conc. of ER degrader 86 is 0 nM, and conc. of Palbociclib is 10 nM, 30 nM, and 100 nM), or with the combination of ER degrader 86 and increasing concentrations of Palbociclib. The cell growth inhibition curve is shown in FIG. 3.

These results indicate that the ER degrader 86 from Table 1B synergizes with CDK4/6 inhibitor Palbociclib in vitro to inhibit cell growth with greater efficacy than the ER degrader or CDK4/6 inhibitor alone.

Example 4. ER Degrader+Abemaciclib

Figure 4:
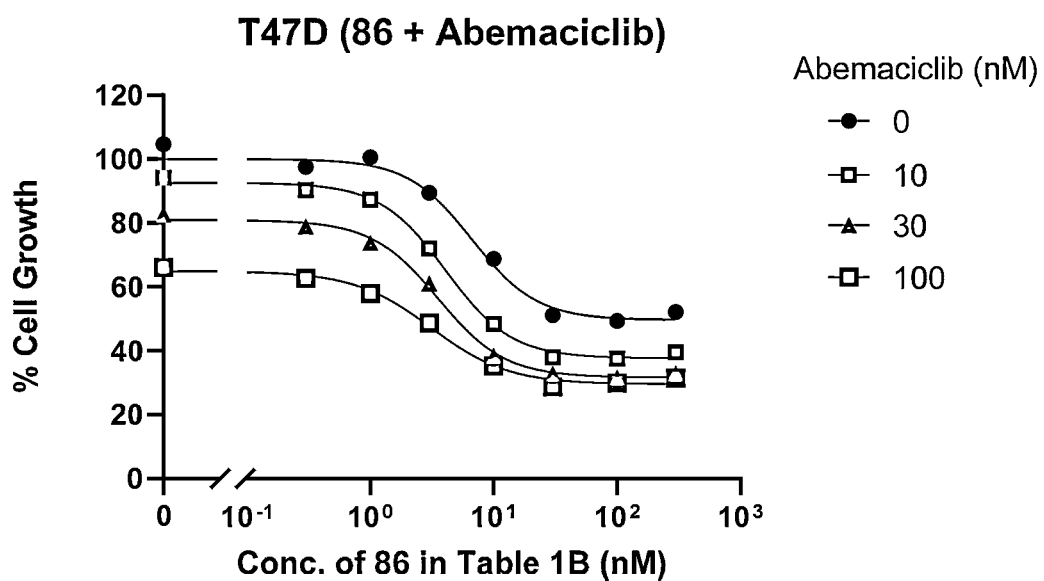
FIG. 4 is a cell growth inhibition curve depicting cell growth (%) in ER-positive T47D cells treated with abemaciclib alone at 10, 30, and 100 nM, and with ER degrader 86 in Table 1B alone or in combination with abemaciclib at 10, 30, and 100 nM.

ER-positive T47D cells were treated with increasing concentrations of ER degrader 86 disclosed herein, alone (FIG. 4, 0 nM Abemaciclib), with increasing concentrations of CDK4/6 inhibitor, Abemaciclib, alone) (as shown on Y axis of FIG. 4 when conc. of ER degrader 86 is 0 nM, and conc. of Abemaciclib is 10 nM, 30 nM, and 100 nM), or with the combination of ER degrader 86 and increasing concentrations of Abemaciclib. The cell growth inhibition curve is shown in FIG. 4.

These results indicate that the ER degrader 86 synergizes with CDK4/6 inhibitor Abemaciclib in vitro to inhibit cell growth with greater efficacy than the ER degrader alone or CDK4/6 inhibitor alone.

Figure 5:
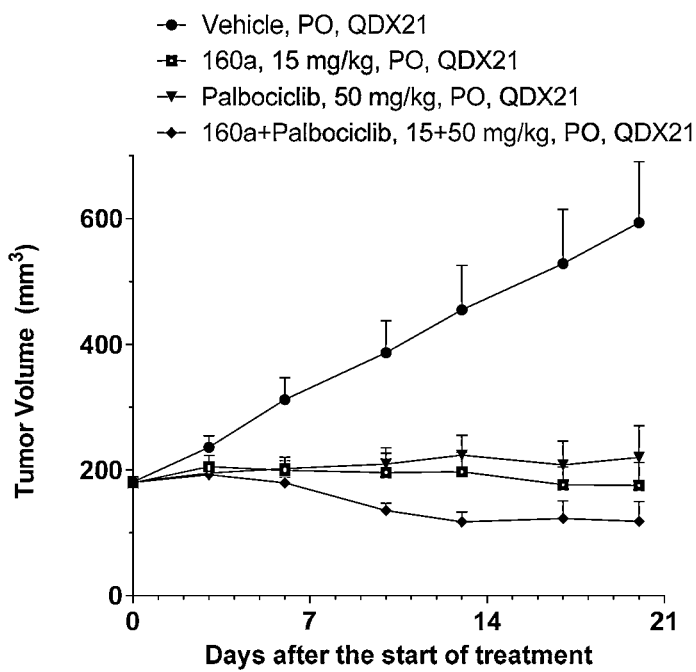
FIG. 5 illustrates antitumor activity from 160a in Table 1A and Palbociclib alone at the indicated doses or their combination in a MCF7 human tumor xenograft model.

Example 5. Anti-Tumor Efficacy of ER Degrader+Palbociclib in MCF7 Human Xenograft Tumors MCF-7 tumor cells (10×10$^6$) in 0.1 mL of PBS mixed with 0.1 mL matrigel (total 0.2 mL) were inoculated subcutaneously at the right flank of each BALB/c nude mouse, which has been implanted with 17β-estradiol (0.18 mg) tablet subcutaneously in the left flank three days before. When the average tumor volume reached approximately 175 mm$^3$, the animals were randomized and treated for 21 days with an ER degrader 160a alone, or with a CDK4/6 inhibitor, Palbociclib, alone, or with the combination of ER degrader 160a and Palbociclib. The tumor growth curve is shown in FIG. 5.

These results indicate that the ER degrader 160a synergizes with CDK4/6 inhibitor Palbociclib in vivo to inhibit tumor growth with greater efficacy than the ER degrader or CDK4/6 inhibitor alone.

Figure 6:
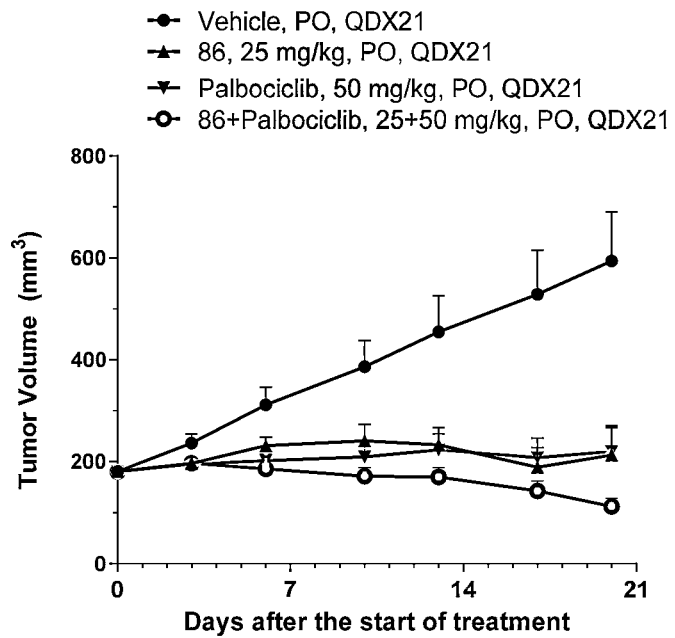
FIG. 6 illustrates antitumor activity from 86 in Table 1B and Palbociclib alone at the indicated doses or their combination in a MCF7 human tumor xenograft model.

Example 6. Anti-Tumor Efficacy of ER Degrader+Palbociclib in MCF7 Human Xenograft Tumors MCF-7 tumor cells (10×10$^6$) in 0.1 mL of PBS mixed with 0.1 mL matrigel (total 0.2 mL) were inoculated subcutaneously at the right flank of each BALB/c nude mouse, which has been implanted with 17β-estradiol (0.18 mg) tablet subcutaneously in the left flank three days before. When the average tumor volume reached approximately 175 mm$^3$, the animals were randomized and treated for 21 days with an ER degrader 86 alone, or with a CDK4/6 inhibitor, Palbociclib, alone, or with the combination of 86 and Palbociclib. The tumor growth curve is shown in FIG. 6.

These results indicate that the ER degrader 86 synergizes with CDK4/6 inhibitor Palbociclib in vivo to inhibit tumor growth with greater efficacy than the ER degrader or CDK4/6 inhibitor alone.

Figure 7:
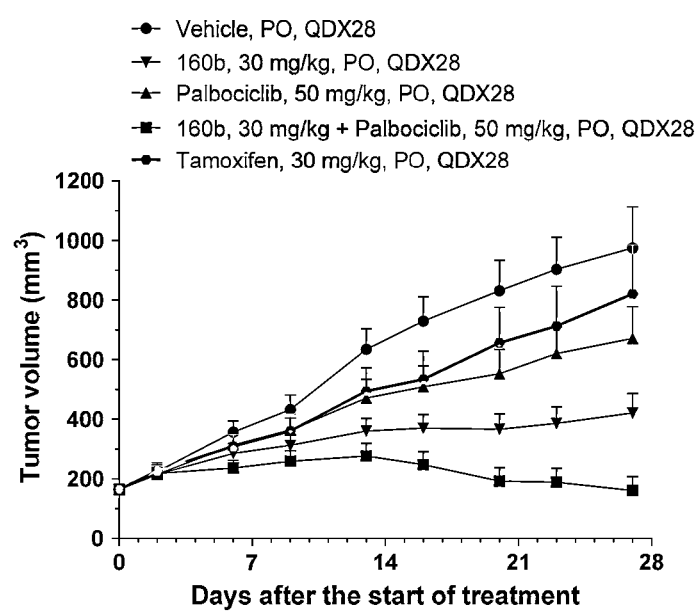
FIG. 7 illustrates antitumor activity from 160b in Table 1A and Palbociclib alone at the indicated doses or their combination in a tamoxifen-resistant MCF7 human tumor xenograft model.

Example 7. Anti-Tumor Efficacy of ER Degrader+Palbociclib in Tamoxifen-Resistant MCF7 Human Xenograft Tumors Tamoxifen-resistant MCF-7 cells were subcutaneously implanted to establish cell line-derived xenograft tumors. 30 mg/kg tamoxifen is administrated until tumor showed continuous growth. This tumor was then defined as passage 0. The tumor fragments were constantly implanted into new animals (per passage) with 30 mg/kg Tamoxifen treatment. For the efficacy study, the passage 9 tamoxifen-resistant tumor fragments (~30 mm3) were inoculated subcutaneously at the right flank of each BALB/c nude mouse, which has been implanted with 17β-estradiol (0.36 mg) tablet subcutaneously in the left flank three days before. When the average tumor volume reached approximately 175 mm3, the animals were randomized and treated for 28. Tamoxifen-resistant MCF7 human xenograft tumors were treated with an ER degrader 160b alone, or with a CDK4/6 inhibitor, Palbociclib, alone, or with the combination of ER degrader 160b and Palbociclib. The tumor growth curve is shown in FIG. 7.

These results indicate that the ER degrader 160b synergizes with CDK4/6 inhibitor Palbociclib in vivo to inhibit tumor growth with greater efficacy than the ER degrader or CDK4/6 inhibitor alone.

What is claimed:

1. A method of treating an estrogen receptor-positive (ER+) cancer in a patient in need thereof, comprising administering an estrogen receptor (ER) degrader having a structure of:

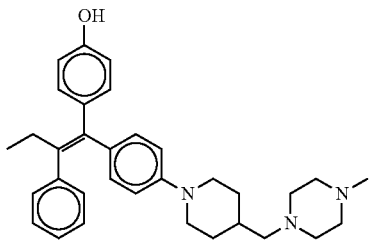

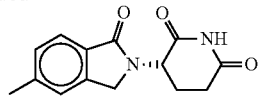

or a pharmaceutically acceptable salt thereof; and
the cyclin dependent kinase (CDK) palbociclib or a pharmaceutically acceptable salt thereof; and
wherein the estrogen receptor-positive (ER+) cancer is breast cancer.

2. The method of claim 1, wherein the estrogen receptor (ER) degrader and the cyclin-dependent kinase (CDK) inhibitor are administered as a pharmaceutical formulation further comprising a pharmaceutically acceptable excipient or a pharmaceutically acceptable carrier.

3. The method of claim 1, wherein the cancer is positive for ERα.

4. The method of claim 1, wherein the estrogen receptor (ER) degrader and the cyclin-dependent kinase (CDK) inhibitor are in separate dosage forms.

5. The method of claim 4, wherein the separate dosage forms are administered via same mode of administration or different modes of administration.

6. The method of claim 4, wherein the separate dosage forms are co-administered via simultaneous administration, sequential administration, overlapping administration, interval administration, or continuous administration.

* * * * *